US009944658B2

(12) United States Patent
Burns et al.

(10) Patent No.: US 9,944,658 B2
(45) Date of Patent: Apr. 17, 2018

(54) BETA-LACTAMASE INHIBITORS

(71) Applicant: VenatoRx Pharmaceuticals, Inc., Malvern, PA (US)

(72) Inventors: Christopher J. Burns, Malvern, PA (US); Denis Daigle, Street, MD (US); Bin Liu, Dayton, NJ (US); Daniel McGarry, Malvern, PA (US); Daniel C. Pevear, Downingtown, PA (US); Robert E. Lee Trout, Collegeville, PA (US)

(73) Assignee: VENATORX PHARMACEUTICALS, INC., Malvern, PA (US)

( * ) Notice: Subject to any disclaimer, the term of this patent is extended or adjusted under 35 U.S.C. 154(b) by 13 days.

(21) Appl. No.: 14/773,717

(22) PCT Filed: Mar. 13, 2014

(86) PCT No.: PCT/US2014/026727
§ 371 (c)(1),
(2) Date: Sep. 8, 2015

(87) PCT Pub. No.: WO2014/151958
PCT Pub. Date: Sep. 25, 2014

(65) Prior Publication Data
US 2016/0024121 A1 Jan. 28, 2016

Related U.S. Application Data

(60) Provisional application No. 61/785,919, filed on Mar. 14, 2013.

(51) Int. Cl.
*C07F 5/02* (2006.01)
*A61K 45/06* (2006.01)
*A61K 31/69* (2006.01)

(52) U.S. Cl.
CPC .............. *C07F 5/025* (2013.01); *A61K 31/69* (2013.01); *A61K 45/06* (2013.01)

(58) Field of Classification Search
CPC .................................... C07F 5/025; A61K 31/69
See application file for complete search history.

(56) References Cited

U.S. PATENT DOCUMENTS

| 4,427,690 | A | 1/1984 | Cole et al. |
| 7,271,186 | B1 | 9/2007 | Shoichet et al. |
| 8,680,136 | B2 | 3/2014 | Hirst et al. |
| 8,912,169 | B2 | 12/2014 | Burns et al. |
| 9,040,504 | B2 | 5/2015 | Burns et al. |
| 9,101,638 | B2 | 8/2015 | Reddy et al. |
| 2010/0056478 | A1 | 3/2010 | Desarbre et al. |
| 2010/0120715 | A1 | 5/2010 | Burns et al. |
| 2010/0286092 | A1* | 11/2010 | Burns .................. C07F 5/025 514/64 |
| 2010/0292185 | A1 | 11/2010 | Burns et al. |
| 2010/0317621 | A1 | 12/2010 | Burns et al. |
| 2011/0294777 | A1 | 12/2011 | Blizzard et al. |
| 2012/0040932 | A1 | 2/2012 | Hirst et al. |
| 2015/0224125 | A1 | 8/2015 | Burns et al. |
| 2015/0361107 | A1* | 12/2015 | Trout .................. A61K 31/69 514/64 |
| 2016/0264598 | A1 | 9/2016 | Burns et al. |

FOREIGN PATENT DOCUMENTS

| WO | WO-2005004799 | A2 | 1/2005 |
| WO | WO-2009064413 | A1 | 5/2009 |
| WO | WO-2009064414 | A1 | 5/2009 |
| WO | WO-2010056827 | A1 | 5/2010 |
| WO | WO-2010130708 | A1 | 11/2010 |
| WO | WO-2012021455 | A1 | 2/2012 |
| WO | WO-2013053372 | A1 | 4/2013 |
| WO | WO-2013092979 | A1 | 6/2013 |
| WO | WO-2013122888 | A2 | 8/2013 |
| WO | WO-2014089365 | A1 | 6/2014 |
| WO | WO-2014107535 | A1 | 7/2014 |
| WO | WO-2014107536 | A1 | 7/2014 |
| WO | WO-2014110442 | A1 | 7/2014 |
| WO | WO-2014151958 | A1 | 9/2014 |
| WO | WO-2014151959 | A1 | 9/2014 |

OTHER PUBLICATIONS

Patani et al. Bioisosterism: A Rational Approach in Drug Design. Chemical Reviews 96:3147-3176 (1996).
Co-pending U.S. Appl. No. 15/194,443, filed Jun. 27, 2016.
Co-pending U.S. Appl. No. 15/212,959, filed Jul. 18, 2016.
Co-pending U.S. Appl. No. 15/261,359, filed Sep. 9, 2016.
Burns et al. CAPLUS AN 2014-1130723 (2014).
Isomer. https://en.wikipedia.org/wiki/Isomer (2015).
PCT/US2015/035407 International Search Report and Written Opinion dated Oct. 20, 2015.
U.S. Appl. No. 14/649,527 Office Action dated Nov. 9, 2015.
U.S. Appl. No. 14/759,853 Office Action dated Dec. 11, 2015.
Bodner Research Web. The Chemistry of the Halogens. Available from http://web.archive.org/web/20090414155348/http://chemechem/topicreview/bp/ch10/group3.php.
Co-pending U.S. Appl. No. 14/649,527, filed Jun. 3, 2015.
Co-pending U.S. Appl. No. 14/736,921, filed Jun. 11, 2015.
Co-pending U.S. Appl. No. 14/737,156, filed Jun. 11, 2015.
Co-pending U.S. Appl. No. 14/737,323, filed Jun. 11, 2015.
Co-pending U.S. Appl. No. 14/759,853, filed Jul. 8, 2015.
Eidam et al. Design, synthesis, crystal structures, and antimicrobial activity of sulfonamide boronic acids as β-lactamase inhibitors. J. Med. Chem. 53(21):7852-7863 (2010).
Ettmayer et al. Lessons Learned from Marketed and Investigational Prodrugs. J Medicinal Chem. 47(10):2393-2404. 2004.

(Continued)

*Primary Examiner* — Joseph R Kosack
(74) *Attorney, Agent, or Firm* — Wilson, Sonsini, Goodrich & Rosati

(57) ABSTRACT

Described herein are compounds and compositions that modulate the activity of beta-lactamases. In some embodiments, the compounds described herein inhibit beta-lactamase. In certain embodiments, the compounds described herein are useful in the treatment of bacterial infections.

19 Claims, No Drawings

(56) References Cited

OTHER PUBLICATIONS

Han. Targeted Prodrug Design to Optimize Drug Delivery. AAPS Pharmsci. 2(1)Article 6:1-11 (2000).
Lima et al. Bioisosterism: A Useful Strategy for Molecular Modificaion and Drug Design. Current Medicinal Chemistry 12:23-49 (2005).
Morandi et al. Structure-based optimization of cephalothin-analogue boronic acids as β-lactamase inhibitors. Bioorg. Med. Chem. 16(3):1195-1205 (2008) (Epub: Nov. 7, 2007).
Ness et al. Structure-based design guides the improved efficacy of deacylation transition state analogue inhibitors of TEM-1 β-lactamase. Biochemistry 39(18):5312-5321 (2000).
PCT/US2013/073428 International Search Report dated Apr. 25, 2014.
PCT/US2014/011144 International Search Report dated May 12, 2014.
PCT/US2014/026727 International Search Report and Written Opinion dated Jul. 25, 2014.
Powers et al. Structure-based approach for binding site identification on AmpC β-lactamase. J. Med. Chem. 45(15):3222-3234 (2002).
Powers et al. Structures of ceftazidime and its transition-state analogue in complex with AmpC β-lactamase: implications for resistance mutations and inhibitor design. Biochemistry 40(31):9207-9214 (2001).
Testa. Prodrug research: futile or fertile? Biochem. Pharm. 68:2097-2106 (2004).
U.S. Appl. No. 14/693,318 Office Action dated Sep. 1, 2015.
U.S. Appl. No. 14/152,916 Office Action dated Aug. 29, 2014.
Weston et al. Structure-based enhancement of boronic acid-based inhibitors of AmpC β-lactamase. J. Med. Chem. 41(23):4577-4586 (1998).
Bacterial Infection 101. Available at http://www.onhealth.com/content/l/bacterial_infections (34 pgs) (2017).
Definition of Quinoxaline from PubChem. http://pubchem.ncbi.nlm.nih.gov/compund/quinoxaline#section=information-sources. (24 pgs) (2005).
Definition of Quinoxaline from Wikipedia. http://en.wikipedia.org/wiki/Quinoxaline (3 pgs.) (2016).
Ishikawa et al. Synthesis and antimicrobial activity of 2,3-bis(bromomethyl)quinoxaline derivatives. Bioorg Chem 41-42:1-5 (2012).
Pub Chem Substance Record for SID 197433672. https://pubchem.ncbi.nim.nih/substance/197433672. Created Aug. 18, 2014. Retrieved Jan. 10, 2017 ( 5 pgs).
U.S. Appl. No. 15/194,433 Office Action dated Feb. 9, 2017.
U.S. Appl. No. 15/212,959 Office Action dated Mar. 23, 2017.
U.S. Appl. No. 90/013,866 Ex Parte Reexam Office Action dated Apr. 20, 2017.
Isomer. https://en.wikipedia.org/wiki/Isomer (5 pgs) (2017).

* cited by examiner

BETA-LACTAMASE INHIBITORS

CROSS-REFERENCE

This application is a U.S. National Stage entry of International Application No. PCT/US14/26727, filed Mar. 13, 2014, which claims the benefit of priority from U.S. provisional application Ser. No. 61/785,919, filed Mar. 14, 2013, all of which are incorporated herein by reference in their entirety.

STATEMENT AS TO FEDERALLY SPONSORED RESEARCH

This invention was made with the support of the United States government under Contract numbers R43AI096679 by National Institutes of Health (NIH), R43AI096613 by National Institutes of Health (NIH), and R01AI089512 by National Institutes of Health (NIH). The government has certain rights in the invention.

FIELD OF INVENTION

The present invention relates to boron-containing compounds, compositions, preparations and their use as inhibitors of beta-lactamase enzymes and as antibacterial agents.

BACKGROUND OF THE INVENTION

Antibiotics are the most effective drugs for curing bacteria-infectious diseases clinically. They have a wide market due to their advantages of good antibacterial effect with limited side effects. Among them, the beta-lactam class of antibiotics (for example, penicillins, cephalosporins, and carbapenems) are widely used because they have a strong bactericidal effect and low toxicity.

To counter the efficacy of the various beta-lactams, bacteria have evolved to produce variants of beta-lactam deactivating enzymes called beta-lactamases, and in the ability to share this tool inter- and intra-species. These beta-lactamases are categorized as "serine" or "metallo" based, respectively, on presence of a key serine or zinc in the enzyme active site. The rapid spread of this mechanism of bacterial resistance can severely limit beta-lactam treatment options in the hospital and in the community. Currently available beta-lactamase inhibitors (for example, clavulanic acid and tazobactam) are poorly active against the diversity of beta-lactamase enzymes (both serine- and metallo-based) now emerging clinically. There is an urgent need for new beta-lactamase inhibitors with broadened enzyme spectrum.

SUMMARY OF THE INVENTION

Described herein are compounds that modulate the activity of beta-lactamases. In some embodiments, the compounds described herein inhibit beta-lactamases. In certain embodiments, the compounds described herein are useful in the treatment of bacterial infections.

In one aspect, provided herein are compounds of Formula I or Formula Ia, or pharmaceutically acceptable salts, polymorphs, solvates, tautomers, metabolites, or N-oxides thereof:

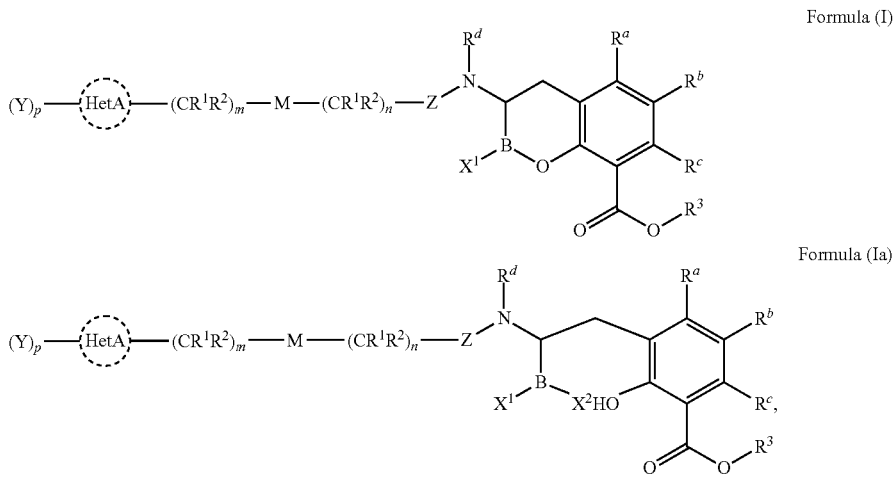

Formula (I)

Formula (Ia)

wherein:
M is a bond, —O—, —S—, —S(O)—, $SO_2$—, or —N($R^4$)—;
m is 0, 1, or 2;
  provided that when HetA is attached to $(CR^1R^2)_m$ through a ring nitrogen atom, m=0 or 2.
n is 0, 1, 2, or 3;
  provided that
    when n is 0, then M is a bond;
p is 0, 1, 2, 3 or 4;
$X^1$ and $X^2$ are independently selected from —OH, —$OR^8$, or F;
Z is >C=O, >C=S, or >$SO_2$;
HetA is an optionally substituted non-aromatic heterocyclic ring system;
Each Y, provided Y is not attached directly to a heteroatom of HetA, is selected from the group consisting of:
  fluoro, chloro, bromo, —CN, optionally substituted $C_1$-$C_6$ alkyl, optionally substituted $C_3$-$C_6$ cycloalkyl, optionally substituted heterocycle, optionally substituted aryl, optionally substituted heteroaryl, —OH, —$OR^{10}$, —$SR^{10}$, —$NR^4R^5$, —$(CR^6R^7)_vNR^4R^5$, —$NR^4(CR^6R^7)_vNR^4R^5$, —$O(CR^6R^7)_vNR^4R^5$, —$S(O)_{0,1,2}(CR^6R^7)_vNR^4R^5$, —$N(R^4)C(O)(CR^6R^7)_vNR^4R^5$, —$(CR^6R^7)_vN(R^4)C(O)(CR^6R^7)_vNR^4R^5$, —$(CR^6R^7)_vNR^4(CR^6R^7)_vNR^4R^5$, —$NR^4(CR^6R^7)_vOR^{10}$, —$NR^4(CR^6R^7)_vS$ $(O)_{0,1,2}R^{10}$, —C(O)NR$^4$(CR$^6$R$^7$)$_v$NR$^4$R$^5$, —S(O)$_{0,1,2}$NR$^4$(CR$^6$R$^7$)$_v$NR$^4$R$^5$, —NR$^5$C(O)NR$^4$(CR$^6$R$^7$)$_v$NR$^4$R$^5$, —OC(O)NR$^4$(CR$^6$R$^7$)$_v$NR$^4$R$^5$, —NR$^5$C(=NR$^7$)NR$^4$(CR$^6$R$^7$)$_v$NR$^4$R$^5$, —N(R$^4$)C(=NR$^5$)R$^6$, —(CR$^6$R$^7$)$_v$N(R$^4$)C(=NR$^5$)R$^6$, —NR$^4$(CR$^6$R$^7$)$_v$N(R$^4$)C(=NR$^5$)R$^6$, —O(CR$^6$R$^7$)$_v$N(R$^4$)C(=NR$^5$)R$^6$, —S(O)$_{0,1,2}$(CR$^6$R$^7$)$_v$N(R$^4$)C(=NR$^5$)R$^6$, —(CR$^6$R$^7$)$_v$C(=NR$^5$)NR$^4$R$^5$, —NR$^4$(CR$^6$R$^7$)$_v$C(=NR$^5$)NR$^4$R$^5$, —O(CR$^6$R$^7$)$_v$C(=NR$^5$)NR$^4$R$^5$, —S(O)$_{0,1,2}$(CR$^6$R$^7$)$_v$C(=NR$^5$)NR$^4$R$^5$, —(CR$^6$R$^7$)$_v$N(R$^4$)C(=NR$^5$)NR$^4$R$^5$, —NR$^4$(CR$^6$R$^7$)$_v$N(R$^4$)C(=NR$^5$)NR$^4$R$^5$, —O(CR$^6$R$^7$)$_v$N(R$^4$)C(=NR$^5$)NR$^4$R$^5$, —S(O)$_{0,1,2}$(CR$^6$R$^7$)$_v$N(R$^4$)C(=NR$^5$)NR$^4$R$^5$, —NR$^4$C(=NR$^5$)NR$^4$C(=NR)NR$^4$R$^5$, —(CR$^6$R$^7$)$_v$C(=NR$^4$)NR$^5$C(=NR$^4$)NR$^4$R$^5$, —NR$^4$(CR$^6$R$^7$)$_v$C(=NR$^4$)NR$^5$C(=NR$^4$)NR$^4$R$^5$, —O(CR$^6$R$^7$)$_v$C(=NR$^4$)NR$^5$C(=NR$^4$)NR$^4$R$^5$, —S(O)$_{0,1,2}$—(CR$^6$R$^7$)$_v$C(=NR$^4$)NR$^5$C(=NR$^4$)NR$^4$R$^5$, —NR$^4$C(=NR$^5$)NR$^4$R$^5$, —C(=NR$^4$)NR$^4$R$^5$, —C(=NR$^4$)NR$^4$C(O)R$^6$, —NR$^4$SO$_2$R$^6$, —NR$^4$C(O)R$^6$, —NR$^4$C(=O)OR$^6$, —C(O)NR$^4$R$^5$, —(CR$^6$R$^7$)$_v$C(O)NR$^4$R$^5$, —SO$_2$NR$^4$R$^5$, -Heteroaryl-NR$^4$R$^5$, -Heterocyclyl-NR$^4$R$^5$, -Heteroaryl-N(R$^4$)C(=NR$^5$)NR$^4$R$^5$, -Heterocyclyl-N(R$^4$)C(=NR$^5$)NR$^4$R$^5$, —N(R$^4$)—Heteroaryl-NR$^4$R$^5$, —N(R$^4$)—Heterocyclyl-NR$^4$R$^5$, —(CR$^6$R$^7$)$_v$Heteroaryl-NR$^4$R$^5$, —(CR$^6$R$^7$)$_v$Heterocyclyl-NR$^4$R$^5$, —(CR$^6$R$^7$)$_v$Heteroaryl-N(R$^4$)C(=NR$^5$)NR$^4$R$^5$, —(CR$^6$R$^7$)$_v$Heterocyclyl-N(R$^4$)C(=NR$^5$)NR$^4$R$^5$, —(CR$^6$R$^7$)$_v$Heteroaryl, —(CR$^6$R$^7$)$_v$Heterocyclyl, —O-Heteroaryl, —O-Heterocyclyl, —NR$^4$(CR$^6$R$^7$)$_v$Heteroaryl, —NR$^4$(CR$^6$R$^7$)$_v$Heterocyclyl, —O(CR$^6$R$^7$)$_v$ Heteroaryl, —O(CR$^6$R$^7$)$_v$Heterocyclyl, —NR$^4$(CR$^6$R$^7$)$_v$NR$^5$-Heteroaryl, —NR$^4$(CR$^6$R$^7$)$_v$NR$^5$-Heterocyclyl, —O(CR$^6$R$^7$)$_v$NR$^5$-Heteroaryl, —O(CR$^6$R$^7$)$_v$NR$^5$-Heterocyclyl, —O(CR$^6$R$^7$)$_v$O-Heterocyclyl, —NR$^4$R$^5$R$^{9+}$Q$^-_2$, —(CR$^6$R$^7$)$_v$NR$^4$R$^5$R$^{9+}$Q$^-$, —NR$^4$(CR$^6$R$^7$)$_v$NR$^4$R$^5$R$^{9+}$Q$^-$, —NR$^4$R$^{9+}$(CR$^6$R$^7$)$_v$NR$^4$R$^5$R$^{9+}$Q$^-_2$, —(CR$^6$R$^7$)$_v$(T)$^+$Q$^-$, and —O(CR$^6$R$^7$)$_v$NR$^4$R$^5$R$^{9+}$Q$^-$;

wherein:
T is pyridine-1-yl, pyrimidin-1-yl, or thiazol-3-yl;
Q is a pharmaceutically acceptable counterion; and
v is 1-4;

or two Ys taken together with the carbon atoms to which they are attached form an optionally substituted carbocycle, an optionally substituted heterocycle, or a carbonyl group; or in the case where Y is attached directly to a heteroatom of HetA, Y is selected from the group consisting of:
—(CR$^6$R$^7$)$_v$NR$^4$R$^5$, —S(O)$_{1,2}$(CR$^6$R$^7$)$_v$NR$^4$R$^5$, —C(O)(CR$^6$R$^7$)$_v$NR$^4$R$^5$, —(CR$^6$R$^7$)$_w$N(R$^4$)C(O)(CR$^6$R$^7$)$_w$NR$^4$R$^5$, —(CR$^6$R$^7$)$_w$NR$^4$(CR$^6$R$^7$)$_w$NR$^4$R$^5$, —NR$^4$(CR$^6$R$^7$)$_w$OR$^{10}$, —(CR$^6$R$^7$)$_w$S(O)$_{0,1,2}$R$^{10}$, —C(O)NR$^4$(CR$^6$R$^7$)$_w$NR$^4$R$^5$, —S(O)$_{1,2}$NR$^4$(CR$^6$R$^7$)$_w$NR$^4$R$^5$, —C(=NR$^7$)NR$^4$(CR$^6$R$^7$)$_v$NR$^4$R$^5$, —C(=NR$^5$)R$^6$, —(CR$^6$R$^7$)$_w$N(R$^4$)C(=NR$^5$)R$^6$, —S(O)$_{1,2}$(CR$^6$R$^7$)$_v$N(R$^4$)C(=NR$^5$)R$^6$, —(CR$^6$R$^7$)$_v$C(=NR$^5$)NR$^4$R$^5$, —(CR$^6$R$^7$)$_w$C(=NR$^5$)NR$^4$R$^5$, —S(O)$_{1,2}$(CR$^6$R$^7$)$_v$C(=NR$^5$)NR$^4$R$^5$, —(CR$^6$R$^7$)$_w$N(R$^4$)C(=NR$^5$)NR$^4$R$^5$, —S(O)$_{1,2}$(CR$^6$R$^7$)$_v$N(R$^4$)C(=NR$^5$)NR$^4$R$^5$, —C(=NR$^5$)NR$^4$C(=NR$^5$)NR$^4$R$^5$, —(CR$^6$R$^7$)$_v$C(=NR$^4$)NR$^5$C(=NR$^4$)NR$^4$R$^5$, —S(O)$_{1,2}$(CR$^6$R$^7$)$_v$C(=NR$^4$)NR$^5$C(=NR$^4$)NR$^4$R$^5$, —C(=NR$^4$)NR$^4$R$^5$, —C(=NR$^4$)NR$^4$C(O)R$^6$, —SO$_2$R$^6$, —C(O)R$^6$, —C(=O)OR$^6$, —C(O)NR$^4$R$^5$, —(CR$^6$R$^7$)$_v$C(O)NR$^4$R$^5$, —SO$_2$NR$^4$R$^5$, -aryl, -heteroaryl, —C(O)N(R$^4$)—Heteroaryl-NR$^4$R$^5$, -Heteroaryl-NR$^4$R$^5$, —C(O)N(R$^4$)—Heteroaryl-NR$^4$R$^5$, -Heteroaryl-NR$^4$R$^5$, -Heterocyclyl-NR$^4$R$^5$, -Heteroaryl-N(R$^4$)C(=NR$^5$)NR$^4$R$^5$, -Heterocyclyl-N(R$^4$)C(=NR$^5$)NR$^4$R$^5$, -Heteroaryl-NR$^4$R$^5$, -Heterocyclyl-NR$^4$R$^5$, —(CR$^6$R$^7$)$_v$Heteroaryl-NR$^4$R$^5$, —(CR$^6$R$^7$)$_v$Heterocyclyl-NR$^4$R$^5$, —(CR$^6$R$^7$)$_v$Heteroaryl-N(R$^4$)C(=NR$^5$)NR$^4$R$^5$, —(CR$^6$R$^7$)$_v$Heterocyclyl-N(R$^4$)C(=NR$^5$)NR$^4$R$^5$, —(CR$^6$R$^7$)$_v$Heteroaryl, —(CR$^6$R$^7$)$_v$Heterocyclyl, —(CR$^6$R$^7$)$_v$NR$^5$-Heteroaryl, —(CR$^6$R$^7$)$_v$NR$^5$-Heterocyclyl, —(CR$^6$R$^7$)$_v$O-Heterocyclyl, —R$^{9+}$Q$^-$, —(CR$^6$R$^7$)$_w$NR$^4$R$^5$R$^{9+}$Q$^-$, —R$^{9+}$(CR$^6$R$^7$)$_v$NR$^4$R$^5$R$^{9+}$Q$^-_2$ and —(CR$^6$R$^7$)$_v$(T)$^+$Q;

wherein:
T is pyridine-1-yl, pyrimidin-1-yl, or thiazol-3-yl;
Q is a pharmaceutically acceptable counterion; and
v is 1-4; w is 2-4;

R$^a$, R$^b$, and R$^c$ are independently selected from the group consisting of hydrogen, fluoro, chloro, bromo, optionally substituted C$_1$-C$_6$ alkyl, optionally substituted C$_3$-C$_6$ cycloalkyl, optionally substituted heterocyclyl, optionally substituted aryl, optionally substituted heteroaryl, —OH, —OR$^{10}$, —NR$^4$R$^5$, and —SR$^{10}$;

R$^1$ and R$^2$ are independently selected from the group consisting of hydrogen, fluoro, chloro, bromo, optionally substituted C$_1$-C$_6$ alkyl, optionally substituted C$_3$-C$_6$ cycloalkyl, —OH, —OR$^{10}$, —SR$^{10}$, and —NR$^4$R$^5$, or R$^1$ and R$^2$ taken together form an oxo, oxime, or an optionally substituted carbocycle or optionally substituted heterocycle with the carbon to which they are attached;

R$^3$ is hydrogen, optionally substituted C$_1$-C$_6$ alkyl, or a pharmaceutically acceptable prodrug;

R$^d$, R$^4$ and R$^5$ are independently selected from the group consisting of hydrogen, —OH, —CN, optionally substituted C$_1$-C$_6$ alkyl, optionally substituted alkoxyalkyl, optionally substituted hydroxyalkyl, optionally substituted aminoalkyl, optionally substituted cycloalkyl, optionally substituted heterocyclyl, optionally substituted aryl, optionally substituted heteroaryl, optionally substituted cycloalkylalkyl, optionally substituted heterocyclylalkyl, optionally substituted aralkyl, optionally substituted heteroaralkyl, (poly-ethylene-glycol)-ethyl, and an optionally substituted saccharide;

or R$^4$ and R$^5$ taken together form an optionally substituted heterocycle with the nitrogen to which they are attached;

R$^6$ and R$^7$ are independently selected from the group consisting of hydrogen, fluoro, chloro, bromo, optionally substituted C$_1$-C$_6$ alkyl, optionally substituted alkoxyalkyl, optionally substituted hydroxyalkyl, optionally substituted C$_3$-C$_6$ cycloalkyl, —OH, —OR$^{10}$, —SR$^{10}$, —NR$^4$R$^5$, —NR$^4$C(O)R$^5$, —C(O)NR$^4$R$^5$, —NR$^4$SO$_2$R$^5$, optionally substituted heterocyclyl, optionally substituted aryl, and optionally substituted heteroaryl;

or R$^6$ and R$^7$ taken together form an oxo, oxime, or an optionally substituted carbocycle or an optionally substituted heterocycle with the carbon to which they are attached;

R$^8$ is optionally substituted C$_1$-C$_6$ alkyl, optionally substituted C$_3$-C$_6$ cycloalkyl, or a pharmaceutically acceptable boronate ester group;

R$^9$ is optionally substituted C$_1$-C$_6$ alkyl; and

R$^{10}$ is optionally substituted C$_1$-C$_6$ alkyl or optionally substituted C$_3$-C$_6$ cycloalkyl.

In some embodiments of a compound of Formula I or Formula Ia, $R^a$, $R^b$, and $R^c$ are independently selected from the group consisting of hydrogen, fluoro, chloro, optionally substituted $C_1$-$C_6$ alkyl, optionally substituted $C_3$-$C_6$ cycloalkyl, —OH, —$OR^{10}$, —$NR^4R^5$, and —$SR^{10}$. In certain embodiments, $R^a$, $R^b$, and $R^c$ are independently hydrogen, fluoro, or chloro. In preferred embodiments, $R^a$, $R^b$, and $R^c$ are hydrogen.

In some embodiments of a compound of Formula I or Formula Ia, $R^3$ is hydrogen, methyl, ethyl, propyl, butyl, or isopropyl. In preferred embodiments, $R^3$ is hydrogen.

In some embodiments of a compound of Formula I or Formula Ia, $X^1$ and $X^2$ are —OH.

In some embodiments of a compound of Formula I or Formula Ia, $R^d$ is hydrogen or $C_1$-$C_4$-alkyl. In preferred embodiments, $R^d$ is hydrogen.

In some embodiments of a compound of Formula I or Formula Ia, Z is >C=O or >$SO_2$. In preferred embodiments, Z is >C=O.

In some embodiments of a compound of Formula I or Formula Ia, HetA is selected from the group consisting of azetidine, oxetane thietane, pyrrolidine, tetrahydrofuran, tetrahydrothiophene, oxazolidine, isoxazolidine, thiazolidine, isothiazolidine, imidazolidine, pyrazolidine, 2,5-dihydro-1H-pyrrole, 3,4-dihydro-2H-pyrrole, 4,5-dihydrooxazole, 4,5-dihydroisoxazole, 4,5-dihydrothiazole, 4,5-dihydroisothiazole, 4,5-dihydro-1H-pyrazole, 4,5-dihydro-1H-imidazole, 2,5-dihydro-1H-pyrrole, piperidine, morpholine, thiomorpholine, tetrahydrothiopyran, tetrahydropyran, 1,4-oxathiane, piperazine, hexahydropyrimidine, hexahydropyridazine, 1,4,5,6-tetrahydropyrimidine, 1,3-oxazinane, 5,6-dihydro-4H-1,3-oxazine, 1,3-thiazinane, 5,6-dihydro-4H-1,3-thiazine, 1,4,5,6-tetrahydropyridazine, 1,2,3,6-tetrahydropyrazine, 1,2,3,6-tetrahydropyridine, 1,2,3,6-tetrahydropyridazine, 1,2,3,6-tetrahydropyridine, 3,6-dihydro-2H-pyran, 3,6-dihydro-2H-thiopyran, azepane, 1,3-oxazepane, 1,4-oxazepane, 1,3-diazepane, 1,4-diazepane, 1,3-thiazepane, 1,4-thiazepane, diazepane, oxazepane, thiazepane, 3,4,5,6-tetrahydro-2H-azepine, 4,5,6,7-tetrahydro-1H-1,3-diazepine, 4,5,6,7-tetrahydro-1,3-oxazepine, 4,5,6,7-tetrahydro-1,3-thiazepine, 2,3,4,7-tetrahydro-1H-1,3-diazepine, 2,3,4,7-tetrahydro-1,3-oxazepine, 2,3,4,7-tetrahydro-1H-azepine, 2,3,6,7-tetrahydro-1H-azepine, oxepane, thiepane, 2,3,6,7-tetrahydrooxepine, 2,3,4,7-tetrahydrooxepine, 2,3,4,7-tetrahydrothiepine, 2,3,6,7-tetrahydrothiepine azocane, oxocane, thiocane, 1,3-diazocane, 1,4-diazocane, 1,5-diazocane, 1,3-oxazocane, 1,4-oxazocane, 1,5-oxazocane, 1,3-thiazocane, 1,4-thiazocane, 1,5-thiazocane, (2Z)-1,4,5,6,7,8-hexahydro-1,3-diazocine, (3Z)-1,2,5,6,7,8-hexahydro-1,4-diazocine, (5Z)-1,2,3,4,7,8-hexahydro-1,5-diazocine, (6Z)-1,2,3,4,5,8-hexahydro-1,3-diazocine, (4Z)-1,2,3,6,7,8-hexahydro-1,4-diazocine, (6Z)-1,2,3,4,5,8-hexahydroazocine, (5Z)-1,2,3,4,7,8-hexahydroazocine, (6Z)-3,4,5,8-tetrahydro-2H-oxocine, (5Z)-3,4,7,8-tetrahydro-2H-oxocine, (6Z)-3,4,5,8-tetrahydro-2H-thiocine, and (5Z)-3,4,7,8-tetrahydro-2H-thiocine.

In some embodiments of a compound of Formula I or Formula Ia, at least one Y is selected from the group consisting fluoro, chloro, bromo, —CN, optionally substituted $C_1$-$C_6$ alkyl, —OH, —$OR^{10}$, —$NR^4R^5$, —$(CR^6R^7)_vNR^4R^5$, —$NR^4(CR^6R^7)_vNR^4R^5$, —$O(CR^6R^7)_vNR^4R^5$, —$N(R^4)C(O)(CR^6R^7)_vNR^4R^5$, —$(CR^6R^7)_vN(R^4)C(O)(CR^6R^7)_vNR^4R^5$, —$C(O)NR^4(CR^6R^7)_vNR^4R^5$, —$S(O)_{0,1,2}NR^4(CR^6R^7)_vNR^4R^5$, —$NR^5C(O)NR^4(CR^6R^7)_vNR^4R^5$, —$OC(O)NR^4(CR^6R^7)_vNR^4R^5$, —$NR^5C(=NR^7)NR^4(CR^6R^7)_vNR^4R^5$, —$N(R^4)C(=NR^5)R^6$, —$(CR^6R^7)_vN(R^4)C(=NR^5)R^6$, —$NR^4(CR^6R^7)_vN(R^4)C(=NR^5)R^6$, —$O(CR^6R^7)_vN(R^4)C(=NR^5)R^6$, —$(CR^6R^7)_vC(=NR^5)NR^4R^5$, —$NR^4(CR^6R^7)_vC(=NR^5)NR^4R^5$, —$O(CR^6R^7)_vC(=NR^5)NR^4R^5$, —$(CR^6R^7)_vN(R^4)C(=NR^5)NR^4R^5$, —$O(CR^6R^7)_vN(R^4)C(=NR^5)NR^4R^5$, —$NR^4C(=NR^5)NR^4C(=NR^5)NR^4R^5$, —$(CR^6R^7)_vC(=NR^4)NR^5C(=NR^4)NR^4R^5$, —$NR^4(CR^6R^7)_vC(=NR^4)NR^5C(=NR^4)NR^4R^5$, —$O(CR^6R^7)_vC(=NR^4)NR^4C(=NR^4)NR^4R^5$, —$NR^4C(=NR^5)NR^4R^5$, —$C(=NR^4)NR^4R^5$, —$C(=NR^4)NR^4C(O)R^6$, —$NR^4SO_2R^6$, —$NR^4C(O)R^6$, —$NR^4C(=O)OR^6$, —$C(O)NR^4R^5$, —$(CR^6R^7)_vC(O)NR^4R^5$, -Heteroaryl-$NR^4R^5$, -Heterocyclyl-$NR^4R^5$, -Heteroaryl-$N(R^4)C(=NR^5)NR^4R^5$, -Heterocyclyl-$N(R^4)C(=NR^5)NR^4R^5$, —$N(R^4)$—Heteroaryl-$NR^4R^5$, —$N(R^4)$—Heterocyclyl-$NR^4R^5$, —$(CR^6R^7)_v$Heteroaryl-$NR^4R^5$, —$(CR^6R^7)_v$Heterocyclyl-$NR^4R^5$, —$(CR^6R^7)_v$Heteroaryl-$N(R^4)C(=NR)NR^4R^5$, —$(CR^6R^7)_v$Heterocyclyl-$N(R^4)C(=NR^5)NR^4R^5$, —$(CR^6R^7)_v$Heteroaryl, —$(CR^6R^7)_v$Heterocyclyl, —O-Heteroaryl, —O-Heterocyclyl, —$NR^4(CR^6R^7)_v$Heteroaryl, —$NR^4(CR^6R^7)_v$Heterocyclyl, —$O(CR^6R^7)_v$Heteroaryl, —$O(CR^6R^7)_v$Heterocyclyl, and —$O(CR^6R^7)_v$O-Heterocyclyl. In certain embodiments, at least one Y is selected from the group consisting of fluoro, chloro, —CN, optionally substituted $C_1$-$C_6$ alkyl, —OH, —$NR^4R^5$, —$(CR^6R^7)_vNR^4R^5$, —$NR^4(CR^6R^7)_vNR^4R^5$, —$O(CR^6R^7)_vNR^4R^5$, —$C(O)NR^4(CR^6R^7)_vNR^4R^5$, —$NR^5C(O)NR^4(CR^6R^7)_vNR^4R^5$, —$NR^5C(=NR^7)NR^4(CR^6R^7)_vNR^4R^5$, —$N(R^4)C(=NR^5)R^6$, —$(CR^6R^7)_vN(R^4)C(=NR^5)R^6$, —$NR^4(CR^6R^7)_vN(R^4)C(=NR^5)R^6$, —$(CR^6R^7)_vC(=NR^5)NR^4R^5$, —$NR^4(CR^6R^7)_vC(=NR^5)NR^4R^5$, —$(CR^6R^7)_vN(R^4)C(=NR^5)NR^4R^5$, —$NR^4(CR^6R^7)_vN(R^4)C(=NR^5)NR^4R^5$, —$NR^4C(=NR^5)NR^4C(=NR^5)NR^4R^5$, —$(CR^6R^7)_vC(=NR^4)NR^5C(=NR^4)NR^4R^5$, —$NR^4(CR^6R^7)_vC(=N R^4)NR^5C(=NR^4)NR^4R^5$, —$NR^4C(=NR^5)NR^4R^5$, —$C(=NR^4)NR^4R^5$, —$C(=NR^4)NR^4C(O)R^6$, —$NR^4C(O)R^6$, —$(CR^6R^7)_vC(O)NR^4R^5$, -Heterocyclyl-$NR^4R^5$, -Heterocyclyl-$N(R^4)C(=NR)NR^4R^5$, —$N(R^4)$-Heterocyclyl-$NR^4R^5$, —$(CR^6R^7)_v$Heterocyclyl-$NR^4R^5$, —$(CR^6R^7)_v$Heterocyclyl-$N(R^4)C(=NR^5)NR^4R^5$, —$(CR^6R^7)_v$Heterocyclyl, and —$NR^4(CR^6R^7)_v$Heterocyclyl. In further embodiments, at least one Y is selected from the group consisting of -Heteroaryl-$NR^4R^5$, -Heterocyclyl-$NR^4R^5$, -Heteroaryl-$N(R^4)C(=NR^5)NR^4R^5$, -Heterocyclyl-$N(R^4)C(=NR^5)NR^4R^5$, —$N(R^4)$—Heteroaryl-$NR^4R^5$, —$N(R^4)$—Heterocyclyl-$NR^4R^5$, -Heteroaryl-$C(=NR^5)NR^4R^5$, -Heterocyclyl-$C(=NR)NR^4R^5$, —$(CR^6R^7)_v$Heteroaryl-$NR^4R^5$, —$(CR^6R^7)_v$Heterocyclyl-$NR^4R^5$, —$(CR^6R^7)_v$Heteroaryl-$N(R^4)C(=NR^5)NR^4R^5$, and —$(CR^6R^7)_v$Heterocyclyl-$N(R^4)C(=NR^5)NR^4R^5$. In preferred embodiments, at least one Y is selected from the group consisting of —$NR^4R^5$, —$NR^4C(=NR^5)NR^4R^5$, —$C(=NR^4)NR^4R^5$, —$N(R^4)C(=NR^5)R^6$, —$(CR^6R^7)_vNR^4R^5$, —$(CR^6R^7)_vN(R^4)C(=NR^5)NR^4R^5$, —$NR^4(CR^6R^7)_vNR^4R^5$, —$NR^4(CR^6R^7)_vOR^{10}$, —$(CR^6R^7)_vNR^4(CR^6R^7)_vNR^4R^5$, $NR^5C(=NR^5)NR^4(CR^6R^7)_vNR^4R^5$, —$NR^4(CR^6R^7)_vN(R^4)C(=NR^5)NR^4R^5$, —$NR^5C(O)CR^6(NR^4R^5)(CR^6R^7)_vNR^4R^5$, —$(CR^6R^7)_vC(=NR^5)NR^4R^5$, —$(CR^6R^7)_vN(R^4)C(O)(CR^6R^7)_vNR^4R^5$, —$C(=NR^4)NR^4C(O)R^6$, —$NR^4(CR^6R^7)_v$Heteroaryl, and —$O(CR^6R^7)_vNR^4R^5$.

In some embodiments, p is 0, 1, 2, or 3. In certain embodiments, p is 1 or 2.

In some embodiments of a compound of Formula I or Formula Ia, $R^4$ and $R^5$ are independently selected from the group consisting of hydrogen, —OH, optionally substituted $C_1$-$C_6$ alkyl, optionally substituted alkoxyalkyl, optionally substituted hydroxyalkyl, and optionally substituted heterocyclyl. In preferred embodiments, $R^4$ and $R^5$ are independently hydrogen or optionally substituted $C_1$-$C_6$ alkyl.

In some embodiments of a compound of Formula I or Formula Ia, $R^6$ and $R^7$ are independently selected from the group consisting of hydrogen, optionally substituted $C_1$-$C_6$ alkyl, —OH, —$NR^4R^5$, and optionally substituted heterocyclyl, or $R^6$ and $R^7$ taken together form an optionally substituted heterocycle with the carbon to which they are attached. In preferred embodiments, $R^6$ and $R^7$ are independently hydrogen, fluoro, or optionally substituted $C_1$-$C_6$ alkyl.

In certain embodiments of a compound of Formula I or Formula Ia, the compound is selected from the group represented by the following structures:

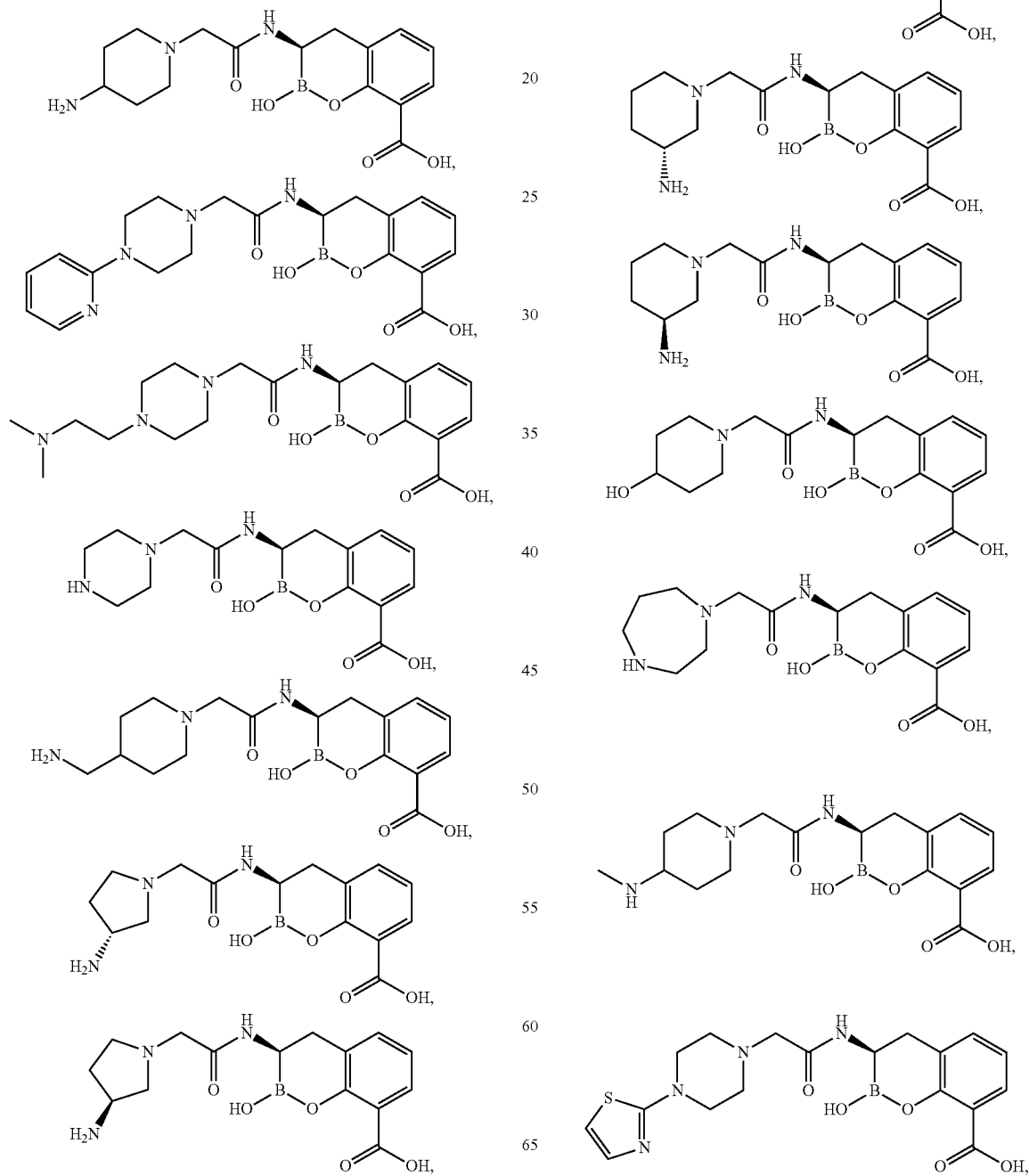

-continued

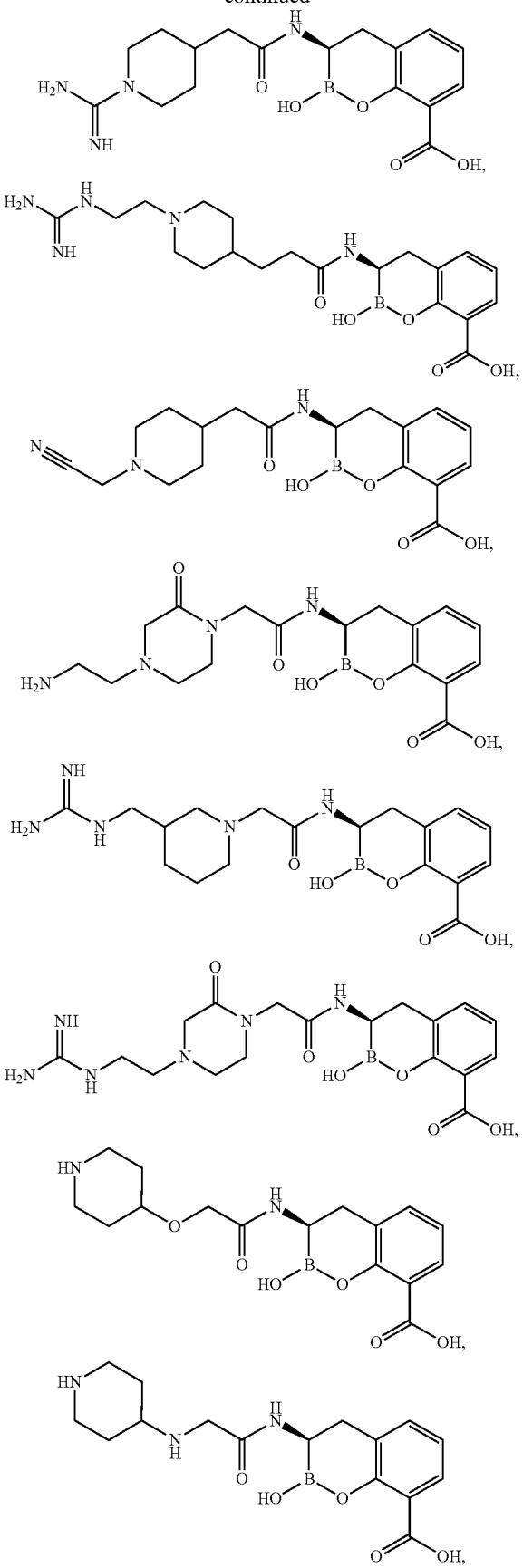
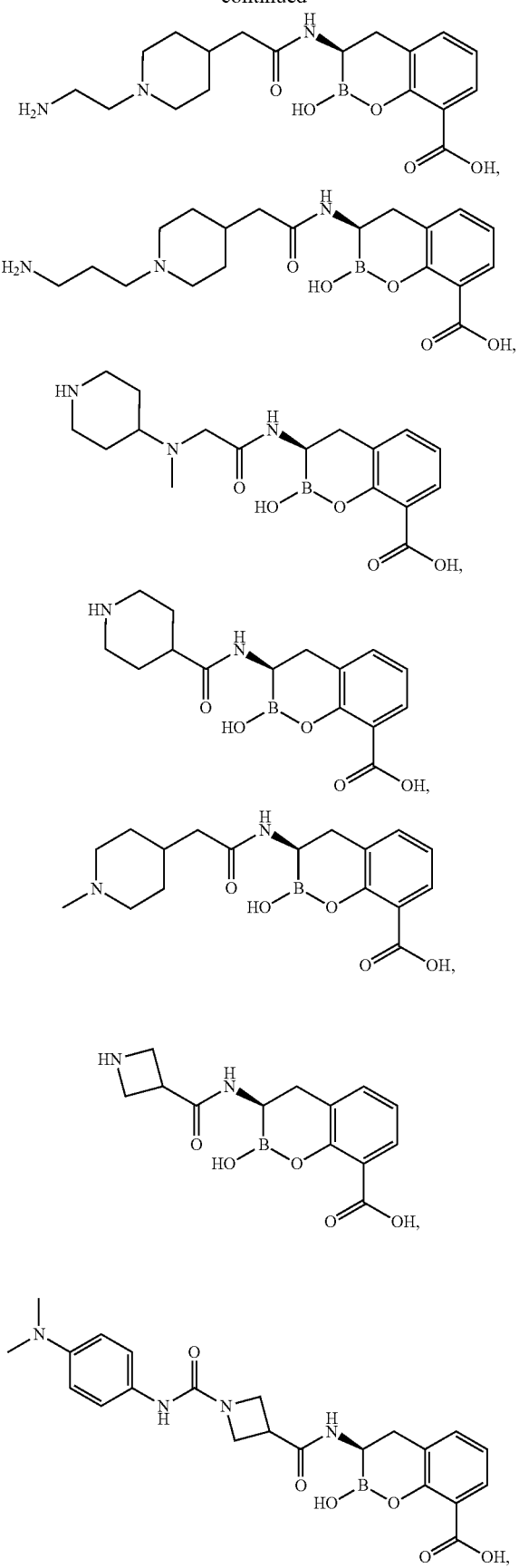

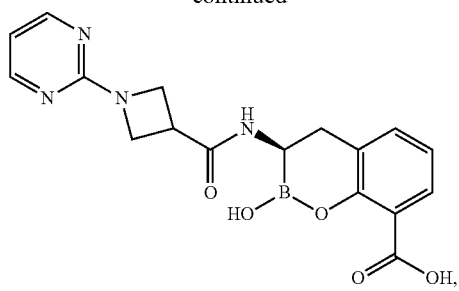
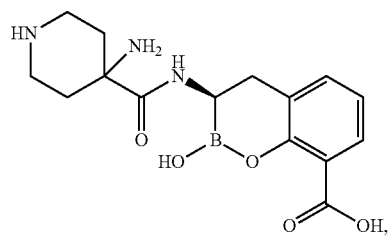
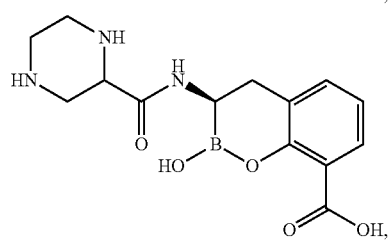
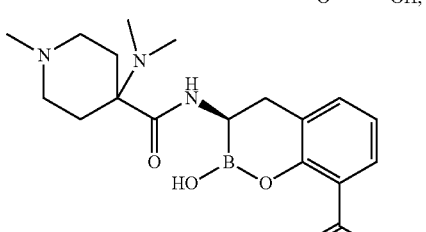
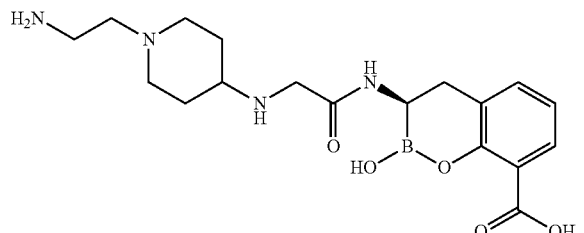
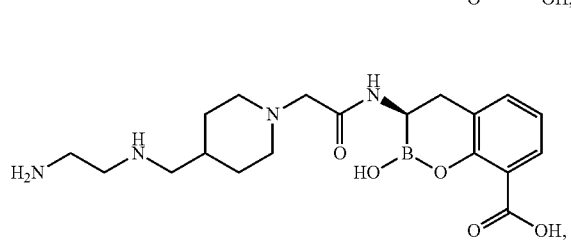
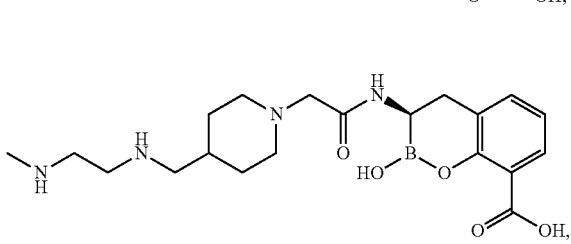
and
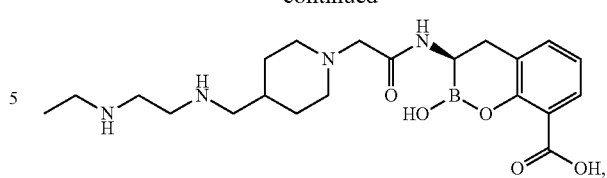
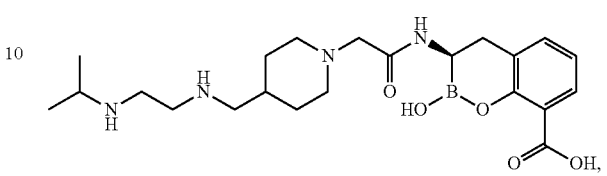
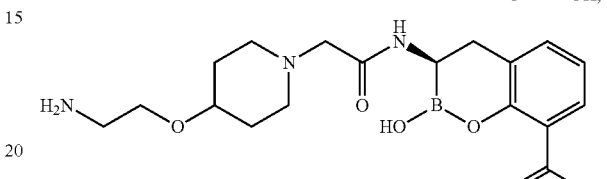
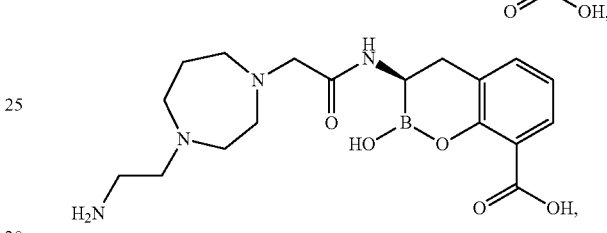
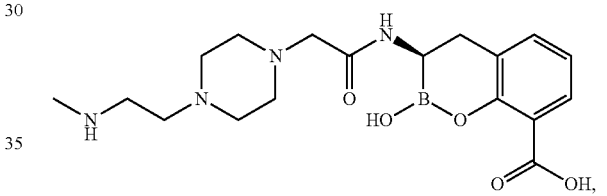
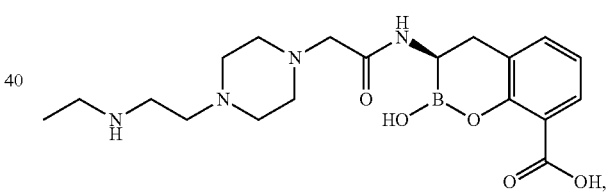
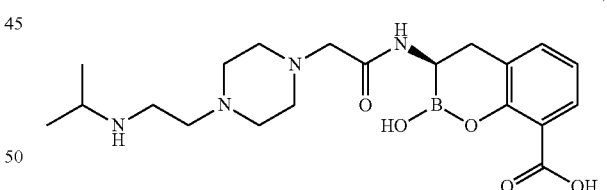
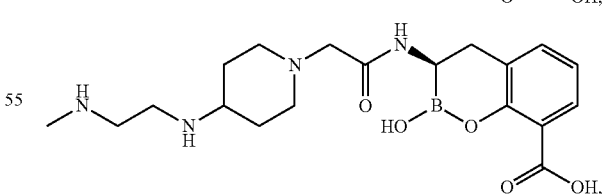
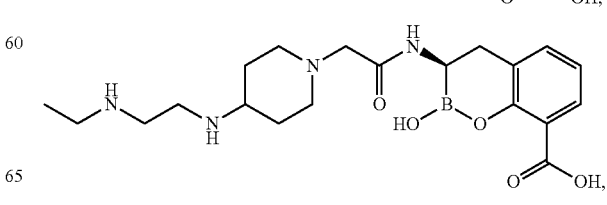

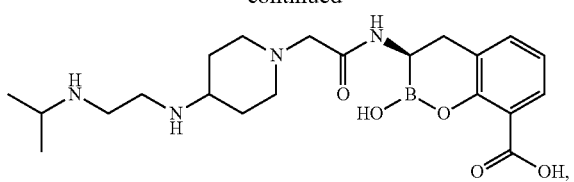
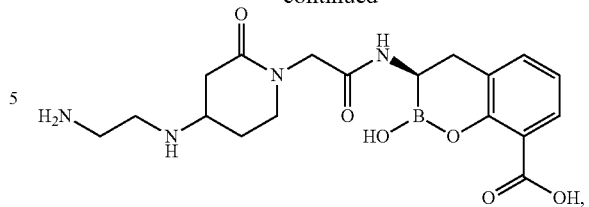
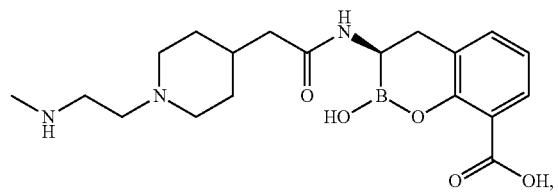
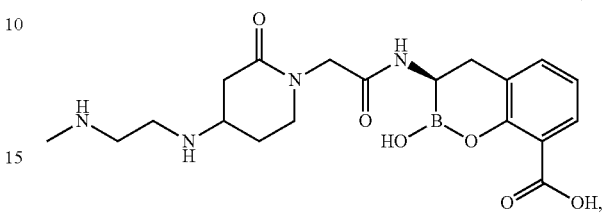
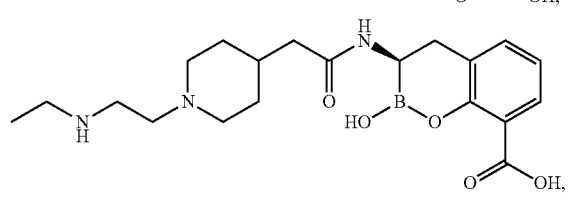
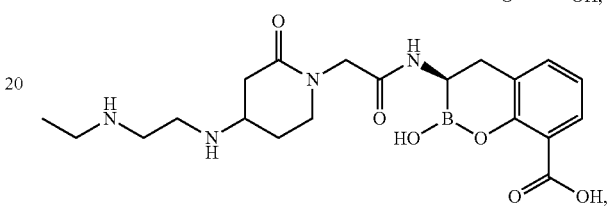
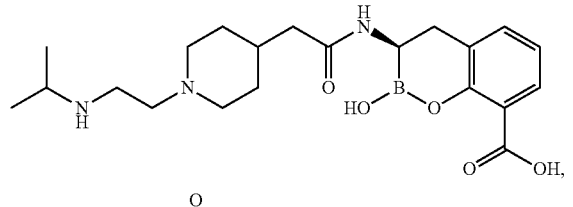
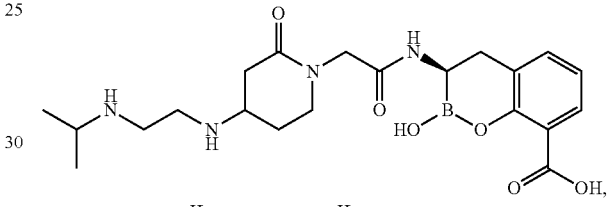
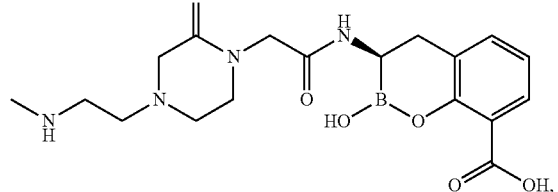
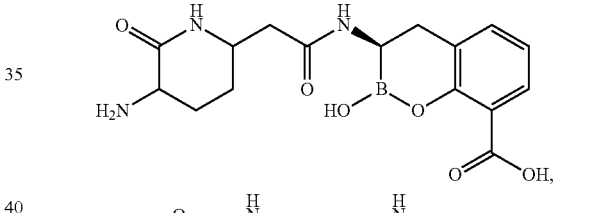
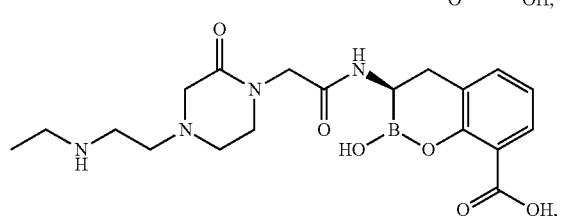
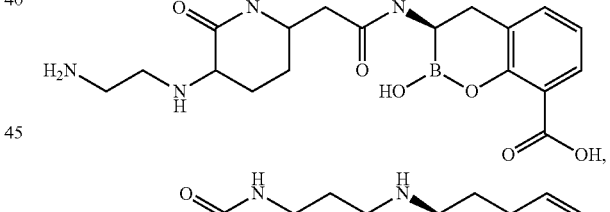
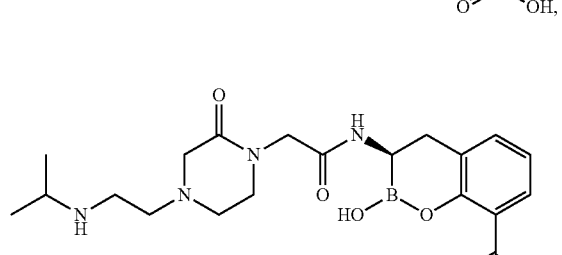
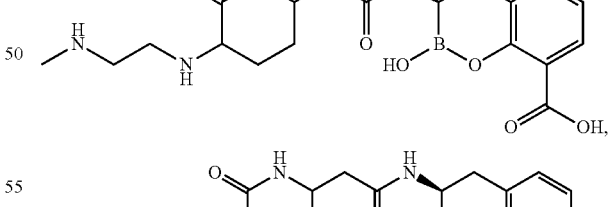
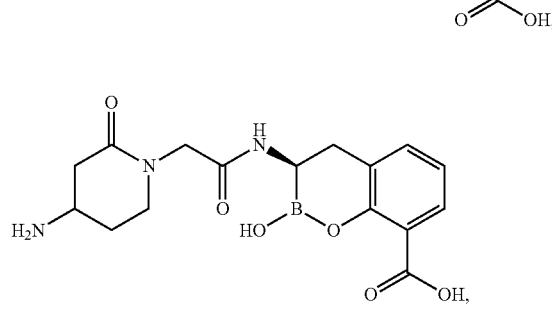
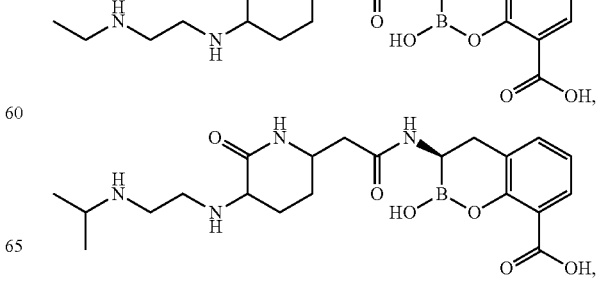

-continued

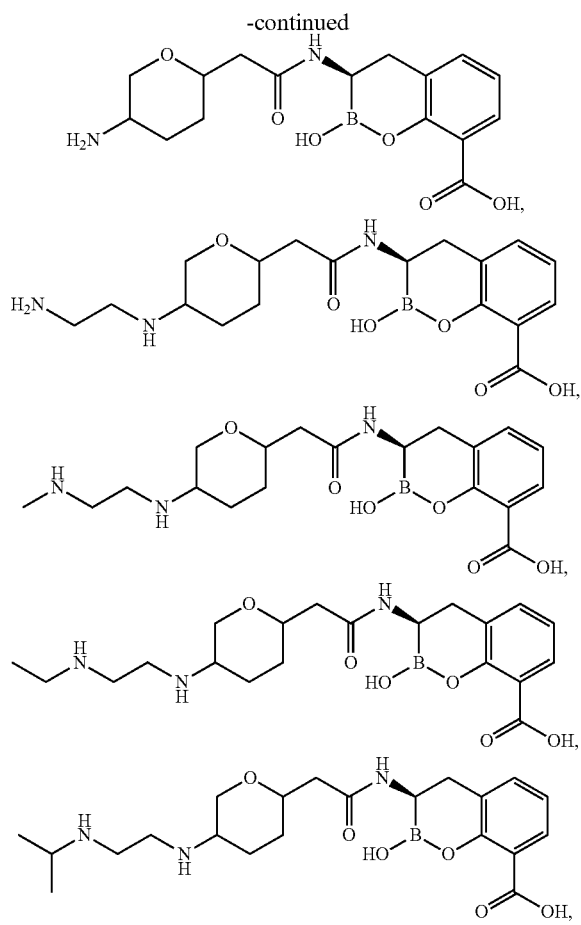

or a pharmaceutically acceptable salt, polymorph, solvate, prodrug, N-oxide, or isomer thereof, wherein the compound is present in a closed, cyclic form according to Formula I and as shown in the structures above, in a open, acyclic form according to Formula Ia, or mixtures thereof.

In some embodiments, the compound of Formula I or Formula Ia is the stereoisomer represented by any of the structures shown herein. In some embodiments, the compound of Formula I or Formula Ia is an enantiomer of the stereoisomer represented by any of the structures shown herein. In certain embodiments, the compound of Formula I or Formula Ia is a diastereomer of the stereoisomer represented by any of the structures shown herein. In some embodiments, the compound of Formula I or Formula Ia is a mixture of enantiomers and/or diastereomers of the stereoisomer represented by any of the structures shown herein. In certain embodiments, the compound of Formula I or Formula Ia is a racemate of the stereoisomer represented by any of the structures herein.

In another aspect, provided herein are pharmaceutical compositions comprising a compound Formula I or Formula Ia as described herein, or a pharmaceutically acceptable salt, polymorph, solvate, prodrug, N-oxide, or isomer thereof, and a pharmaceutically acceptable excipient. In some embodiments, the pharmaceutical composition further comprises a beta-lactam antibiotic. In certain embodiments, the beta-lactam antibiotic is a penicillin, cephalosporin, carbapenem, monobactam, bridged monobactam, or a combination thereof.

In an additional aspect, provided herein are methods of treating a bacterial infection in a subject, comprising administering to the subject a compound of Formula I or Formula Ia as described herein in combination with a therapeutically effective amount of beta lactam antibiotic.

In a further aspect, provided herein are methods of treating a bacterial infection in a subject, comprising administering to the subject a pharmaceutical composition as described herein, optionally in combination with a beta-lactam antibiotic. In certain embodiments, the methods of treating a bacterial infection in a subject comprise administering to the subject a pharmaceutical composition as described herein in combination with a beta-lactam antibiotic.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Beta-lactamases are typically grouped into 4 classes: Ambler classes A, B, C, and D, based on their amino acid sequences. Enzymes in classes A, C, and D are active-site serine beta-lactamases, while class B enzymes are Zn-dependent. Newer generation cephalosporins and carbapenems were developed partly based on their ability to evade the deactivating effect of the early serine-based beta-lactamase variants. However, a recent surge in new versions of serine-based beta-lactamases—for example Class A Extended-Spectrum Beta-Lactamase (ESBL) enzymes, Class A carbapenemases (e.g. KPC-2), chromosomal and plasmid mediated Class C cephalosporinases (AmpC, CMY, etc.), and Class D oxacillinases—as well as Class B metallo-beta-lactamases (e.g. VIM, NDM) has begun to diminish the utility of the beta-lactam antibiotic family, including the more recent generation beta-lactam drugs, leading to a serious medical problem. Indeed the number of catalogued serine-based beta-lactamases has exploded from less than ten in the 1970s to over 750 variants (see, e.g., Jacoby & Bush, "Amino Acid Sequences for TEM, SHV and OXA Extended-Spectrum and Inhibitor Resistant β-Lactamases", on the Lahey Clinic website).

The commercially available beta-lactamase inhibitors (clavulanic acid, sulbactam, tazobactam) were developed to address the beta-lactamases that were clinically relevant in the 1970s and 1980s (e.g. penicillinases). These beta-lactamase inhibitors are poorly active against the diversity of beta-lactamase enzymes (both serine- and metallo-based) now emerging clinically. In addition, these enzyme inhibitors are available only as fixed combinations with penicillin derivatives. No combinations with cephalosporins (or carbapenems) are clinically available. This fact, combined with the increased use of newer generation cephalosporins and carbapenems, is driving the selection and spread of the new beta-lactamase variants (ESBLs, carbapenemases, chromosomal and plasmid-mediated Class C, Class D oxacillinases, etc.). While maintaining good inhibitory activity against ESBLs, the legacy beta-lactamase inhibitors are largely ineffective against the new Class A and Class B carbapenemases, against the chromosomal and plasmid-mediated Class C cephalosporinases and against many of the Class D oxacillinases.

To address this growing therapeutic vulnerability, and because there are three major molecular classes of serine-based beta-lactamases, and one major class of metallo-beta-lactamases, and each of these classes contains significant numbers of beta-lactamase variants, we have identified an approach for developing novel beta-lactamase inhibitors with broad spectrum functionality. In particular, we have identified an approach for developing compounds that are active against both serine- and metallo-based beta-lactamase enzymes. Compounds of the current invention demonstrate potent activity across all four major classes of beta-lactamases.

The present invention is directed to certain boron-based compounds (boronic acids and cyclic boronic acid esters) which are beta-lactamase inhibitors and antibacterial compounds. The compounds and their pharmaceutically acceptable salts are useful alone and in combination with beta-lactam antibiotics for the treatment of bacterial infections, particularly antibiotic resistant bacterial infections. Some embodiments include compounds, compositions, pharmaceutical compositions, use and preparation thereof.

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The term "antibiotic" refers to a compound or composition which decreases the viability of a microorganism, or which inhibits the growth or proliferation of a microorganism. The phrase "inhibits the growth or proliferation" means increasing the generation time (i.e., the time required for the bacterial cell to divide or for the population to double) by at least about 2-fold. Preferred antibiotics are those which can increase the generation time by at least about 10-fold or more (e.g., at least about 100-fold or even indefinitely, as in total cell death). As used in this disclosure, an antibiotic is further intended to include an antimicrobial, bacteriostatic, or bactericidal agent. Examples of antibiotics suitable for use with respect to the present invention include penicillins, cephalosporins and carbapenems.

The term "β-lactam antibiotic" refers to a compound with antibiotic properties that contains a β-lactam functionality. Non-limiting examples of β-lactam antibiotics useful with respect to the invention include penicillins, cephalosporins, penems, carbapenems, and monobactams.

The term "β-lactamase" denotes a protein capable of inactivating a β-lactam antibiotic. The β-lactamase can be an enzyme which catalyzes the hydrolysis of the β-lactam ring of a β-lactam antibiotic. Of particular interest herein are microbial β-lactamases. The β-lactamase may be, for example, a serine β-lactamase or a metallo-β-lactamase. β-Lactamases of interest include those disclosed in an ongoing website that monitors beta-lactamase nomenclature (www.lahey.org) and in Bush, K. and G. A. Jacoby. 2010. An updated functional classification of β-lactamases. Antimicrob. Agents Chemother. 54:969-976. β-Lactamases of particular interest herein include β-lactamases found in bacteria such as class A β-lactamases including the SHV, CTX-M and KPC subclasses, class B β-lactamases such as VIM, class C β-lactamases (both chromosomal and plasmid-mediated), and class D β-lactamases. The term "β-lactamase inhibitor" refers to a compound which is capable of inhibiting β-lactamase activity. Inhibiting β-lactamase activity means inhibiting the activity of a class A, B, C, or D β-lactamase. For antimicrobial applications inhibition at a 50% inhibitory concentration is preferably achieved at or below about 100 micrograms/mL, or at or below about 50 micrograms/mL, or at or below about 25 micrograms/mL. The terms "class A", "class B", "class C", and "class D" β-lactamases are understood by those skilled in the art and are described in Bush, K. and G. A. Jacoby. 2010. An updated functional classification of β-lactamases. Antimicrob. Agents Chemother. 54:969-976.

The terms below, as used herein, have the following meanings, unless indicated otherwise:

"Amino" refers to the —NH$_2$ radical.
"Cyano" or "nitrile" refers to the —CN radical.
"Hydroxy" or "hydroxyl" refers to the —OH radical.
"Nitro" refers to the —NO$_2$ radical.
"Oxo" refers to the =O substituent.
"Oxime" refers to the =N—OH substituent.
"Thioxo" refers to the =S substituent.
"Alkyl" refers to an optionally substituted straight-chain, or optionally substituted branched-chain saturated hydrocarbon monoradical having from one to about ten carbon atoms, more preferably one to six carbon atoms, wherein an sp3-hybridized carbon of the alkyl residue is attached to the rest of the molecule by a single bond. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$ alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. Unless stated otherwise specifically in the specification, an alkyl group may be optionally substituted as described below, for example, with oxo, amino, nitrile, nitro, hydroxyl, alkyl, alkylene, alkynyl, alkoxy, aryl, cycloalkyl, heterocyclyl, heteroaryl, and the like.

"Alkenyl" refers to an optionally substituted straight-chain, or optionally substituted branched-chain hydrocarbon monoradical having one or more carbon-carbon double-bonds and having from two to about ten carbon atoms, more preferably two to about six carbon atoms, wherein an sp2-hybridized carbon of the alkenyl residue is attached to the rest of the molecule by a single bond. The group may be in either the cis or trans conformation about the double bond(s), and should be understood to include both isomers. Examples include, but are not limited to ethenyl (—CH=CH$_2$), 1-propenyl (—CH$_2$CH=CH$_2$), isopropenyl [—C(CH$_3$)=CH$_2$], butenyl, 1,3-butadienyl and the like. Whenever it appears herein, a numerical range such as "C$_2$-C$_6$ alkenyl" or "C$_2$-6 alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated.

"Alkynyl" refers to an optionally substituted straight-chain or optionally substituted branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "C$_2$-C$_6$ alkynyl" or "C$_{2-6}$ alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated.

"Alkylene" or "alkylene chain" refers to a straight or branched divalent hydrocarbon chain. Unless stated otherwise specifically in the specification, an alkylene group may be optionally substituted as described below.

"Alkoxy" refers to a radical of the formula —OR$_a$ where R$_a$ is an alkyl radical as defined. Unless stated otherwise specifically in the specification, an alkoxy group may be optionally substituted as described below.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from the hydrocarbon ring systems of aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Cycloalkyl" or "carbocycle" refers to a stable, non-aromatic, monocyclic or polycyclic carbocyclic ring, which may include fused or bridged ring systems, which is saturated or unsaturated. Representative cycloalkyls or carbocycles include, but are not limited to, cycloalkyls having from three to fifteen carbon atoms, from three to ten carbon atoms, from three to eight carbon atoms, from three to six carbon atoms, from three to five carbon atoms, or three to four carbon atoms. Monocyclic cycloalkyls or carbocycles include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0] nonane, cis-decalin, trans-decalin, bicyclo[2.1.1]hexane, bicyclo[2.2.1]heptane, bicyclo[2.2.2]octane, bicyclo[3.2.2] nonane, and bicyclo[3.3.2]decane, and 7,7-dimethyl-bicyclo [2.2.1]heptanyl. Unless otherwise stated specifically in the specification, a cycloalkyl or carbocycle group may be optionally substituted. Illustrative examples of cycloalkyl groups include, but are not limited to, the following moieties:

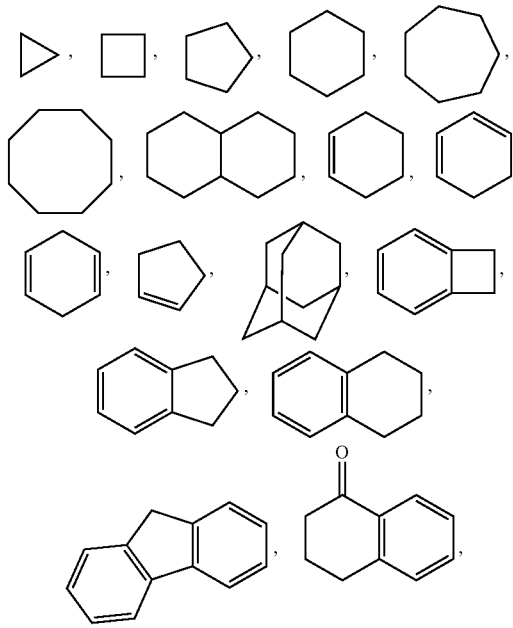

and the like.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" similarly refers to a radical of the formula —OR$_a$ where R$_a$ is a haloalkyl radical as defined. Unless stated otherwise specifically in the specification, a haloalkoxy group may be optionally substituted as described below.

"Heterocycloalkyl" or "heterocyclyl" or "heterocyclic ring" or "heterocycle" refers to a stable 3- to 24-membered non-aromatic ring radical comprising 2 to 23 carbon atoms and from one to 8 heteroatoms selected from the group consisting of nitrogen, oxygen, phosphorous and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated.

Examples of such heterocyclyl radicals include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 12-crown-4, 15-crown-5, 18-crown-6, 21-crown-7, aza-18-crown-6, diaza-18-crown-6, aza-21-crown-7, and diaza-21-crown-7. Unless stated otherwise specifically in the specification, a heterocyclyl group may be optionally substituted. Illustrative examples of heterocycloalkyl groups, also referred to as non-aromatic heterocycles, include:

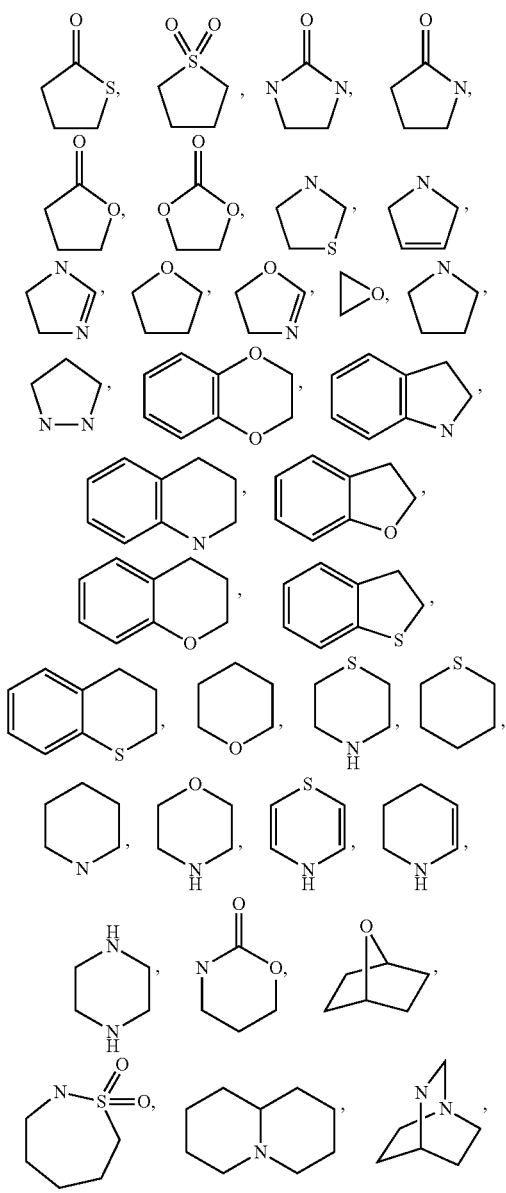

and the like. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

All the above groups may be either substituted or unsubstituted. The term "substituted" as used herein means any of the above groups (e.g, alkyl, alkylene, alkoxy, aryl, cycloalkyl, haloalkyl, heterocyclyl and/or heteroaryl) may be further functionalized wherein at least one hydrogen atom is replaced by a bond to a non-hydrogen atom substituent. Unless stated specifically in the specification, a substituted group may include one or more substituents selected from: oxo, amino, —CO$_2$H, nitrile, nitro, hydroxyl, thiooxy, alkyl, alkylene, alkoxy, aryl, cycloalkyl, heterocyclyl, heteroaryl, dialkylamines, arylamines, alkylarylamines, diarylamines, trialkylammonium (—N+R$_3$), N-oxides, imides, and enamines; a silicon atom in groups such as trialkylsilyl groups, dialkylarylsilyl groups, alkyldiarylsilyl groups, triarylsilyl groups, perfluoroalkyl or perfluoroalkoxy, for example, trifluoromethyl or trifluoromethoxy. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NH$_2$, —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. In the foregoing, R$_g$ and R$_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. In addition, each of the foregoing substituents may also be optionally substituted with one or more of the above substituents. Furthermore, any of the above groups may be substituted to include one or more internal oxygen, sulfur, or nitrogen atoms. For example, an alkyl group may be substituted with one or more internal oxygen atoms to form an ether or polyether group. Similarly, an alkyl group may be substituted with one or more internal sulfur atoms to form a thioether, disulfide, etc.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons.

An "effective amount" or "therapeutically effective amount" refers to an amount of a compound administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. In some embodiments, treatment includes administration of a pharmaceutical composition, subsequent to the initiation of a pathologic event or contact with an etiologic agent and includes stabilization of the condition (e.g., condition does not worsen) or alleviation of the condition. In other embodiments, treatment also includes prophylactic treatment (e.g., administration of a composition described herein when an individual is suspected to be suffering from a bacterial infection).

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

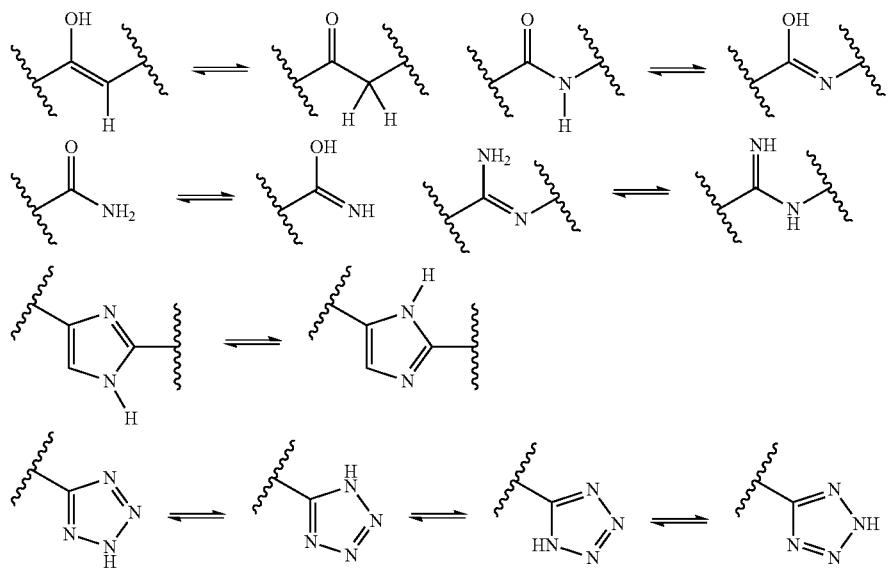

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism may be obtained from The Pharmacological Basis of Therapeutics, 9th Edition, McGraw-Hill (1996).

Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites.

Compounds

Described herein are compounds that modulate the activity of beta-lactamase. In some embodiments, the compounds described herein inhibit beta-lactamase. In certain embodiments, the compounds described herein are useful in the treatment of bacterial infections. In some embodiments, the bacterial infection is an upper or lower respiratory tract infection, a urinary tract infection, an intra-abdominal infection, or a skin infection.

In one aspect, provided herein are compounds of Formula I or Formula Ia, or pharmaceutically acceptable salts, polymorphs, solvates, tautomers, metabolites, or N-oxides thereof:

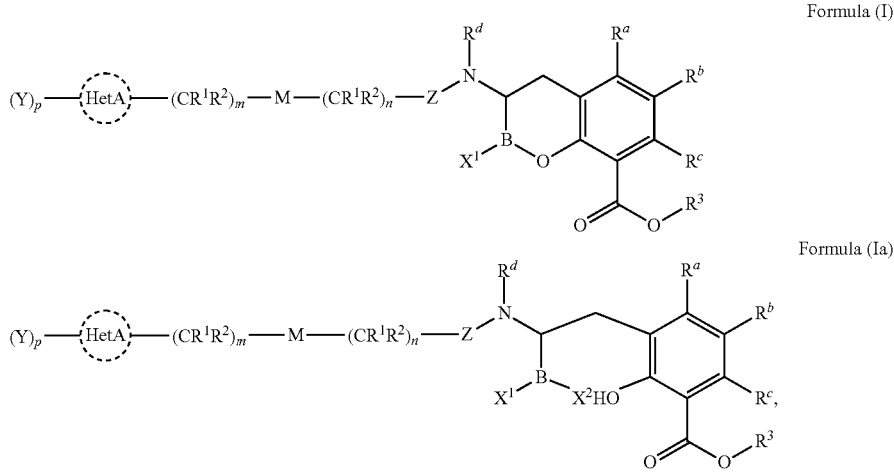

Formula (I)

Formula (Ia)

wherein:
M is a bond, —O—, —S—, —S(O)—, $SO_2$—, or —N($R^4$)—;
m is 0, 1, or 2;
provided that when HetA is attached to $(CR^1R^2)_m$ through a ring nitrogen atom, m=0 or 2.
n is 0, 1, 2, or 3;
provided that
when n is 0, then M is a bond;
p is 0, 1, 2, or 3;
$X^1$ and $X^2$ are independently selected from —OH, —$OR^8$, or F;
Z is >C=O, >C=S, or >$SO_2$;
HetA is an optionally substituted non-aromatic heterocyclic ring system;
each Y, provided Y is not attached directly to a heteroatom of HetA, is selected from the group consisting of:
fluoro, chloro, bromo, —CN, optionally substituted $C_1$-$C_6$ alkyl, optionally substituted $C_3$-$C_6$ cycloalkyl, optionally substituted heterocycle, optionally substituted aryl, optionally substituted heteroaryl, —OH, —$OR^{10}$, —$SR^{10}$, —$NR^4R^5$, —$(CR^6R^7)_vNR^4R^5$, —$NR^4(CR^6R^7)_vNR^4R^5$, —O$(CR^6R^7)_vNR^4R^5$, —S(O)$_{0,1,2}$$(CR^6R^7)_vNR^4R^5$, —N($R^4$)C(O)$(CR^6R^7)_vNR^4R^5$, —$(CR^6R^7)_vN(R^4)$C(O) $(CR^6R^7)_vNR^4R^5$, —$(CR^6R^7)_vNR^4(CR^6R^7)_v$ $NR^4R^5$, —$NR^4(CR^6R^7)_vOR^{10}$, —$NR^4(CR^6R^7)_v$ S(O)$_{0,1,2}R^{10}$, —C(O)$NR^4(CR^6R^7)_vNR^4R^5$, —S(O)$_{0,1,2}NR^4(CR^6R^7)_vNR^4R^5$, —$NR^5C(O)NR^4$ $(CR^6R^7)_vNR^4R^5$, —OC(O)$NR^4(CR^6R^7)_vNR^4R^5$, —$NR^5C(=NR^7)NR^4(CR^6R^7)_vNR^4R^5$, —N($R^4$)C (=$NR^5$) $R^6$, —$(CR^6R^7)_vN(R^4)C(=NR^5)R^6$, —$NR^4$ $(CR^6R^7)_vN(R^4)C(=NR^5)R^6$, —O$(CR^6R^7)_vN(R^4)C$ (=$NR^5$)$R^6$, —S(O)$_{0,1,2}$$(CR^6R^7)_vN(R^4)C(=NR^5)$ $R^6$, —$(CR^6R^7)_vC(=NR^5)NR^4R^5$, —$NR^4(CR^6R^7)_vC$ (=$NR^5$)$NR^4R^5$, —O$(CR^6R^7)_vC(=NR^5)NR^4R^5$, —S(O)$_{0,1,2}$$(CR^6R^7)_vC(=NR^5)NR^4R^5$, —$(CR^6R^7)_v$ N($R^4$)C(=$NR^5$)$NR^4R^5$, —$NR^4(CR^6R^7)_vN(R^4)C$ (=$NR^5$)$NR^4R^5$, —O$(CR^6R^7)_vN(R^4)C(=NR^5)$ $NR^4R^5$, —S(O)$_{0,1,2}$$(CR^6R^7)_vN(R^4)C(=NR^5)$ $NR^4R^5$, —$NR^4C(=NR^5)NR^4C(=NR)NR^4R^5$, —$(CR^6R^7)_vC(=NR^4)NR^5C(=NR^4)NR^4R^5$, —$NR^4$ $(CR^6R^7)_vC(=NR^4)NR^5C(=NR^4)NR^4R^5$, —O$(CR^6R^7)_vC(=NR^4)NR^5C(=NR^4)NR^4R^5$, —S(O)$_{0,1,2}$—$(CR^6R^7)_vC(=NR^4)NR^5C(=NR^4)$ $NR^4R^5$, —$NR^4C(=NR^5)NR^4R^5$, —C(=$NR^4$) $NR^4R^5$, —C(=$NR^4$)$NR^4C(O)R^6$, —$NR^4SO_2R^6$, —$NR^4C(O)R^6$, —$NR^4C(=O)OR^6$, —C(O)$NR^4R^5$, —$(CR^6R^7)_vC(O)NR^4R^5$, —$SO_2NR^4R^5$, -Heteroaryl-$NR^4R^5$, -Heterocyclyl-$NR^4R^5$, -Heteroaryl-N($R^4$)C(=$NR^5$)$NR^4R^5$, -Heterocyclyl-N($R^4$)C (=$NR^5$)$NR^4R^5$, —N($R^4$)—Heteroaryl-$NR^4R^5$, —N($R^4$)—Heterocyclyl-$NR^4R^5$, —$(CR^6R^7)_v$Heteroaryl-$NR^4R^5$, —$(CR^6R^7)_v$Heterocyclyl-$NR^4R^5$, —$(CR^6R^7)_v$Heteroaryl-N($R^4$)C(=$NR^5$)$NR^4R^5$, —$(CR^6R^7)_v$Heterocyclyl-N($R^4$)C(=$NR^5$)$NR^4R^5$, —$(CR^6R^7)_v$Heteroaryl, —$(CR^6R^7)_v$Heterocyclyl, —O-Heteroaryl, —O-Heterocyclyl, —$NR^4(CR^6$ $R^7)_v$Heteroaryl, —$NR^4(CR^6R^7)_v$Heterocyclyl, —O$(CR^6R^7)_v$ Heteroaryl, —O$(CR^6R^7)_v$Heterocyclyl, —$NR^4(CR^6R^7)_vNR^5$-Heteroaryl, —$NR^4$ $(CR^6R^7)_vNR^5$-Heterocyclyl, —O$(CR^6R^7)_vNR^5$-Heteroaryl, —O$(CR^6R^7)_vNR^5$-Heterocyclyl, —O$(CR^6R^7)_v$O-Heterocyclyl, —$NR^4R^5R^{9+}Q^-$, —$(CR^6R^7)_vNR^4R^5R^{9+}Q^-$, —$NR^4(CR^6R^7)_v$ $NR^4R^5R^{9+}Q^-$, —$NR^4R^{9+}(CR^6R^7)_vNR^4R^5R^{9+}Q^-_2$, —$(CR^6R^7)_v(T)^+Q^-$, and —O$(CR^6R^7)_vNR^4R^5R^{9+}Q^-$;

wherein:
T is pyridine-1-yl, pyrimidin-1-yl, or thiazol-3-yl;
Q is a pharmaceutically acceptable counterion; and
v is 1-4;
or two Ys taken together with the carbon atoms to which they are attached form an optionally substituted carbocycle, an optionally substituted heterocycle, or a carbonyl group;
in the case where Y is attached directly to a heteroatom of HetA, Y is selected from the group consisting of —(CR$^6$R$^7$)$_v$NR$^4$R$^5$, —S(O)$_{1,2}$(CR$^6$R$^7$)$_v$NR$^4$R$^5$, —C(O)(CR$^6$R$^7$)$_v$NR$^4$R$^5$, —(CR$^6$R$^7$)$_w$N(R$^4$)C(O)(CR$^6$R$^7$)$_v$NR$^4$R$^5$, —(CR$^6$R$^7$)$_w$NR$^4$(CR$^6$R$^7$)$_w$NR$^4$R$^5$, —NR$^4$(CR$^6$R$^7$)$_w$OR$^{10}$, —(CR$^6$R$^7$)$_w$S(O)$_{0,1,2}$R$^{10}$, —C(O)NR$^4$(CR$^6$R$^7$)$_w$NR$^4$R$^5$, —S(O)$_{1,2}$NR$^4$(CR$^6$R$^7$)$_w$NR$^4$R$^5$, —C(=NR$^7$)NR$^4$(CR$^6$R$^7$)$_v$NR$^4$R$^5$, —C(=NR$^5$)R$^6$, —(CR$^6$R$^7$)$_w$N(R$^4$)C(=NR$^5$)R$^6$, —S(O)$_{1,2}$(CR$^6$R$^7$)$_v$N(R$^4$)C(=NR$^5$)R$^6$, —(CR$^6$R$^7$)$_v$C(=NR$^5$)NR$^4$R$^5$, —(CR$^6$R$^7$)$_w$C(=NR$^5$)NR$^4$R$^5$, —S(O)$_{1,2}$(CR$^6$R$^7$)$_v$C(=NR$^5$)NR$^4$R$^5$, —(CR$^6$R$^7$)$_w$N(R$^4$)C(=NR$^5$)NR$^4$R$^5$, —S(O)$_{1,2}$(CR$^6$R$^7$)$_v$N(R$^4$)C(=NR$^5$)NR$^4$R$^5$, —C(=NR$^5$)NR$^4$C(=NR$^5$)NR$^4$R$^5$, —(CR$^6$R$^7$)$_v$C(=NR$^4$)NR$^5$C(=NR$^4$)NR$^4$R$^5$, —S(O)$_{1,2}$(CR$^6$R$^7$)$_v$C(=NR$^4$)NR$^5$C(=NR$^4$)NR$^4$R$^5$, —C(=NR$^4$)NR$^4$R$^5$, —C(=NR$^4$)NR$^4$C(O)R$^6$, —SO$_2$R$^6$, —C(O)R$^6$, —C(=O)OR$^6$, —C(O)NR$^4$R$^5$, —(CR$^6$R$^7$)$_v$C(O)NR$^4$R$^5$, —SO$_2$NR$^4$R$^5$, -aryl, -heteroaryl, —C(O)N(R$^4$)—Heteroaryl-NR$^4$R$^5$, -Heteroaryl-NR$^4$R$^5$, -Heterocyclyl-NR$^4$R$^5$, —Heteroaryl-N(R$^4$)C(=NR$^5$)NR$^4$R$^5$, -Heterocyclyl-N(R$^4$)C(=NR$^5$)NR$^4$R$^5$, -Heteroaryl-NR$^4$R$^5$, -Heterocyclyl-NR$^4$R$^5$, —(CR$^6$R$^7$)$_v$Heteroaryl-NR$^4$R$^5$, —(CR$^6$R$^7$)$_v$Heterocyclyl-NR$^4$R$^5$, —(CR$^6$R$^7$)$_v$Heteroaryl-N(R$^4$)C(=NR$^5$)NR$^4$R$^5$, —(CR$^6$R$^7$)$_v$Heterocyclyl-N(R$^4$)C(=NR$^5$)NR$^4$R$^5$, —(CR$^6$R$^7$)$_v$Heteroaryl, —(CR$^6$R$^7$)$_v$Heterocyclyl, —(CR$^6$R$^7$)$_v$NR$^5$-Heteroaryl, —(CR$^6$R$^7$)$_v$NR$^5$-Heterocyclyl, —(CR$^6$R$^7$)$_v$O-Heterocyclyl, —R$^{9+}$Q$^-$, —(CR$^6$R$^7$)$_w$NR$^4$R$^5$R$^{9+}$ Q$^-$, —R$^{9+}$(CR$^6$R$^7$)$_v$NR$^4$R$^5$R$^{9+}$Q$^-_2$ and —(CR$^6$R$^7$)$_v$(T)$^+$Q
wherein:
T is pyridine-1-yl, pyrimidin-1-yl, or thiazol-3-yl;
Q is a pharmaceutically acceptable counterion; and
v is 1-4; w is 2-4;
R$^a$, R$^b$, and R$^c$ are independently selected from the group consisting of hydrogen, fluoro, chloro, bromo, optionally substituted C$_1$-C$_6$ alkyl, optionally substituted C$_3$-C$_6$ cycloalkyl, optionally substituted heterocyclyl, optionally substituted aryl, optionally substituted heteroaryl, —OH, —OR$^{10}$, —NR$^4$R$^5$, and —SR$^{10}$;

R$^1$ and R$^2$ are independently selected from the group consisting of hydrogen, fluoro, chloro, bromo, optionally substituted C$_1$-C$_6$ alkyl, optionally substituted C$_3$-C$_6$ cycloalkyl, —OH, —OR$_{10}$, —SR$^{10}$, and —NR$^4$R$^5$,
or R$^1$ and R$^2$ taken together form an oxo, oxime, or an optionally substituted carbocycle or optionally substituted heterocycle with the carbon to which they are attached;

R$^3$ is hydrogen, optionally substituted C$_1$-C$_6$ alkyl, or a pharmaceutically acceptable prodrug;

R$^d$, R$^4$ and R$^5$ are independently selected from the group consisting of hydrogen, —OH, —CN, optionally substituted C$_1$-C$_6$ alkyl, optionally substituted alkoxyalkyl, optionally substituted hydroxyalkyl, optionally substituted aminoalkyl, optionally substituted cycloalkyl, optionally substituted heterocyclyl, optionally substituted aryl, optionally substituted heteroaryl, optionally substituted cycloalkylalkyl, optionally substituted heterocyclylalkyl, optionally substituted aralkyl, optionally substituted heteroaralkyl, (poly-ethylene-glycol)-ethyl, and an optionally substituted saccharide;
or R$^4$ and R$^5$ taken together form an optionally substituted heterocycle with the nitrogen to which they are attached;

R$^6$ and R$^7$ are independently selected from the group consisting of hydrogen, fluoro, chloro, bromo, optionally substituted C$_1$-C$_6$ alkyl, optionally substituted alkoxyalkyl, optionally substituted hydroxyalkyl, optionally substituted C$_3$-C$_6$ cycloalkyl, —OH, —OR$^{10}$, —SR$^{10}$, —NR$^4$R$^5$, —NR$^4$C(O)R$^5$, —C(O)NR$^4$R$^5$, —NR$^4$SO$_2$R$^5$, optionally substituted heterocyclyl, optionally substituted aryl, and optionally substituted heteroaryl;
or R$^6$ and R$^7$ taken together form an oxo, oxime, or an optionally substituted carbocycle or an optionally substituted heterocycle with the carbon to which they are attached;

R$^8$ is optionally substituted C$_1$-C$_6$ alkyl, optionally substituted C$_3$-C$_6$ cycloalkyl, or a pharmaceutically acceptable boronate ester group;

R$^9$ is optionally substituted C$_1$-C$_6$ alkyl; and

R$^{10}$ is optionally substituted C$_1$-C$_6$ alkyl or optionally substituted C$_3$-C$_6$ cycloalkyl.

In some embodiments, provided herein are compounds of Formula I or Formula Ia, or pharmaceutically acceptable salts, polymorphs, solvates, tautomers, metabolites, or N-oxides thereof:

Formula (I)

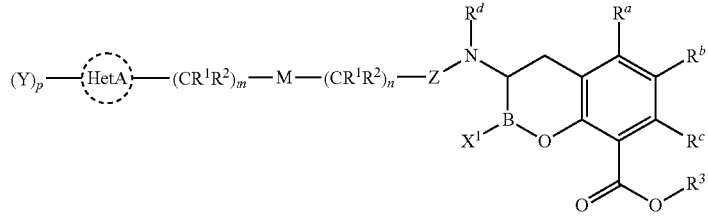

-continued

Formula (Ia)

$$(Y)_p-\text{HetA}-(CR^1R^2)_m-M-(CR^1R^2)_n-Z-N(R^d)-\text{...}$$

wherein:
  M is a bond, —O—, —S—, —S(O)—, SO$_2$—, or —N(R$^4$)—;
  m is 0, 1, or 2;
    provided that when HetA is attached to (CR$^1$R$^2$)$_m$ through a ring nitrogen atom, m=0 or 2.
  n is 0, 1, 2, or 3;
    provided that
      when n is 0, then M is a bond;
  p is 1, 2, or 3;
  X$^1$ and X$^2$ are independently selected from —OH, —OR$^8$, or F;
  Z is >C=O, >C=S, or >SO$_2$;
  HetA is an optionally substituted non-aromatic heterocyclic ring system;
  each Y, provided Y is not attached directly to a heteroatom of HetA, is selected from the group consisting of:
    fluoro, chloro, bromo, —CN, optionally substituted C$_1$-C$_6$ alkyl, optionally substituted C$_3$-C$_6$ cycloalkyl, optionally substituted heterocycle, optionally substituted aryl, optionally substituted heteroaryl, —OH, —OR$^{10}$, —SR$^{10}$, —NR$^4$R$^5$, —(CR$^6$R$^7$)$_v$NR$^4$R$^5$, —NR$^4$(CR$^6$R$^7$)$_v$NR$^4$R$^5$, —O(CR$^6$R$^7$)$_v$NR$^4$R$^5$, —S(O)$_{0,1,2}$(CR$^6$R$^7$)$_v$NR$^4$R$^5$, —N(R$^4$)C(O)(CR$^6$R$^7$)$_v$NR$^4$R$^5$, —(CR$^6$R$^7$)$_v$N(R$^4$)C(O)(CR$^6$R$^7$)$_v$NR$^4$R$^5$, —(CR$^6$R$^7$)$_v$NR$^4$(CR$^6$R$^7$)$_v$NR$^4$R$^5$, —NR$^4$(CR$^6$R$^7$)$_v$OR$^{10}$, —NR$^4$(CR$^6$R$^7$)$_v$S(O)$_{0,1,2}$R$^{10}$, —C(O)NR$^4$(CR$^6$R$^7$)$_v$NR$^4$R$^5$, —S(O)$_{0,1,2}$NR$^4$(CR$^6$R$^7$)$_v$NR$^4$R$^5$, —NR$^5$C(O)NR$^4$(CR$^6$R$^7$)$_v$NR$^4$R$^5$, —OC(O)NR$^4$(CR$^6$R$^7$)$_v$NR$^4$R$^5$, —NR$^5$C(=NR$^7$)NR$^4$(CR$^6$R$^7$)$_v$NR$^4$R$^5$, —N(R$^4$)C(=NR$^5$)R$^6$, —(CR$^6$R$^7$)$_v$N(R$^4$)C(=NR$^5$)R$^6$, —NR$^4$(CR$^6$R$^7$)$_v$N(R$^4$)C(=NR$^5$)R$^6$, —O(CR$^6$R$^7$)$_v$N(R$^4$)C(=NR$^5$)R$^6$, —S(O)$_{0,1,2}$(CR$^6$R$^7$)$_v$N(R$^4$)C(=NR$^5$)R$^6$, —(CR$^6$R$^7$)$_v$C(=NR$^5$)NR$^4$R$^5$, —NR$^4$(CR$^6$R$^7$)$_v$C(=NR$^5$)NR$^4$R$^5$, —O(CR$^6$R$^7$)$_v$C(=NR$^5$)NR$^4$R$^5$, —S(O)$_{0,1,2}$(CR$^6$R$^7$)$_v$C(=NR$^5$)NR$^4$R$^5$, —(CR$^6$R$^7$)$_v$N(R$^4$)C(=NR$^5$)NR$^4$R$^5$, —NR$^4$(CR$^6$R$^7$)$_v$N(R$^4$)C(=NR$^5$)NR$^4$R$^5$, —O(CR$^6$R$^7$)$_v$N(R$^4$)C(=NR$^5$)NR$^4$R$^5$, —S(O)$_{0,1,2}$(CR$^6$R$^7$)$_v$N(R$^4$)C(=NR$^5$)NR$^4$R$^5$, —NR$^4$C(=NR$^5$)NR$^4$C(=NR)NR$^4$R$^5$, —(CR$^6$R$^7$)$_v$C(=NR$^4$)NR$^5$C(=NR$^4$)NR$^4$R$^5$, —NR$^4$(CR$^6$R$^7$)$_v$C(=NR$^4$)NR$^5$C(=NR$^4$)NR$^4$R$^5$, —O(CR$^6$R$^7$)$_v$C(=NR$^4$)NR$^5$C(=NR$^4$)NR$^4$R$^5$, —S(O)$_{0,1,2}$—(CR$^6$R$^7$)$_v$C(=NR$^4$)NR$^5$C(=NR$^4$)NR$^4$R$^5$, —NR$^4$C(=NR$^5$)NR$^4$R$^5$, —C(=NR$^4$)NR$^4$R$^5$, —C(=NR$^4$)NR$^4$C(O)R$^6$, —NR$^4$SO$_2$R$^6$, —NR$^4$C(O)R$^6$, —NR$^4$C(=O)OR$^6$, —C(O)NR$^4$R$^5$, —(CR$^6$R$^7$)$_v$C(O)NR$^4$R$^5$, —SO$_2$NR$^4$R$^5$, -Heteroaryl-NR$^4$R$^5$, -Heterocyclyl-NR$^4$R$^5$, -Heteroaryl-N(R$^4$)C(=NR$^5$)NR$^4$R$^5$, -Heterocyclyl-N(R$^4$)C(=NR$^5$)NR$^4$R$^5$, —N(R$^4$)—Heteroaryl-NR$^4$R$^5$, —N(R$^4$)—Heterocyclyl-NR$^4$R$^5$, —(CR$^6$R$^7$)$_v$Heteroaryl-NR$^4$R$^5$, —(CR$^6$R$^7$)$_v$Heterocyclyl-NR$^4$R$^5$, —(CR$^6$R$^7$)$_v$Heteroaryl-N(R$^4$)C(=NR$^5$)NR$^4$R$^5$, —(CR$^6$R$^7$)$_v$Heterocyclyl-N(R$^4$)C(=NR$^5$)NR$^4$R$^5$, —(CR$^6$R$^7$)$_v$Heteroaryl, —(CR$^6$R$^7$)$_v$Heterocyclyl, —O-Heteroaryl, —O-Heterocyclyl, —NR$^4$(CR$^6$R$^7$)$_v$Heteroaryl, —NR$^4$(CR$^6$R$^7$)$_v$Heterocyclyl, —O(CR$^6$R$^7$)$_v$Heteroaryl, —O(CR$^6$R$^7$)$_v$Heterocyclyl, —NR$^4$(CR$^6$R$^7$)$_v$NR$^5$-Heteroaryl, —NR$^4$(CR$^6$R$^7$)$_v$NR$^5$-Heterocyclyl, —O(CR$^6$R$^7$)$_v$NR$^5$-Heteroaryl, —O(CR$^6$R$^7$)$_v$NR$^5$-Heterocyclyl, —O(CR$^6$R$^7$)$_v$O-Heterocyclyl, —NR$^4$R$^5$R$^{9+}$Q$^-$, —(CR$^6$R$^7$)$_v$NR$^4$R$^5$R$^{9+}$Q$^-$, —NR$^4$(CR$^6$R$^7$)$_v$NR$^4$R$^5$R$^{9+}$Q$^-$, —NR$^4$R$^{9+}$(CR$^6$R$^7$)$_v$NR$^4$R$^5$R$^{9+}$Q$^-_2$, —(CR$^6$R$^7$)$_v$(T)$^+$Q$^-$, and —O(CR$^6$R$^7$)$_v$NR$^4$R$^5$R$^{9+}$Q$^-$;
wherein:
  T is pyridine-1-yl, pyrimidin-1-yl, or thiazol-3-yl;
  Q is a pharmaceutically acceptable counterion; and
  v is 1-4;
  or two Ys taken together with the carbon atoms to which they are attached form an optionally substituted carbocycle, an optionally substituted heterocycle, or a carbonyl group;
  in the case where Y is attached directly to a heteroatom of HetA, Y is selected from the group consisting of —(CR$^6$R$^7$)$_v$NR$^4$R$^5$, —S(O)$_{1,2}$(CR$^6$R$^7$)$_v$NR$^4$R$^5$, —C(O)(CR$^6$R$^7$)$_v$NR$^4$R$^5$, —(CR$^6$R$^7$)$_w$N(R$^4$)C(O)(CR$^6$R$^7$)$_v$NR$^4$R$^5$, —(CR$^6$R$^7$)$_w$NR$^4$(CR$^6$R$^7$)$_w$NR$^4$R$^5$, —NR$^4$(CR$^6$R$^7$)$_w$OR$^{10}$, —(CR$^6$R$^7$)$_w$S(O)$_{0,1,2}$R$^{10}$, —C(O)NR$^4$(CR$^6$R$^7$)$_w$NR$^4$R$^5$, —S(O)$_{1,2}$NR$^4$(CR$^6$R$^7$)$_w$NR$^4$R$^5$, —C(=NR$^7$)NR$^4$(CR$^6$R$^7$)$_v$NR$^4$R$^5$, —C(=NR$^5$)R$^6$, —(CR$^6$R$^7$)$_w$N(R$^4$)C(=NR$^5$)R$^6$, —S(O)$_{1,2}$(CR$^6$R$^7$)$_v$N(R$^4$)C(=NR$^5$)R$^6$, —(CR$^6$R$^7$)$_v$C(=NR$^5$)NR$^4$R$^5$, —(CR$^6$R$^7$)$_w$C(=NR$^5$)NR$^4$R$^5$, —S(O)$_{1,2}$(CR$^6$R$^7$)$_v$C(=NR$^5$)NR$^4$R$^5$, —(CR$^6$R$^7$)$_w$N(R$^4$)C(=NR$^5$)NR$^4$R$^5$, —S(O)$_{1,2}$(CR$^6$R$^7$)$_v$N(R$^4$)C(=NR$^5$)NR$^4$R$^5$, —C(=NR$^5$)NR$^4$C(=NR$^5$)NR$^4$R$^5$, —(CR$^6$R$^7$)$_v$C(=NR$^4$)NR$^5$C(=NR$^4$)NR$^4$R$^5$, —S(O)$_{1,2}$—(CR$^6$R$^7$)$_v$C(=NR$^4$)NR$^5$C(=NR$^4$)NR$^4$R$^5$, —C(=NR$^4$)NR$^4$R$^5$, —C(=NR$^4$)NR$^4$C(O)R$^6$, —SO$_2$R$^6$, —C(=O)OR$^6$, —C(O)NR$^4$R$^5$, —(CR$^6$R$^7$)$_v$C(O)NR$^4$R$^5$, —SO$_2$NR$^4$R$^5$, -aryl, -heteroaryl, —C(O)N(R$^4$)—Heteroaryl-NR$^4$R$^5$, -Heteroaryl-NR$^4$R$^5$, -Heterocyclyl-NR$^4$R$^5$, -Heteroaryl-N(R$^4$)C(=NR$^5$)NR$^4$R$^5$, -Heterocyclyl-N(R$^4$)C(=NR$^5$)NR$^4$R$^5$, -Heteroaryl-NR$^4$R$^5$, -Heterocyclyl-NR$^4$R$^5$, —(CR$^6$R$^7$)$_v$Heteroaryl-NR$^4$R$^5$, —(CR$^6$R$^7$)$_v$Heterocyclyl-NR$^4$R$^5$, —(CR$^6$R$^7$)$_v$Heteroaryl-N(R$^4$)C(=NR$^5$)NR$^4$R$^5$, —(CR$^6$R$^7$)$_v$Heterocyclyl-N(R$^4$)C(=NR$^5$)NR$^4$R$^5$, —(CR$^6$R$^7$)$_v$Heteroaryl, —(CR$^6$R$^7$)$_v$Heterocyclyl, —(CR$^6$R$^7$)$_v$NR$^5$-Heteroaryl, —(CR$^6$R$^7$)$_v$NR$^5$-Heterocyclyl, —(CR$^6$R$^7$)$_v$O-Heterocyclyl, —R$^{9+}$Q$^-$, —(CR⁶R⁷)_wNR⁴R⁵R⁹⁺Q⁻, —R⁹⁺(CR⁶R⁷)_v
NR⁴R⁵R⁹⁺Q⁻₂ and —(CR⁶R⁷)_v(T)⁺Q wherein:
T is pyridine-1-yl, pyrimidin-1-yl, or thiazol-3-yl;
Q is a pharmaceutically acceptable counterion; and
v is 1-4; w is 2-4;

$R^a$, $R^b$, and $R^c$ are independently selected from the group consisting of hydrogen, fluoro, chloro, bromo, optionally substituted $C_1$-$C_6$ alkyl, optionally substituted $C_3$-$C_6$ cycloalkyl, optionally substituted heterocyclyl, optionally substituted aryl, optionally substituted heteroaryl, —OH, —OR¹⁰, —NR⁴R⁵, and —SR¹⁰;

$R^1$ and $R^2$ are independently selected from the group consisting of hydrogen, fluoro, chloro, bromo, optionally substituted $C_1$-$C_6$ alkyl, optionally substituted $C_3$-$C_6$ cycloalkyl, —OH, —OR¹⁰, —SR¹⁰, and —NR⁴R⁵,
or $R^1$ and $R^2$ taken together form an oxo, oxime, or an optionally substituted carbocycle or optionally substituted heterocycle with the carbon to which they are attached;

$R^3$ is hydrogen, optionally substituted $C_1$-$C_6$ alkyl, or a pharmaceutically acceptable prodrug;

$R^d$, $R^4$ and $R^5$ are independently selected from the group consisting of hydrogen, —OH, —CN, optionally substituted $C_1$-$C_6$ alkyl, optionally substituted alkoxyalkyl, optionally substituted hydroxyalkyl, optionally substituted aminoalkyl, optionally substituted cycloalkyl, optionally substituted heterocyclyl, optionally substituted aryl, optionally substituted heteroaryl, optionally substituted cycloalkylalkyl, optionally substituted heterocyclylalkyl, optionally substituted aralkyl, optionally substituted heteroaralkyl, (poly-ethylene-glycol)-ethyl, and an optionally substituted saccharide;
or $R^4$ and $R^5$ taken together form an optionally substituted heterocycle with the nitrogen to which they are attached;

$R^6$ and $R^7$ are independently selected from the group consisting of hydrogen, fluoro, chloro, bromo, optionally substituted $C_1$-$C_6$ alkyl, optionally substituted alkoxyalkyl, optionally substituted hydroxyalkyl, optionally substituted $C_3$-$C_6$ cycloalkyl, —OH, —OR¹⁰, —SR¹⁰, —NR⁴R⁵, —NR⁴C(O)R⁵, —C(O)NR⁴R⁵, —NR⁴SO₂R⁵, optionally substituted heterocyclyl, optionally substituted aryl, and optionally substituted heteroaryl;
or $R^6$ and $R^7$ taken together form an oxo, oxime, or an optionally substituted carbocycle or an optionally substituted heterocycle with the carbon to which they are attached;

$R^8$ is optionally substituted $C_1$-$C_6$ alkyl, optionally substituted $C_3$-$C_6$ cycloalkyl, or a pharmaceutically acceptable boronate ester group;

$R^9$ is optionally substituted $C_1$-$C_6$ alkyl; and $R^{10}$ is optionally substituted $C_1$-$C_6$ alkyl or optionally substituted $C_3$-$C_6$ cycloalkyl.

In some embodiments, provided herein are compounds of Formula I or Formula Ia, or pharmaceutically acceptable salts, polymorphs, solvates, tautomers, metabolites, or N-oxides thereof:

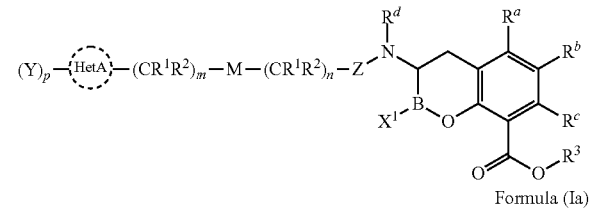

Formula (I)

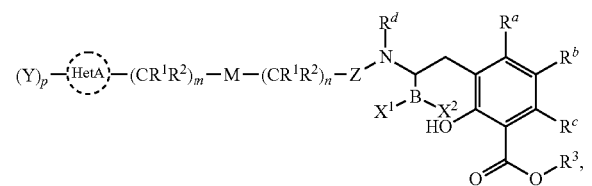

Formula (Ia)

wherein:
M is a bond, —O—, —S—, —S(O)—, SO₂—, or —N(R⁴)—;
m is 0, 1, or 2;
provided that when HetA is attached to (CR¹R²)_m through a ring nitrogen atom, m=0 or 2.
n is 0, 1, 2, or 3;
provided that
when n is 0, then M is a bond;
p is 0, 1, 2, or 3;
$X^1$ and $X^2$ are independently selected from —OH, —OR⁸, or F;
Z is >C=O, >C=S, or >SO₂;
HetA is an optionally substituted non-aromatic heterocyclic ring system, provided that HetA is not 2-pyrrolidinyl or 4-piperidinyl;
each Y, provided Y is not attached directly to a heteroatom of HetA, is selected from the group consisting of:
fluoro, chloro, bromo, —CN, optionally substituted $C_1$-$C_6$ alkyl, optionally substituted $C_3$-$C_6$ cycloalkyl, optionally substituted heterocycle, optionally substituted aryl, optionally substituted heteroaryl, —OH, —OR¹⁰, —SR¹⁰, —NR⁴R⁵, —(CR⁶R⁷)_vNR⁴R⁵, —NR⁴(CR⁶R⁷)_vNR⁴R⁵, —O(CR⁶R⁷)_vNR⁴R⁵, —S(O)_{0,1,2}(CR⁶R⁷)_vNR⁴R⁵, —N(R⁴)C(O)(CR⁶R⁷)_vNR⁴R⁵, —(CR⁶R⁷)_vN(R⁴)C(O)(CR⁶R⁷)_vNR⁴R⁵, —(CR⁶R⁷)_vNR⁴(CR⁶R⁷)_vNR⁴R⁵, —NR⁴(CR⁶R⁷)_vOR¹⁰, —NR⁴(CR⁶R⁷)_vS(O)_{0,1,2}R¹⁰, —C(O)NR⁴(CR⁶R⁷)_vNR⁴R⁵, —S(O)_{0,1,2}NR⁴(CR⁶R⁷)_vNR⁴R⁵, —NR⁵C(O)NR⁴(CR⁶R⁷)_vNR⁴R⁵, —OC(O)NR⁴(CR⁶R⁷)_vNR⁴R⁵, —NR⁵C(=NR⁷)NR⁴(CR⁶R⁷)_vNR⁴R⁵, —N(R⁴)C(=NR⁵)R⁶, —(CR⁶R⁷)_vN(R⁴)C(=NR⁵)R⁶, —NR⁴(CR⁶R⁷)_vN(R⁴)C(=NR⁵)R⁶, —O(CR⁶R⁷)_vN(R⁴)C(=NR⁵)R⁶, —S(O)_{0,1,2}(CR⁶R⁷)_vN(R⁴)C(=NR⁵)R⁶, —(CR⁶R⁷)_vC(=NR⁵)NR⁴R⁵, —NR⁴(CR⁶R⁷)_vC(=NR⁵)NR⁴R⁵, —O(CR⁶R⁷)_vC(=NR⁵)NR⁴R⁵, —S(O)_{0,1,2}(CR⁶R⁷)_vC(=NR⁵)NR⁴R⁵, —(CR⁶R⁷)_vN(R⁴)C(=NR⁵)NR⁴R⁵, —NR⁴(CR⁶R⁷)_vN(R⁴)C(=NR⁵)NR⁴R⁵, —O(CR⁶R⁷)_vN(R⁴)C(=NR⁵)NR⁴R⁵, —S(O)_{0,1,2}(CR⁶R⁷)_vN(R⁴)C(=NR⁵)NR⁴R⁵, —NR⁴C(=NR⁵)NR⁴C(=NR)NR⁴R⁵, —(CR⁶R⁷)_vC(=NR⁴)NR⁵C(=NR⁴)NR⁴R⁵, —NR⁴(CR⁶R⁷)_vC(=NR⁴)NR⁵C(=NR⁴)NR⁴R⁵, —O(CR⁶R⁷)_vC(=NR⁴)NR⁵C(=NR⁴)NR⁴R⁵, —S(O)_{0,1,2}—(CR⁶R⁷)_vC(=NR⁴)NR⁵C(=NR⁴)NR⁴R⁵, —NR⁴C(=NR⁵)NR⁴R⁵, —C(=NR⁴)

NR$^4$R$^5$, —C(=NR$^4$)NR$^4$C(O)R$^6$, —NR$^4$SO$_2$R$^6$, —NR$^4$C(O)R$^6$, —NR$^4$C(=O)OR$^6$, —C(O)NR$^4$R$^5$, —(CR$^6$R$^7$)$_v$C(O)NR$^4$R$^5$, —SO$_2$NR$^4$R$^5$, -Heteroaryl-NR$^4$R$^5$, -Heterocyclyl-NR$^4$R$^5$, -Heteroaryl-N(R$^4$)C(=NR$^5$)NR$^4$R$^5$, -Heterocyclyl-N(R$^4$)C(=NR$^5$)NR$^4$R$^5$, —N(R$^4$)—Heteroaryl-NR$^4$R$^5$, —N(R$^4$)—Heterocyclyl-NR$^4$R$^5$, —(CR$^6$R$^7$)$_v$Heteroaryl-NR$^4$R$^5$, —(CR$^6$R$^7$)$_v$Heterocyclyl-NR$^4$R$^5$, —(CR$^6$R$^7$)$_v$Heteroaryl-N(R$^4$)C(=NR$^5$)NR$^4$R$^5$, —(CR$^6$R$^7$)$_v$Heterocyclyl-N(R$^4$)C(=NR$^5$)NR$^4$R$^5$, —(CR$^6$R$^7$)$_v$Heteroaryl, —(CR$^6$R$^7$)$_v$Heterocyclyl, —O-Heteroaryl, —O-Heterocyclyl, —NR$^4$(CR$^6$R$^7$)$_v$Heteroaryl, —NR$^4$(CR$^6$R$^7$)$_v$Heterocyclyl, —O(CR$^6$R$^7$)$_v$ Heteroaryl, —O(CR$^6$R$^7$)$_v$Heterocyclyl, —NR$^4$(CR$^6$R$^7$)$_v$NR$^5$-Heteroaryl, —NR$^4$(CR$^6$R$^7$)$_v$NR$^5$-Heterocyclyl, —O(CR$^6$R$^7$)$_v$NR$^5$-Heteroaryl, —O(CR$^6$R$^7$)$_v$NR$^5$-Heterocyclyl, —O(CR$^6$R$^7$)$_v$O-Heterocyclyl, —NR$^4$R$^5$R$^{9+}$Q$^-$, —(CR$^6$R$^7$)$_v$NR$^4$R$^5$R$^{9+}$Q$^-$, —NR$^4$(CR$^6$R$^7$)$_v$NR$^4$R$^5$R$^{9+}$Q$^-$, —NR$^4$R$^{9+}$(CR$^6$R$^7$)$_v$NR$^4$R$^5$R$^{9+}$Q$^-$$_2$, —(CR$^6$R$^7$)$_v$(T)$^+$Q$^-$, and —O(CR$^6$R$^7$)$_v$NR$^4$R$^5$R$^{9+}$Q$^-$;

wherein:
T is pyridine-1-yl, pyrimidin-1-yl, or thiazol-3-yl;
Q is a pharmaceutically acceptable counterion; and
v is 1-4;
or two Ys taken together with the carbon atoms to which they are attached form an optionally substituted carbocycle, an optionally substituted heterocycle, or a carbonyl group;

in the case where Y is attached directly to a heteroatom of HetA, Y is selected from the group consisting of —(CR$^6$R$^7$)$_v$NR$^4$R$^5$, —S(O)$_{1,2}$(CR$^6$R$^7$)$_v$NR$^4$R$^5$, —C(O)(CR$^6$R$^7$)$_v$NR$^4$R$^5$, —(CR$^6$R$^7$)$_w$N(R$^4$)C(O)(CR$^6$R$^7$))$_v$NR$^4$R$^5$, —(CR$^6$R$^7$)$_v$NR$^4$(CR$^6$R$^7$)$_w$NR$^4$R$^5$, —NR$^4$(CR$^6$R$^7$)$_w$OR$^{10}$, —(CR$^6$R$^7$)$_w$S(O)$_{0,1,2}$R$^{10}$, —C(O)NR$^4$(CR$^6$R$^7$)$_w$NR$^4$R$^5$, —S(O)$_{1,2}$NR$^4$(CR$^6$R$^7$)$_w$NR$^4$R$^5$, —C(=NR$^7$)NR$^4$(CR$^6$R$^7$)$_v$NR$^4$R$^5$, —C(=NR$^5$)R$^6$, —(CR$^6$R$^7$)$_w$N(R$^4$)C(=NR$^5$)R$^6$, —S(O)$_{1,2}$(CR$^6$R$^7$)$_v$N(R$^4$)C(=NR$^5$)R$^6$, —(CR$^6$R$^7$)$_v$C(=NR$^5$)NR$^4$R$^5$, —(CR$^6$R$^7$)$_w$C(=NR$^5$)NR$^4$R$^5$, —S(O)$_{1,2}$(CR$^6$R$^7$)$_v$C(=NR$^5$)NR$^4$R$^5$, —(CR$^6$R$^7$)$_w$N(R$^4$)C(=NR$^5$)NR$^4$R$^5$, —S(O)$_{1,2}$(CR$^6$R$^7$)$_v$N(R$^4$)C(=NR$^5$)NR$^4$R$^5$, —C(=NR$^5$)NR$^4$C(=NR$^5$)NR$^4$R$^5$, —(CR$^6$R$^7$)$_v$C(=NR$^4$)NR$^5$C(=NR$^4$)NR$^4$R$^5$, —S(O)$_{1,2}$—(CR$^6$R$^7$)$_v$C(=NR$^4$)NR$^5$C(=NR$^4$)NR$^4$R$^5$, —C(=NR$^4$)NR$^4$R$^5$, —C(=NR$^4$)NR$^4$C(O)R$^6$, —SO$_2$R$^6$, —C(=O)OR$^6$, —C(O)NR$^4$R$^5$, —(CR$^6$R$^7$)$_v$C(O)NR$^4$R$^5$, —SO$_2$NR$^4$R$^5$, -aryl, -heteroaryl, —C(O)N(R$^4$)—Heteroaryl-NR$^4$R$^5$, -Heteroaryl-NR$^4$R$^5$, -Heterocyclyl-NR$^4$R$^5$, -Heteroaryl-N(R$^4$)C(=NR$^5$)NR$^4$R$^5$, -Heterocyclyl-N(R$^4$)C(=NR$^5$)NR$^4$R$^5$, -Heteroaryl-NR$^4$R$^5$, -Heterocyclyl-NR$^4$R$^5$, —(CR$^6$R$^7$)$_v$Heteroaryl-NR$^4$R$^5$, —(CR$^6$R$^7$)$_v$Heterocyclyl-NR$^4$R$^5$, —(CR$^6$R$^7$)$_v$Heteroaryl-N(R$^4$)C(=NR$^5$)NR$^4$R$^5$, —(CR$^6$R$^7$)$_v$Heterocyclyl-N(R$^4$)C(=NR$^5$)NR$^4$R$^5$, —(CR$^6$R$^7$)$_v$Heteroaryl, —(CR$^6$R$^7$)$_v$Heterocyclyl, —(CR$^6$R$^7$)$_v$NR$^5$-Heteroaryl, —(CR$^6$R$^7$)$_v$ NR$^5$-Heterocyclyl, —(CR$^6$R$^7$)$_v$O-Heterocyclyl, —R$^{9+}$Q$^-$, —(CR$^6$R$^7$)$_w$NR$^4$R$^5$R$^{9+}$Q$^-$, —R$^{9+}$(CR$^6$R$^7$)$_v$NR$^4$R$^5$R$^{9+}$Q$^-$$_2$ and —(CR$^6$R$^7$)$_v$(T)$^+$Q wherein:
T is pyridine-1-yl, pyrimidin-1-yl, or thiazol-3-yl;
Q is a pharmaceutically acceptable counterion; and
v is 1-4; w is 2-4;

R$^a$, R$^b$, and R$^c$ are independently selected from the group consisting of hydrogen, fluoro, chloro, bromo, optionally substituted C$_1$-C$_6$ alkyl, optionally substituted C$_3$-C$_6$ cycloalkyl, optionally substituted heterocyclyl, optionally substituted aryl, optionally substituted heteroaryl, —OH, —OR$^{10}$, —NR$^4$R$^5$, and —SR$^{10}$;

R$^1$ and R$^2$ are independently selected from the group consisting of hydrogen, fluoro, chloro, bromo, optionally substituted C$_1$-C$_6$ alkyl, optionally substituted C$_3$-C$_6$ cycloalkyl, —OH, —OR$^{10}$, —SR$^{10}$, and —NR$^4$R$^5$,
or R$^1$ and R$^2$ taken together form an oxo, oxime, or an optionally substituted carbocycle or optionally substituted heterocycle with the carbon to which they are attached;

R$^3$ is hydrogen, optionally substituted C$_1$-C$_6$ alkyl, or a pharmaceutically acceptable prodrug;

R$^d$, R$^4$ and R$^5$ are independently selected from the group consisting of hydrogen, —OH, —CN, optionally substituted C$_1$-C$_6$ alkyl, optionally substituted alkoxyalkyl, optionally substituted hydroxyalkyl, optionally substituted aminoalkyl, optionally substituted cycloalkyl, optionally substituted heterocyclyl, optionally substituted aryl, optionally substituted heteroaryl, optionally substituted cycloalkylalkyl, optionally substituted heterocyclylalkyl, optionally substituted aralkyl, optionally substituted heteroaralkyl, (poly-ethylene-glycol)-ethyl, and an optionally substituted saccharide;
or R$^4$ and R$^5$ taken together form an optionally substituted heterocycle with the nitrogen to which they are attached;

R$^6$ and R$^7$ are independently selected from the group consisting of hydrogen, fluoro, chloro, bromo, optionally substituted C$_1$-C$_6$ alkyl, optionally substituted alkoxyalkyl, optionally substituted hydroxyalkyl, optionally substituted C$_3$-C$_6$ cycloalkyl, —OH, —OR$^{10}$, —SR$^{10}$, —NR$^4$R$^5$, —NR$^4$C(O)R$^5$, —C(O)NR$^4$R$^5$, —NR$^4$SO$_2$R$^5$,
optionally substituted heterocyclyl, optionally substituted aryl, and optionally substituted heteroaryl;
or R$^6$ and R$^7$ taken together form an oxo, oxime, or an optionally substituted carbocycle or an optionally substituted heterocycle with the carbon to which they are attached;

R$^8$ is optionally substituted C$_1$-C$_6$ alkyl, optionally substituted C$_3$-C$_6$ cycloalkyl, or a pharmaceutically acceptable boronate ester group;

R$^9$ is optionally substituted C$_1$-C$_6$ alkyl; and

R$^{10}$ is optionally substituted C$_1$-C$_6$ alkyl or optionally substituted C$_3$-C$_6$ cycloalkyl.

In some embodiments of a compound of Formula I or Formula Ia, R$^a$, R$^b$, and R$^c$ are independently selected from the group consisting of hydrogen, fluoro, chloro, optionally substituted C$_1$-C$_6$ alkyl, optionally substituted C$_3$-C$_6$ cycloalkyl, —OH, —OR$^{10}$, —NR$^4$R$^5$, and —SR$^{10}$. In certain embodiments, R$^a$, R$^b$, and R$^c$ are independently hydrogen, fluoro, or chloro. In preferred embodiments, R$^a$, R$^b$, and R$^c$ are hydrogen.

In some embodiments of a compound of Formula I or Formula Ia, R$^3$ is hydrogen, methyl, ethyl, propyl, butyl, or isopropyl. In preferred embodiments, R$^3$ is hydrogen.

In some embodiments of a compound of Formula I or Formula Ia, X$^1$ and X$^2$ are —OH.

In some embodiments of a compound of Formula I or Formula Ia, R$^d$ is hydrogen or C$_1$-C$_4$-alkyl. In preferred embodiments, R$^d$ is hydrogen.

In some embodiments of a compound of Formula I or Formula Ia, Z is Z is >C=O or >SO$_2$. In preferred embodiments, Z is >C=O.

In some embodiments of a compound of Formula I or Formula Ia, HetA is selected from the group consisting of azetidine, oxetane thietane, pyrrolidine, oxazolidine, isoxazolidine, thiazolidine, isothiazolidine, imidazolidine, pyrazolidine, 2,5-dihydro-1H-pyrrole, 3,4-dihydro-2H-pyrrole, 4,5-dihydrooxazole, 4,5-dihydroisoxazole, 4,5-dihydrothiazole, 4,5-dihydroisothiazole, 4,5-dihydro-1H-pyrazole, 4,5-dihydro-1H-imidazole, 2,5-dihydro-1H-pyrrole, piperidine, morpholine, thiomorpholine, tetrahydrothiopyran, tetrahydropyran, 1,4-oxathiane, piperazine, hexahydropyrimidine, hexahydropyridazine, 1,4,5,6-tetrahydropyrimidine, 1,3-oxazinane, 5,6-dihydro-4H-1,3-oxazine, 1,3-thiazinane, 5,6-dihydro-4H-1,3-thiazine, 1,4,5,6-tetrahydropyridazine, 1,2,3,6-tetrahydropyrazine, 1,2,3,6-tetrahydropyridine, 1,2,3,6-tetrahydropyridazine, azepane, 1,3-oxazepane, 1,4-oxazepane, 1,3-diazepane, 1,4-diazepane, 1,3-thiazepane, 1,4-thiazepane, diazepane, oxazepane, thiazepane, 3,4,5,6-tetrahydro-2H-azepine, 4,5,6,7-tetrahydro-1H-1,3-diazepine, 4,5,6,7-tetrahydro-1,3-oxazepine, 4,5,6,7-tetrahydro-1,3-thiazepine, 2,3,4,7-tetrahydro-1H-1,3-diazepine, and 2,3,4,7-tetrahydro-1,3-oxazepine.

In some embodiments of a compound of Formula I or Formula Ia, at least one Y is selected from the group consisting fluoro, chloro, —CN, optionally substituted $C_1$-$C_6$ alkyl, —OH, —$OR^{10}$, —$NR^4R^5$, —$(CR^6R^7)_vNR^4R^5$, —$NR^4(CR^6R^7)_vNR^4R^5$, —$O(CR^6R^7)_vNR^4R^5$, —$N(R^4)C(O)(CR^6R^7)_vNR^4R^5$, —$(CR^6R^7)_vN(R^4)C(O)(CR^6R^7)_vNR^4R^5$, —$C(O)NR^4(CR^6R^7)_vNR^4R^5$, —$S(O)_{0,1,2}NR^4(CR^6R^7)_vNR^4R^5$, —$NR^5C(O)NR^4(CR^6R^7)_vNR^4R^5$, —$OC(O)NR^4(CR^6R^7)_vNR^4R^5$, —$NR^5C(=NR^7)NR^4(CR^6R^7)_vNR^4R^5$, —$N(R^4)C(=NR^5)R^6$, —$(CR^6R^7)_vN(R^4)C(=NR^5)R^6$, —$NR^4(CR^6R^7)_vN(R^4)C(=NR^5)R^6$, —$O(CR^6R^7)_vN(R^4)C(=NR^5)R^6$, —$(CR^6R^7)_vC(=NR^5)NR^4R^5$, —$NR^4(CR^6R^7)_vC(=NR^5)NR^4R^5$, —$O(CR^6R^7)_vC(=NR^5)NR^4R^5$, —$(CR^6R^7)_vN(R^4)C(=NR^5)NR^4R^5$, —$NR^4(CR^6R^7)_vN(R^4)C(=NR^5)NR^4R^5$, —$O(CR^6R^7)_vN(R^4)C(=NR^5)NR^4R^5$, —$NR^4C(=NR^5)NR^4C(=NR^5)NR^4R^5$, —$(CR^6R^7)_vC(=NR^4)NR^5C(=NR^4)NR^4R^5$, —$NR^4(CR^6R^7)_vC(=NR^4)NR^5C(=NR^4)NR^4R^5$, —$O(CR^6R^7)_vC(=NR^4)NR^5C(=NR^4)NR^4R^5$, —$NR^4C(=NR^5)NR^4R^5$, —$C(=NR^4)NR^4R^5$, —$C(=NR^4)NR^4C(O)R^6$, —$NR^4SO_2R^6$, —$NR^4C(O)R^6$, —$NR^4C(=O)OR^6$, —$C(O)NR^4R^5$, —$(CR^6R^7)_vC(O)NR^4R^5$, -Heteroaryl-$NR^4R^5$, -Heterocyclyl-$NR^4R^5$, -Heteroaryl-$N(R^4)C(=NR^5)NR^4R^5$, -Heterocyclyl-$N(R^4)C(=NR^5)NR^4R^5$, —$N(R^4)$—Heteroaryl-$NR^4R^5$, —$N(R^4)$—Heterocyclyl-$NR^4R^5$, —$(CR^6R^7)_v$Heteroaryl-$NR^4R^5$, —$(CR^6R^7)_v$Heterocyclyl-$NR^4R^5$, —$(CR^6R^7)_v$Heteroaryl-$N(R^4)C(=NR^5)NR^4R^5$, —$(CR^6R^7)_v$Heterocyclyl-$N(R^4)C(=NR^5)NR^4R^5$, —$(CR^6R^7)_v$Heteroaryl, —$(CR^6R^7)_v$Heterocyclyl, —O-Heteroaryl, —O-Heterocyclyl, —$NR^4(CR^6R^7)_v$Heteroaryl, —$NR^4(CR^6R^7)_v$Heterocyclyl, —$O(CR^6R^7)_v$Heteroaryl, —$O(CR^6R^7)_v$Heterocyclyl, and —$O(CR^6R^7)_v$O-Heterocyclyl. In certain embodiments, at least one Y is selected from the group consisting fluoro, chloro, —CN, optionally substituted $C_1$-$C_6$ alkyl, —OH, —$NR^4R^5$, —$(CR^6R^7)_vNR^4R^5$, —$NR^4(CR^6R^7)_vNR^4R^5$, —$O(CR^6R^7)_vNR^4R^5$, —$C(O)NR^4(CR^6R^7)_vNR^4R^5$, —$NR^5C(O)NR^4(CR^6R^7)_vNR^4R^5$, —$NR^5C(=NR^7)NR^4(CR^6R^7)_vNR^4R^5$, —$N(R^4)C(=NR^5)R^6$, —$(CR^6R^7)_vN(R^4)C(=NR^5)R^6$, —$NR^4(CR^6R^7)_vN(R^4)C(=NR^5)R^6$, —$(CR^6R^7)_vC(=NR^5)NR^4R^5$, —$NR^4(CR^6R^7)_vC(=NR^5)NR^4R^5$, —$(CR^6R^7)_vN(R^4)C(=NR^5)NR^4R^5$, —$NR^4(CR^6R^7)_vN(R^4)C(=NR^5)NR^4R^5$, —$NR^4C(=NR^5)NR^4C(=NR^5)NR^4R^5$, —$(CR^6R^7)_vC(=NR^4)NR^5C(=NR^4)NR^4R^5$, —$NR^4(CR^6R^7)_vC(=NR^4)NR^5C(=NR^4)NR^4R^5$, —$C(=NR^4)NR^4R^5$, —$C(=NR^4)NR^4C(O)R^6$, —$NR^4C(O)R^6$, —$(CR^6R^7)_vC(O)NR^4R^5$, -Heterocyclyl-$NR^4R^5$, -Heterocyclyl-$N(R^4)C(=NR^5)NR^4R^5$, —$N(R^4)$—Heterocyclyl-$NR^4R^5$, —$(CR^6R^7)_v$Heterocyclyl-$NR^4R^5$, —$(CR^6R^7)_v$Heterocyclyl-$N(R^4)C(=NR^5)NR^4R^5$, —$(CR^6R^7)_v$Heterocyclyl, and —$NR^4(CR^6R^7)_v$Heterocyclyl. In further embodiments, at least one Y is selected from the group consisting of -Heteroaryl-$NR^4R^5$, -Heterocyclyl-$NR^4R^5$, -Heteroaryl-$N(R^4)C(=NR^5)NR^4R^5$, -Heterocyclyl-$N(R^4)C(=NR^5)NR^4R^5$, —$N(R^4)$—Heteroaryl-$NR^4R^5$, —$N(R^4)$—Heterocyclyl-$NR^4R^5$, -Heteroaryl-$C(=NR^5)NR^4R^5$, -Heterocyclyl-$C(=NR^5)NR^4R^5$, —$(CR^6R^7)_v$Heteroaryl-$NR^4R^5$, —$(CR^6R^7)_v$Heterocyclyl-$NR^4R^5$, —$(CR^6R^7)_v$Heteroaryl-$N(R^4)C(=NR^5)NR^4R^5$, and —$(CR^6R^7)_v$Heterocyclyl-$N(R^4)C(=NR^5)NR^4R^5$. In specific embodiments, at least one Y is 2-($NR_4R_5$)-pyridyl, 2-($NR_4R_5$)-pyrimidinyl, 2-($NR_4R_5$)-thiazolyl, 2-($NR_4R_5$)-imidazolyl, 3-($NR_4R_5$)-pyrazolyl, 3-($R_4R_5N$)-isothiazolyl, 2-($R_4R_5N$)-oxazolyl, piperidine, pyrrolidine, 4-amino-piperidinyl, 3-amino-pyrrolidinyl, piperazine, or 4-carboximidoyl-piperazinyl. In preferred embodiments, at least one Y is selected from the group consisting of —$NR^4R^5$, —$NR^4C(=NR^5)NR^4R^5$, —$C(=NR^4)NR^4R^5$, —$N(R^4)C(=NR^5)R^6$, —$(CR^6R^7)_vNR^4R^5$, —$(CR^6R^7)_vN(R^4)C(=NR^5)NR^4R^5$, —$NR^4(CR^6R^7)_vNR^4R^5$, —$NR^4(CR^6R^7)_vOR^{10}$, —$(CR^6R^7)_vNR^4(CR^6R^7)_vNR^4R^5$, $NR^5C(=NR^5)NR^4(CR^6R^7)_vNR^4R^5$, —$NR^4(CR^6R^7)_vN(R^4)C(=NR^5)NR^4R^5$, $C(=NR^5)NR^4R^5$, —$NR^5C(O)CR^6(NR^4R^5)(CR^6R^7)_vNR^4R^5$, —$(CR^6R^7)_vC(=NR^5)NR^4R^5$, —$(CR^6R^7)_vN(R^4)C(O)(CR^6R^7)_vNR^4R^5$, —$C(=NR^4)NR^4C(O)R^6$, —$NR^4(CR^6R^7)_v$Heteroaryl, and —$O(CR^6R^7)_vNR^4R^5$.

In some embodiments, p is 0, 1, 2, or 3. In certain embodiments, p is 1 or 2. In some embodiments, p is 2. In other embodiments, p is 1.

In some embodiments of a compound of Formula I or Formula Ia, $R^4$ and $R^5$ are independently selected from the group consisting of hydrogen, —OH, optionally substituted $C_1$-$C_6$ alkyl, optionally substituted alkoxyalkyl, optionally substituted hydroxyalkyl, and optionally substituted heterocyclyl. In preferred embodiments, $R^4$ and $R^5$ are independently hydrogen or optionally substituted $C_1$-$C_6$ alkyl.

In some embodiments of a compound of Formula I or Formula Ia, $R^6$ and $R^7$ are independently selected from the group consisting of hydrogen, optionally substituted $C_1$-$C_6$ alkyl, —OH, —$NR^4R^5$, and optionally substituted heterocyclyl, or $R^6$ and $R^7$ taken together form an optionally substituted heterocycle with the carbon to which they are attached. In preferred embodiments, $R^6$ and $R^7$ are independently hydrogen, fluoro, or optionally substituted $C_1$-$C_6$ alkyl.

Preparation of Compounds

Described herein are compounds of Formula I or Formula Ia that inhibit the activity of beta-lactamases, and processes for their preparation. Also described herein are pharmaceutically acceptable salts, pharmaceutically acceptable solvates, pharmaceutically active metabolites, and pharmaceutically acceptable prodrugs of such compounds. Pharmaceutical compositions comprising at least one such compound or a pharmaceutically acceptable salt, pharmaceutically acceptable solvate, pharmaceutically active metabolite or pharmaceutically acceptable prodrug of such compound, and a pharmaceutically acceptable excipient are also provided.

Compounds of Formula I or Formula Ia may be synthesized using standard synthetic reactions known to those of skill in the art or using methods known in the art. The reactions can be employed in a linear sequence to provide the compounds or they may be used to synthesize fragments which are subsequently joined by the methods known in the art.

The starting material used for the synthesis of the compounds described herein may be synthesized or can be obtained from commercial sources, such as, but not limited to, Aldrich Chemical Co. (Milwaukee, Wis.), Bachem (Torrance, Calif.), or Sigma Chemical Co. (St. Louis, Mo.). The compounds described herein, and other related compounds having different substituents can be synthesized using techniques and materials known to those of skill in the art, such as described, for example, in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001); Green and Wuts, PROTECTIVE GROUPS IN ORGANIC SYNTHESIS 3$^{rd}$ Ed., (Wiley 1999); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989). (all of which are incorporated by reference in their entirety). Other methods for the synthesis of compounds described herein may be found in International Patent Publication No. WO 01/01982901, Arnold et al. *Bioorganic & Medicinal Chemistry Letters* 10 (2000) 2167-2170; Burchat et al. *Bioorganic & Medicinal Chemistry Letters* 12 (2002) 1687-1690. General methods for the preparation of compounds as disclosed herein may be derived from known reactions in the field, and the reactions may be modified by the use of appropriate reagents and conditions, as would be recognized by the skilled person, for the introduction of the various moieties found in the formulas as provided herein.

The products of the reactions may be isolated and purified, if desired, using conventional techniques, including, but not limited to, filtration, distillation, crystallization, chromatography and the like. Such materials may be characterized using conventional means, including physical constants and spectral data.

Compounds described herein may be prepared as a single isomer or a mixture of isomers.

Further Forms of Compounds Disclosed Herein

Isomers

In some embodiments, due to the oxophilic nature of the boron atom, the compounds described herein may convert to or exist in equilibrium with alternate forms, particularly in milieu that contain water (aqueous solution, plasma, etc.). Accordingly, the compounds described herein may exist in an equilibrium between the "closed" cyclic form shown in Formula I and the "open" acyclic form shown in Figure Ia. In addition, the compounds described herein may associate into intramolecular dimers, trimers, and related combinations.

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chloride, such as $^{2}$H, $^{3}$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds described herein, and the metabolites, pharmaceutically acceptable salts, esters, prodrugs, solvate, hydrates or derivatives thereof which contain the aforementioned isotopes and/or other isotopes of other atoms are within the scope of this invention. Certain isotopically-labeled compounds, for example those into which radioactive isotopes such as $^{3}$H and $^{14}$C are incorporated, are useful in drug and/or substrate tissue distribution assays. Tritiated, i. e., $^{3}$H and carbon-14, i. e., $^{14}$C, isotopes are particularly preferred for their ease of preparation and detectability. Further, substitution with heavy isotopes such as deuterium, i.e., $^{2}$H, produces certain therapeutic advantages resulting from greater metabolic stability, for example increased in vivo half-life or reduced dosage requirements. In some embodiments, the isotopically labeled compounds, pharmaceutically acceptable salt, ester, prodrug, solvate, hydrate or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate undeconate and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds of the invention and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4}$ alkyl$)_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. It should be understood that the compounds described herein also include the quaternization of any boron-containing groups they contain. Such a quarternization could result from the treatment of the Lewis acidic boron with a Lewis base to form a complex or salt. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Polymorphs

In some embodiments, the compounds described herein exist as polymorphs. The invention provides for methods of treating diseases by administering such polymorphs. The invention further provides for methods of treating diseases by administering such polymorphs as pharmaceutical compositions.

Thus, the compounds described herein include all their crystalline forms, known as polymorphs. Polymorphs include the different crystal packing arrangements of the same elemental composition of a compound. In certain instances, polymorphs have different X-ray diffraction patterns, infrared spectra, melting points, density, hardness, crystal shape, optical and electrical properties, stability, and solubility. In certain instances, various factors such as the recrystallization solvent, rate of crystallization, and storage temperature cause a single crystal form to dominate.

Prodrugs

In some embodiments, the compounds described herein exist in prodrug form. The invention provides for methods of treating diseases by administering such prodrugs. The invention further provides for methods of treating diseases by administering such prodrugs as pharmaceutical compositions.

Prodrugs are generally drug precursors that, following administration to an individual and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some situations, they are easier to administer than the parent drug. They are, for instance, bioavailable by oral administration whereas the parent is not. In certain instances, the prodrug also has improved solubility in pharmaceutical compositions over the parent drug. An example, without limitation, of a prodrug would be a compound as described herein which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyamino acid) bonded to an acid group where the peptide is metabolized to reveal the active moiety. (See for example Bundgaard, "Design and Application of Prodrugs" in *A Textbook of Drug Design and Development*, Krosgaard-Larsen and Bundgaard, Ed., 1991, Chapter 5, 113-191, which is incorporated herein by reference).

In some embodiments, prodrugs are designed as reversible drug derivatives, for use as modifiers to enhance drug transport to site-specific tissues. The design of prodrugs to date has been to increase the effective water solubility of the therapeutic compound for targeting to regions where water is the principal solvent.

Additionally, prodrug derivatives of compounds described herein can be prepared by methods described herein are otherwise known in the art (for further details see Saulnier et al., *Bioorganic and Medicinal Chemistry Letters*, 1994, 4, 1985). By way of example only, appropriate prodrugs can be prepared by reacting a non-derivatized compound with a suitable carbamylating agent, such as, but not limited to, 1,1-acyloxyalkylcarbanochloridate, para-nitrophenyl carbonate, or the like. Prodrug forms of the herein described compounds, wherein the prodrug is metabolized in vivo to produce a derivative as set forth herein are included within the scope of the claims. Indeed, some of the herein-described compounds are prodrugs for another derivative or active compound.

In some embodiments, prodrugs include compounds wherein an amino acid residue, or a polypeptide chain of two or more (e. g., two, three or four) amino acid residues is covalently joined through an amide or ester bond to a free amino, hydroxy or carboxylic acid group of compounds of the present invention. The amino acid residues include but are not limited to the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. In other embodiments, prodrugs include compounds wherein a nucleic acid residue, or an oligonucleotide of two or more (e. g., two, three or four) nucleic acid residues is covalently joined to a compound of the present invention.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. Compounds having free amino, amido, hydroxy or carboxylic groups can be converted into prodrugs. For instance, free carboxyl groups can be derivatized as amides or alkyl esters. In certain instances, all of these prodrug moieties incorporate groups including but not limited to ether, amine and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters and disulfide containing esters; ethers, amides, carbamates, hemisuccinates, dimethylaminoacetates and phosphoryloxymethyloxycarbonyls, as outlined in *Advanced Drug Delivery Reviews* 1996, 19, 115.

Amine derived prodrugs include, but are not limited to the following groups and combinations of groups:

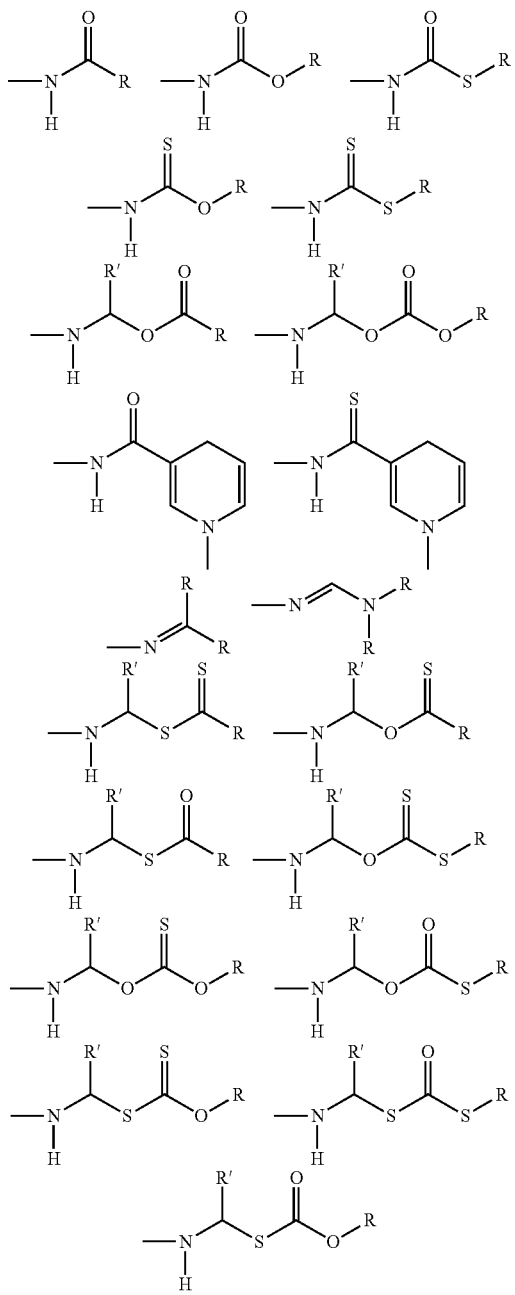

as well as sulfonamides and phosphonamides.

In certain instances, sites on any aromatic ring portions are susceptible to various metabolic reactions, therefore incorporation of appropriate substituents on the aromatic ring structures, can reduce, minimize or eliminate this metabolic pathway.

Metabolites

In some embodiments, compounds of Formula I or Formula Ia are susceptible to various metabolic reactions. Therefore, in some embodiments, incorporation of appropriate substituents into the structure will reduce, minimize, or eliminate a metabolic pathway. In specific embodiments, the appropriate substituent to decrease or eliminate the susceptibility of an aromatic ring to metabolic reactions is, by way of example only, a halogen, or an alkyl group.

In additional or further embodiments, the compounds of Formula I or Formula Ia described herein are metabolized upon administration to an organism in need to produce a metabolite that is then used to produce a desired effect, including a desired therapeutic effect.

Pharmaceutical Compositions/Formulations

In another aspect, provided herein are pharmaceutical compositions comprising a compound of Formula I or Formula Ia as described herein, or a pharmaceutically acceptable salt, polymorph, solvate, prodrug, N-oxide, or isomer thereof, and a pharmaceutically acceptable excipient. In some embodiments, the pharmaceutical composition further comprises a beta-lactam antibiotic. In certain embodiments, the beta-lactam antibiotic is a penicillin, cephalosporin, carbapenem, monobactam, bridged monobactam, or a combination thereof.

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

Provided herein are pharmaceutical compositions that include a compound of Formula I or Formula Ia and at least one pharmaceutically acceptable inactive ingredient. In some embodiments, the compounds described herein are administered as pharmaceutical compositions in which a compound of Formula I or Formula Ia is mixed with other active ingredients, as in combination therapy. In other embodiments, the pharmaceutical compositions include other medicinal or pharmaceutical agents, carriers, adjuvants, preserving, stabilizing, wetting or emulsifying agents, solution promoters, salts for regulating the osmotic pressure, and/or buffers. In yet other embodiments, the pharmaceutical compositions include other therapeutically valuable substances.

A pharmaceutical composition, as used herein, refers to a mixture of a compound of Formula I or Formula Ia with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combinations thereof. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, liquids, gels, syrups, elixirs, slurries, suspensions, self-emulsifying dispersions, solid solutions, liposomal dispersions, aerosols, solid oral dosage forms, powders, immediate release formulations, controlled release formulations, fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Pharmaceutical compositions including a compound of Formula I or Formula Ia are manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound of Formula I or Formula Ia as an active ingredient in free-acid or free-base form, or in a pharmaceutically acceptable salt form. In addition, the methods and pharmaceutical compositions described herein include the use of N-oxides (if appropriate), crystalline forms, amorphous phases, as well as active metabolites of these compounds having the same type of activity. In some embodiments, compounds described herein exist in unsolvated form or in solvated forms with pharmaceutically acceptable solvents such as water, ethanol, and the like. The solvated forms of the compounds presented herein are also considered to be disclosed herein.

Pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active compound doses.

Pharmaceutical preparations that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In soft capsules, the active compounds are dissolved or suspended in suitable liquids, such as fatty oils, liquid paraffin, or liquid polyethylene glycols. In some embodiments, stabilizers are added.

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

Combination Treatment

The compounds according to Formula I or Formula Ia may be used in combination with one or more antibiotics in the treatment of bacterial infections. Such antibiotics may be administered, by a route and in an amount commonly used therefore, contemporaneously or sequentially with a compound of Formula I or Ia. When a compound of Formula I or Ia is used contemporaneously with one or more antibiotic, a pharmaceutical composition in unit dosage form containing such other drugs and the compound of the present invention is preferred. However, the combination therapy may also include therapies in which the compound of Formula I or Ia and one or more antibiotics are administered on different overlapping schedules. It is also contemplated that when used in combination with one or more antibiotics, the antibiotics may be used in lower doses than when each is used singly.

Accordingly, the pharmaceutical compositions of the present invention also include those that contain one or more antibiotics, in addition to a compound according to Formula I or Formula Ia. In some embodiments, a pharmaceutical composition comprising a compound of Formula I or Ia further comprises a beta-lactam antibiotic. In certain embodiments, the beta-lactam antibiotic is a penicillin, cephalosporin, carbapenem, monobactam, bridged monobactam, or a combination thereof.

The above combinations include combinations of a compound of Formula I or Ia not only with one antibiotic, but also with two or more antibiotics. Likewise, compounds of Formula I or Ia, either in combination with an antibiotic or by themselves, may be used in combination with other drugs that are used in the prevention, treatment, control, amelioration, or reduction of risk of bacterial infections or conditions associated with bacterial infections. Such other drugs may be administered, by a route and in an amount commonly used therefore, contemporaneously or sequentially with a compound of Formula I or Ia. When a compound of Formula I or Ia is used contemporaneously with one or more other drugs, a pharmaceutical composition containing such other drugs in addition to the compound of the present invention is preferred. Accordingly, the pharmaceutical compositions of the present invention also include those that also contain one or more other active ingredients, in addition to a compound of Formula I or Ia. The weight ratio of the compound of Formula I or Ia to the second active ingredient may be varied and will depend upon the effective dose of each ingredient. Generally, an effective dose of each will be used.

In some embodiments, the compounds according to Formula I or Formula Ia are used in combination with one or more antibiotics in the treatment of bacterial infections. In certain embodiments, the bacterial infection is an upper or lower respiratory tract infection, a urinary tract infection, an intra-abdominal infection, or a skin infection. In some embodiments, the one or more antibiotics are selected from β-lactam antibiotics. β-Lactam antibiotics include, but are not limited to, penicillins, penems, carbapenems, cephalosporins, cephamycins, monobactams, or combinations thereof. Penicillins include, but are not limited to, amoxicillin, ampicillin, azidocillin, azlocillin, bacampicillin, benzathine benzylpenicillin, benzathine phenoxymethylpenicillin, benzylpenicillin (G), carbenicillin, carindacillin, clometocillin, cloxacillin, dicloxacillin, epicillin, flucloxacillin, hetacillin, mecillinam, metampicillin, meticillin, mezlocillin, nafcillin, oxacillin, penamecillin, pheneticillin, phenoxymethylpenicillin (V), piperacillin, pivampicillin, pivmecillinam, procaine benzylpenicillin, propicillin, sulbenicillin, talampicillin, temocillin, ticarcillin. Penems include, but are not limited to, faropenem. Carbapenems include, but are not limited to, biapenem, ertapenem, doripenem, imipenem, meropenem, panipenem. Cephalosprins/Cephamycins include, but are not limited to, cefacetrile, cefaclor, cefadroxil, cefalexin, cefaloglycin, cefalonium, cefaloridine, cefalotin, cefamandole, cefapirin, cefatrizine, cefazaflur, cefazedone, cefazolin, cefbuperazone, cefcapene, cefdaloxime, cefdinir, cefditoren, cefepime, cefetamet, cefixime, cefmenoxime, cefmetazole, cefminox, cefodizime, cefonicid, cefoperazone, ceforanide, cefotaxime, cefotetan, cefotiam, cefovecin, cefoxitin, cefozopran, cefpimizole, cefpiramide, cefpirome, cefpodoxime, cefprozil, cefquinome, cefquinome, cefradine, cefroxadine, cefsulodin, ceftaroline fosamil, ceftazidime, cefteram, ceftezole, ceftibuten, ceftiofur, ceftiolene, ceftizoxime, ceftobiprole, ceftriaxone, cefuroxime, cefuzonam, flomoxef, latamoxef, loracarbef. Monobactams include, but are not limited to, aztreonam, carumonam, nocardicin A, tigemonam.

Administration of Pharmaceutical Composition

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In some embodiments, compounds of Formula I or Formula Ia and compositions thereof are administered in any suitable manner. The manner of administration can be chosen based on, for example, whether local or systemic treatment is desired, and on the area to be treated. For example, the compositions can be administered orally, parenterally (e.g., intravenous, subcutaneous, intraperitoneal, or intramuscular injection), by inhalation, extracorporeally, topically (including transdermally, ophthalmically, vaginally, rectally, intranasally) or the like.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained.

Assays for Antibacterial Activity

Assays for the inhibition of beta-lactamase activity are well known in the art. For instance, the ability of a compound to inhibit beta-lactamase activity in a standard enzyme inhibition assay may be used (see, e.g., Page, *Biochem J*, 295:295-304 (1993)). Beta-lactamases for use in such assays may be purified from bacterial sources or preferably, are produced by recombinant DNA techniques, since genes and cDNA clones coding for many beta-lactamases are known (see, e g, Cartwright & Waley, *Biochem J* 221:505-12 (1984)).

Alternatively, the sensitivity of bacteria known, or engineered, to produce a beta-lactamase to an inhibitor may be determined. Other bacterial inhibition assays include agar disk diffusion and agar dilution (see, e.g, Traub & Leonhard, *Chemotherapy* 43 159-67 (1997)). Thus, a beta-lactamase may be inhibited by contacting the beta-lactamase enzyme with an effective amount of an inventive compound or by contacting bacteria that produce the beta-lactamase enzymes with an effective amount of such a compound so that the beta-lactamase in the bacteria is contacted with the inhibitor. The contacting may take place in vitro or in vivo. "Contacting" means that the beta-lactamase and the inhibitor are brought together so that the inhibitor can bind to the beta-lactamase. Amounts of a compound effective to inhibit a beta-lactamase may be determined empirically, and making such determinations is within the skill in the art. Inhibition includes both reduction and elimination of beta-lactamase activity.

Methods

The present disclosure also provides methods for inhibiting bacterial growth, by, e.g., reducing bacterial resistance to a β-lactam antibiotic, such methods comprising contacting a bacterial cell culture, or a bacterially infected cell culture, tissue, or organism, with a beta-lactamase inhibitor described herein. Preferably, the bacteria to be inhibited by administration of a beta-lactamase inhibitor of Formula I or Ia are bacteria that are resistant to beta-lactam antibiotics. The term "resistant" is well-understood by those of ordinary skill in the art (see, e g Payne et al., *Antimicrobial Agents and Chemotherapy* 38 767-772 (1994), Hanaki et al., *Antimicrobial Agents and Chemotherapy* 30 1120-1126 (1995)).

These methods are useful for inhibiting bacterial growth in a variety of contexts. In certain embodiments, a compound of Formula I or Ia is administered to an experimental cell culture in vitro to prevent the growth of beta-lactam resistant bacteria. In certain other embodiments, a compound of Formula I or Ia is administered to a mammal, including a human to prevent the growth of beta-lactam resistant bacteria in vivo. The method according to this embodiment comprises administering a therapeutically effective amount of a beta-lactamase inhibitor for a therapeutically effective period of time to a mammal, including a human. Preferably, the beta-lactamase inhibitor is administered in the form of a pharmaceutical composition as described above. In some embodiments, a beta-lactam antibiotic is co-administered with the beta-lactamase inhibitor as described above.

In another aspect provided herein are methods of treating a bacterial infection, which method comprises administering to a subject a pharmaceutical composition comprising a compound of Formula I or Formula Ia, or a pharmaceutically acceptable salt thereof, and a pharmaceutically acceptable excipient. In some embodiments, the methods of treating a bacterial infection in a subject comprises administering to the subject a pharmaceutical composition as described herein, optionally in combination with a beta-lactam antibiotic. In some embodiments, the bacterial infection is an upper or lower respiratory tract infection, a urinary tract infection, an intra-abdominal infection, or a skin infection.

In some embodiments, the infection that is treated or prevented comprises a bacteria that includes *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcusfaecalis, Enterococcusfaecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, or *Staphylococcus saccharolyticus*.

In some embodiments, the infection that is treated or prevented comprises a bacteria that includes *Pseudomonas aeruginosa, Pseudomonas fluorescens, Stenotrophomonas maltophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Acinetobacter calcoaceticus, Acinetobacter haemolyticus, Yersinia enterocolitica, Yersinia pestis, Yersinia pseudotuberculosis, Yersinia intermedia, Haemophilus influenzae, Haemophilus parainfluenzae, Haemophilus haemolyticus, Haemophilus parahaemolyticus, Helicobacter pylori, Campylobacter fetus, Campylobacter jejuni, Campylobacter coli, Vibrio cholerae, Vibrio parahaemolyticus, Legionella pneumophila, Listeria monocytogenes, Neisseria gonorrhoeae, Neisseria meningitidis, Moraxella, Bacteroides fragilis, Bacteroides vulgatus, Bacteroides ovalus, Bacteroides thetaiotaomicron, Bacteroides uniformis, Bacteroides eggerthii*, or *Bacteroides splanchnicus*.

EXAMPLES

List of Abbreviations

As used above, and throughout the description of the invention, the following abbreviations, unless otherwise indicated, shall be understood to have the following meanings:

ACN acetonitrile
Bn benzyl
BOC or Boc tert-butyl carbamate
BOP benzotriazol-1-yl-oxytris (dimethylamino) phosphonium
t-Bu tert-butyl
Cbz benzyl carbamate
Cy Cyclohexyl
DBU 1,8-Diazabicyclo[5.4.0]undec-7-ene
DCC dicyclohexylcarbodiimide
DCM dichloromethane ($CH_2Cl_2$)
DIC 1,3-diisopropylcarbodiimide
DEAD diethyl azodicarboxylate
DIAD diisopropyl azodicarboxylate
DIEA diisopropylethylamine
DMAP 4-(N,N-dimethylamino)pyridine
DMP reagent Dess-Martin Periodinane reagent
DMF dimethylformamide
DMA N,N-Dimethylacetamide
DME 1,2-Dimethoxy-ethane
DMSO dimethylsulfoxide
Dppf 1,1'-Bis(diphenylphosphino)ferrocene
EDCI 1-ethyl-3-(3-dimethylaminopropyl) carbodiimide HCl
eq equivalent(s)
Et ethyl
$Et_2O$ diethyl ether
EtOH ethanol
EtOAc ethyl acetate
HOAt 1-hydroxy-7-azabenzotriazole
HOBT 1-hydroxybenztriazole
HOSu N-hydroxysuccinamide
HPLC high performance liquid chromatography
LAH lithium aluminum anhydride
LC liquid chromatography
Me methyl
MeI methyliodide
MeOH methanol
MOMCl methoxymethylchloride
MOM methoxymethyl
MS mass spectroscopy
NMP N-methyl-pyrrolidin-2-one
NMR nuclear magnetic resonance
PyBOP benzotriazole-1-yl-oxytris-pyrrolidino-phosphonium Hexafluorophosphate
SPHOS 2-Dicyclohexylphosphino-2',6'-dimethoxybiphenyl
TBD 1,5,7-triazabicyclo[4.4.0]-dec-5-ene
RP-HPLC reverse phase-high pressure liquid chromatography
TBS tert-butyldimethylsilyl
TBSCl tert-butyldimethylsilyl chloride
TBTU O-(Benzotriazol-1-yl)-N,N,N',N'-tetramethyluronium
TEOC 2-Trimethylsilylethyl Carbamate
TFA trifluoroacetic acid
$Tf_2O$ triflate anhydride
TMG 1,1,3,3-Tetramethylguanidine
THF tetrahydrofuran
THP tetrahydropyran
TLC thin layer chromatography
XPHOS 2-Dicyclohexylphosphino-2',4',6'-triisopropylbiphenyl

General Examples for the Preparation of Compounds of the Invention

The starting materials and intermediates for the compounds of this invention may be prepared by the application or adaptation of the methods described below, their obvious chemical equivalents, or, for example, as described in literature such as The Science of Synthesis, Volumes 1-8. Editors E. M. Carreira et al. Thieme publishers (2001-2008). Details of reagent and reaction options are also available by structure and reaction searches using commercial computer search engines such as Scifinder (www.cas.org) or Reaxys (www.reaxys.com).

Certain compounds of the invention (I) (SCHEME 1) are prepared from the corresponding functional-group-protected boronic acid esters (II) by treatment with a Lewis acid such as $BCl_3$, in a solvent such as dichloromethane, at a temperature between −78° C. and 0° C. followed by an aqueous quench.

SCHEME 1

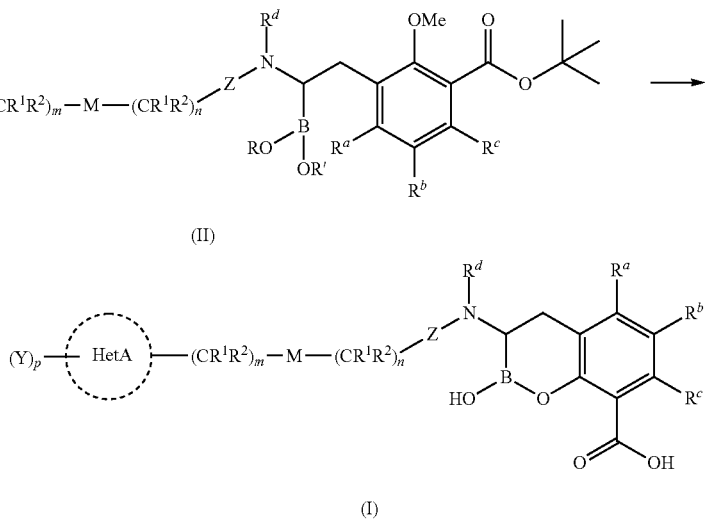

Alternatively, (I) is obtained from (II) by treatment of (II) with aqueous hydrochloric acid (around 3-5 Molar) in dioxane at a temperature between room temperature and 100° C.

The requisite boronic acid esters (II) are obtained (SCHEME 2) by coupling of amine (III) with (carboxylic or sulphonic) acid (IV). This transformation is effected by first activating the acid functionality as an acid chloride, anhydride or reactive ester (Va, Vb or Vc), followed by treatment of the activated substrate with (III) in a solvent such as DMF, DMA, NMP, THF or dichloromethane (or a mixture thereof) at about room temperature, usually in the presence of a non-nucleophilic base such as 4-methyl-morpholine, triethylamine or diisopropylethylamine.

ester (Vc) involves treatment of (IV) with an activating reagent system such as EDCI, DCC/HOBt, HATU, BOP reagents or TBTU, in a solvent such as DMF, DMA, NMP or dichloromethane at room temperature or below (*International Journal of Pharmaceutical Sciences Review and Research* (2011), 8(1), 108-119).

In certain instances (SCHEME 3), (II) is prepared from the α-bromo or chloro-acyl amino intermediate (VI) by treatment with a suitable heterocyclylamine (VII) in a solvent such as THF in the presence of a base such as potassium carbonate.

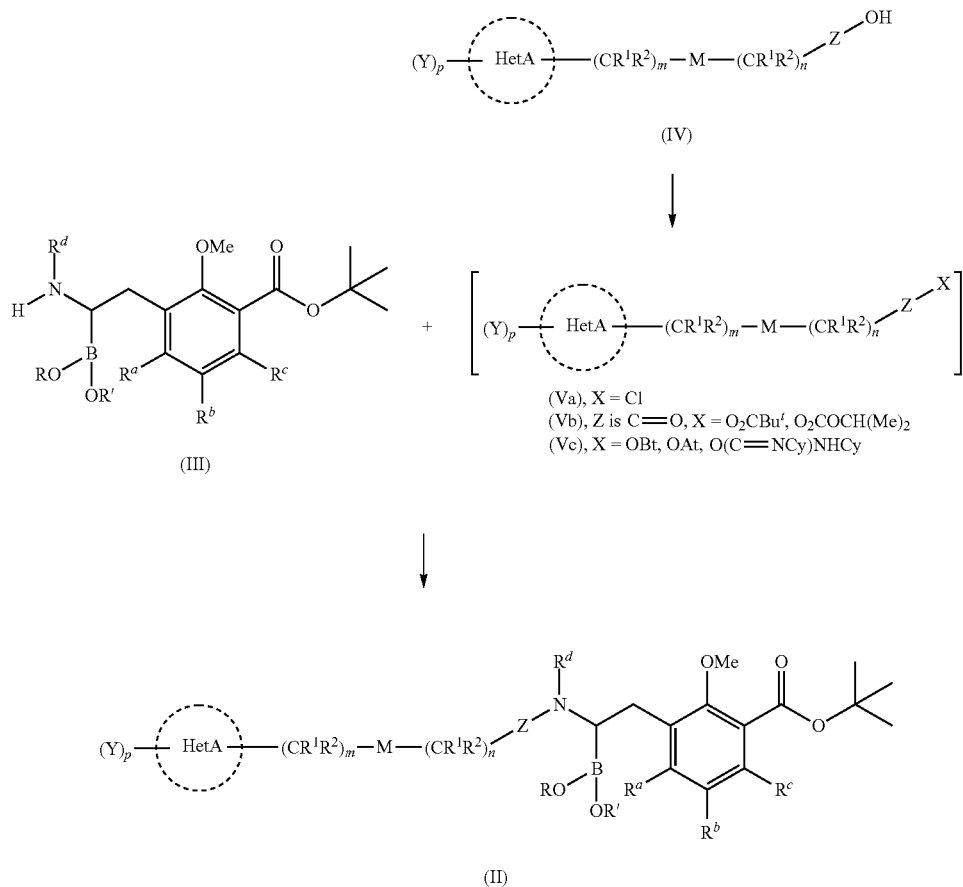

Formation of the acid chloride (Va) involves treatment of (IV) with a chlorinating agent such as thionyl chloride, phosphorous pentachloride or oxalyl chloride, in a solvent such as dichloromethane, in the presence of a catalyst such as DMF, at around room temperature. In certain cases, DMF is also used as a co-solvent. Formation of the anhydride (Vb) (Z is C=O) involves treatment of (IV) with a sterically hindered acid chloride or chloroformate, such as trimethylacetyl chloride or isopropylchloroformate, in an inert solvent such as dichloromethane, in the presence of a non-nucleophilic base, such as triethylamine or diisopropylamine at room temperature or below. Formation of the activated

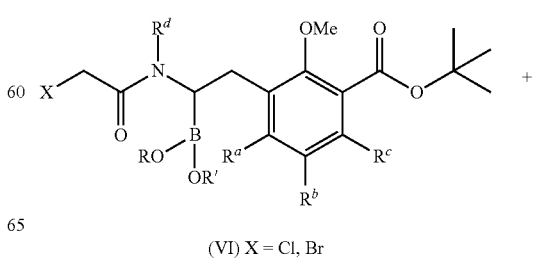

-continued

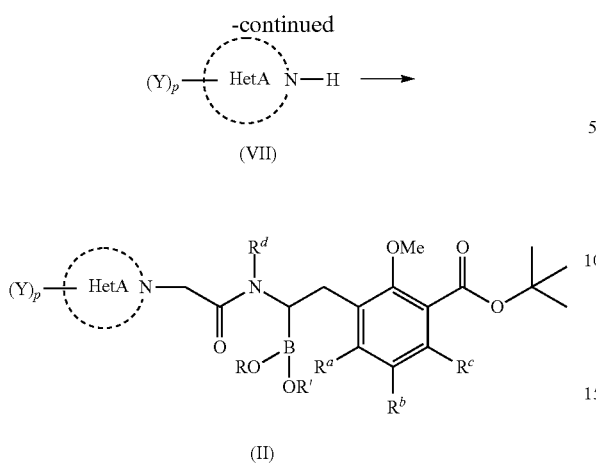

(II)

Intermediate (VI) is prepared from (III) by treatment with bromoacetyl bromide or chloroacetyl chloride in a solvent such as THF at a temperature between −20° C. and room temperature.

The requisite acids (IV) and amines (VII) are prepared by a number of different reaction sequences. While there are common themes and strategies among the illustrative examples cited below, the selection of an appropriate reaction sequence (including protecting group requirements) is dictated by the nature and arrangement of the functionality present in the target molecule and, therefore, may involve obvious adaptations of the illustrated methods in order to be applied in a particular case.

In the case where HetA is connected to $(CR^1R^2)_m$ via a ring nitrogen atom and $Y_1$ is connected to HetA through an amino functionality, the requisite acids (IV) and amines (VII) are conveniently prepared from an appropriately substituted-heterocyclic ketone (VIII) (SCHEME 4). For example, treatment of (VIII) with a suitable amine (IX) in the presence of a reducing agent such as sodium tri-acetoxyborohydride, sodium cyanoborohydride or sodium borohydride in a solvent such as dichloromethane, 1,2-dichloroethane, THF, methanol, acetic acid or a mixture thereof, at a temperature around room temperature gives the carbamate protected heterocycle (X). In the case where the use of a primary amine (IX, $R^5$=H) is called for, (X) can also be prepared by treatment of an equimolar mixture of (VIII) and (IX, $R^5$=H) with a Lewis acid/dessicant, such as $Ti(OEt)_4$, in a solvent such as dichloromethane or 1,2-dichloroethane, at room temperature or above to provide the intermediate imine. This is followed by reduction of the imine with sodium borohydride, in a solvent such as methanol, at a temperature between −78° C. and room temperature

SCHEME 4

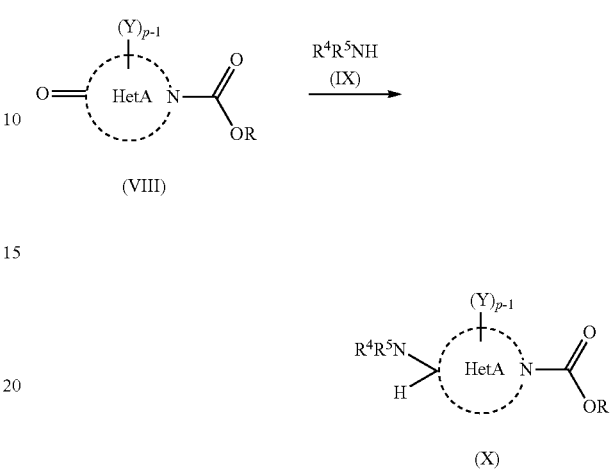

Acid (IV) is obtained from heterocycle (X) by formal hydrolysis of the carbamate functionality followed by derivitization of the resulting amine (VII) (SCHEME 5). The reaction conditions employed to cleave the carbamate depend on the type of carbamate used. In the case of a t-butyl carbamate, cleavage is effected by treatment with an acid such as trifluoroacetic acid in dichloromethane at around room temperature or with HCl in a solvent such as ethyl acetate, ether or 1,4 dioxane. In the case of a benzyl carbamate, cleavage is achieved by hydrogenolysis at around atmospheric pressure, using a catalyst such as palladium on carbon in a solvent such as ethyl acetate, methanol, THF or a combination thereof. Other carbamate protecting groups can also be used, such as allyl, 2-trimethylsilyl-ethyl or 2,2,2-trichloroethyl. In these cases, conversion of the carbamate to the corresponding amine is achieved using the standard deprotection procedures in the literature (*Greene's Protective Groups in Organic Synthesis*. Fourth Edition. John Wiley & Sons, Inc. 2006). It should be understood that the amine functionality in $Y_1$ may also be protected as a carbamate during this sequence (i.e. $R^5$=$CO_2R'$) and that this protecting group should be selected to be orthogonal to the carbamate protecting the HetA amine functionality.

SCHEME 5

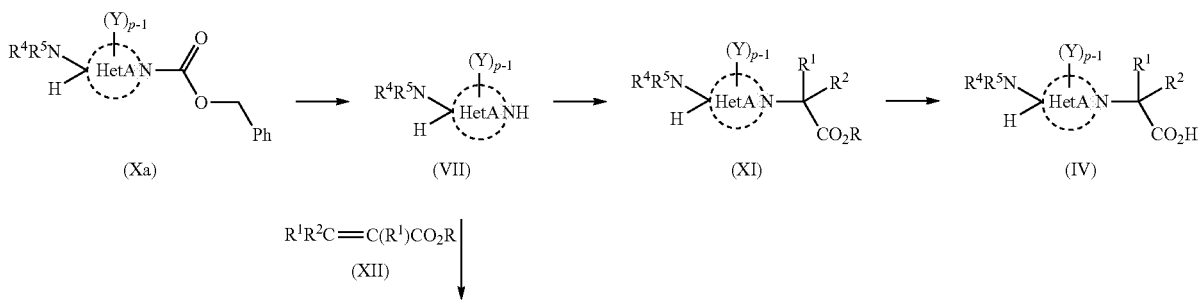

-continued

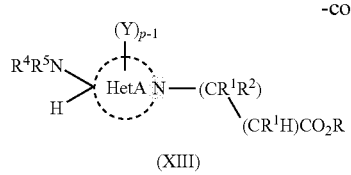
(XIII)

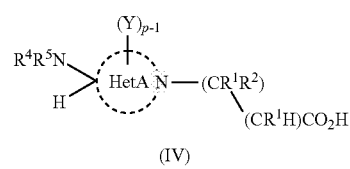
(IV)

For an example of the preparation of (IV) from (VII) consider the case of (IV) where m=1, M=a bond, n=0. Treatment of (Xa) (R=benzyl) with hydrogen in the presence of a catalyst such as palladium on carbon in a solvent such as methanol provides the heterocyclic amine (VII). Condensation of (VII) with an appropriate α-halo-acetic acid ester in a solvent such as acetonitrile, DMF, DMA or ethanol, in the presence of a non nucleophilic base such as diisopropylethylamine, triethylamine or potassium carbonate furnishes the ester (XI). Ester hydrolysis by brief treatment with an aqueous base such as sodium hydroxide or lithium hydroxide in a solvent such as ethanol or THF/methanol provides the acid (IV).

For the case of (IV) where m=2, M=a bond, n=0, treatment of (VII) with an appropriate α,β-unsaturated ester (XII) in the presence of a catalyst such as potassium carbonate, cesium fluoride (*Monatshefte fuer Chemie*, (2011), 142(10), 1055-1059) cerium ammonium nitrate (Synlett, (2006), 10, 1549-1553) copper acetate (*Synlett*, (2003), 15, 2425-2427) in a solvent such as DMA or ethanol or water yields (XIII). Hydrolysis of the ester group in (XIII), as described above, provides the acid (IV).

dichloromethane or pyridine, at around 0° C. provides the corresponding sulfonate ester (XV). Displacement of the sulfonate group with azide by treatment of (XV) with sodium azide or a tetra-alkylammonium azide in a solvent such as DMA, DMF, NMP, acetonitrile or DMSO, at a temperature between room temperature and 120° C., yields the azide (XVI). Reduction of the azide with triphenylphosphine and water in THF at around room temperature (Staudinger reaction) yields the primary amine (XVII). Further derivatization of (XVII), where appropriate, can be accomplished by reductive amination with an appropriate aldehyde or ketone, using conditions already described to give (XX).

Alternatively, formation of the N-BOC derivative of (XVII) by treatment with Boc₂O, in the presence of a non nucleophilic base such as triethylamine or DIEA, in a solvent such as dichloromethane, at around room temperature gives carbamate (XVIII). Treatment of (XVIII) with an alkyl halide or sulphonate in the presence of a base, such as sodium hydride, potassium carbonate or tetramethylguanidine, in a solvent such as DMF, DMA, NMP, THF, DMPU

SCHEME 6

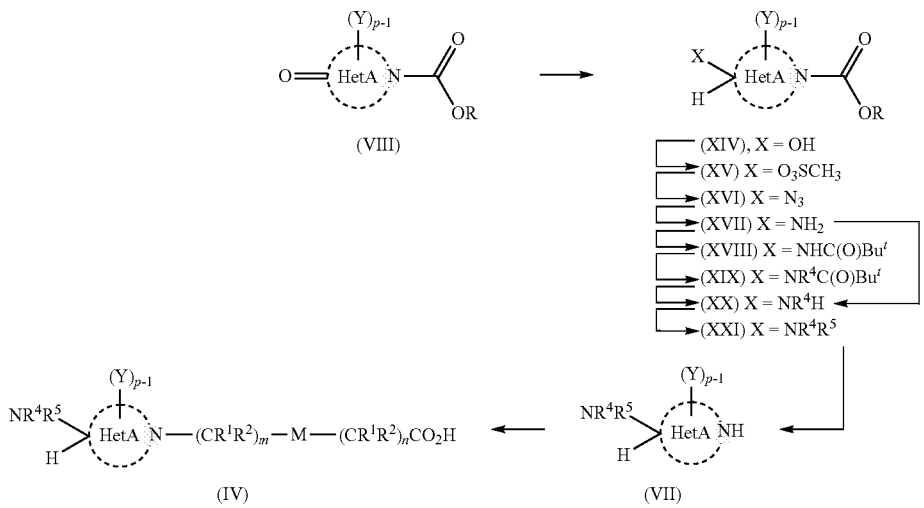

In an alternative approach to systems wherein HetA is connected to $(CR^1R^2)_m$ via a ring nitrogen atom and $Y_1$ is connected to HetA through an amino functionality, the requisite acids (IV) and amines (VII) are prepared (SCHEME 6) by treatment of ketone (VIII) with a reducing agent, such as sodium borohydride in methanol at around 0° C. or L-selectride in THF, at a temperature between −78° C. and room temperature to give alcohol (XIV). Treatment of the alcohol (XIV) with methanesulfonyl chloride or p-toluene-sulfonyl chloride, in the presence of a non nucleophilic base, such as triethylamine or DIEA, in a solvent such as or ethanol (or a mixture thereof), at room temperature or below, provides (XIX). Cleavage of the BOC group with an acid, such as TFA in dichloromethane or HCl in dioxane, ethyl acetate or ether, at around room temperature, provides the secondary amine (XX). Further derivatization of (XX), where appropriate, can be accomplished by reductive amination with an appropriate aldehyde or ketone, using conditions already described, to give (XXI). Carbamate cleavage in (XXI) provides (VII) and derivitization of the heterocyclic ring nitrogen as already described, yields (IV).

SCHEME 7

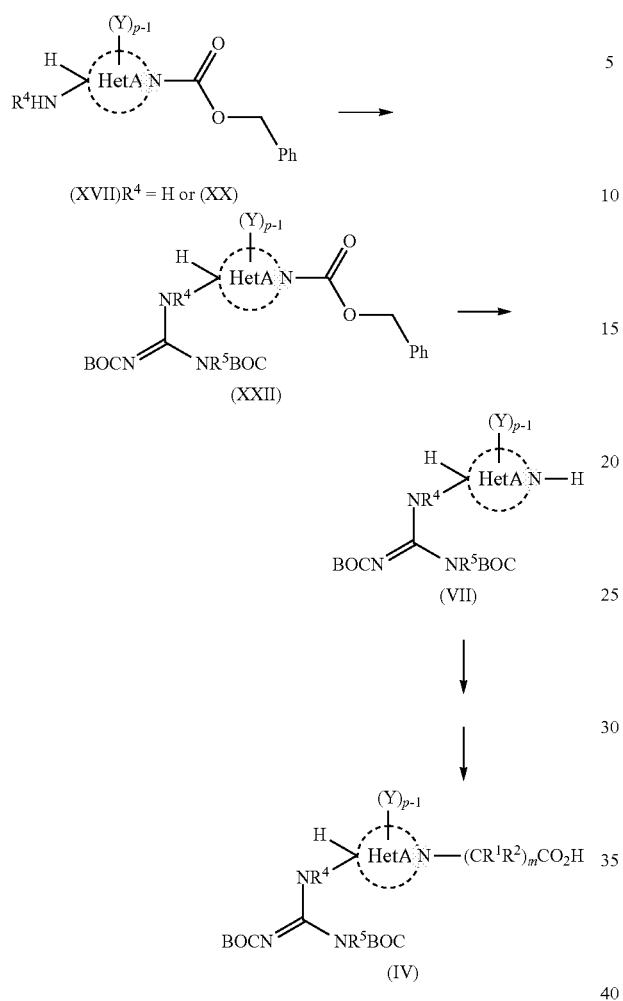

SCHEME 8

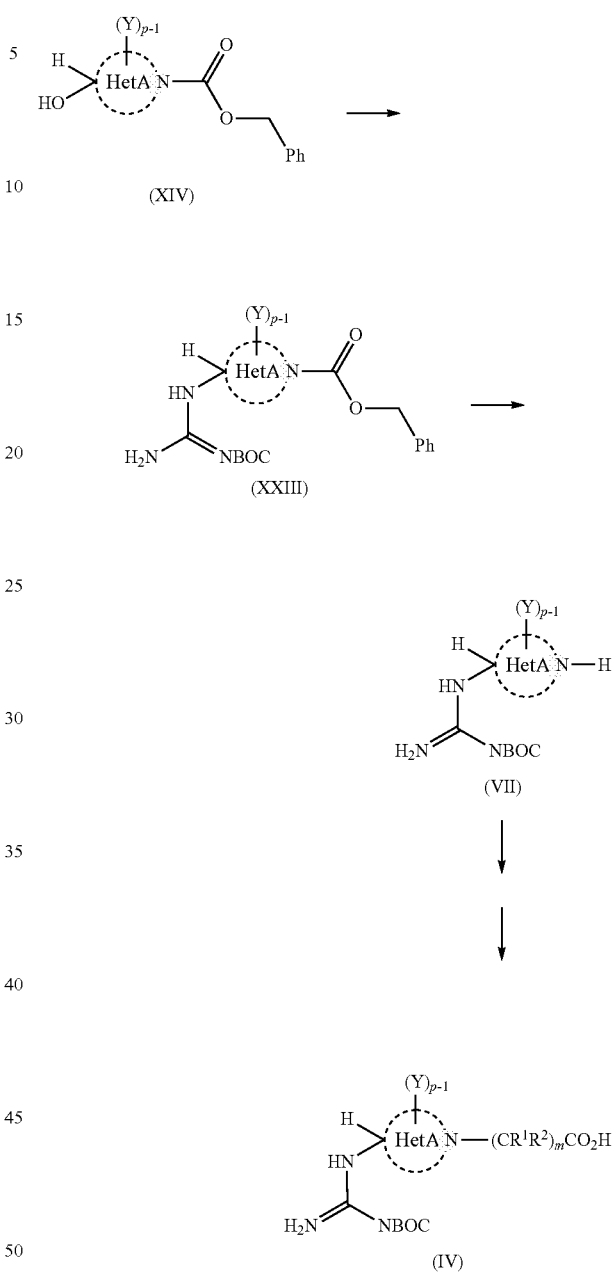

In the case where $Y_1$ is a guanidine, the guanidino group is derived from the appropriate heterocyclic primary (XVII) or secondary (XX) amine (SCHEME 7) by treatment with a reagent such as 1,3-Di-tert-butyloxycarbonyl-S-methylisothiourea, in a solvent such as DMF, (*Synthesis*, (2004), 37-42) or pyridine at room temperature or above, or by treatment with N,N'Bis-(BOC)-1H-pyrazole-1-carboxamidine in the presence of a base such as diisopropylethylamine, in a solvent such as DMF or DMA at around room temperature to give (XXII). Selective cleavage of the heterocyclic ring carbamate and derivitization of the resulting heterocyclic amine (VII), as already described, provides the corresponding acid (IV).

Alternatively, the guanidinyl group can be introduced by treatment of an appropriate heterocyclic alcohol (XIV) (SCHEME 8) with a reagent such as BOC-guanidine, in the presence of triphenylphosphine and diethyl-azo-dicarboxylate, in a solvent such as THF (Mitsunobu conditions: *Chemical Reviews*, (2009), 109, 2551-2651) to give (XXIII) directly. Benzyl carbamate cleavage provides (VII) which is processed to yield (IV) as already described.

In the case where $Y_1$ is an amidine linked to HetA through nitrogen, the requisite acids (SCHEME 9) are prepared from the appropriate primary (XVII) or secondary amine (XX) by treatment with a suitable alkyl thioimidate, such as the 2-napthylmethylthioimidate derivative (XXIV), in a solvent such as ethanol at a temperature between 0° C. and room temperature (*Tetrahedron Letters*, (1997), 38(2), 179-182) to give (XXV). Protection of the amidine (XXV) as an orthogonal carbamate derivative such as BOC is effected under standard conditions (BOC anhydride/triethylamine in methanol) to give (XXVI). Selective cleavage of the heterocyclic ring carbamate functionality and derivitization of the heterocyclic amine (VII), as already described, provides the corresponding acid (IV).

SCHEME 9

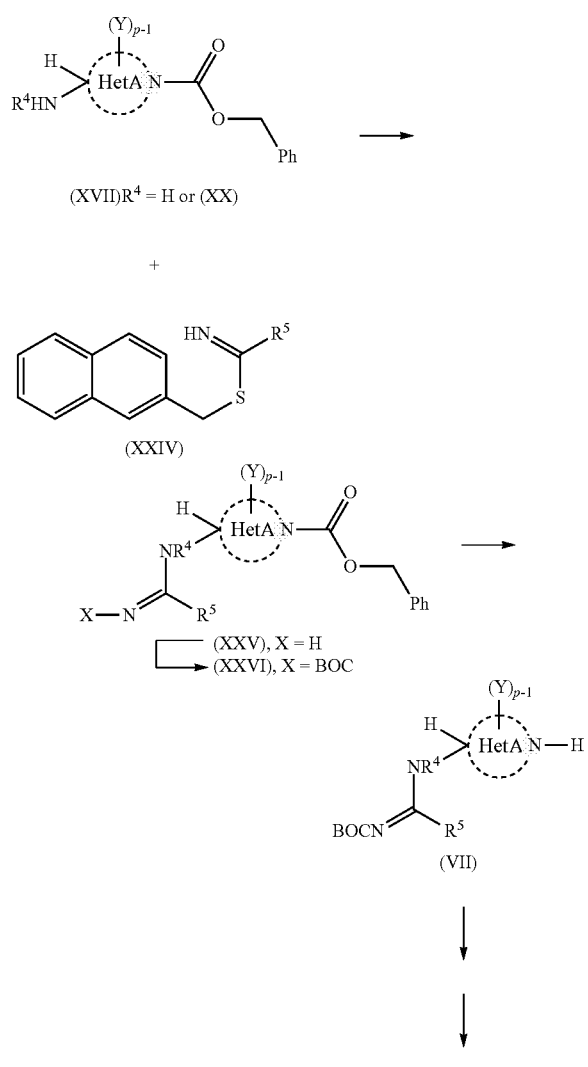

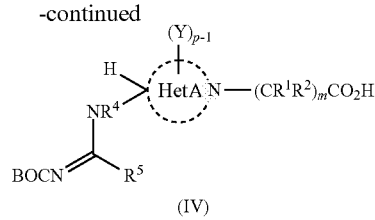

In the case where $Y_1$ is an amidine linked to HetA through carbon (SCHEME 10), the amidine functionality is introduced by conversion of an appropriate heterocyclic ketone (VIII) to the corresponding exocyclic nitrile (XXVII) by treatment with toluenesulfonyl-methylisocyanide (*Journal of Organic Chemistry* (1977), 42(19), 3114-18) in the presence of a base such as KOBu$^t$ in a solvent such as DMSO or DME containing about 2% of t-butanol or ethanol at a temperature between 0° C. and 50° C. Treatment of (XXVII) with HCl in methanol to form the corresponding imidate ester (XXVIII) is followed by reaction of this intermediate with an appropriate amine (XXIX) in a solvent such as methanol or THF at around room temperature to give the amidine (XXX). Protection of the amidine functionality as a BOC derivative (XXXI) is accomplished by treatment of (XXX) with BOC anhydride in the presence of a base such as triethylamine in a solvent such as methanol at a temperature between room temperature and 60° C. Removal of the Cbz group, as previously described, furnishes the heterocyclic amine (VII). (VII) is processed to the corresponding acid (IV) as already described.

In certain cases, it is convenient to effect direct amidine formation from the nitrile (XXVII) (SCHEME 10) using a suitable methyl-chloroaluminum amide (XXXII), in a solvent such as toluene at around 80° C. (*Tetrahedron Letters*, (1990), 31(14), 1969-1972).

SCHEME 10

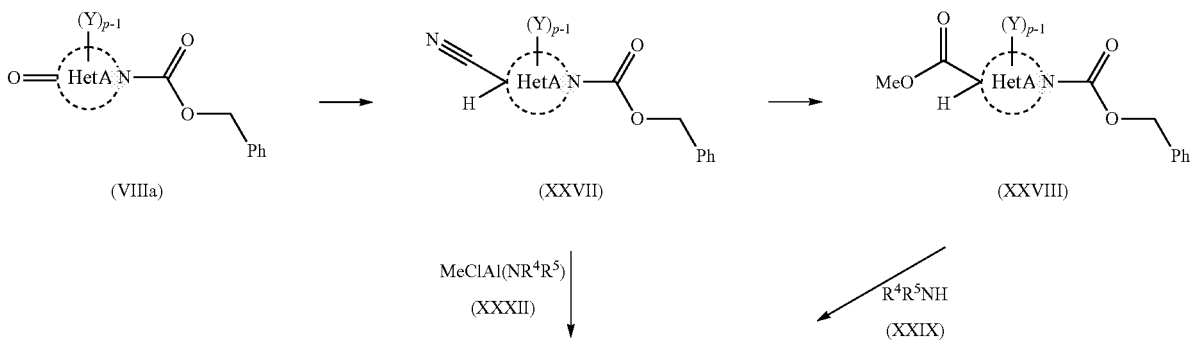

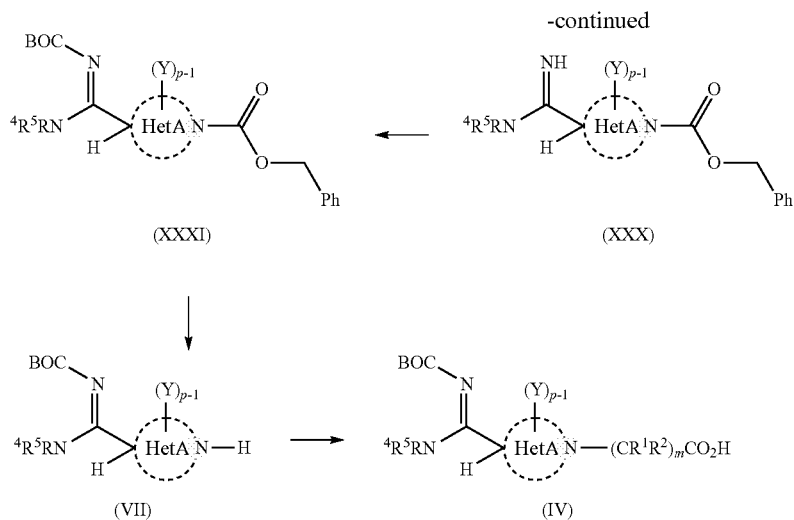

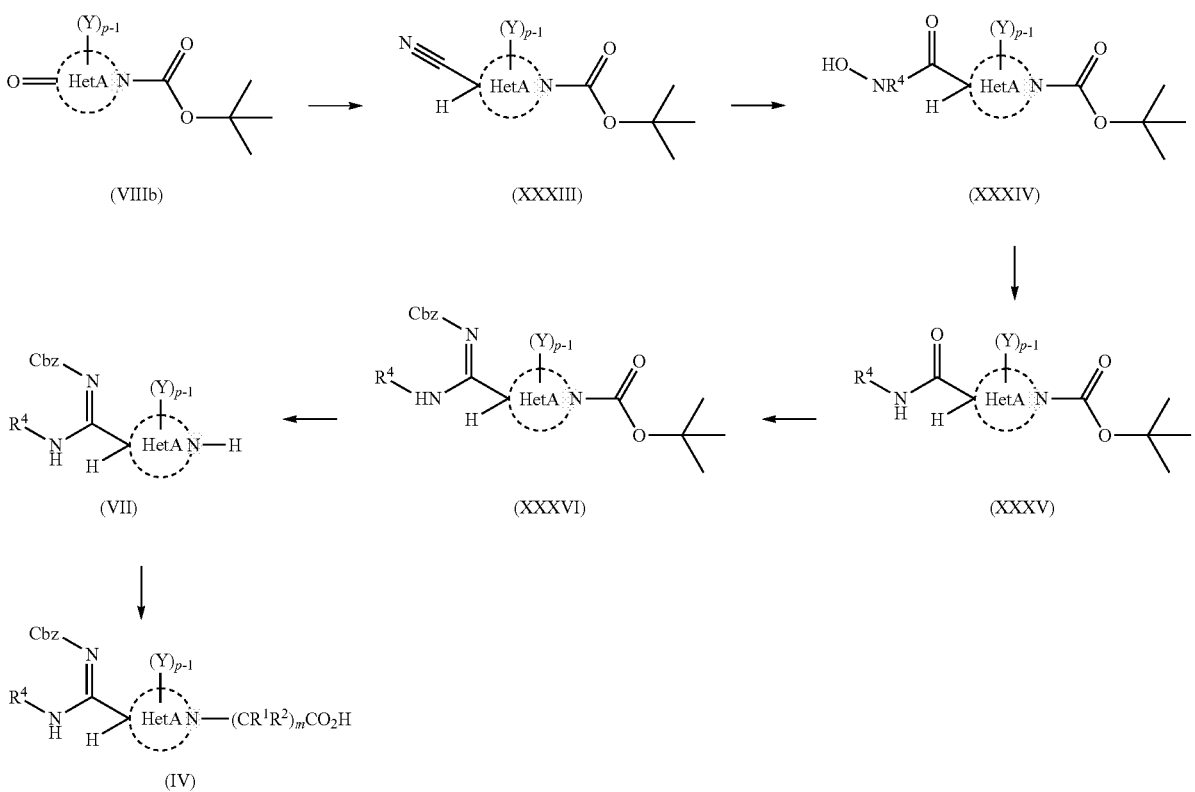

In the case where R⁵═H (SCHEME 11), the amidine functionality can also be introduced by treatment of the appropriate carbocyclic nitrile (XXXIII) with hydroxylamine or an O-alkyl-hydroxylamine to give the N-hydroxyl-(or alkoxy)-amidine (XXXIV). This is followed by N—O bond cleavage by catalytic hydrogenolysis to provide the amidine (XXXV). Benzyl carbamate derivitization of the amidine functionality in (XXXV) by treatment with Cbz chloride in the presence of a base such as DIEA in a solvent such as dichloromethane or by treatment with Cbz chloride in a solvent such as aqueous THF or aqueous 1,4-dioxane in the presence of a base such as sodium hydroxide provides (XXXVI). Cleavage of the heterocyclic ring carbamate yields (VII) which is further processed to provide acid (IV) as previously described.

In the case where $Y_1$ is a nitrogen substituted methylene group, the requisite amines (VII) and acids (IV) (SCHEME 12) are prepared from the appropriate heterocyclic-ketones (VIII) by conversion of the ketone functionality into, first, the corresponding hydroxyl-methyl derivative by treatment with an olefination reagent such as methyltriphenylphosphonium bromide in the presence of sodium hexamethyldisilazide, in a solvent such as THF at around 0° C. (Wittig reaction) or by treatment with lithium trimethylsilylmethane/CeCl₃ at around 0° C. to room temperature, in a solvent such as THF or ether (Peterson reaction) (*Journal of Organic Chemistry*, (1987) 52(2), 281-3) or by reaction with the Petasis modified Tebbe reagent (dicyclopentadienyldimethyltitanium) in THF/toluene at around 60° C. (*Journal of the American Chemical Society*, (1990), 112 (17) 6392-6394) to give (XXXVII). This is followed by hydroboration of the exocyclic alkene in (XXXVII) with a reagent such as borane THF or an alkyl derivative, at around 0° C., in a solvent such as THF, followed by oxidative workup with hydrogen peroxide/NaOH (aq.) to provide (XXXVIII). Conversion of the hydroxymethyl (XXXVIII) into the functionalized amino-methyl derivative (XL) can be accomplished by conversion to the corresponding tosylate, azide and primary amine as described above. Alternatively, oxidation of (XXXVIII) to the aldehyde (XXXIX) followed by reductive amination of (XXXIX) with an amine ($R^4R^5NH$), as already described, also provides amine (XL). Conversion of (XL) to the requisite amine (VII) and or acid (IV) is accomplished by side chain modification as previously described.

SCHEME 12

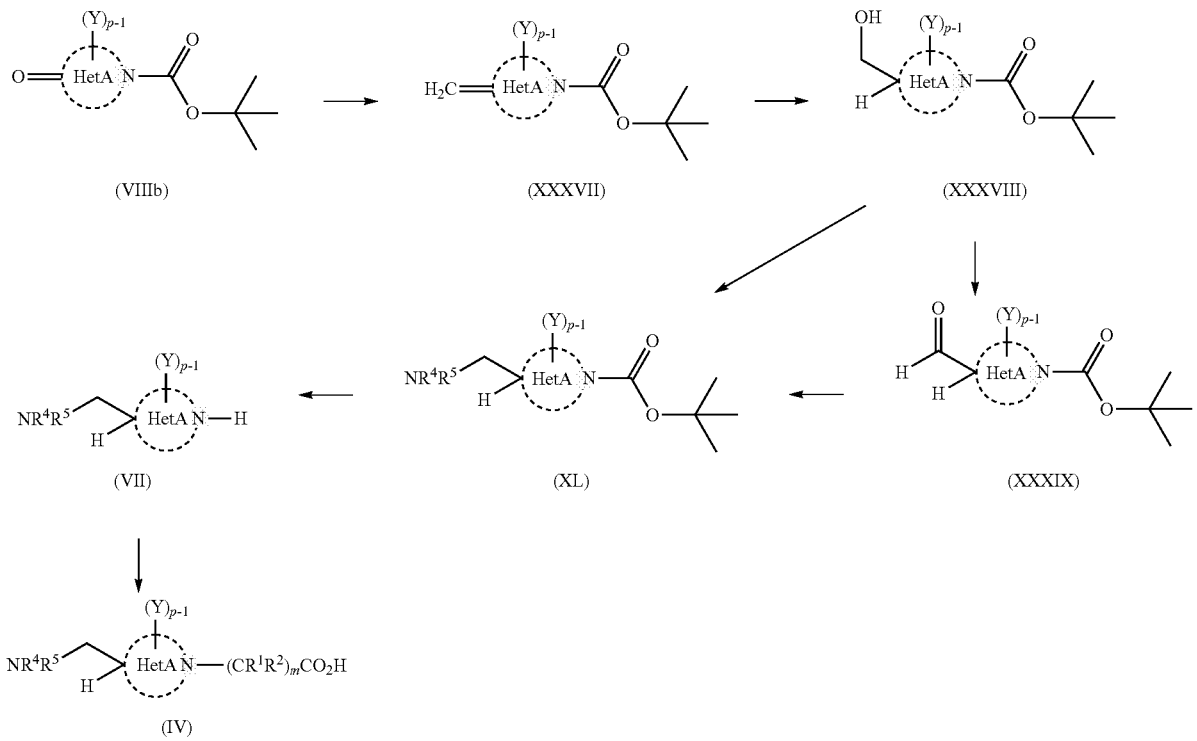

Alternatively, aminomethylene-substituted heterocycles are also prepared from the appropriate heterocyclic nitriles (XXXIII) (SCHEME 13) by treatment with a reagent such as nickel chloride hexahydrate with sodium borohydride in a solvent such as methanol (*J. Am. Chem. Soc.*, (2006) 128, 15996-15997) to give the primary amine (XLI). Derivitization of the primary amine as previously outlined provides (XL) which is, in turn, processed to give (VII) and (IV) as described above.

SCHEME 13

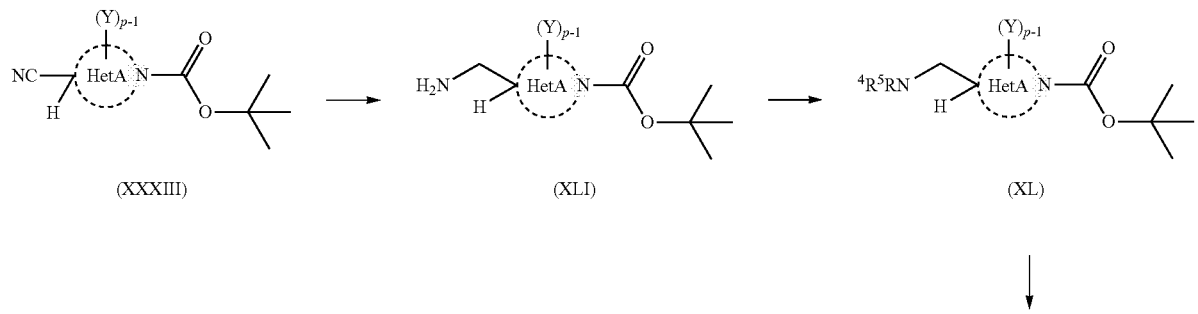

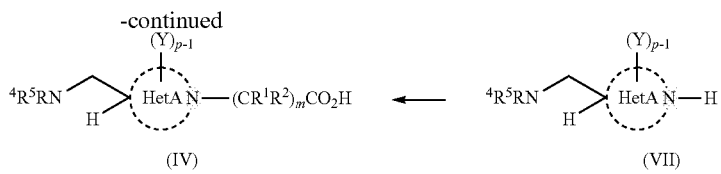

In the case where $Y_1$ is an optionally substituted aminoethyl group, the requisite amine (VII) and acids (IV) are prepared from the corresponding heterocyclic ketone (VIIIb) (SCHEME 14) by treatment with an appropriate trialkyl-phosphonoacetate, such as triethylphosphonoacetate, in a solvent such as THF, in the presence of a base such as sodium hydride, at a temperature between about −5° C. and room temperature to give the corresponding α,β-unsaturated ester (XLII) (*Liebigs Annalen/Recueil*, (1997), 7, 1283-1301). Reduction of the enone double bond is achieved by treatment of (XLII) with a heterogeneous Pd, Rh or Pt catalyst, such as 10% Pd on carbon, under an atmosphere of hydrogen gas (1-4 atm), in a solvent such as ethyl acetate, methanol or THF (or a mixture thereof) at room temperature to 70 OC to give the saturated ester (XLIII). Alternatively, in certain cases, unsaturated-ester (XLII) may be reduced by treatment with excess magnesium, in a solvent such as methanol, at around room temperature (*Tetrahedron Letters*, (1986); 27(21), 2409-2410) to provide (XLIII). The ester functionality in (XLIII) is hydrolyzed to give the corresponding acid (XLIV) by brief treatment with a base such as sodium hydroxide or lithium hydroxide, in a solvent such as THF/methanol/water at around room temperature. Selective reduction of the acid functionality in (XLIV) by treatment with borane in a solvent such as THF at a temperature between 0° C. and room temperature provides primary alcohol (XLV). Alcohol (XLV) is processed to the optionally substituted amine (XLVIII) via the corresponding tosylate, azide and primary amine (XLVI) or by oxidation to the corresponding aldehyde (XLVII) and reductive amination using the reagent systems already outlined. Deprotection of the heterocyclic amine in (XLVIII) yields (VII) which is converted to the corresponding acid (IV) as already described.

SCHEME 14

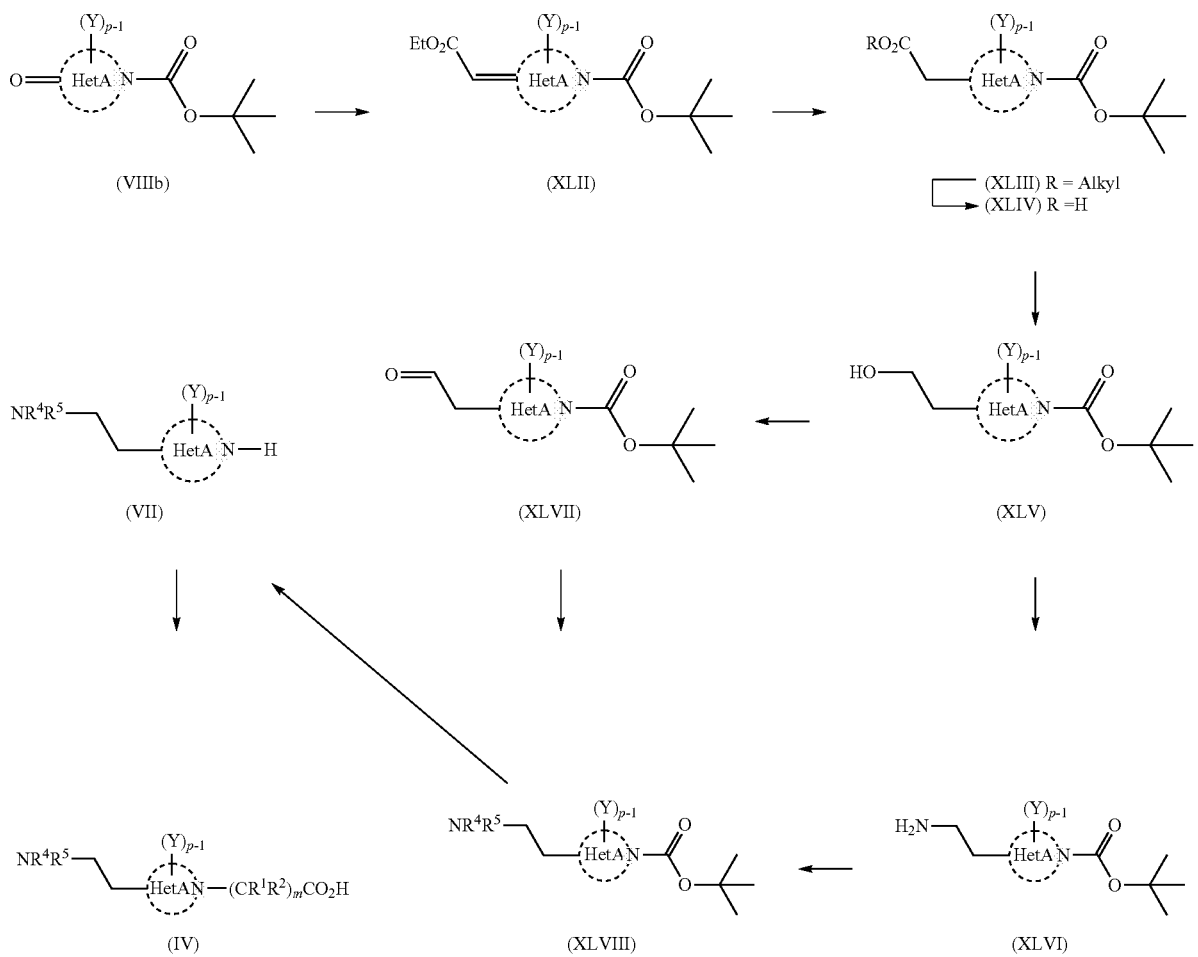

In the case where $Y_1$ and $Y_2$ are each linked to HetA through a nitrogen atom and $Y_1$ and $Y_2$ are positioned vicinally to each other on the heterocycle, the requisite amines (VII) and acids (IV) (SCHEME 15) are prepared from the appropriate heterocyclic olefins (XLIX). For example, treatment of (XLIX) with sodium azide, in the presence of a mild oxidant, such as $Mn(OAc)_3(H_2O)_2$ and an acid such as acetic acid or trifluoroacetic acid, in a solvent such as acetonitrile, at a temperature between –30° C. and 0° C. provides the diazide (L) in predominantly the trans a base, such as $K_2CO_3$, in a solvent such as DMF, DMA, or acetonitrile to give (LIII). Removal of the carbamate protecting group to give (LIV), followed by treatment of the resulting secondary amine with an aldehyde or ketone in the presence of a reducing agent such as sodium borohydride, sodium cyanoborohydride or sodium triacetoxyborohydride in a solvent such as dichloromethane, 1,2-dichloroethane, methanol or THF at around room temperature provides (LV). Processing of (LV), as already described, yields (VII) and (IV).

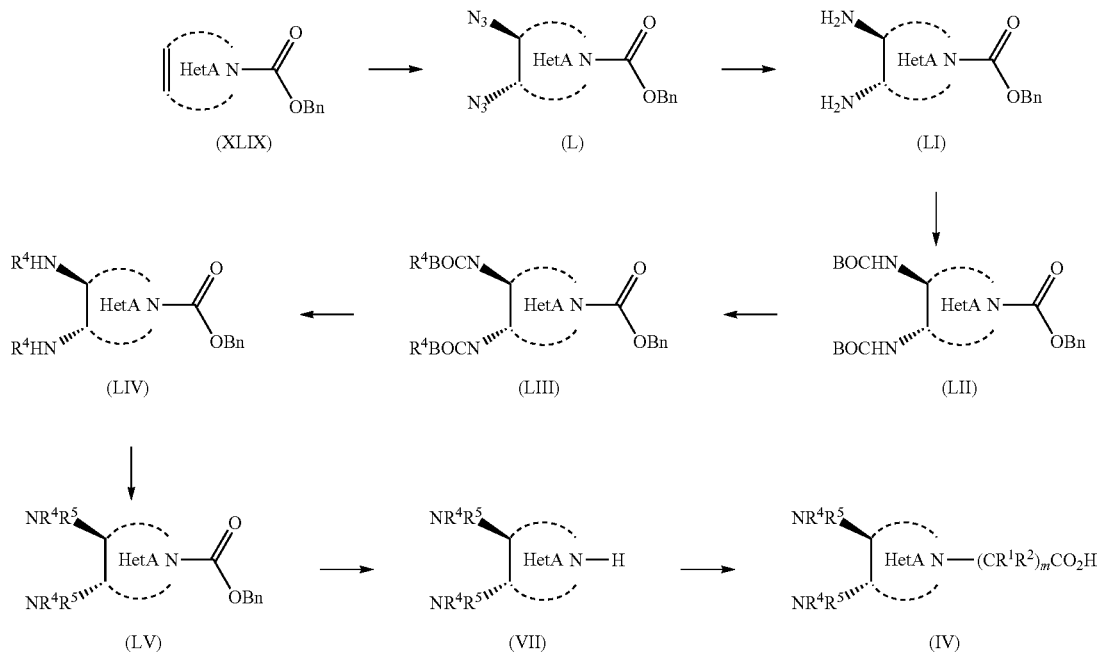

isomer configuration (*Synthetic Communications*, 28(10), 1913-1922; 1998). Subsequent reduction of the bis-azide by treatment with a reducing agent, such as triphenylphosphine, in a solvent such as THF, followed by in situ hydrolysis of the intermediate aza-phosphorane by the addition of excess water yields the bis-amine (LI). This bis-primary-amine (LI) is protected as a BOC or other suitable N-protected derivative (Greene's Protective Groups in Organic Synthesis; 4th Edition: John Wiley & Sons, Inc., 2006). For example, treatment of (LI) with an appropriate anhydride or chloroformate, in the presence of a base such as triethylamine, in a solvent such as THF or dichloromethane, at around room temperature provides the carbamate intermediate (LII). Where appropriate, the carbamate is further derivatized by treatment with a suitable alkylating agent, in the presence of Alternatively, treatment of the appropriate heterocyclic olefin (XLIX) (SCHEME 16) with an oxidant such as meta-chloroperbenzoic acid in a solvent such as dichloromethane at around 0° C. provides the corresponding cyclic epoxide (LVI). Ring opening of the epoxide by treatment with sodium azide and ammonium chloride in a solvent such as ethanol, poly-ethylene-glycol, or DMF/water at a temperature between room temperature and 80° C., provides the trans hydroxyl azide (LVII). Reaction of (LVII) with methanesulfonyl chloride in pyridine at around 0° C. yields the mesylate (LVIII). Treatment of (LVIII) with tetrabutylammonium azide in a solvent such as toluene provides the cis-oriented bis azide (LIX). Processing of intermediate (LIX) is carried out as previously described to provide (LX), amine (VII) and acid (IV).

SCHEME 16

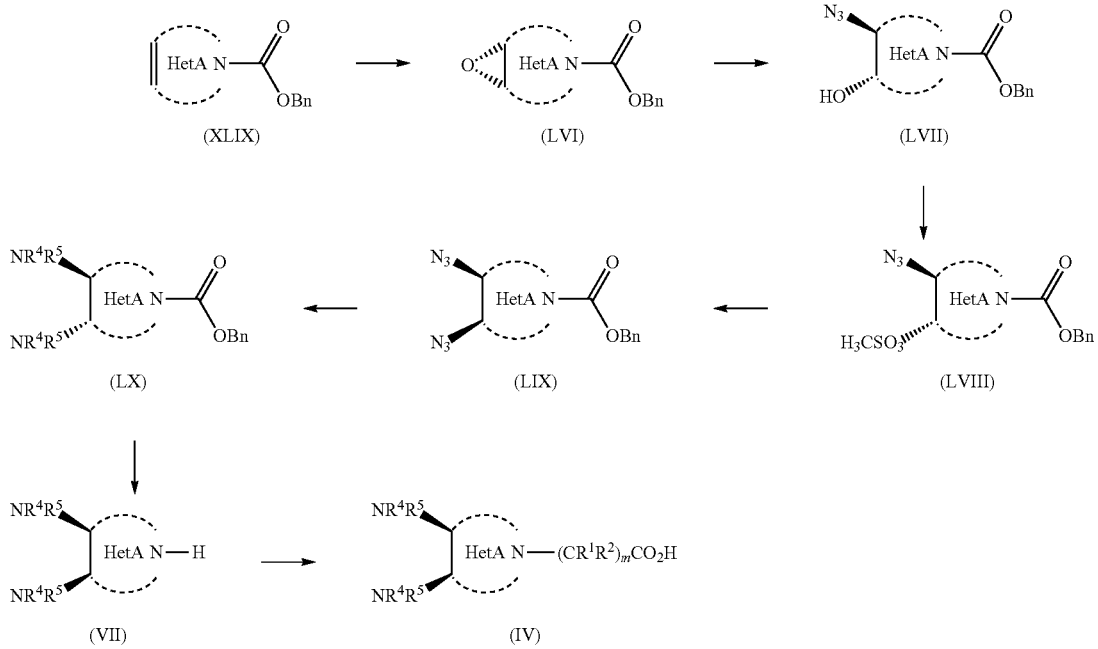

In the case where $Y_1$ is linked to HetA through a nitrogen atom:$Y_2$ is an optionally substituted aminomethyl and $Y_1$ and $Y_2$ are positioned vicinally to each other on the heterocycle, the requisite amines (VII) and acids (IV) (SCHEME 17) are prepared from the appropriate α-azido-alcohol (LVII) by processing the azide as previously described to give aminoalcohol (LXI). Treatment of (LXI) with methanesulfonyl chloride in pyridine at around 0° C. yields the mesylate (LXII). Displacement of the mesylate with cyanide by treatment of (LXII) with tetrabutylammonium cyanide in a solvent such as acetonitrile (*Bioorg. Med. Chem. Lett.*, (2009), 19, 1084-1088) yields (LXIII). Reduction of the nitrile in (LXIII) by treatment with sodium borohydride in the presence of a catalyst such as nickel chloride hexahydrate (*J. Am. Chem. Soc.*, (2006), 128, 15996-15997) provides (LXIV). Derivitization of the primary amine in (LXIV) as previously outlined yields (LXV). This intermediate is, in turn, processed to provide (VII) and (IV) as previously described.

SCHEME 17

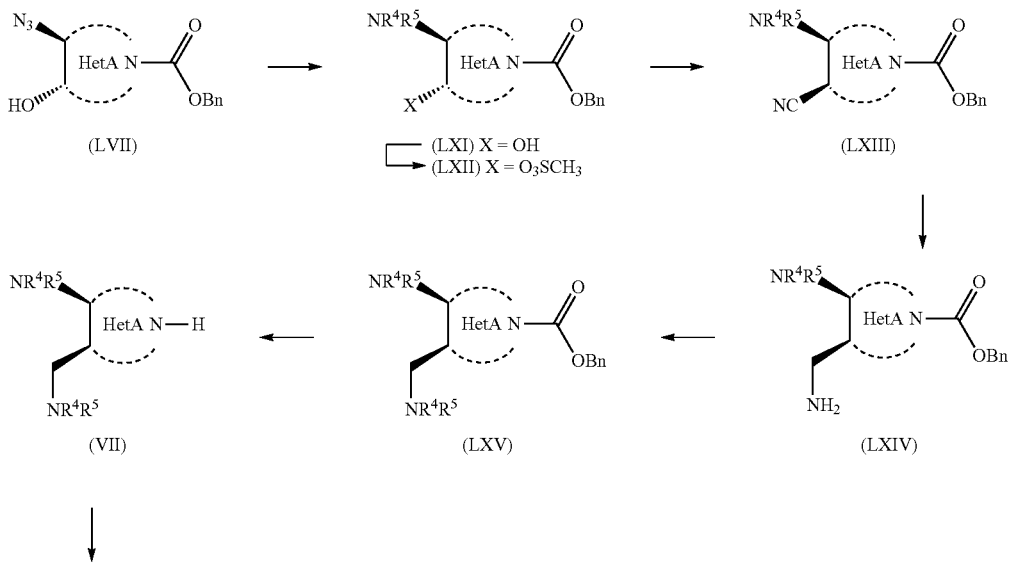

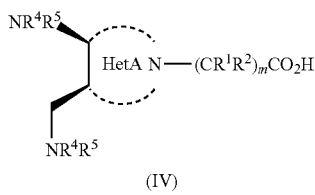

(IV)

In the case where $Y_1$ is linked to HetA through a nitrogen atom:$Y_2$ is an optionally substituted aminoethyl and $Y_1$ and $Y_2$ are positioned vicinally to each other on the heterocycle, the requisite amines (VI) and acids (IV) (SCHEME 18) are prepared from the appropriate heterocyclic ketone (VIII) by reaction with a base such as LDA in a solvent such as THF, HMPA or THF/TBTU at a temperature between −78° C. and 0° C. to form the corresponding enolate in situ. This is followed by treatment of the enolate with an allylic bromide to give (LXVI). Derivitization of the heterocyclic ketone as previously outlined yields the heterocyclic amine (LXVII). Oxidation of the olefin by treatment with catalytic amounts of osmium tetroxide (Org. Synth. Oxid. Met. Compd. (1986), 633-93. Publisher: Plenum, N.Y.) in the presence of a co-oxidant such as N-methyl morpholine N-oxide, in a solvent such as tert-butanol/water to yield the corresponding di-hydroxy-derivative (LXVIII). This diol is then oxidatively cleaved using sodium periodate, in a solvent such as THF/water, at around room temperature, to give carbonyl compound (LXIX). This intermediate is processed as previously described to give amine (LXX). Removal of the heterocyclic nitrogen carbamate protecting group yields (VII) which is further derivitized to yield (IV) as previously described.

SCHEME 18

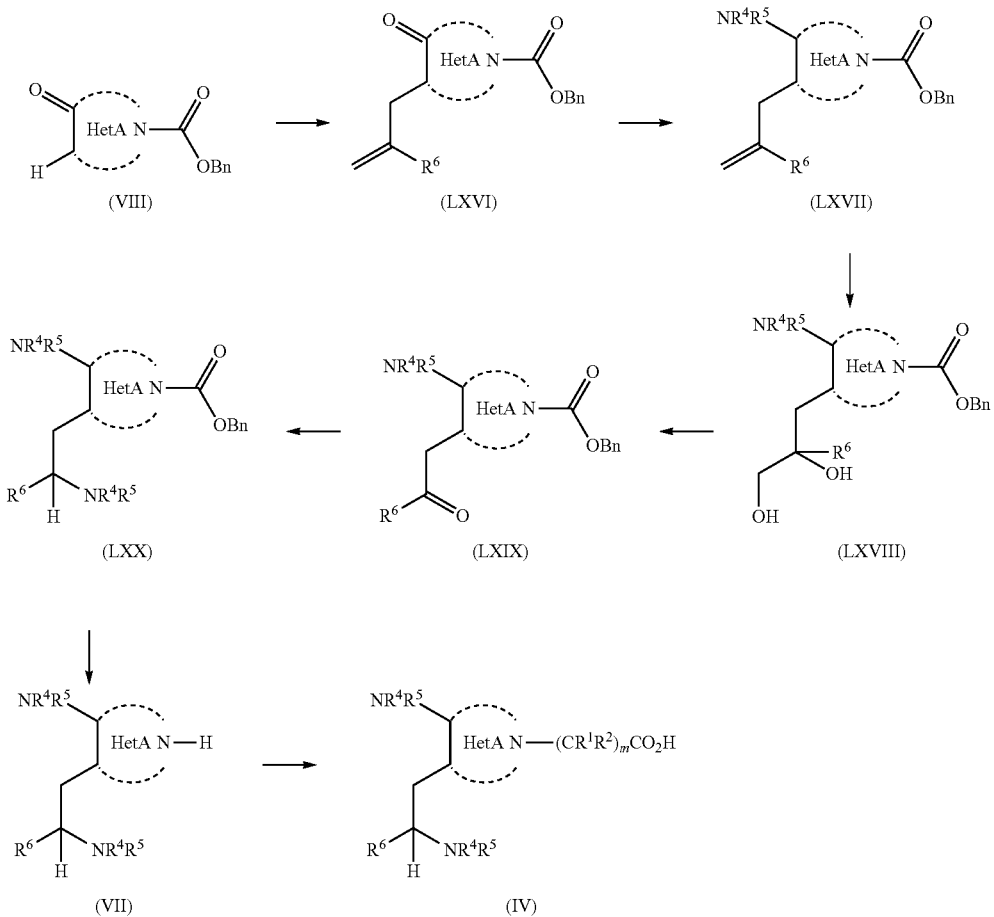

In the case where $Y_1$ is attached to HetA through a ring nitrogen, the requisite acids (IV) (SCHEME 19) are prepared from heterocyclic ketone (VIII) by elaboration of the ketone functionality to $(CR^1R^2)_mCO_2H$ and derivitization of the heterocyclic ring nitrogen as previously described for amine $(NR^4R^5)$, amidinyl $(R^5C(=NR^4)-)$ or guanidinyl $(R^4R^5NC(=NR^4)-)$ above. For example, in the case where M=bond and m=1 (SCHEME 19), (IV) is prepared from (VIII) by treatment with triethylphosphonoacetate as described above to give enone (LXXI). Reduction of the double bond in (LXXI) with concomitant cleavage of the benzyl carbamate is accomplished by treatment with hydrogen in the presence of a catalyst such as palladium on carbon in a solvent such as methanol, ethanol, ethyl acetate or THF to provide the amine (LXXII). Processing of the amino functionality in (LXXII), as previously outlined, provides the ring amino substituted derivatives (LXXIII). Finally, (LXXIII) is converted to the requisite acid (IV) by brief treatment with aqueous base as previously described.

SCHEME 19

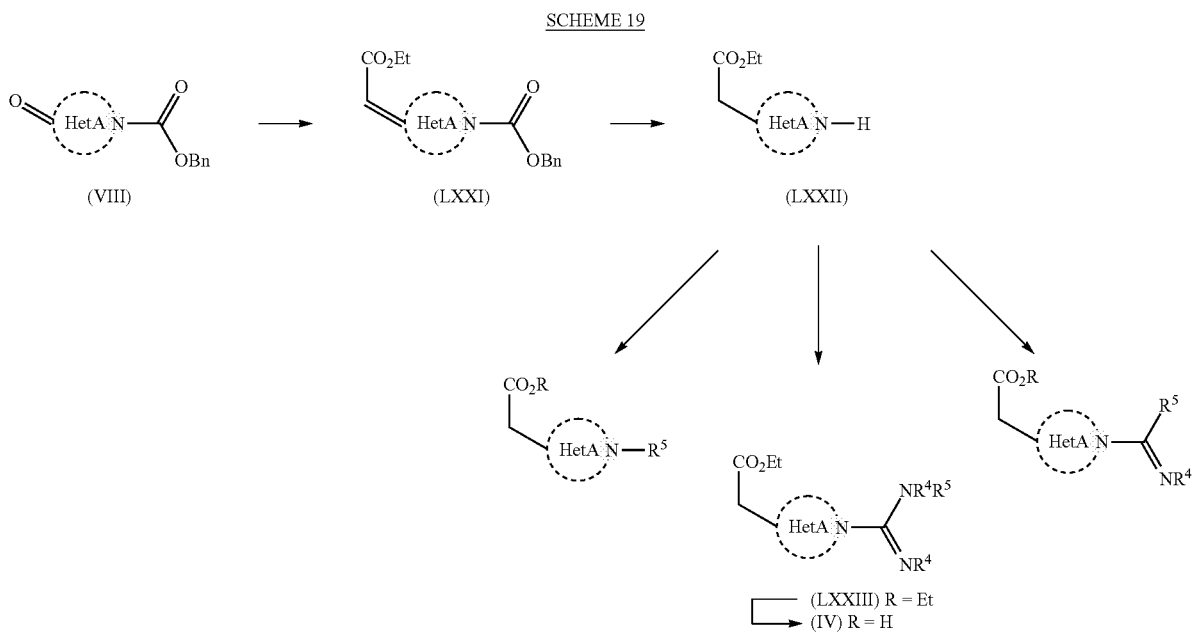

In the case where M=bond and m=0, the requisite acids (IV) (SCHEME 20) are prepared from aldehyde (XXXIX). Oxidation of (XXXIX) is accomplished by treatment with sodium chlorite/sodium dihydrogenphosphate in the presence of tetramethylethylene, in a solvent such as t-butanol/water at around room temperature (*Journal of Organic Chemistry*, (1980), 45, 4825). This is followed by esterification of the intermediate acid with methyl iodide in a solvent such as DMF in the presence of a base such as potassium carbonate to yield ester (LXXIII). Removal of the heterocyclic t-butyl carbonate protecting group under standard conditions yields secondary amine (LXXIV). Processing of (LXXIV) to the derivitized intermediates (LXXV) is accomplished as previously described. (LXXV) is converted to the requisite acid (IV) by ester hydrolysis under standard conditions.

SCHEME 20

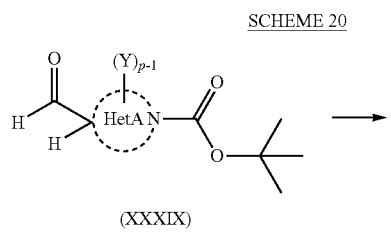

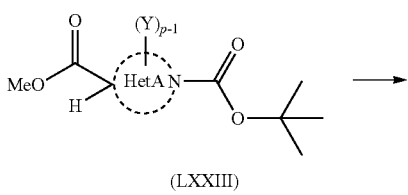

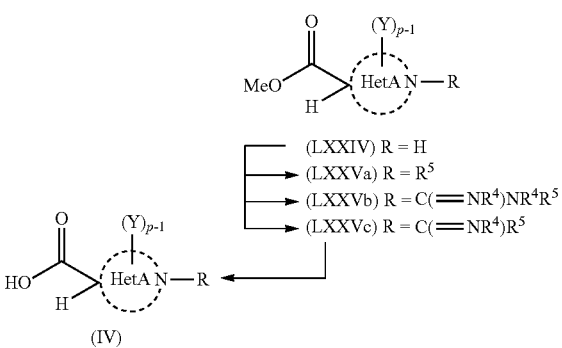

In the case where M=bond and m=2, the requisite acids (IV) (SCHEME 21) are prepared from aldehyde (XXXIX) by treatment with a trialkylphosphonoacetate reagent as previously described to provide ester (LXXVI). Hydrogenation of the double bond of the enone using hydrogen in the presence of a palladium catalyst as previously described yields (LXXVII). Cleavage of the t-butyl carbamate then provides secondary amine (LXXVIII). Subsequent processing of (LXXVIII) via (LXXIX) to yield (IV) is accomplished as outlined above for m=1.

SCHEME 21

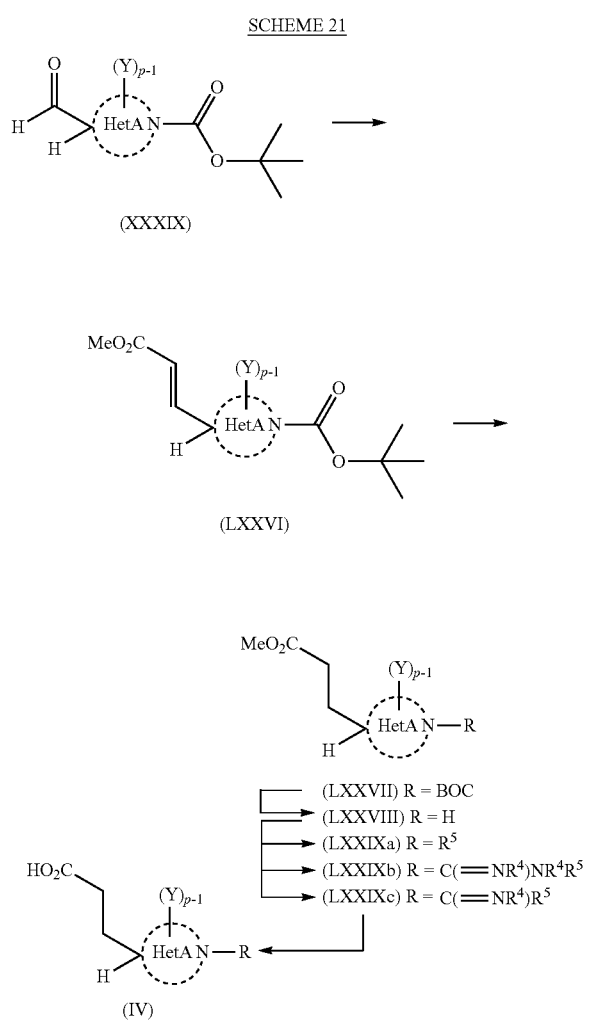

In the case where M=O, m=1, the requisite acids (IV) (SCHEME 22) are prepared from alcohol (XIV) by condensation with ethyl diazoacetate in the presence of a catalyst such as Rh(acac) dimer in a solvent such as dichloromethane to provide the alkoxyacetate derivative (LXXX). Cleavage of the heterocyclic ring nitrogen protected carbamate under standard conditions yields (LXXXI). This intermediate is processed to acid (IV) by amine derivitization and ester hydrolysis as previously outlined.

SCHEME 22

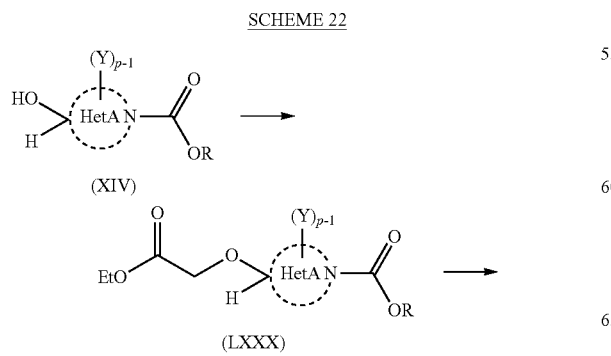

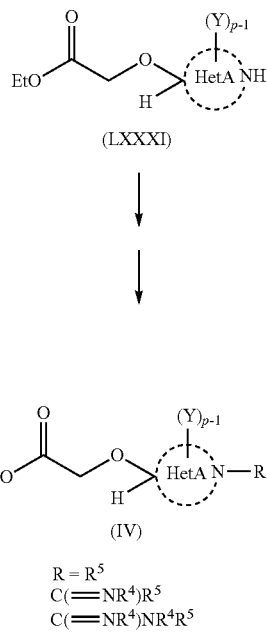

In the case where M=NR$^4$, m=1, the requisite acids (IV) (SCHEME 23) are prepared from ketone (VIII) by reductive amination with a suitable α-amino acid ester (LXXXII) to give (LXXXIII). Subsequent cleavage of the heterocyclic nitrogen carbamate and processing of the resulting secondary amine as described above provides ester (LXXXIV). Hydrolysis of the ester under standard conditions yields (IV).

SCHEME 23

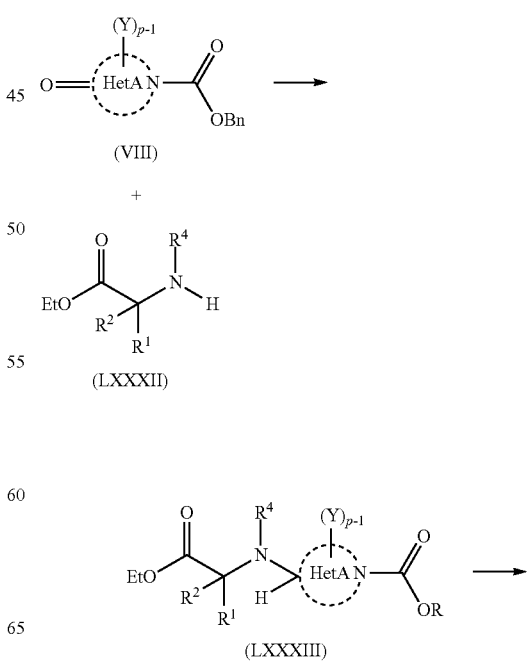

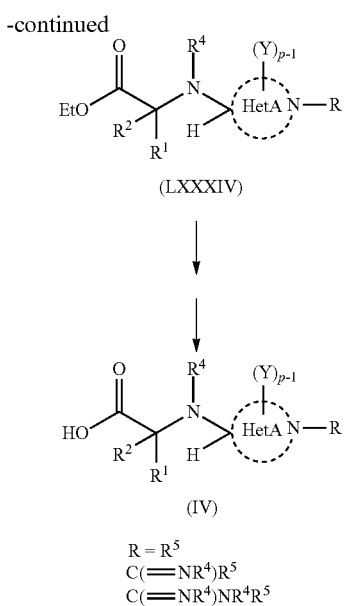

In the case where both $Y_1$ and $M(CR^1R^2)_mCO_2H$ are each connected to HetA at carbon atoms of HetA (SCHEME 24), the requisite acids (IV) can be prepared from a suitable protected keto-alcohol such as (LXXXV) by elaboration of the ketone functionality into $M(CR^1R^2)_mCO_2R$ by adaptation of the methods described above to give (LXXXVI). This sequence is followed by elaboration of the protected alcohol into $Y_1$ again, following the methods already outlined for this type of transformation.

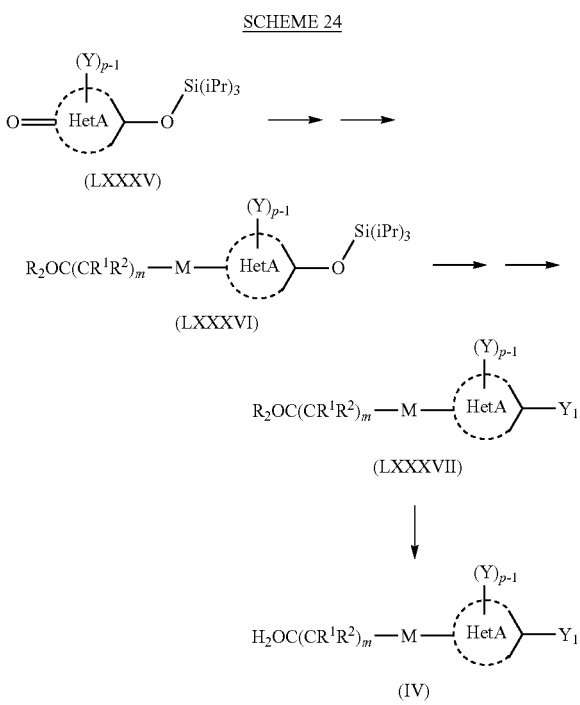

The requisite functionalized heterocycles are known compounds or are prepared by various synthetic pathways depending on the nature of the heterocycle in question. For example, in the case where HetA is a piperidine, $Y_1$ is connected to HetA through the ring nitrogen and $Y_2$ is an optionally substituted aminomethyl (SCHEME 25), the requisite ketone (VIII) is prepared from amino aldehyde (LXXXVIII). Imine formation with diphenylmethylamine under standard conditions affords (LXXXIX). A tandem Mannich-Michael reaction with Danishefsky's diene (XC) in the presence of a Lewis acid such as zinc iodide in a solvent such as acetonitrile at a temperature of 0° C. or lower provides the desired enaminone which is selectively reduced using a reducing agent such as L-selectride in a solvent such as THF at a low temperature (−50° C. or below) to provide the piperidinone (XCI) (*Tetrahedron*, (1999) 55, 7601-7612). A standard protecting group switch, where appropriate by hydrogenolysis and BOC formation provides (VIII).

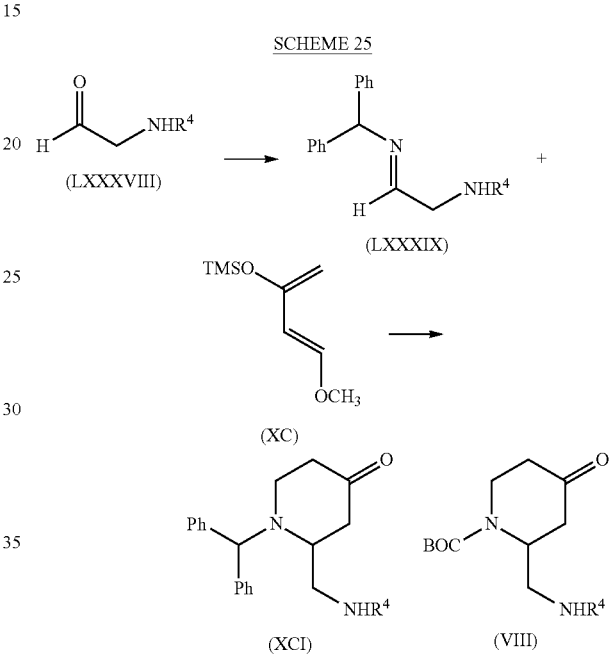

In the case where HetA is a pyrrolidine, $Y_1$ is connected to HetA through the ring nitrogen and $Y_2$ is an optionally substituted aminomethyl (SCHEME 26), the requisite ketone (VIII) is prepared from the known hydroxyl proline aldehyde (XCII) (*Tetrahedron*, (1991), 47(27), 5051-5070) by reductive amination with a suitable amine under conditions described previously to give (XCIII). This is followed by removal of the silyl protecting group using a reagent such as tetrabutylammonium fluoride in THF at around room temperature and oxidation of the intermediate alcohol with Dess-Martin periodinane in dichloromethane at room temperature to give (VIII).

SCHEME 26

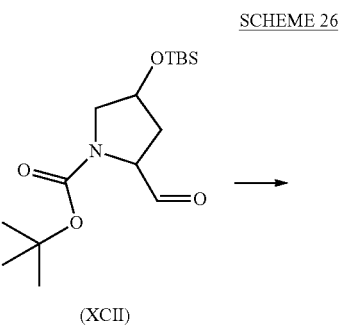

(XCII)

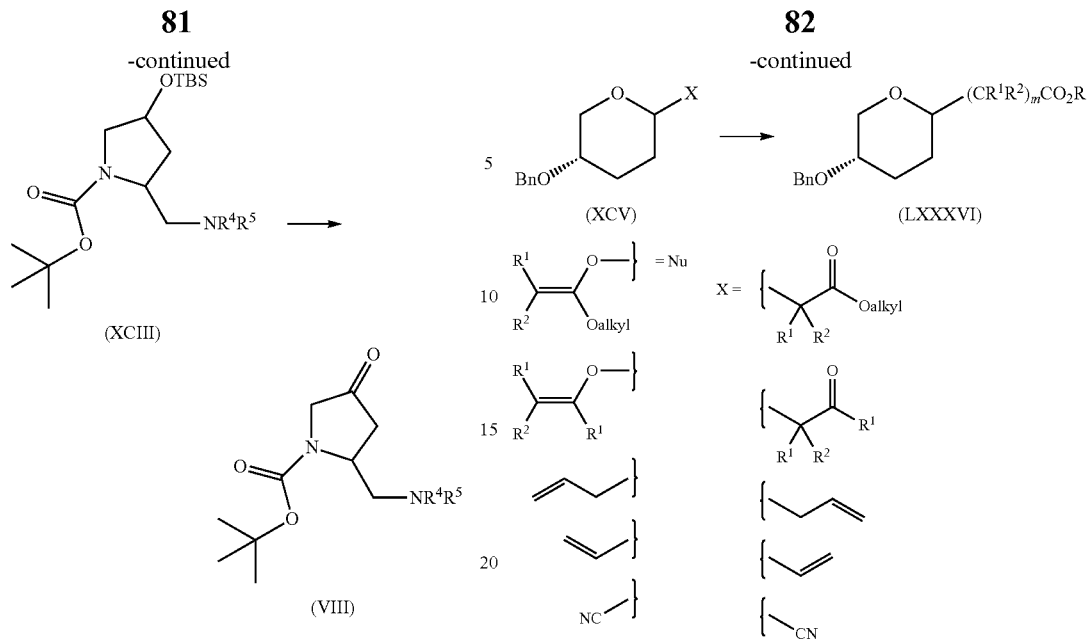

(XCIII)

(VIII)

In the case where HetA is a pyran ring, the requisite protected alcohol (LXXXVI) (SCHEME 27) is prepared

SCHEME 28

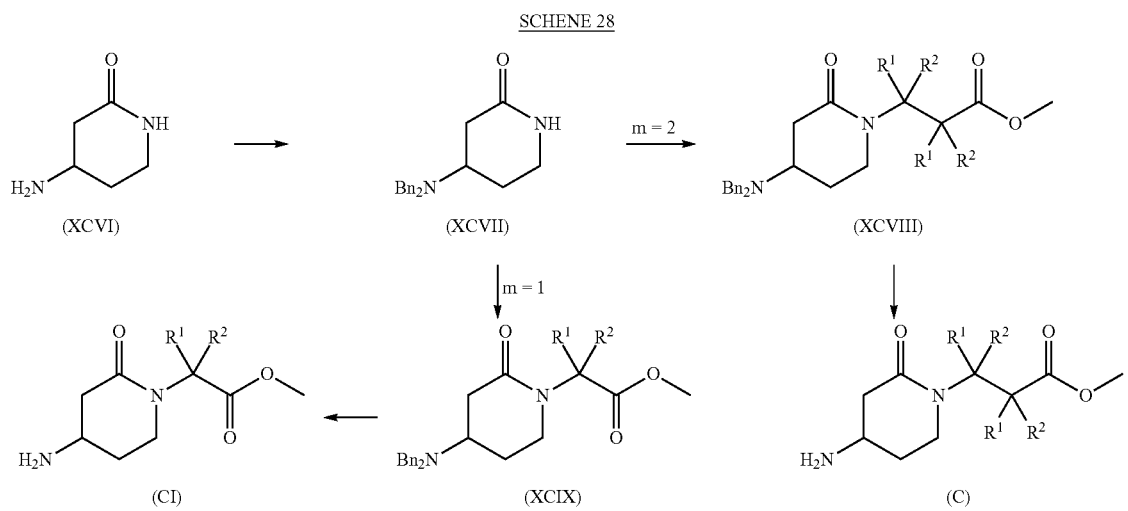

from the known 2-acetoxy-4-benzyloxy-pyran (*Organic Letters*, (2008), 10(21), 4907-491) by Lewis acid mediated C—C bond formation using an allyl silane, vinyl silane, TMS cyanide, silylketene acetal or silyl enol ether to generate a range of side chains that can be elaborated into $M(CR^1R^2)CO_2R$ using methods described above.

SCHEME 27

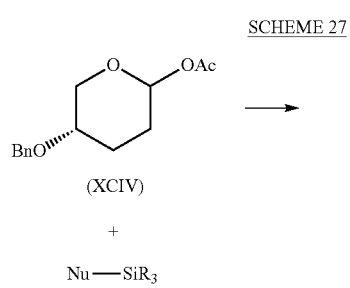

In the case where HetA is a piperidin-2-one and $Y_1$ is linked to HetA through an amine functionality (SCHEME 28), the requisite substituted heterocycles are prepared from the known 4-amino-piperidin-2-one (XCVI) by reductive amination with excess benzophenone as described above to provide (XCVII). This is followed by elaboration of the piperidin-one nitrogen to install the $(CR^1R^2)_mCO_2R$ functionality. For example, in the case where m=2, the requisite side chain is introduced by treatment of (XCVII) with an acrylate derivative in the presence of a base such as cesium fluoride and a Lewis acid such as tetraethoxysilane (*Tetrahedron Letters*, (1994), 35(12), 1875-8) to give ester (XCVIII). In the case where m=1, treatment of (XCVII) with a bromo-acetate derivative in the presence of a base such as sodium hydride in a solvent such as DMF, DMA or NMP provides (XCIX). Hydrogenolysis of the N-benzyl groups in (XCVIII) or (XCIX) using palladium hydroxide in methanol at a hydrogen pressure of 1-4 atm yields the free amines (C) and (CI) respectively. These intermediates are derivatized as previously described for compound (XVIII).

In the case where HetA is a pyrrolidin-2-one and $Y_1$ is linked to HetA through an amine functionality, the requisite amines (CII) and (CIII) are prepared (SCHEME 29) as described above for the case of the piperidin-2-one, except starting with lactams (CIV) (*Organic Letters* (2012), 14(1), 218-221 and *Journal of Organic Chemistry* (2009), 74(11), 4177-4187).

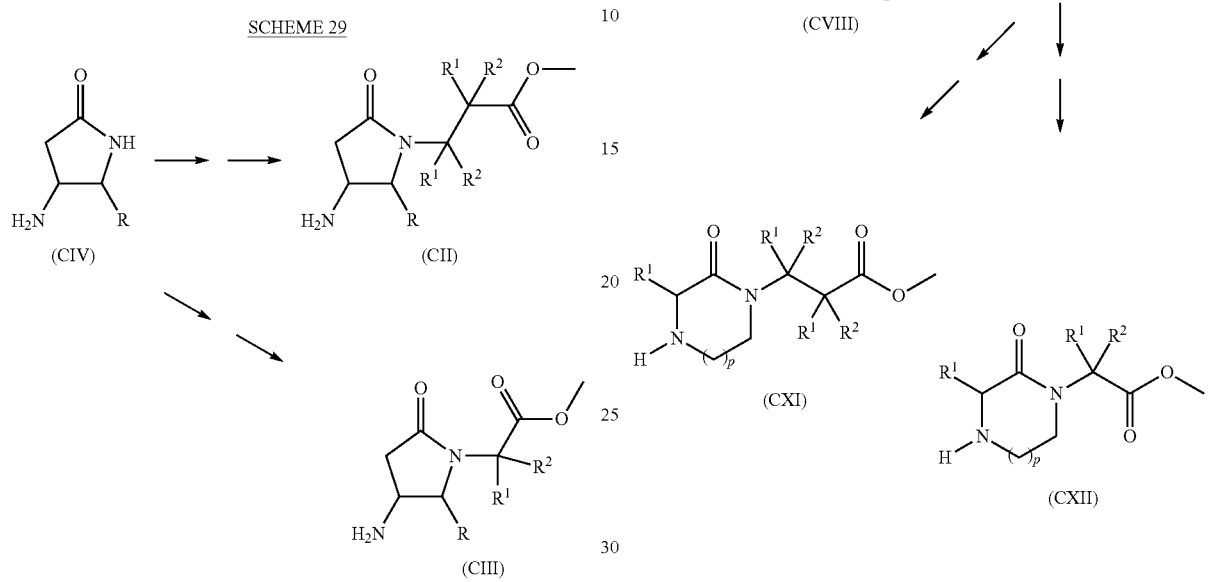

In the case where HetA is a piperazin-2-one or 1,4-diazepan-2-one: $Y_1$ is attached to hetA at N-4 and $(CR^1R^2)_m$ is attached to HetA at N-1 (SCHEME 30), the requisite functionalized heterocycles are prepared from a suitable diamine (CV) by treatment with an appropriate α-keto ester substrate (CVI) under the reductive amination conditions described above to give intermediate (CVII). Deprotection of the carbamate and acid functionality by treatment with an acid such as trifluoroacetic acid in a solvent such as dichloromethane at around room temperature gives amino acid (CVIII). Cyclization is affected by treatment of (CVIII) with a reagent system such as pyridyldisulfide/triphenylphosphine in a solvent such as toluene at a temperature between room temperature and reflux to give (CIX). Elaboration of N-1 to install $(CR^1R^2)_m CO_2R$ is achieved, as previously described for the case of (XCVII), to provide the requisite intermediates (CXI) and (CXII).

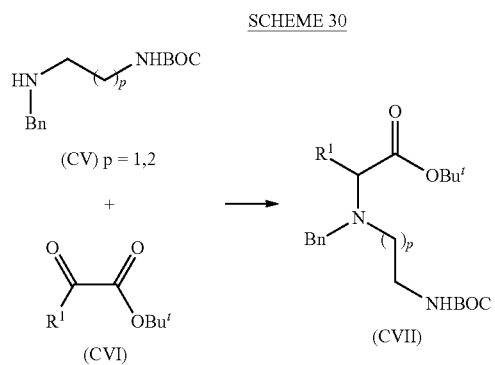

In the case where HetA is a piperazine or 1,4-diazepane: $Y_1$ is attached to HetA at N-1 and $(CR^1R^2)_m$ is attached to HetA at N-4 and $Y_2$ is an aminomethyl group attached to HetA and C-2 (SCHEME 31), the requisite functionalized heterocycles are prepared from the C-2 carboxy-piperazine or 2-carboxy-1,4 diazepane (CXIII). Differential protection of the heterocyclic ring nitrogens is achieved using such reagents as 2-(Boc-oxyimino)-2-methylacetonitrile in the presence of camphorsulfonic acid to install a BOC group selectively at N-4. This is followed by standard CBZ protection at N-1 (*Enantiomer* (2001), 6(6), 343-345) to give (CXIV). Conversion of (CXIV) to the corresponding Weinreb amide using a reagent such as N,O-dimethylhydroxylamine hydrochloride with a coupling reagent such as N-(3-dimethylaminopropyl)-N'-ethylcarbodiimide hydrochloride and an organic base such as triethylamine and/or dimethylaminopyridine in a solvent such as dichloromethane affords (CXV). The activated amide is reduced using a reducing agent such as sodium borohydride in a solvent such as methanol to provide the alcohol (CXVI). Reaction (CXVI) with a sulfonyl halide such as methanesulfonyl chloride with an organic base such as triethylamine in a solvent such as dichloromethane at room temperature or below is followed by displacement of the sulfonate with an azide source such as sodium azide in a solvent such as DMF at room temperature or higher to yield the azide (CXVIII) (*Bioorg. Med. Chem. Lett.*, (2009) 19, 5440-5443). The azide is reduced following one of the procedures described previously and the resulting primary amine (CXIX) is derivitized as previously described. Deprotection of the BOC protecting group provides (CXX).

SCHEME 31

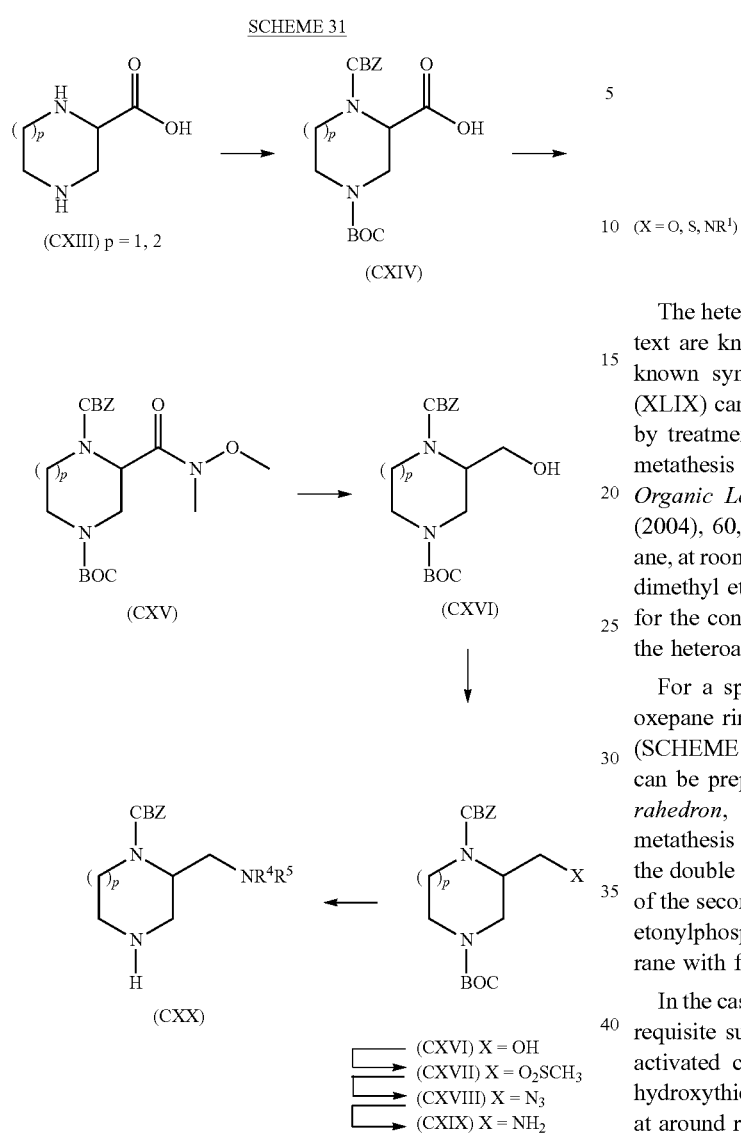

(CXVI) X = OH
(CXVII) X = O$_2$SCH$_3$
(CXVIII) X = N$_3$
(CXIX) X = NH$_2$

SCHEME 32

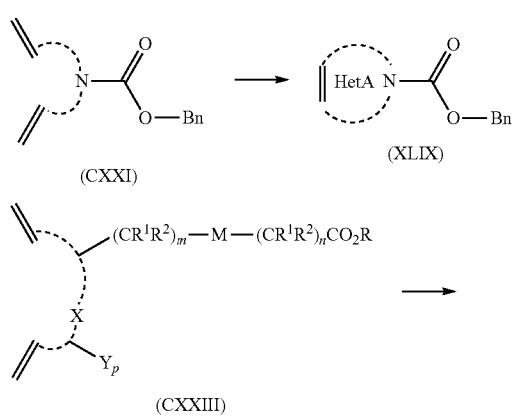

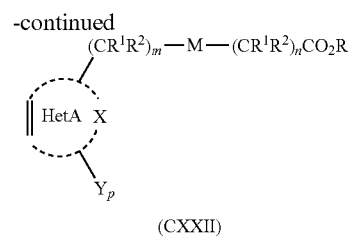

(X = O, S, NR$^1$)

The heterocyclic olefins (such as XLIX) described in this text are known compounds or are prepared by a range of known synthetic methods. For example (SCHEME 32), (XLIX) can be prepared from an acyclic precursor (CXXI) by treatment with one of a range of Grubb's or Schrock metathesis catalysts (*Tetrahedron*, (2012), 68(2) 397-421; *Organic Letters*, (2007), 9(23), 4885-4888; *Tetrahedron*, (2004), 60, 7117-7139) in a solvent such as dichloromethane, at room temperature or above, or in an aqueous PEGs$_{500}$ dimethyl ether solution. These conditions are also suitable for the construction of heterocyclic olefins (CXXII) where the heteroatom is not attached to —Y$_p$ or —(CR$^1$R$^2$)$_m$.

For a specific example, in the case where HetA is an oxepane ring linked to (CR$^1$R$^2$)$_m$ at C-2 and to Y$_1$ at C-5 (SCHEME 33), the requisite ketone intermediate (CXXIV) can be prepared from the acyclic precursor (CXXV) (*Tetrahedron*, (2007), 63(21), 4472-4490) by ring closure metathesis to give (CXXVI) followed by hydrogenation of the double bond. (CXXV) is, in turn, prepared by treatment of the secondary alcohol (CXXVII) with triphenylchloroacetonylphosphorane and olefination of the resulting phosphorane with formaldehyde.

In the case where Z is a sulfonyl group (SCHEME 34), the requisite sulfonic acid is prepared from the corresponding activated carboxylic acid (V) by treatment with sodium hydroxythiopyridone in a solvent such as dichloromethane, at around room temperature to yield the Barton ester intermediate (CXXVII). (CXXVII) is treated with iodoform in CCl$_4$ under a tungsten UV lamp at around reflux temperature to provide the de-carboxylative-iodination product (CXXVIII) (*Journal of Organic Chemistry*, 75(19), 6489-6501; 2010). Alternatively, treatment of acid (IV) with iodosobenzene-diacetate and iodine in CCl$_4$, under a tungsten UV lamp, at around reflux temperature (*Journal of Organic Chemistry*, (1986), 51, 402) provides (CXXVIII) directly. Treatment of (CXXVIII) with sodium sulfite in aqueous ethanol, isopropanol or acetone, at a temperature between 60 and 90° C., followed by acidification yields the sulfonic acid (IV). Alternatively, treatment of (CXXVIII) with thiourea in acetone, at around 60° C., provides the isothiouronium salt derivative (CXXIX) (*Synthetic Letters*, (2010), 7, 1037). Cleavage of (CXXIX) with aq. sodium thiosulphate gives thiol (CXXX). Treatment of (CXXX) with performic acid (formic acid and aqueous H$_2$O$_2$ at around 0° C. to room temperature) provides (IV).

The requisite amines (III) are prepared according to literature methods (WO2010/130708).

SCHEME 33
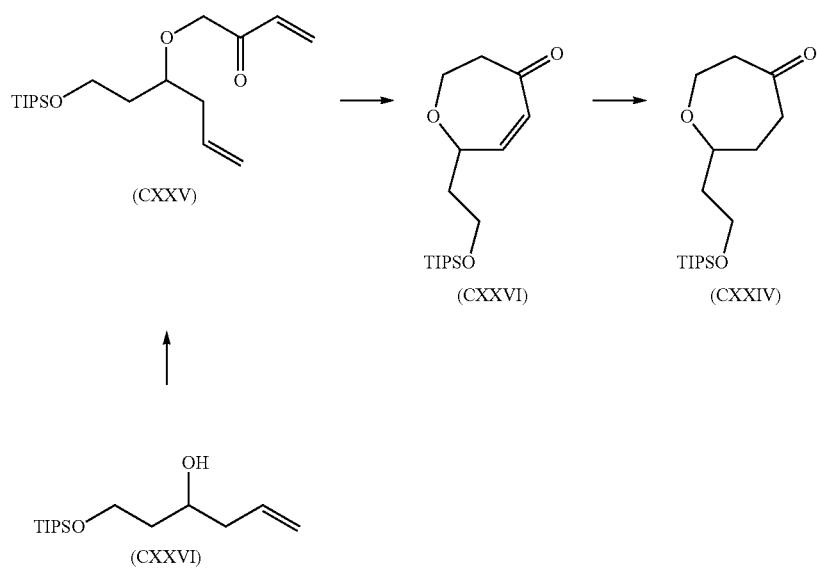
Synthetic Examples
SCHEME 34
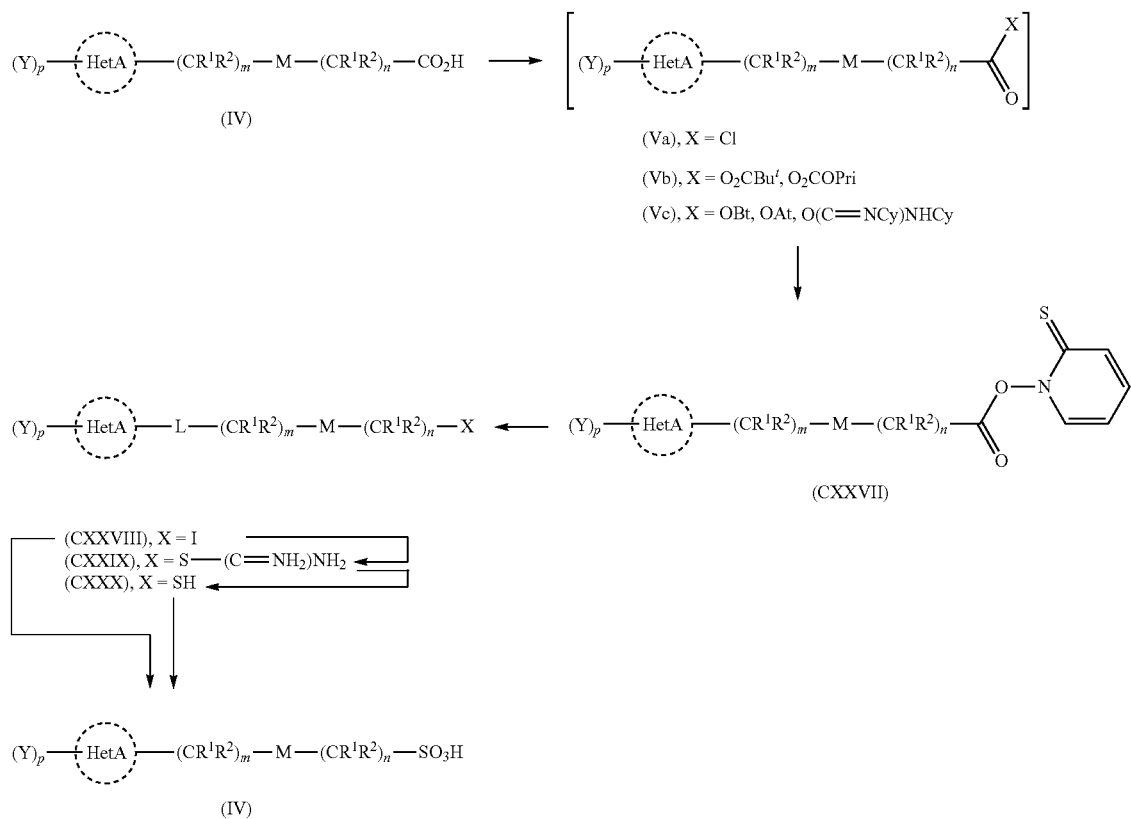
The following preparations of compounds of Formula I or Formula Ia and intermediates are given to enable those of skill in the art to more clearly understand and to practice the present invention. They should not be considered as limiting the scope of the invention, but merely as illustrative and representative thereof.

Example 1: 3-[2-(4-Amino-piperidin-1-yl)-acetylamino]-2-hydroxy-3,4-dihydro-2H-benzo[e][1,2]oxaborinine-8-carboxylic acid

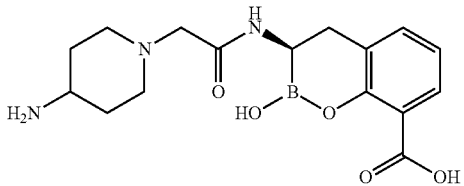 [SMILES: NC1CCN(CC(=O)N[C@H]2Cc3cccc(C(=O)O)c3OB2O)CC1]

Step 1. Synthesis of 2-Methoxy-3-(2,9,9-trimethyl-3,5-dioxa-4-bora-tricyclo[6.1.1.02,6]dec-4-yl)-benzoic acid A solution of 3-borono-2-methoxybenzoic acid (Combi-Blocks, 7.42 g, 37.9 mmol) and (+)-pinanediol (6.44 g, 37.8 mmol) in tetrahydrofuran (THF, 56 mL) was stirred at room temperature for 91 h. The solution was concentrated in vacuo and triturated twice with hexanes to afford 12.50 g (~100%) of product as a white solid. ESI-MS m/z 331 (MH)+.

Step 2. Synthesis of 2-Methoxy-3-(2,9,9-trimethyl-3,5-dioxa-4-bora-tricyclo[6.1.1.02,6]dec-4-yl)-benzoic acid tert-butyl ester Phosphorous pentachloride (7.90 g, 37.9 mmol) was added in one portion to a solution of 2-Methoxy-3-(2,9,9-trimethyl-3,5-dioxa-4-bora-tricyclo[6.1.1.02,6]dec-4-yl)-benzoic acid (12.50 g, 37.9 mmol) in toluene (105 mL) under argon. The reaction was stirred until homogeneous (~40 minutes). The reaction mixture was poured into t-butanol (105 mL) and stirred under argon for 18.5 h. The reaction was concentrated in vacuo and the residue purified by flash column chromatography on silica gel with 0-6% EtOAc/hexane to afford 9.78 g (67%) of product. ESI-MS m/z 409 (M+Na)+.

Step 3. Synthesis of 2-Methoxy-3-(2,9,9-trimethyl-3,5-dioxa-4-bora-tricyclo[6.1.1.02,6]dec-4-ylmethyl)-benzoic acid tert-butyl ester A solution of 2-Methoxy-3-(2,9,9-trimethyl-3,5-dioxa-4-bora-tricyclo[6.1.1.02,6]dec-4-yl)-benzoic acid tert-butyl ester (9.78 g, 25.3 mmol) and chloroiodomethane (2.9 mL, 39.8 mmol) in THF (72 mL) under argon was cooled to −100° C. (MeOH, liquid N₂ slush bath). n-BuLi (15.0 mL, 2.5M in hexanes, 37.5 mmol) was added dropwise over 25 minutes. The reaction was allowed to slowly warm to room temperature and stirred for a total of 17.5 h. The reaction was quenched with H₂O and extracted with EtOAc (3×). The combined organic layers were washed with brine, dried over Na₂SO₄, filtered, and concentrated in vacuo. Purification by flash chromatography (0-7% EtOAc/hexane) provided 8.92 g (88%) of product as a clear oil. ESI-MS m/z 401 (MH)+.

Step 4. Synthesis of 3-[2-[2-(4-tert-Butoxycarbonylamino-piperidin-1-yl)-acetylamino]-2-(2,9,9-trimethyl-3,5-dioxa-4-bora-tricyclo[6.1.1.02,6]dec-4-yl)-ethyl]-2-methoxy-benzoic acid tert-butyl ester A solution of dichloromethane (DCM, 0.58 mL, 9.08 mmol) in THF (6.2 mL) under argon was cooled to −100° C. (MeOH, liquid N₂ slush bath). n-BuLi (3.9 mL, 2.5M in hexane, 7.80 mmol) was added dropwise over 15 minutes and the reaction stirred at −100° C. for 30 minutes. A THF (5.7 mL) solution of 2-Methoxy-3-(2,9,9-trimethyl-3,5-dioxa-4-bora-tricyclo[6.1.1.02,6]dec-4-ylmethyl)-benzoic acid tert-butyl ester (2.13 g, 5.33 mmol) was added dropwise over 15 minutes. After 10 minutes, the cooling bath was removed and the reaction stirred at 0° C. for 1 h. The reaction was then cooled to −78° C. for 30 minutes. LiHMDS (8.0 mL, 1.0M in THF, 8.0 mmol) was added dropwise over 10 minutes and the reaction allowed to slowly warm to room temperature while stirring overnight. Upon cooling to −10° C., anhydrous MeOH (0.28 mL, 6.92 mmol) was added and the reaction stirred at −10° C. for 1 h then warmed to room temperature for 1 h. The reaction was cooled back down to −20° C. and bromoacetyl bromide (0.61 mL, 7.00 mmol) was added slowly. After 10 minutes, the cooling bath was removed and the reaction stirred at room temperature for 3.5 h. At this stage, LCMS indicated the formation of the 3-[2-(2-Bromo-acetylamino)-2-(2,9,9-trimethyl-3,5-dioxa-4-bora-tricyclo[6.1.1.02,6]dec-4-yl)-ethyl]-2-methoxy-benzoic acid tert-butyl ester intermediate.

In a separate dry round bottom flask under argon containing 4-(N-boc-amino)piperidine (1.58 g, 7.88 mmol), THF (5.0 mL) and potassium carbonate (0.74 g, 6.23 mmol) were added. To this flask was added the previously prepared bromide solution and the reaction stirred at room temperature for 16 h. The reaction was quenched with H₂O and extracted with EtOAc (3×). The combined organic layers were dried over Na₂SO₄, filtered, and concentrated. The residue was purified by a reverse phase preparative HPLC [Waters Sunfire C18 OBD, 5 μm, 19×50 mm, 5-100% AcCN:H₂O (with 0.1% TFA)] to afford 0.52 g of product. ESI-MS m/z 670 (MH)+.

Step 5. Synthesis of 3-[2-(4-Amino-piperidin-1-yl)-acetylamino]-2-hydroxy-3,4-dihydro-2H-benzo[e][1,2]oxaborinine-8-carboxylic acid A solution of 3-[2-[2-(4-tert-Butoxycarbonylamino-piperidin-1-yl)-acetylamino]-2-(2,9,9-trimethyl-3,5-dioxa-4-bora-tricyclo[6.1.1.02,6]dec-4-yl)-ethyl]-2-methoxy-benzoic acid tert-butyl ester (0.52 g, 0.78 mmol) in DCM (12 mL) under argon was cooled to −78° C. Boron trichloride (4.0 mL, 1.0M in DCM, 4.0 mmol) was added dropwise over 5 minutes. The reaction was stirred at −78° C. for 1 h then warmed to 0° C. for 30 minutes. The reaction was quenched with H₂O (6 mL), warmed to room temperature over 15 minutes, and concentrated in vacuo to remove DCM. The remaining aqueous layer was extracted with diethyl ether (3×). The product remained in the aqueous layer and was purified by reverse phase preparative HPLC [Waters Sunfire C18 OBD, 5 μm, 19×50 mm, 5-50% AcCN:H₂O (with 0.1% TFA)] to afford 3.4 mg of product as a white solid. ESI-MS m/z 348 (MH)+.

Example 2: 2-Hydroxy-3-[2-(4-pyridin-2-yl-piperazin-1-yl)-acetylamino]-3,4-dihydro-2H-benzo[e][1,2]oxaborinine-8-carboxylic acid

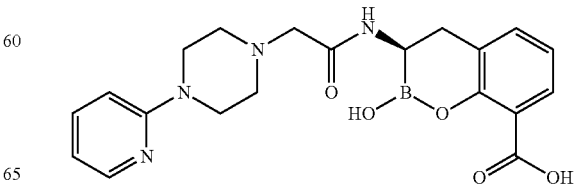

Step 1. Synthesis of 2-Methoxy-3-[2-[2-(4-pyridin-2-yl-piperazin-1-yl)-acetylamino]-2-(2,9,9-trimethyl-3,5-dioxa-4-bora-tricyclo[6.1.1.02,6]dec-4-yl)-ethyl]-benzoic acid tert-butyl ester Prepared from 2-Methoxy-3-(2,9,9-trimethyl-3,5-dioxa-4-bora-tricyclo[6.1.1.02,6]dec-4-ylmethyl)-benzoic acid tert-butyl ester and 1-(2-Pyridyl)piperazine following the procedure described in Step 4 of Example 1. The crude product was purified by a reverse phase preparative HPLC [Waters Sunfire C18 OBD, 5 μm, 19×50 mm, 5-100% AcCN:H$_2$O (with 0.1% TFA)] to give an 8% yield of product. ESI-MS m/z 633 (MH)$^+$.

Step 2. Synthesis of 2-Hydroxy-3-[2-(4-pyridin-2-yl-piperazin-1-yl)-acetylamino]-3,4-dihydro-2H-benzo[e][1,2]oxaborinine-8-carboxylic acid Prepared from 2-Methoxy-3-[2-[2-(4-pyridin-2-yl-piperazin-1-yl)-acetylamino]-2-(2,9,9-trimethyl-3,5-dioxa-4-bora-tricyclo[6.1.1.02,6]dec-4-yl)-ethyl]-benzoic acid tert-butyl ester and BCl$_3$ following the procedure described in Step 5 of Example 1. The crude product was purified by reverse phase preparative HPLC [Waters Sunfire C18 OBD, 5 μm, 19×50 mm, 5-50% AcCN:H$_2$O (with 0.1% TFA)] to give a 4% yield of product as a white solid. ESI-MS m/z 411 (MH)$^+$.

Example 3: 3-{2-[4-(2-Dimethylamino-ethyl)-piperazin-1-yl]-acetylamino}-2-hydroxy-3,4-dihydro-2H-benzo[e][1,2]oxaborinine-8-carboxylic acid

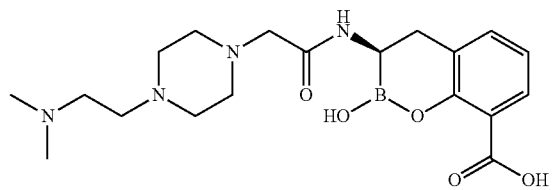 [SMILES: CN(C)CCN1CCN(CC(=O)N[C@H]2Cc3cccc(C(=O)O)c3OB2O)CC1]

Step 1. Synthesis of 3-[2-{2-[4-(2-Dimethylamino-ethyl)-piperazin-1-yl]-acetylamino}-2-(2,9,9-trimethyl-3,5-dioxa-4-bora-tricyclo[6.1.1.02,6]dec-4-yl)-ethyl]-2-methoxy-benzoic acid tert-butyl ester Prepared from 2-Methoxy-3-(2,9,9-trimethyl-3,5-dioxa-4-bora-tricyclo[6.1.1.02,6]dec-4-ylmethyl)-benzoic acid tert-butyl ester and 1-[2-(Dimethylamino)ethyl]piperazine following the procedure described in Step 4 of Example 1. The crude product was purified by a reverse phase preparative HPLC [Waters Sunfire C18 OBD, 5 μm, 19×50 mm, 5-60% AcCN:H$_2$O (with 0.1% TFA)] to give a 2% yield of product. ESI-MS m/z 627 (MH)$^+$.

Step 2. Synthesis of 3-{2-[4-(2-Dimethylamino-ethyl)-piperazin-1-yl]-acetylamino}-2-hydroxy-3,4-dihydro-2H-benzo[e][1,2]oxaborinine-8-carboxylic acid Prepared from 3-[2-{2-[4-(2-Dimethylamino-ethyl)-piperazin-1-yl]-acetylamino}-2-(2,9,9-trimethyl-3,5-dioxa-4-bora-tricyclo[6.1.1.02,6]dec-4-yl)-ethyl]-2-methoxy-benzoic acid tert-butyl ester and BCl$_3$ following the procedure described in Step 5 of Example 1. The crude product was purified by reverse phase preparative HPLC [Waters Sunfire C18 OBD, 5 μm, 19×50 mm, 5-50% AcCN:H$_2$O (with 0.1% TFA)] to give a 7% yield of product as a white solid. ESI-MS m/z 405 (MH)$^+$.

Example 4: 2-Hydroxy-3-(2-piperazin-1-yl-acetylamino)-3,4-dihydro-2H-benzo[e][1,2]oxaborinine-8-carboxylic acid

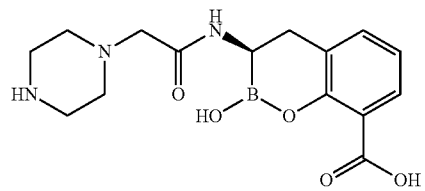

Step 1. Synthesis of 4-{[2-(3-tert-Butoxycarbonyl-2-methoxy-phenyl)-1-(2,9,9-trimethyl-3,5-dioxa-4-bora-tricyclo[6.1.1.02,6]dec-4-yl)-ethylcarbamoyl]-methyl}-piperazine-1-carboxylic acid tert-butyl ester Prepared from 2-Methoxy-3-(2,9,9-trimethyl-3,5-dioxa-4-bora-tricyclo[6.1.1.02,6]dec-4-ylmethyl)-benzoic acid tert-butyl ester and 1-Boc-piperazine following the procedure described in Step 4 of Example 1. The crude product was purified by a reverse phase preparative HPLC [Waters Sunfire C18 OBD, 5 μm, 19×50 mm, 5-100% AcCN:H$_2$O (with 0.1% TFA)] to give a 10% yield of product. ESI-MS m/z 656 (MH)$^+$.

Step 2. Synthesis of 2-Hydroxy-3-(2-piperazin-1-yl-acetylamino)-3,4-dihydro-2H-benzo[e][1,2]oxaborinine-8-carboxylic acid Prepared from 4-{[2-(3-tert-Butoxycarbonyl-2-methoxy-phenyl)-1-(2,9,9-trimethyl-3,5-dioxa-4-bora-tricyclo[6.1.1.02,6]dec-4-yl)-ethylcarbamoyl]-methyl}-piperazine-1-carboxylic acid tert-butyl ester and BCl$_3$ following the procedure described in Step 5 of Example 1. The crude product was purified by reverse phase preparative HPLC [Waters Sunfire C18 OBD, 5 μm, 19×50 mm, 5-20% AcCN:H$_2$O (with 0.1% TFA)] to give a 8% yield of product as a white solid. ESI-MS m/z 334 (MH)$^+$.

Example 5: 3-[2-(4-Aminomethyl-piperidin-1-yl)-acetylamino]-2-hydroxy-3,4-dihydro-2H-benzo[e][1,2]oxaborinine-8-carboxylic acid

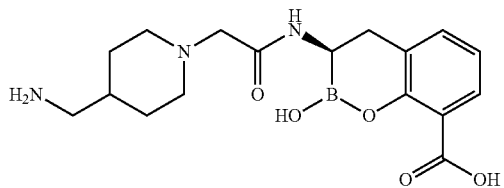 [SMILES: NCC1CCN(CC(=O)N[C@H]2Cc3cccc(C(=O)O)c3OB2O)CC1]

Step 1. Synthesis of 3-[2-(2-Chloro-acetylamino)-2-(2,9,9-trimethyl-3,5-dioxa-4-bora-tricyclo[6.1.1.02,6]dec-4-yl)-ethyl]-2-methoxy-benzoic acid tert-butyl ester A solution of DCM (1.1 mL, 17.2 mmol) in THF (12 mL) under argon was cooled to −100° C. (MeOH, liquid $N_2$ slush bath). n-BuLi (7.1 mL, 2.5M in hexane, 17.8 mmol) was added dropwise over 15 minutes and the reaction stirred at −100° C. for 30 minutes. A THF (9.0 mL) solution of 2-Methoxy-3-(2,9,9-trimethyl-3,5-dioxa-4-bora-tricyclo[6.1.1.02,6]dec-4-ylmethyl)-benzoic acid tert-butyl ester (4.00 g, 10.0 mmol) was added dropwise over 15 minutes. After 10 minutes, the cooling bath was removed and the reaction stirred at 0° C. for 1 h. The reaction was then cooled to −78° C. for 30 minutes. LiHMDS (15.0 mL, 1.0M in THF, 15.0 mmol) was added dropwise over 10 minutes and the reaction allowed to slowly warm to room temperature while stirring overnight. Upon cooling to −10° C., anhydrous MeOH (0.50 mL, 12.4 mmol) was added and the reaction stirred at −10° C. for 1 h then warmed to room temperature for 1 h. A portion (~2.50 mmol) of the reaction mixture was transferred to a separate round bottom flask under argon. Chloroacetyl chloride (0.29 mL, 3.65 mmol) was added dropwise and the reaction was stirred at room temperature for 3 h. The reaction was quenched with $H_2O$ and extracted with EtOAc (3×). The combined organic layers were dried over $Na_2SO_4$, filtered, and concentrated. The crude product was carried to the next step without purification.

Step 2. Synthesis of 3-[2-{2-[4-(tert-Butoxycarbonylamino-methyl)-piperidin-1-yl]-acetylamino}-2-(2,9,9-trimethyl-3,5-dioxa-4-bora-tricyclo[6.1.1.02,6]dec-4-yl)-ethyl]-2-methoxy-benzoic acid tert-butyl ester To a solution of 3-[2-(2-Chloro-acetylamino)-2-(2,9,9-trimethyl-3,5-dioxa-4-bora-tricyclo[6.1.1.02,6]dec-4-yl)-ethyl]-2-methoxy-benzoic acid tert-butyl ester (1.26 g, 2.50 mmol) in N,N-dimethylformamide (DMF, 11.0 mL) was added t-butyl N-(4-piperidinylmethyl)carbonate (0.550 g, 2.57 mmol), potassium carbonate (0.361 g, 3.05 mmol), and tetrabutylammonium bromide (0.038 g, 0.118 mmol) under argon. The reaction was stirred at room temperature for 65 h. The reaction was quenched with $H_2O$ and extracted with EtOAc (3×). The combined organic layers were washed with brine, dried over $Na_2SO_4$, filtered, and concentrated. The residue was purified by a reverse phase preparative HPLC [Waters Sunfire C18 OBD, 5 μm, 19×50 mm, 5-50% AcCN:$H_2O$ (with 0.1% TFA)] to afford 0.066 g (4% over 2 steps) of product. ESI-MS m/z 684 (MH)⁺.

Step 3. Synthesis of 3-[2-(4-Aminomethyl-piperidin-1-yl)-acetylamino]-2-hydroxy-3,4-dihydro-2H-benzo[e][1,2]oxaborinine-8-carboxylic acid Prepared from 3-[2-{2-[4-(tert-Butoxycarbonylamino-methyl)-piperidin-1-yl]-acetylamino}-2-(2,9,9-trimethyl-3,5-dioxa-4-bora-tricyclo[6.1.1.02,6]dec-4-yl)-ethyl]-2-methoxy-benzoic acid tert-butyl ester and $BCl_3$ following the procedure described in Step 5 of Example 1. The crude product was purified by reverse phase preparative HPLC [Waters Sunfire C18 OBD, 5 μm, 19×50 mm, 5-50% AcCN:$H_2O$ (with 0.1% TFA)] to give a 11% yield of product as a white solid. ESI-MS m/z 362 (MH)⁺.

Example 6: 3-[2-(R-3-Amino-pyrrolidin-1-yl)-acetylamino]-2-hydroxy-3,4-dihydro-2H-benzo[e][1,2]oxaborinine-8-carboxylic acid

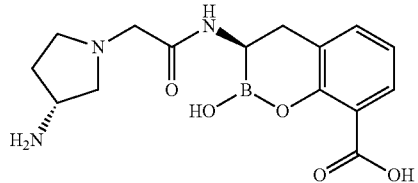 [SMILES: N[C@@H]1CCN(CC(=O)N[C@H]2Cc3cccc(C(=O)O)c3OB2O)C1]

Step 1. Synthesis of 3-[2-[2-(3-tert-Butoxycarbonylamino-pyrrolidin-1-yl)-acetylamino]-2-(2,9,9-trimethyl-3,5-dioxa-4-bora-tricyclo[6.1.1.02,6]dec-4-yl)-ethyl]-2-methoxy-benzoic acid tert-butyl ester Prepared from 2-Methoxy-3-(2,9,9-trimethyl-3,5-dioxa-4-bora-tricyclo[6.1.1.02,6]dec-4-ylmethyl)-benzoic acid tert-butyl ester and (R)-3-N-Boc-aminopyrrolidine following the procedure described in Step 4 of Example 1. The crude product was purified by a reverse phase preparative HPLC [Waters Sunfire C18 OBD, 5 μm, 19×50 mm, 5-100% AcCN:$H_2O$ (with 0.1% TFA)] to give a 24% yield of product. ESI-MS m/z 656 (MH).

Step 2. Synthesis of 3-[2-(R-3-Amino-pyrrolidin-1-yl)-acetylamino]-2-hydroxy-3,4-dihydro-2H-benzo[e][1,2]oxaborinine-8-carboxylic acid Prepared from 3-[2-[2-(3-tert-Butoxycarbonylamino-pyrrolidin-1-yl)-acetylamino]-2-(2,9,9-trimethyl-3,5-dioxa-4-bora-tricyclo[6.1.1.02,6]dec-4-yl)-ethyl]-2-methoxy-benzoic acid tert-butyl ester and $BCl_3$ following the procedure described in Step 5 of Example 1. The crude product was purified by reverse phase preparative HPLC [Waters Sunfire C18 OBD, 5 μm, 19×50 mm, 5-50% AcCN:$H_2O$ (with 0.1% TFA)] to give a 5% yield of product as a white solid. ESI-MS m/z 334 (MH)⁺.

Example 7: 3-[2-(S-3-Amino-pyrrolidin-1-yl)-acetylamino]-2-hydroxy-3,4-dihydro-2H-benzo[e][1,2]oxaborinine-8-carboxylic acid

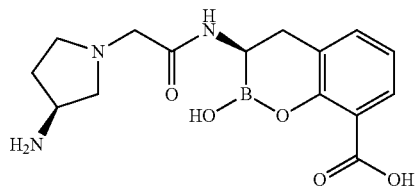

Step 1. Synthesis of 3-[2-[2-(3-tert-Butoxycarbonylamino-pyrrolidin-1-yl)-acetylamino]-2-(2,9,9-trimethyl-3,5-dioxa-4-bora-tricyclo[6.1.1.02,6]dec-4-yl)-ethyl]-2-methoxy-benzoic acid tert-butyl ester Prepared from 2-Methoxy-3-(2,9,9-trimethyl-3,5-dioxa-4-bora-tricyclo[6.1.1.02,6]dec-4-ylmethyl)-benzoic acid tert-butyl ester and (S)-3-N-Boc-aminopyrrolidine following the procedure described in Step 4 of Example 1. The crude product was purified by a reverse phase preparative HPLC [Waters Sunfire C18 OBD, 5 µm, 19×50 mm, 5-100% AcCN:H$_2$O (with 0.1% TFA)] to give a 28% yield of product. ESI-MS m/z 656 (MH)$^+$.

Step 2. Synthesis of 3-[2-(S-3-Amino-pyrrolidin-1-yl)-acetylamino]-2-hydroxy-3,4-dihydro-2H-benzo[e][1,2]oxaborinine-8-carboxylic acid Prepared from 3-[2-[2-(3-tert-Butoxycarbonylamino-pyrrolidin-1-yl)-acetylamino]-2-(2,9,9-trimethyl-3,5-dioxa-4-bora-tricyclo[6.1.1.0$^{2,6}$]dec-4-yl)-ethyl]-2-methoxy-benzoic acid tert-butyl ester and BCl$_3$ following the procedure described in Step 5 of Example 1. The crude product was purified by reverse phase preparative HPLC [Waters Sunfire C18 OBD, 5 µm, 19×50 mm, 5-50% AcCN:H$_2$O (with 0.1% TFA)] to give a 29% yield of product as a white solid. ESI-MS m/z 334 (MH)$^+$.

Example 8: 2-Hydroxy-3-[2-(2-oxo-piperazin-1-yl)-acetylamino]-3,4-dihydro-2H-benzo[e][1,2]oxaborinine-8-carboxylic acid

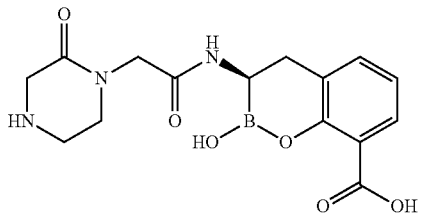 [SMILES: O=C(CN1CCNCC1=O)N[C@H]1Cc2cccc(C(=O)O)c2OB1O]

Step 1. Synthesis of 4-{[2-(3-tert-Butoxycarbonyl-2-methoxy-phenyl)-1-(2,9,9-trimethyl-3,5-dioxa-4-bora-tricyclo[6.1.1.0$^{2,6}$]dec-4-yl)-ethylcarbamoyl]-methyl}-3-oxo-piperazine-1-carboxylic acid tert-butyl ester A solution of dichloromethane (0.58 mL, 9.08 mmol) in THF (6.2 mL) under argon was cooled to −100° C. (MeOH, liquid N$_2$ slush bath). n-BuLi (3.9 mL, 2.5M in hexane, 7.80 mmol) was added dropwise over 15 minutes and the reaction stirred at −100° C. for 30 minutes. A THF (5.7 mL) solution of 2-Methoxy-3-(2,9,9-trimethyl-3,5-dioxa-4-bora-tricyclo[6.1.1.0$^{2,6}$]dec-4-ylmethyl)-benzoic acid tert-butyl ester (2.13 g, 5.33 mmol) was added dropwise over 15 minutes. After 10 minutes, the cooling bath was removed and the reaction stirred at 0° C. for 1 h. The reaction was then cooled to −78° C. for 30 minutes. LiHMDS (8.0 mL, 1.0M in THF, 8.0 mmol) was added dropwise over 10 minutes and the reaction allowed to slowly warm to room temperature while stirring overnight. Upon cooling to −10° C., anhydrous MeOH (0.28 mL, 6.92 mmol) was added and the reaction stirred at −10° C. for 1 h then warmed to room temperature for 1 h.

To a separate dry round bottom flask under argon containing 4-N-Boc-2-oxo-piperazine-1-acetic acid (0.318 g, 1.23 mmol) and DCM (3.4 mL) was added N-methylmorpholine (0.20 mL, 1.82 mmol) and HATU (0.494 g, 1.70 mmol). DMF (1.6 mL) was added to make the reaction homogeneous. The reaction was stirred at room temperature for 3 h. A portion of the solution (~2.44 mmol) prepared above was added slowly at 0° C. and the reaction was gradually warmed to room temperature and stirred for 44 h. The reaction was quenched with H$_2$O and extracted with EtOAc (3×). The combined organic layers were dried over Na$_2$SO$_4$, filtered, and concentrated. The residue was purified by a reverse phase preparative HPLC [Waters Sunfire C18 OBD, 5 µm, 19×50 mm, 5-100% AcCN:H$_2$O (with 0.1% TFA)] to afford 0.158 g (19%) of product. ESI-MS m/z 670 (MH)$^+$.

Step 2. Synthesis of 2-Hydroxy-3-[2-(2-oxo-piperazin-1-yl)-acetylamino]-3,4-dihydro-2H-benzo[e][1,2]oxaborinine-8-carboxylic acid Prepared from 4-{[2-(3-tert-Butoxycarbonyl-2-methoxy-phenyl)-1-(2,9,9-trimethyl-3,5-dioxa-4-bora-tricyclo[6.1.1.0$^{2,6}$]dec-4-yl)-ethylcarbamoyl]-methyl}-3-oxo-piperazine-1-carboxylic acid tert-butyl ester and BCl$_3$ following the procedure described in Step 5 of Example 1. The crude product was purified by reverse phase preparative HPLC [Waters Sunfire C18 OBD, 5 µm, 19×50 mm, 5-50% AcCN:H$_2$O (with 0.1% TFA)] to give a 13% yield of product as a white solid. ESI-MS m/z 348 (MH)$^+$.

Example 9: 2-Hydroxy-3-[2-(pyrrolidin-3-ylamino)-acetylamino]-3,4-dihydro-2H-benzo[e][1,2]oxaborinine-8-carboxylic acid

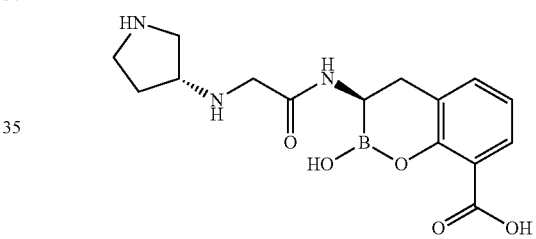

Step 1. Synthesis of 3-({[2-(3-tert-Butoxycarbonyl-2-methoxy-phenyl)-1-(2,9,9-trimethyl-3,5-dioxa-4-bora-tricyclo[6.1.1.0$^{2,6}$]dec-4-yl)-ethylcarbamoyl]-methyl}-amino)-pyrrolidine-1-carboxylic acid tert-butyl ester Prepared from 2-Methoxy-3-(2,9,9-trimethyl-3,5-dioxa-4-bora-tricyclo[6.1.1.0$^{2,6}$]dec-4-ylmethyl)-benzoic acid tert-butyl ester and (R)-(+)-1-Boc-3-aminopyrrolidine following the procedure described in Step 4 of Example 1. The crude product was purified by a reverse phase preparative HPLC [Waters Sunfire C18 OBD, 5 µm, 19×50 mm, 5-100% AcCN:H$_2$O (with 0.1% TFA)] to give a 9% yield of product. ESI-MS m/z 656 (MH)$^+$.

Step 2. Synthesis of 2-Hydroxy-3-[2-(pyrrolidin-3-ylamino)-acetylamino]-3,4-dihydro-2H-benzo[e][1,2]oxaborinine-8-carboxylic acid Prepared from 3-({[2-(3-tert-Butoxycarbonyl-2-methoxy-phenyl)-1-(2,9,9-trimethyl-3,5-dioxa-4-bora-tricyclo[6.1.1.0$^{2,6}$]dec-4-yl)-ethylcarbamoyl]-methyl}-amino)-pyrrolidine-1-carboxylic acid tert-butyl ester and BCl$_3$ following the procedure described in Step 5 of Example 1. The crude product was purified by reverse phase preparative HPLC [Waters Sunfire C18 OBD, 5 µm, 19×50 mm, 5-30%

AcCN:H₂O (with 0.1% TFA)] to give a 6% yield of product as a white solid. ESI-MS m/z 334 (MH)⁺.

Example 10: 3-[2-(R-3-Amino-piperidin-1-yl)-acetylamino]-2-hydroxy-3,4-dihydro-2H-benzo[e][1,2]oxaborinine-8-carboxylic acid

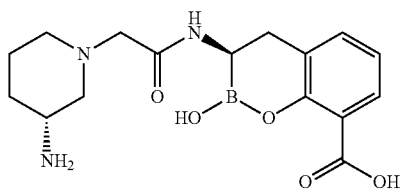 [SMILES: N[C@@H]1CCCN(CC(=O)N[C@H]2Cc3cccc(C(=O)O)c3OB2O)C1]

Step 1. Synthesis of 3-[2-[2-(3-tert-Butoxycarbo-nylamino-piperidin-1-yl)-acetylamino]-2-(2,9,9-trimethyl-3,5-dioxa-4-bora-tricyclo[6.1.1.0²,⁶]dec-4-yl)-ethyl]-2-methoxy-benzoic acid tert-butyl ester Prepared from 2-Methoxy-3-(2,9,9-trimethyl-3,5-dioxa-4-bora-tricyclo[6.1.1.0²,⁶]dec-4-ylmethyl)-benzoic acid tert-butyl ester and (R)-3-(Boc-amino)piperidine following the procedure described in Step 4 of Example 1. The crude product was purified by a reverse phase preparative HPLC [Waters Sunfire C18 OBD, 5 μm, 19×50 mm, 5-100% AcCN:H₂O (with 0.1% TFA)] to give a 10% yield of product. ESI-MS m/z 670 (MH)⁺.

Step 2. Synthesis of 3-[2-(R-3-Amino-piperidin-1-yl)-acetylamino]-2-hydroxy-3,4-dihydro-2H-benzo[e][1,2]oxaborinine-8-carboxylic acid Prepared from –[2-[2-(3-tert-Butoxycarbonylamino-piperidin-1-yl)-acetylamino]-2-(2,9,9-trimethyl-3,5-dioxa-4-bora-tricyclo[6.1.1.0²,⁶]dec-4-yl)-ethyl]-2-methoxy-benzoic acid tert-butyl ester ester and BCl₃ following the procedure described in Step 5 of Example 1. The crude product was purified by reverse phase preparative HPLC [Waters Sunfire C18 OBD, 5 μm, 19×50 mm, 5-50% AcCN:H₂O (with 0.1% TFA)] to give a 10% yield of product as a white solid. ESI-MS m/z 348 (MH)⁺.

Example 11: 3-[2-(S-3-Amino-piperidin-1-yl)-acetylamino]-2-hydroxy-3,4-dihydro-2H-benzo[e][1,2]oxaborinine-8-carboxylic acid

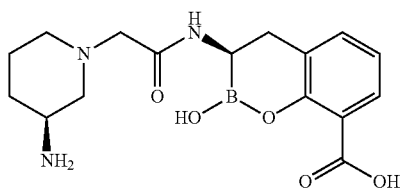 [SMILES: N[C@H]1CCCN(CC(=O)N[C@H]2Cc3cccc(C(=O)O)c3OB2O)C1]

Step 1. Synthesis of 3-[2-[2-(3-tert-Butoxycarbo-nylamino-piperidin-1-yl)-acetylamino]-2-(2,9,9-trimethyl-3,5-dioxa-4-bora-tricyclo[6.1.1.0²,⁶]dec-4-yl)-ethyl]-2-methoxy-benzoic acid tert-butyl ester Prepared from 2-Methoxy-3-(2,9,9-trimethyl-3,5-dioxa-4-bora-tricyclo[6.1.1.0²,⁶]dec-4-ylmethyl)-benzoic acid tert-butyl ester and (S)-3-(Boc-amino)piperidine following the procedure described in Step 4 of Example 1. The crude product was purified by a reverse phase preparative HPLC [Waters Sunfire C18 OBD, 5 μm, 19×50 mm, 5-100% AcCN:H₂O (with 0.1% TFA)] to give a 10% yield of product. ESI-MS m/z 670 (MH)⁺.

Step 2. Synthesis of 3-[2-(S-3-Amino-piperidin-1-yl)-acetylamino]-2-hydroxy-3,4-dihydro-2H-benzo[e][1,2]oxaborinine-8-carboxylic acid Prepared from –[2-[2-(3-tert-Butoxycarbonylamino-piperidin-1-yl)-acetylamino]-2-(2,9,9-trimethyl-3,5-dioxa-4-bora-tricyclo[6.1.1.0²,⁶]dec-4-yl)-ethyl]-2-methoxy-benzoic acid tert-butyl ester and BCl₃ following the procedure described in Step 5 of Example 1. The crude product was purified by reverse phase preparative HPLC [Waters Sunfire C18 OBD, 5 μm, 19×50 mm, 5-50% AcCN:H₂O (with 0.1% TFA)] to give a 6% yield of product as a white solid. ESI-MS m/z 348 (MH)⁺.

Example 12: 2-Hydroxy-3-[2-(4-Hydroxy-piperidin-1-yl)-acetylamino]-3,4-dihydro-2H-benzo[e][1,2]oxaborinine-8-carboxylic acid

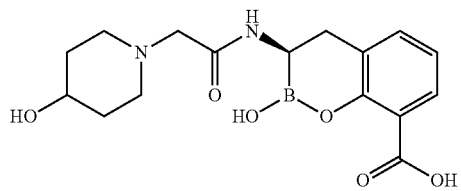 [SMILES: O=C(CN1CCC(O)CC1)N[C@H]1Cc2cccc(C(=O)O)c2OB1O]

Step 1. Synthesis of 3-[2-[2-(4-Hydroxy-piperidin-1-yl)-acetylamino]-2-(2,9,9-trimethyl-3,5-dioxa-4-bora-tricyclo[6.1.1.0²,⁶]dec-4-yl)-ethyl]-2-methoxy-benzoic acid tert-butyl ester Prepared from 2-Methoxy-3-(2,9,9-trimethyl-3,5-dioxa-4-bora-tricyclo[6.1.1.0²,⁶]dec-4-ylmethyl)-benzoic acid tert-butyl ester and 4-hydroxypiperidine following the procedure described in Step 4 of Example 1. The crude product was purified by a reverse phase preparative HPLC [Waters Sunfire C18 OBD, 5 μm, 19×50 mm, 5-100% AcCN:H₂O (with 0.1% TFA)] to give a 15% yield of product. ESI-MS m/z 571 (MH)⁺.

Step 2. Synthesis of 2-Hydroxy-3-[2-(4-hydroxy-piperidin-1-yl)-acetylamino]-3,4-dihydro-2H-benzo[e][1,2]oxaborinine-8-carboxylic acid Prepared from 3-[2-[2-(4-Hydroxy-piperidin-1-yl)-acetylamino]-2-(2,9,9-trimethyl-3,5-dioxa-4-bora-tricyclo[6.1.1.0²,⁶]dec-4-yl)-ethyl]-2-methoxy-benzoic acid tert-butyl ester and BCl₃ following the procedure described in Step 5 of Example 1. The crude product was purified by reverse phase preparative HPLC [Waters Sunfire C18 OBD, 5 μm, 19×50 mm, 5-50% AcCN:H₂O (with 0.1% TFA)] to give a 4% yield of product as a white solid. ESI-MS m/z 349 (MH)⁺.

Example 13: 3-(2-[1,4]Diazepan-1-yl-acetylamino)-2-hydroxy-3,4-dihydro-2H-benzo[e][1,2]oxaborinine-8-carboxylic acid

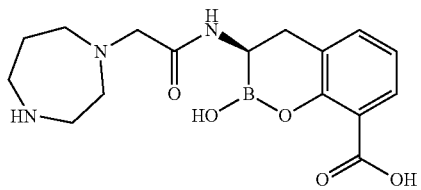 [SMILES: O=C(CN1CCCNCC1)N[C@H]1Cc2cccc(C(=O)O)c2OB1O]

Step 1. Synthesis of 4-{[2-(3-tert-Butoxycarbonyl-2-methoxy-phenyl)-1-(2,9,9-trimethyl-3,5-dioxa-4-bora-tricyclo[6.1.1.02,6]dec-4-yl)-ethylcarbamoyl]-methyl}-[1,4]diazepane-1-carboxylic acid tert-butyl ester Prepared from 2-Methoxy-3-(2,9,9-trimethyl-3,5-dioxa-4-bora-tricyclo[6.1.1.02,6]dec-4-ylmethyl)-benzoic acid tert-butyl ester and 1-Boc-homopiperazine following the procedure described in Step 4 of Example 1. The crude product was purified by a reverse phase preparative HPLC [Waters Sunfire C18 OBD, 5 μm, 19×50 mm, 5-100% AcCN:H$_2$O (with 0.1% TFA)] to give a 13% yield of product. ESI-MS m/z 670 (MH)$^+$.

Step 2. Synthesis of 3-(2-[1,4]Diazepan-1-yl-acetylamino)-2-hydroxy-3,4-dihydro-2H-benzo[e][1,2]oxaborinine-8-carboxylic acid Prepared from 4-{[2-(3-tert-Butoxycarbonyl-2-methoxy-phenyl)-1-(2,9,9-trimethyl-3,5-dioxa-4-bora-tricyclo[6.1.1.02,6]dec-4-yl)-ethylcarbamoyl]-methyl}-[1,4]diazepane-1-carboxylic acid tert-butyl ester and BCl$_3$ following the procedure described in Step 5 of Example 1. The crude product was purified by reverse phase preparative HPLC [Waters Sunfire C18 OBD, 5 μm, 19×50 mm, 5-50% AcCN:H$_2$O (with 0.1% TFA)] to give a 9% yield of product as a white solid. ESI-MS m/z 348 (MH)$^+$.

Example 14: 2-Hydroxy-3-[2-(4-methylamino-piperidin-1-yl)-acetylamino]-3,4-dihydro-2H-benzo[e][1,2]oxaborinine-8-carboxylic acid

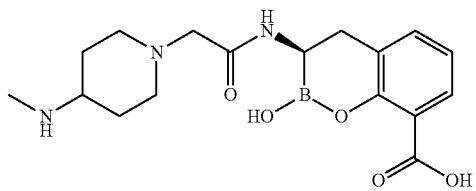 [SMILES: CNC1CCN(CC(=O)N[C@H]2Cc3cccc(C(=O)O)c3OB2O)CC1]

Step 1. Synthesis of 3-[2-{2-[4-(tert-Butoxycarbonyl-methyl-amino)-piperidin-1-yl]-acetylamino}-2-(2,9,9-trimethyl-3,5-dioxa-4-bora-tricylo[6.1.1.02,6]dec-4-yl)-ethyl]-2-methoxy-benzoic acid tert-butyl ester Prepared from 2-Methoxy-3-(2,9,9-trimethyl-3,5-dioxa-4-bora-tricyclo[6.1.1.02,6]dec-4-ylmethyl)-benzoic acid tert-butyl ester and 4-N-Boc-4-N-methylaminopiperidine following the procedure described in Step 4 of Example 1. The crude product was purified by a reverse phase preparative HPLC [Waters Sunfire C18 OBD, 5 μm, 19×50 mm, 5-100% AcCN:H$_2$O (with 0.1% TFA)] to give a 14% yield of product. ESI-MS m/z 684 (MH)$^+$.

Step 2. Synthesis of 2-Hydroxy-3-[2-(4-methyl-amino-piperidin-1-yl)-acetylamino]-3,4-dihydro-2H-benzo[e][1,2]oxaborinine-8-carboxylic acid Prepared from 3-[2-{2-[4-(tert-Butoxycarbonyl-methyl-amino)-piperidin-1-yl]-acetylamino}-2-(2,9,9-trimethyl-3,5-dioxa-4-bora-tricyclo[6.1.1.02,6]dec-4-yl)-ethyl]-2-methoxy-benzoic acid tert-butyl ester and BCl$_3$ following the procedure described in Step 5 of Example 1. The crude product was purified by reverse phase preparative HPLC [Waters Sunfire C18 OBD, 5 μm, 19×50 mm, 5-50% AcCN:H$_2$O (with 0.1% TFA)] to give a 23% yield of product as a white solid. ESI-MS m/z 362 (MH)$^+$.

Example 15: 2-Hydroxy-3-[2-(4-thiazol-2-yl-piperazin-1-yl)-acetylamino]-3,4-dihydro-2H-benzo[e][1,2]oxaborinine-8-carboxylic acid

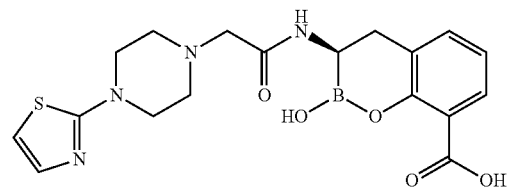 [SMILES: O=C(CN1CCN(c2nccs2)CC1)N[C@H]1Cc2cccc(C(=O)O)c2OB1O]

Step 1. Synthesis of 2-Methoxy-3-[2-[2-(4-thiazol-2-yl-piperazin-1-yl)-acetylamino]-2-(2,9,9-trimethyl-3,5-dioxa-4-bora-tricyclo[6.1.1.02,6]dec-4-yl)-ethyl]-benzoic acid tert-butyl ester Prepared from 2-Methoxy-3-(2,9,9-trimethyl-3,5-dioxa-4-bora-tricyclo[6.1.1.02,6]dec-4-ylmethyl)-benzoic acid tert-butyl ester and 1-thiazole-2-yl-piperazine following the procedure described in Step 4 of Example 1. The crude product was purified by a reverse phase preparative HPLC [Waters Sunfire C18 OBD, 5 μm, 19×50 mm, 5-100% AcCN:H$_2$O (with 0.1% TFA)] to give a 24% yield of product. ESI-MS m/z 639 (MH)$^+$.

Step 2. Synthesis of 2-Hydroxy-3-[2-(4-thiazol-2-yl-piperazin-1-yl)-acetylamino]-3,4-dihydro-2H-benzo[e][1,2]oxaborinine-8-carboxylic acid Prepared from 2-Methoxy-3-[2-[2-(4-thiazol-2-yl-piperazin-1-yl)-acetylamino]-2-(2,9,9-trimethyl-3,5-dioxa-4-bora-tricyclo[6.1.1.02,6]dec-4-yl)-ethyl]-benzoic acid tert-butyl ester and BCl$_3$ following the procedure described in Step 5 of Example 1. The crude product was purified by reverse phase preparative HPLC [Waters Sunfire C18 OBD, 5 μm, 19×50 mm, 5-50% AcCN:H$_2$O (with 0.1% TFA)] to give a 25% yield of product as a white solid. ESI-MS m/z 417 (MH)$^+$.

Example 16: 3-{2-[4-(2-Amino-ethyl)-piperazin-1-yl]-acetylamino}-2-hydroxy-3,4-dihydro-2H-benzo[e][1,2]oxaborinine-8-carboxylic acid

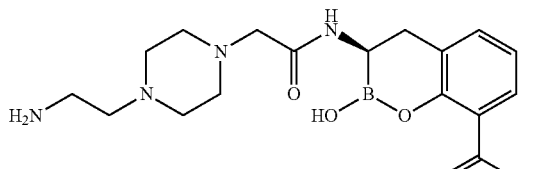

Step 1. Synthesis of 3-[2-{2-[4-(2-tert-Butoxycarbonylamino-ethyl)-piperazin-1-yl]-acetylamino}-2-(2,9,9-trimethyl-3,5-dioxa-4-bora-tricyclo[6.1.1.02,6]dec-4-yl)-ethyl]-2-methoxy-benzoic acid tert-butyl ester Prepared from 2-Methoxy-3-(2,9,9-trimethyl-3,5-dioxa-4-bora-tricyclo[6.1.1.02,6]dec-4-ylmethyl)-benzoic acid tert-butyl ester and 1-(2-N-Boc-aminoethyl)piperazine following the procedure described in Step 4 of Example 1. The crude product was purified by a reverse phase preparative HPLC [Waters Sunfire C18 OBD, 5 μm, 19×50 mm, 5-100% AcCN:H$_2$O (with 0.1% TFA)] to give a 18% yield of product. ESI-MS m/z 699 (MH)$^+$.

Step 2. Synthesis of 3-{2-[4-(2-Amino-ethyl)-piperazin-1-yl]-acetylamino}-2-hydroxy-3,4-dihydro-2H-benzo[e][1,2]oxaborinine-8-carboxylic acid Prepared from 3-[2-{2-[4-(2-tert-Butoxycarbonylamino-ethyl)-piperazin-1-yl]-acetylamino}-2-(2,9,9-trimethyl-3,5-dioxa-4-bora-tricyclo[6.1.1.02,6]dec-4-yl)-ethyl]-2-methoxy-benzoic acid tert-butyl ester and BCl$_3$ following the procedure described in Step 5 of Example 1. The crude product was purified by reverse phase preparative HPLC [Waters Sunfire C18 OBD, 5 μm, 19×50 mm, 5-50% AcCN:H$_2$O (with 0.1% TFA)] to give a 7% yield of product as a white solid. ESI-MS m/z 377 (MH)$^+$.

Example 17: 3-{2-[4-(2-Amino-acetyl)-piperazin-1-yl]-acetylamino}-2-hydroxy-3,4-dihydro-2H-benzo[e][1,2]oxaborinine-8-carboxylic acid

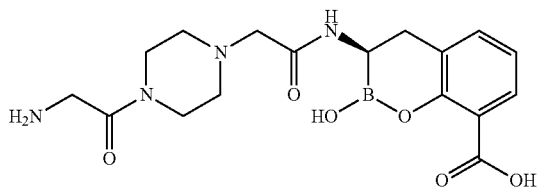 [SMILES: NCC(=O)N1CCN(CC(=O)N[C@H]2Cc3cccc(C(=O)O)c3OB2O)CC1]

Step 1. Synthesis of 3-[2-{2-[4-(2-tert-Butoxycarbonylamino-acetyl)-piperazin-1-yl]-acetylamino}-2-(2,9,9-trimethyl-3,5-dioxa-4-bora-tricylo[6.1.1.02,6]dec-4-yl)-ethyl]-2-methoxy-benzoic acid tert-butyl ester Prepared from 2-Methoxy-3-(2,9,9-trimethyl-3,5-dioxa-4-bora-tricyclo[6.1.1.02,6]dec-4-ylmethyl)-benzoic acid tert-butyl ester and (2-oxo-2-piperazin-1-yl-ethyl)carbamic acid t-butylester following the procedure described in Step 4 of Example 1. The crude product was purified by a reverse phase preparative HPLC [Waters Sunfire C18 OBD, 5 μm, 19×50 mm, 5-100% AcCN:H$_2$O (with 0.1% TFA)] to give a 15% yield of product. ESI-MS m/z 713 (MH)$^+$.

Step 2. Synthesis of 3-{2-[4-(2-Amino-acetyl)-piperazin-1-yl]-acetylamino}-2-hydroxy-3,4-dihydro-2H-benzo[e][1,2]oxaborinine-8-carboxylic acid Prepared from 3-[2-{2-[4-(2-tert-Butoxycarbonylamino-acetyl)-piperazin-1-yl]-acetylamino}-2-(2,9,9-trimethyl-3,5-dioxa-4-bora-tricyclo[6.1.1.02,6]dec-4-yl)-ethyl]-2-methoxy-benzoic acid tert-butyl ester and BCl$_3$ following the procedure described in Step 5 of Example 1. The crude product was purified by reverse phase preparative HPLC [Waters Sunfire C18 OBD, 5 μm, 19×50 mm, 5-50% AcCN:H$_2$O (with 0.1% TFA)] to give a 14% yield of product as a white solid. ESI-MS m/z 391 (MH)$^+$.

Example 18: 2-Hydroxy-3-{2-[4-(2-hydroxy-ethyl)-piperazin-1-yl]-acetylamino}-3,4-dihydro-2H-benzo[e][1,2]oxaborinine-8-carboxylic acid

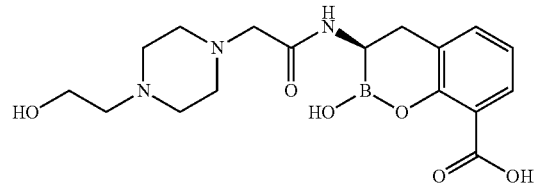 [SMILES: O=C(CN1CCN(CCO)CC1)N[C@H]1Cc2cccc(C(=O)O)c2OB1O]

Step 1. Synthesis of 3-[2-{2-[4-(2-Benzyloxy-ethyl)-piperazin-1-yl]-acetylamino}-2-(2,9,9-trimethyl-3,5-dioxa-4-bora-tricyclo[6.1.1.02,6]dec-4-yl)-ethyl]-2-methoxy-benzoic acid tert-butyl ester Prepared from 2-Methoxy-3-(2,9,9-trimethyl-3,5-dioxa-4-bora-tricyclo[6.1.1.02,6]dec-4-ylmethyl)-benzoic acid tert-butyl ester and 1-(2-benzyloxyethyl)piperazine following the procedure described in Step 4 of Example 1. The crude product was purified by a reverse phase preparative HPLC [Waters Sunfire C18 OBD, 5 μm, 19×50 mm, 5-100% AcCN:H$_2$O (with 0.1% TFA)] to give a 9% yield of product. ESI-MS m/z 690 (MH)$^+$.

Step 2. Synthesis of 2-Hydroxy-3-{2-[4-(2-hydroxy-ethyl)-piperazin-1-yl]-acetylamino}-3,4-dihydro-2H-benzo[e][1,2]oxaborinine-8-carboxylic acid Prepared from 3-[2-{2-[4-(2-Benzyloxy-ethyl)-piperazin-1-yl]-acetylamino}-2-(2,9,9-trimethyl-3,5-dioxa-4-bora-tricyclo[6.1.1.02,6]dec-4-yl)-ethyl]-2-methoxy-benzoic acid tert-butyl ester and BCl$_3$ following the procedure described in Step 5 of Example 1. The crude product was purified by reverse phase preparative HPLC [Waters Sunfire C18 OBD, 5 μm, 19×50 mm, 5-40% AcCN:H$_2$O (with 0.1% TFA)] to give a 8% yield of product as a white solid.

ESI-MS m/z 378 (MH).

Example 19: 3-[2-(3-Aminomethyl-piperidin-1-yl)-acetylamino]-2-hydroxy-3,4-dihydro-2H-benzoe[e][1,2]oxaborinine-8-carboxylic acid

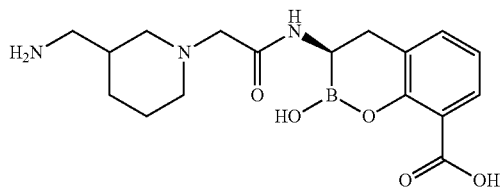 [SMILES: NCC1CCCN(CC(=O)N[C@H]2Cc3cccc(C(=O)O)c3OB2O)C1]

Step 1. Synthesis of 3-[2-{2-[3-(tert-Butoxycarbonylamino-methyl)-piperidin-1-yl]-acetylamino}-2-(2,9,9-trimethyl-3,5-dioxa-4-bora-tricyclo[6.1.1.02,6]dec-4-yl)-ethyl]-2-methoxy-benzoic acid tert-butyl ester Prepared from 2-Methoxy-3-(2,9,9-trimethyl-3,5-dioxa-4-bora-tricyclo[6.1.1.02,6]dec-4-ylmethyl)-benzoic acid tert-butyl ester and 3-(Boc-aminomethyl)piperidine following the procedure described in Step 4 of Example 1. The crude product was purified by a reverse phase preparative HPLC [Waters Sunfire C18 OBD, 5 μm, 19×50 mm, 5-100% AcCN:H$_2$O (with 0.1% TFA)] to give a 15% yield of product. ESI-MS m/z 684 (MH)$^+$.

Step 2. Synthesis of 3-[2-(3-Aminomethyl-piperidin-1-yl)-acetylamino]-2-hydroxy-3,4-dihydro-2H-benzo[e][1,2]oxaborinine-8-carboxylic acid Prepared from 3-[2-{2-[3-(tert-Butoxycarbonylaminomethyl)-piperidin-1-yl]-acetylamino}-2-(2,9,9-trimethyl-3,5-dioxa-4-bora-tricyclo[6.1.1.02,6]dec-4-yl)-ethyl]-2-methoxy-benzoic acid tert-butyl ester and BCl$_3$ following the procedure described in Step 5 of Example 1. The crude product was purified by reverse phase preparative HPLC [Waters Sunfire C18 OBD, 5 μm, 19×50 mm, 5-40% AcCN:H$_2$O (with 0.1% TFA)] to give a 28% yield of product as a white solid. ESI-MS m/z 362 (MH)$^+$.

Example 20: 2-Hydroxy-3-[2-(3-hydroxy-4-methyl-amino-piperidin-1-yl)-acetylamino]-3,4-dihydro-2H-benzo[e][1,2]oxaborinine-8-carboxylic acid

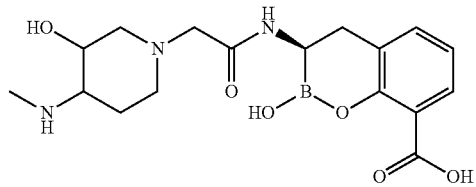 [SMILES: CNC1CCN(CC(=O)N[C@H]2Cc3cccc(C(=O)O)c3OB2O)CC1O]

Step 1. Synthesis of 3,6-Dihydro-2H-pyridine-1-carboxylic acid benzyl ester

Triethylamine (16.8 mL, 120.5 mmol) was added to a solution of 1,2,3,6-tetrahydropyridine (5.5 mL, 60.3 mmol) in DCM (50 mL) under argon. The solution was cooled to 0° C. for 15 minutes. Benzyl chloroformate (9.5 mL, 66.5 mmol) was added slowly. The reaction was stirred at 0° C. for 30 minutes then allowed to come to room temperature overnight. The reaction was diluted with diethyl ether (300 mL) and washed successively with 0.5N HCl (2×), saturated NaHCO$_3$, and brine. The organic layer was dried over Na$_2$SO$_4$, filtered, and concentrated in vacuo to afford 8.58 g (65%) of product as a clear oil. ESI-MS m/z 218 (MH)$^+$.

Step 2. Synthesis of 7-Oxa-3-aza-bicyclo[4.1.0]heptane-3-carboxylic acid benzyl ester A solution of 3,6-Dihydro-2H-pyridine-1-carboxylic acid benzyl ester (8.58 g, 39.5 mmol) in DCM (80 mL) under argon was cooled to 0° C. m-Chloroperoxybenzoic acid (10.95 g, 75%, 47.6 mmol) in DCM (60 mL) was added dropwise over 20 minutes. The reaction was stirred at 0° C. for 30 minutes then allowed to come to room temperature overnight. The reaction was diluted with DCM and washed successively with aqueous Na$_2$S$_2$O$_3$, saturated NaHCO$_3$, and brine. The organic layer was dried over Na$_2$SO$_4$, filtered, and concentrated to provide 8.45 g (92%) of a white solid. ESI-MS m/z 256 (M+Na)$^+$.

Step 3. Synthesis of 4-Azido-3-hydroxy-piperidine-1-carboxylic acid benzyl ester and 3-Azido-4-hydroxy-piperidine-1-carboxylic acid benzyl ester Sodium azide (3.56 g, 54.8 mmol) in acetone (50 mL)/H$_2$O (25 mL) was added slowly to a solution of 7-Oxa-3-aza-bicyclo[4.1.0]heptane-3-carboxylic acid benzyl ester (8.45 g, 36.2 mmol) in DMF (72 mL). The reaction was heated at 80° C. for 24 h. The reaction was cooled to room temperature and concentrated in vacuo. The residue was diluted with ethyl acetate and washed with H$_2$O, 10% aqueous LiCl, and brine. The organic layer was dried over Na$_2$SO$_4$, filtered, and concentrated. Purification by flash chromatography (0-50% EtOAc/hexane) afforded 6.51 g of 4-Azido-3-hydroxy-piperidine-1-carboxylic acid benzyl ester and 1.12 g of 3-Azido-4-hydroxy-piperidine-1-carboxylic acid benzyl ester for a total 76% yield. ESI-MS m/z 299 (M+Na)$^+$.

Step 4. Synthesis of 4-tert-Butoxycarbonylamino-3-hydroxy-piperidine-1-carboxylic acid benzyl ester A solution of 4-Azido-3-hydroxy-piperidine-1-carboxylic acid benzyl ester (6.51 g, 23.6 mmol), triphenylphosphine (12.52 g, 47.7 mmol), H$_2$O (1.8 mL, 100 mmol), and THF (180 mL) was heated at 70° C. for 17 h. The reaction was cooled to room temperature, diluted with ethyl acetate, and washed with 1N HCl (2×). The combined aqueous layers were basified to pH~12 with 10 ON NaOH and extracted with ethyl acetate (3×). The combined organic layers were dried over Na$_2$SO$_4$, filtered, and concentrated. The product was dissolved in DCM (130 mL) under argon. Triethylamine (4.0 mL, 28.7 mmol) and di-tert-butyldicarbonate (5.70 g, 26.1 mmol) in DCM (30 mL) were added and the reaction stirred at room temperature for 18 h. The reaction was quenched with saturated NaHCO$_3$ and extracted with DCM. The organic layer was dried over Na$_2$SO$_4$, filtered, and concentrated. Flash chromatography (0-60% EtOAc/hexane) provided 6.48 g (78%) of product as a white solid. ESI-MS m/z 351 (MH)$^+$.

Step 5. Synthesis of 4-tert-Butoxycarbonylamino-3-(tert-butyl-dimethyl-silanyloxy)-piperidine-1-carboxylic acid benzyl ester A mixture of 4-tert-Butoxycarbonylamino-3-hydroxy-piperidine-1-carboxylic acid benzyl ester (0.725 g, 2.07 mmol), imidazole (0.360 g, 5.29 mmol), and DMF (6.0 mL) under argon was cooled to 0° C. for 15 minutes. tert-Butyldimethylsilyl chloride (0.382 g, 2.53 mmol) was added in one portion and the reaction was warmed to room temperature for 15 h. The reaction was quenched with brine and extracted with diethyl ether (2×). The combined organic layers were dried over MgSO$_4$, filtered, and concentrated to afford 1.08 g of crude product which was carried to the next step without purification. ESI-MS m/z 465 (MH)$^+$.

Step 6. Synthesis of 4-(tert-Butoxycarbonyl-methyl-amino)-3-(tert-butyl-dimethyl-silanyloxy)-piperidine-1-carboxylic acid benzyl ester A solution of 4-tert-Butoxycarbonylamino-3-(tert-butyl-dimethyl-silanyloxy)-piperidine-1-carboxylic acid benzyl ester (0.961 g, 2.07 mmol) in DMF (15 mL) under argon was cooled to 0° C. Sodium hydride (0.206 g, 60% in mineral oil, 5.15 mmol) was added in one portion and the reaction stirred at 0° C. for 35 minutes. Iodomethane (0.32 mL, 5.14 mmol) was added dropwise and the reaction warmed to room temperature for 22 h. The reaction was quenched with H$_2$O and extracted with diethyl ether (2×). The combined organic layers were dried over MgSO$_4$, filtered, and concentrated to give 1.01 g of crude product which was carried to the next step without purification. ESI-MS m/z 479 (MH)$^+$.

Step 7. Synthesis of [3-(tert-Butyl-dimethyl-silanyloxy)-piperidin-4-yl]-methyl-carbamic acid tert-butyl ester A solution of 4-(tert-Butoxycarbonyl-methyl-amino)-3-(tert-butyl-dimethyl-silanyloxy)-piperidine-1-carboxylic acid benzyl ester (0.990 g, 2.07 mmol) in methanol (20 mL) was purged with argon for 5 minutes. Pd(OH)$_2$ (0.080 g, 20% on carbon) was added, the flask evacuated, and the reaction placed under a hydrogen atmosphere for 24 h. The reaction was filtered through a Celite-plugged filter frit, washed with methanol and DCM, and concentrated in vacuo to afford 0.750 g of crude product as a white solid. ESI-MS m/z 345 (MH)$^+$.

Step 8. Synthesis of 3-[2-{2-[4-(tert-Butoxycarbonyl-methyl-amino)-3-(tert-butyl-dimethyl-silanyloxy)-piperidin-1-yl]-acetylamino}-2-(2,9,9-trimethyl-3,5-dioxa-4-bora-tricyclo[6.1.1.0$^{2,6}$]dec-4-yl)-ethyl]-2-methoxy-benzoic acid tert-butyl ester Prepared from 2-Methoxy-3-(2,9,9-trimethyl-3,5-dioxa-4-bora-tricyclo[6.1.1.0$^{2,6}$]dec-4-ylmethyl)-benzoic acid tert-butyl ester and [3-(tert-Butyl-dimethyl-silanyloxy)-piperidin-4-yl]-methyl-carbamic acid tert-butyl ester following the procedure described in Step 4 of Example 1.

The crude product was purified by a reverse phase preparative HPLC [Waters Sunfire C18 OBD, 5 µm, 19×50 mm, 5-100% AcCN:H$_2$O (with 0.1% TFA)] to give a 6% yield of product.
ESI-MS m/z 814 (MH)$^+$.

Step 9. Synthesis of 2-Hydroxy-3-[2-(3-hydroxy-4-methylamino-piperidin-1-yl)-acetylamino]-3,4-dihydro-2H-benzo[e][1,2]oxaborinine-8-carboxylic acid Prepared from 3-[2-{2-[4-(tert-Butoxycarbonyl-methyl-amino)-3-(tert-butyl-dimethyl-silanyloxy)-piperidin-1-yl]-acetylamino}-2-(2,9,9-trimethyl-3,5-dioxa-4-bora-tricyclo[6.1.1.0$^{2,6}$]dec-4-yl)-ethyl]-2-methoxy-benzoic acid tert-butyl ester and BCl$_3$ following the procedure described in Step 5 of Example 1. The crude product was purified by reverse phase preparative HPLC [Waters Sunfire C18 OBD, 5 µm, 19×50 mm, 5-50% AcCN:H$_2$O (with 0.1% TFA)] to give a 5% yield of product as a white solid. ESI-MS m/z 378 (MH)$^+$.

Example 21: 3-[2-(4-Amino-3-methoxy-piperidin-1-yl)-acetylamino]-2-hydroxy-3,4-dihydro-2H-benzo[e][1,2]oxaborinine-8-carboxylic acid

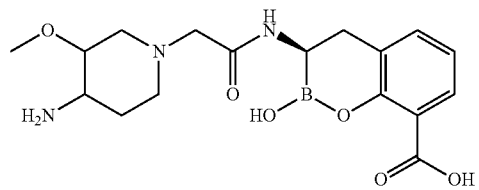 [SMILES: COC1CN(CC(=O)N[C@H]2Cc3cccc(C(=O)O)c3OB2O)CCC1N]

Step 1. Synthesis of 4-tert-Butoxycarbonylamino-3-methoxy-piperidine-1-carboxylic acid benzyl ester A solution of 4-tert-Butoxycarbonylamino-3-hydroxy-piperidine-1-carboxylic acid benzyl ester (prepared in Example 20, Step 4, 0.840 g, 2.40 mmol) in THF (6.0 mL) under argon was cooled to 0° C. Sodium hydride (0.123 g, 60%, 3.08 mmol) was added in one portion and the reaction stirred at 0° C. for 30 minutes. Iodomethane (0.16 mL, 2.57 mmol) was added slowly and the reaction warmed to room temperature for 17 h. The reaction was quenched with H$_2$O and extracted with ethyl acetate (2×). The combined organic layers were washed with saturated NaHCO$_3$ and brine, dried over Na$_2$SO$_4$, filtered, and concentrated to provide 0.840 g (96%) of product. ESI-MS m/z 365 (MH)$^+$.

Step 2. Synthesis of (3-Methoxy-piperidin-4-yl)-carbamic acid tert-butyl ester

A solution of 4-tert-Butoxycarbonylamino-3-methoxy-piperidine-1-carboxylic acid benzyl ester (0.840 g, 2.31 mmol) in methanol (24 mL) was purged with argon for 5 minutes. Pd(OH)$_2$ (0.067, 20% on carbon) was added, flask evacuated, and the reaction stirred under hydrogen atmosphere for 24 h. The reaction was filtered through a Celite-plugged filter frit, washed with methanol and DCM, and concentrated to afford 0.490 g (92%) of product as a white solid. ESI-MS m/z 365 (MH)$^+$.

Step 3. Synthesis of 3-[2-{2-[4-(tert-Butoxycarbonyl-methyl-amino)-3-methoxy-piperidin-1-yl]-acetylamino}-2-(2,9,9-trimethyl-3,5-dioxa-4-bora-tricyclo[6.1.1.0$^{2,6}$]dec-4-yl)-ethyl]-2-methoxy-benzoic acid tert-butyl ester Prepared from 2-Methoxy-3-(2,9,9-trimethyl-3,5-dioxa-4-bora-tricyclo[6.1.1.0$^{2,6}$]dec-4-ylmethyl)-benzoic acid tert-butyl ester and (3-Methoxy-piperidin-4-yl)-carbamic acid tert-butyl ester following the procedure described in Step 4 of Example 1. The crude product was purified by a reverse phase preparative HPLC [Waters Sunfire C18 OBD, 5 µm, 19×50 mm, 5-100% AcCN:H$_2$O (with 0.1% TFA)] to give a 11% yield of product. ESI-MS m/z 700 (MH)$^+$.

Step 4. Synthesis of 3-[2-(4-Amino-3-methoxy-piperidin-1-yl)-acetylamino]-2-hydroxy-3,4-dihydro-2H-benzo[e][1,2]oxaborinine-8-carboxylic acid Prepared from 3-[2-{2-[4-(tert-Butoxycarbonyl-methyl-amino)-3-methoxy-piperidin-1-yl]-acetylamino}-2-(2,9,9-trimethyl-3,5-dioxa-4-bora-tricyclo[6.1.1.0²,⁶]dec-4-yl)-ethyl]-2-methoxy-benzoic acid tert-butyl ester and $BCl_3$ following the procedure described in Step 5 of Example 1. The crude product was purified by reverse phase preparative HPLC [Waters Sunfire C18 OBD, 5 μm, 19×50 mm, 5-40% AcCN:H$_2$O (with 0.1% TFA)] to give a 3% yield of product as a white solid. ESI-MS m/z 378 (MH)⁺.

Example 22: 3-[3-(4-Amino-piperidin-1-yl)-propionylamino]-2-hydroxy-3,4-dihydro-2H-benzo[e][1,2]oxaborinine-8-carboxylic acid

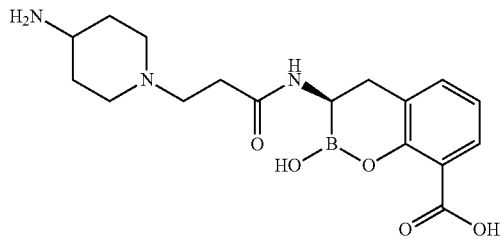 [SMILES: NC1CCN(CCC(=O)N[C@H]2Cc3cccc(C(=O)O)c3OB2O)CC1]

Step 1. Synthesis of 3-[2-[3-(4-tert-Butoxycarbonylamino-piperidin-1-yl)-propionylamino]-2-(2,9,9-trimethyl-3,5-dioxa-4-bora-tricyclo[6.1.1.0²,⁶]dec-4-yl)-ethyl]-2-methoxy-benzoic acid tert-butyl ester A solution of dichloromethane (0.31 mL, 4.85 mmol) in THF (3.4 mL) under argon was cooled to −100° C. (MeOH, liquid N$_2$ slush bath). n-BuLi (1.7 mL, 2.5M in hexane, 4.25 mmol) was added dropwise over 10 minutes and the reaction stirred at −100° C. for 30 minutes. A THF (3.0 mL) solution of 2-Methoxy-3-(2,9,9-trimethyl-3,5-dioxa-4-bora-tricyclo[6.1.1.0²,⁶]dec-4-ylmethyl)-benzoic acid tert-butyl ester (1.14 g, 2.85 mmol) was added dropwise over 12 minutes. After 10 minutes, the cooling bath was removed and the reaction stirred at 0° C. for 1 h. The reaction was then cooled to −78° C. for 30 minutes. LiHMDS (4.4 mL, 1.0M in THF, 4.4 mmol) was added dropwise over 10 minutes and the reaction allowed to slowly warm to room temperature while stirring overnight. Upon cooling to −10° C., anhydrous MeOH (0.16 mL, 3.96 mmol) was added and the reaction stirred at −10° C. for 1 h then warmed to room temperature for 1 h. The reaction was cooled back down to −20° C. and 3-bromopropionyl chloride (0.37 mL, 3.67 mmol) was added slowly. After 10 minutes, the cooling bath was removed and the reaction stirred at room temperature for 4.5 h. At this stage, LCMS indicated the formation of the 3-[2-(3-Bromo-propionylamino)-2-(2,9,9-trimethyl-3,5-dioxa-4-bora-tricyclo[6.1.1.0²,⁶]dec-4-yl)-ethyl]-2-methoxy-benzoic acid tert-butyl ester intermediate.

In a separate dry round bottom flask under argon, 4-(N-Boc-amino)piperidine (0.715 g, 3.57 mmol) and THF (2.6 mL) were added. Sodium hydride (0.177 g, 60%, 4.42 mmol) was added followed by the previously prepared bromide solution and the reaction stirred at room temperature for 17 h. The reaction was quenched with H$_2$O and extracted with EtOAc (3×). The combined organic layers were dried over Na$_2$SO$_4$, filtered, and concentrated. The residue was purified by a reverse phase preparative HPLC [Waters Sunfire C18 OBD, 5 μm, 19×50 mm, 5-100% AcCN:H$_2$O (with 0.1% TFA)] to afford 0.112 g (11%) of product. ESI-MS m/z 684 (MH)⁺.

Step 2. Synthesis of 3-[3-(4-Amino-piperidin-1-yl)-propionylamino]-2-hydroxy-3,4-dihydro-2H-benzo[e][1,2]oxaborinine-8-carboxylic acid Prepared from 3-[2-[3-(4-tert-Butoxycarbonylamino-piperidin-1-yl)-propionylamino]-2-(2,9,9-trimethyl-3,5-dioxa-4-bora-tricyclo[6.1.1.0²,⁶]dec-4-yl)-ethyl]-2-methoxy-benzoic acid tert-butyl ester and $BCl_3$ following the procedure described in Step 5 of Example 1. The crude product was purified by reverse phase preparative HPLC [Waters Sunfire C18 OBD, 5 μm, 19×50 mm, 5-50% AcCN:H$_2$O (with 0.1% TFA)] to give a 42% yield of product as a white solid. ESI-MS m/z 362 (MH)⁺.

Example 23: 2-Hydroxy-3-(3-piperazin-1-yl-propionylamino)-3,4-dihydro-2H-benzo[e][1,2]oxaborinine-8-carboxylic acid

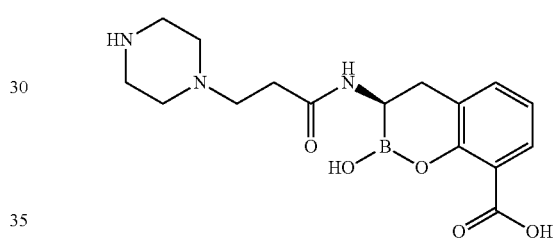

Step 1. Synthesis of 4-{2-[2-(3-tert-Butoxycarbonyl-2-methoxy-phenyl)-1-(2,9,9-trimethyl-3,5-dioxa-4-bora-tricyclo[6.1.1.0²,⁶]dec-4-yl)-ethylcarbamoyl]-ethyl}-piperazine-1-carboxylic acid tert-butyl ester Prepared from 2-Methoxy-3-(2,9,9-trimethyl-3,5-dioxa-4-bora-tricyclo[6.1.1.0²,⁶]dec-4-ylmethyl)-benzoic acid tert-butyl ester and 1-Z-piperazine following the procedure described in Step 1 of Example 22. The crude product was purified by a reverse phase preparative HPLC [Waters Sunfire C18 OBD, 5 μm, 19×50 mm, 5-100% AcCN:H$_2$O (with 0.1% TFA)] to give a 9% yield of product. ESI-MS m/z 704 (MH)⁺.

Step 2. Synthesis of 2-Hydroxy-3-(3-piperazin-1-yl-propionylamino)-3,4-dihydro-2H-benzo[e][1,2]oxaborinine-8-carboxylic acid Prepared from 4-{2-[2-(3-tert-Butoxycarbonyl-2-methoxy-phenyl)-1-(2,9,9-trimethyl-3,5-dioxa-4-bora-tricyclo[6.1.1.0²,⁶]dec-4-yl)-ethylcarbamoyl]-ethyl}-piperazine-1-carboxylic acid tert-butyl ester and $BCl_3$ following the procedure described in Step 5 of Example 1. The crude product was purified by reverse phase preparative HPLC [Waters Sunfire C18 OBD, 5 m, 19×50 mm, 5-95% AcCN:H$_2$O (with 0.1% TFA)] to give a 35% yield of product as a white solid. ESI-MS m/z 348 (MH)⁺.

Example 24: 3-[2-(4-Amino-3-hydroxy-piperidin-1-yl)-acetylamino]-2-hydroxy-3,4-dihydro-2H-benzo[e][1,2]oxaborinine-8-carboxylic acid

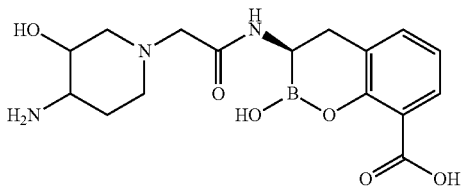

Step 1. Synthesis of [3-(tert-Butyl-dimethyl-silanyloxy)-piperidin-4-yl]-carbamic acid tert-butyl ester A solution of 4-tert-Butoxycarbonylamino-3-(tert-butyl-dimethyl-silanyloxy)-piperidine-1-carboxylic acid benzyl ester (0.907 g, 1.95 mmol) in methanol (22 mL) was purged with argon for 5 minutes. Pd(OH)$_2$ (0.073 g, 20% on carbon) was added, the flask evacuated, and the reaction placed under a hydrogen atmosphere for 22 h. The reaction was filtered through a Celite-plugged filter frit, washed with methanol and DCM, and concentrated in vacuo to afford 0.656 g of crude product as a white solid. ESI-MS m/z 331 (MH)$^+$.

Step 2. Synthesis of 3-[2-{2-[4-tert-Butoxycarbonylamino-3-(tert-butyl-dimethyl-silanyloxy)-piperidin-1-yl]-acetylamino}-2-(2,9,9-trimethyl-3,5-dioxa-4-bora-tricyclo[6.1.1.0 2,6]dec-4-yl)-ethyl]-2-methoxy-benzoic acid tert-butyl ester Preparation of the 3-[2-(2-Bromo-acetylamino)-2-(2,9,9-trimethyl-3,5-dioxa-4-bora-tricyclo[6.1.1.02,6]dec-4-yl)-ethyl]-2-methoxy-benzoic acid tert-butyl ester intermediate was carried out as in Step 4 of Example 1.

In a separate dry round bottom flask under argon, [3-(tert-Butyl-dimethyl-silanyloxy)-piperidin-4-yl]-carbamic acid tert-butyl ester (0.656 g, 1.98 mmol) and THF (2.6 mL) were added. Sodium hydride (0.098 g, 60%, 2.45 mmol) was added followed by the previously prepared bromide solution and the reaction stirred at room temperature for 17 h. The reaction was quenched with H$_2$O and extracted with EtOAc (3×). The combined organic layers were dried over Na$_2$SO$_4$, filtered, and concentrated. The residue was purified by a reverse phase preparative HPLC [Waters Sunfire C18 OBD, 5 µm, 19×50 mm, 5-100% AcCN:H$_2$O (with 0.1% TFA)] to afford 0.084 g (8%) of product. ESI-MS m/z 801 (MH)$^+$.

Step 3. Synthesis of 3-[2-(4-Amino-3-hydroxy-piperidin-1-yl)-acetylamino]-2-hydroxy-3,4-dihydro-2H-benzo[e][1,2]oxaborinine-8-carboxylic acid Prepared from 3-[2-{2-[4-tert-Butoxycarbonylamino-3-(tert-butyl-dimethyl-silanyloxy)-piperidin-1-yl]-acetylamino}-2-(2,9,9-trimethyl-3,5-dioxa-4-bora-tricyclo[6.1.1.02,6]dec-4-yl)-ethyl]-2-methoxy-benzoic acid tert-butyl ester and BCl$_3$ following the procedure described in Step 5 of Example 1. The crude product was purified by reverse phase preparative HPLC [Waters Sunfire C18 OBD, 5 µm, 19×50 mm, 5-50% AcCN:H$_2$O (with 0.1% TFA)] to give a 4% yield of product as a white solid. ESI-MS m/z 364 (MH)$^+$.

Example 25: 3-[2-(4-Carboxymethyl-piperazin-1-yl)-acetylamino]-2-hydroxy-3,4-dihydro-2H-benzo[e][1,2]oxaborinine-8-carboxylic acid

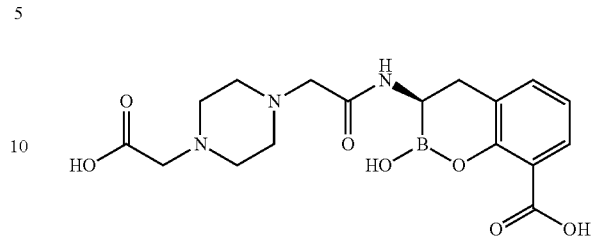

Step 1. Synthesis of 3-[2-[2-(4-tert-Butoxycarbonylmethyl-piperazin-1-yl)-acetylamino]-2-(2,9,9-trimethyl-3,5-dioxa-4-bora-tricyclo[6.1.1.02,6]dec-4-yl)-ethyl]-2-methoxy-benzoic acid tert-butyl ester Prepared from 2-Methoxy-3-(2,9,9-trimethyl-3,5-dioxa-4-bora-tricyclo[6.1.1.02,6]dec-4-ylmethyl)-benzoic acid tert-butyl ester and tert-butylpiperazin-1-ylacetate following the procedure described in Step 2 of Example 24. The crude product was purified by a reverse phase preparative HPLC [Phenomenex Luna, 5 µm, 30×75 mm, 5-100% AcCN:H$_2$O (with 0.1% TFA)] to give a 8% yield of product. ESI-MS m/z 670 (MH)$^+$.

Step 2. Synthesis of 3-[2-(4-Carboxymethyl-piperazin-1-yl)-acetylamino]-2-hydroxy-3,4-dihydro-2H-benzo[e][1,2]oxaborinine-8-carboxylic acid Prepared from 3-[2-[2-(4-tert-Butoxycarbonylmethyl-piperazin-1-yl)-acetylamino]-2-(2,9,9-trimethyl-3,5-dioxa-4-bora-tricyclo[6.1.1.02,6]dec-4-yl)-ethyl]-2-methoxy-benzoic acid tert-butyl ester and BCl$_3$ following the procedure described in Step 5 of Example 1. The crude product was purified by reverse phase preparative HPLC [Waters Sunfire C18 OBD, 5 µm, 19×50 mm, 5-50% AcCN:H$_2$O (with 0.1% TFA)] to give a 12% yield of product as a white solid. ESI-MS m/z 392 (MH)$^+$.

Example 26: 3-[2-(3-Amino-4-hydroxy-piperidin-1-yl)-acetylamino]-2-hydroxy-3,4-dihydro-2H-benzo[e][1,2]oxaborinine-8-carboxylic acid

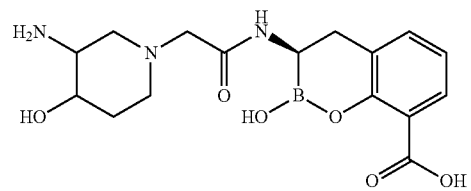 [SMILES: NC1CN(CC(=O)N[C@H]2Cc3cccc(C(=O)O)c3OB2O)CCC1O]

Step 1. Synthesis of 3-tert-Butoxycarbonylamino-4-hydroxy-piperidine-1-carboxylic acid benzyl ester A solution of 3-Azido-4-hydroxy-piperidine-1-carboxylic acid benzyl ester (prepared in Step 3, Example 20) (1.12 g, 4.05 mmol), triphenylphosphine (2.12 g, 8.10 mmol), H$_2$O (0.40 mL, 22.2 mmol), and THF (31 mL) was heated at 70° C. for 17 h. The reaction was cooled to room temperature, diluted with ethyl acetate, and washed with 1N HCl (2×). The combined aqueous layers were basified to pH~12 with 10N NaOH and extracted with ethyl acetate (3×). The combined organic layers were dried over $Na_2SO_4$, filtered, and concentrated. The product was dissolved in DCM (22 mL) under argon. Triethylamine (0.70 mL, 5.02 mmol) and di-tert-butyldicarbonate (0.991 g, 4.54 mmol) in DCM (8 mL) were added and the reaction stirred at room temperature for 18 h. The reaction was quenched with saturated $NaHCO_3$ and extracted with DCM. The organic layer was dried over $Na_2SO_4$, filtered, and concentrated. Flash chromatography (0-100% EtOAc/hexane) provided 1.08 g (76%) of product as a white solid.

ESI-MS m/z 351 (MH).

Step 2. Synthesis of (4-Hydroxy-piperidin-3-yl)-carbamic acid tert-butyl ester A solution of 3-tert-Butoxycarbonylamino-4-hydroxy-piperidine-1-carboxylic acid benzyl ester (1.08 g, 3.08 mmol) in methanol (32 mL) was purged with argon for 10 minutes. $Pd(OH)_2$ (0.086 g, 20% on carbon) was added, the flask evacuated, and the reaction placed under a hydrogen atmosphere for 23 h. The reaction was filtered through a Celite-plugged filter frit, washed with methanol and DCM, and concentrated in vacuo to afford 0.676 g of crude product as a white solid. ESI-MS m/z 217 $(MH)^+$.

Step 3. Synthesis of 3-[2-[2-(3-tert-Butoxycarbonylamino-4-hydroxy-piperidin-1-yl)-acetylamino]-2-(2,9,9-trimethyl-3,5-dioxa-4-bora-tricyclo[6.1.1.02,6]dec-4-yl)-ethyl]-2-methoxy-benzoic acid tert-butyl ester Prepared from 2-Methoxy-3-(2,9,9-trimethyl-3,5-dioxa-4-bora-tricyclo[6.1.1.02,6]dec-4-ylmethyl)-benzoic acid tert-butyl ester and (4-Hydroxy-piperidin-3-yl)-carbamic acid tert-butyl ester following the procedure described in Step 2 of Example 24. The crude product was purified by a reverse phase preparative HPLC [Phenomenex Luna, 5 μm, 30×75 mm, 5-100% AcCN:$H_2O$ (with 0.1% TFA)] to give a 3% yield of product. ESI-MS m/z 686 $(MH)^+$.

Step 4. Synthesis of 3-[2-(3-Amino-4-hydroxy-piperidin-1-yl)-acetylamino]-2-hydroxy-3,4-dihydro-2H-benzo[e][1,2]oxaborinine-8-carboxylic acid Prepared from 3-[2-[2-(3-tert-Butoxycarbonylamino-4-hydroxy-piperidin-1-yl)-acetylamino]-2-(2,9,9-trimethyl-3,5-dioxa-4-bora-tricyclo[6.1.1.02,6]dec-4-yl)-ethyl]-2-methoxy-benzoic acid tert-butyl ester and $BCl_3$ following the procedure described in Step 5 of Example 1. The crude product was purified by reverse phase preparative HPLC [Waters Sunfire C18 OBD, 5 μm, 19×50 mm, 5-40% AcCN: $H_2O$ (with 0.1% TFA)] to give a 34% yield of product as a white solid. ESI-MS m/z 364 $(MH)^+$.

Example 27: 3-{2-[4-(3-Amino-propionylamino)-piperidin-1-yl]-acetylamino}-2-hydroxy-3,4-dihydro-2H-benzo[e][1,2]oxaborinine-8-carboxylic acid

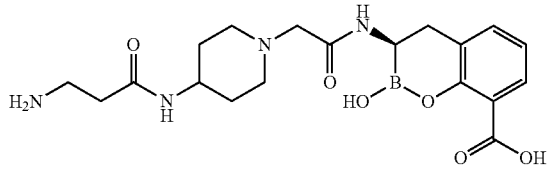 [SMILES: NCCC(=O)NC1CCN(CC(=O)N[C@H]2Cc3cccc(C(=O)O)c3OB2O)CC1]

Step 1. Synthesis of 4-(3-tert-Butoxycarbonylamino-propionylamino)-piperidine-1-carboxylic acid benzyl ester N-Methylmorpholine (0.44 mL, 4.00 mmol) and HATU (1.05 g, 2.76 mmol) were added to a solution of Boc-β-Ala-OH (0.501 g, 2.65 mmol) in DCM (24 mL) under argon and the reaction was stirred at room temperature for 30 minutes. 4-Amino-1-N-CBz-piperidine (0.588 g, 2.51 mmol) was added in one portion and the reaction stirred for 95 h. The reaction was quenched with 0.25M HCl and extracted with DCM. The organic layer was washed with saturated $NaHCO_3$ and brine, dried over $Na_2SO_4$, filtered, and concentrated to provide 1.00 g of crude product which was carried to the next step without purification. ESI-MS m/z 406 $(MH)^+$.

Step 2. Synthesis of [2-(Piperidin-4-ylcarbamoyl)-ethyl]-carbamic acid tert-butyl ester A solution of 4-(3-tert-Butoxycarbonylamino-propionylamino)-piperidine-1-carboxylic acid benzyl ester (1.00 g, 2.47 mmol) in methanol (25 mL) was purged with argon for 8 minutes. $Pd(OH)_2$ (0.088 g, 20% on carbon) was added, the flask evacuated, and the reaction placed under a hydrogen atmosphere for 23 h. The reaction was filtered through a Celite-plugged filter frit, washed with methanol and DCM, and concentrated in vacuo to afford 0.699 g of crude product as a white solid. ESI-MS m/z 272 $(MH)^+$.

Step 3. Synthesis of 3-[2-{2-[4-(3-tert-Butoxycarbonylamino-propionylamino)-piperidin-1-yl]-acetylamino}-2-(2,9,9-trimethyl-3,5-dioxa-4-bora-tricyclo[6.1.1.02,6]dec-4-yl)-ethyl]-2-methoxy-benzoic acid tert-butyl ester Prepared from 2-Methoxy-3-(2,9,9-trimethyl-3,5-dioxa-4-bora-tricyclo[6.1.1.02,6]dec-4-ylmethyl)-benzoic acid tert-butyl ester and [2-(Piperidin-4-ylcarbamoyl)-ethyl]-carbamic acid tert-butyl ester following the procedure described in Step 2 of Example 24. The crude product was purified by a reverse phase preparative HPLC [Phenomenex Luna, 5 μm, 30×75 mm, 5-100% AcCN:$H_2O$ (with 0.1% TFA)] to give a 9% yield of product. ESI-MS m/z 741 $(MH)^+$.

Step 4. Synthesis of 3-{2-[4-(3-Amino-propionylamino)-piperidin-1-yl]-acetylamino}-2-hydroxy-3,4-dihydro-2H-benzo[e][1,2]oxaborinine-8-carboxylic acid Prepared from 3-[2-{2-[4-(3-tert-Butoxycarbonylamino-propionylamino)-piperidin-1-yl]-acetylamino}-2-(2,9,9- trimethyl-3,5-dioxa-4-bora-tricyclo[6.1.1.02,6]dec-4-yl)-ethyl]-2-methoxy-benzoic acid tert-butyl ester and $BCl_3$ following the procedure described in Step 5 of Example 1. The crude product was purified by reverse phase preparative HPLC [Waters Sunfire C18 OBD, 5 μm, 19×50 mm, 5-50% AcCN:$H_2O$ (with 0.1% TFA)] to give a 29% yield of product as a white solid. ESI-MS m/z 419 (MH)$^+$.

Example 28: 3-[2-(3,4-Diamino-piperidin-1-yl)-acetylamino]-2-hydroxy-3,4-dihydro-2H-benzo[e][1,2]oxaborinine-8-carboxylic acid

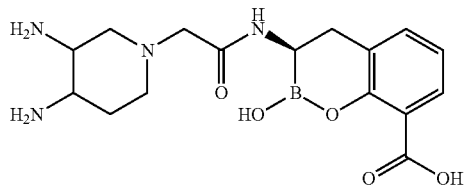 [SMILES: NC1CCN(CC(=O)N[C@H]2Cc3cccc(C(=O)O)c3OB2O)CC1N]

Step 1. Synthesis of 3,4-Dihydroxy-piperidine-1-carboxylic acid benzyl ester

To a mixture of AD-mix-α (5.02 g), t-butanol (60 mL), and $H_2O$ (60 mL) was added 3,6-Dihydro-2H-pyridine-1-carboxylic acid benzyl ester (prepared in Step 1, Example 20) (2.08 g, 9.57 mmol) in t-butanol/$H_2O$ (10 mL/10 mL). The reaction was stirred at room temperature for 42 h. Additional AD-mix-α (1.50 g) was added and the reaction was stirred for an additional 24 h. Sodium sulfite (2.08 g) was added and the reaction stirred for 4 h. The reaction was diluted with saturated $NaHCO_3$ and extracted with DCM (2×). The combined organic layers were washed with brine, dried over $Na_2SO_4$, filtered, and concentrated in vacuo. Flash chromatography (0-100% EtOAc/hexane followed by 10% $CH_3OH$/DCM) afforded 1.51 g (63%) of product. ESI-MS m/z 252 (MH)$^+$.

Step 2. Synthesis of 3,4-Bis-methanesulfonyloxy-piperidine-1-carboxylic acid benzyl ester A solution of 3,4-Dihydroxy-piperidine-1-carboxylic acid benzyl ester (1.51 g, 6.01 mmol) in DCM (30 mL) under argon was cooled to 0° C. Pyridine (2.5 mL, 30.9 mmol) was added followed by slow addition of methanesulfonyl chloride (1.2 mL, 15.5 mmol). The reaction was warmed to room temperature and stirred overnight. The reaction was diluted with DCM and washed with 1N HCl, saturated $NaHCO_3$, and brine. The organic layer was dried over $Na_2SO_4$, filtered, and concentrated. Flash chromatography (0-20% $CH_3OH$/DCM) afforded 1.62 g (66%) of product. ESI-MS m/z 252 (MH)$^+$.

Step 3. Synthesis of 3,4-Diazido-piperidine-1-carboxylic acid benzyl ester

Sodium azide (2.58 g, 39.8 mmol) was added to a solution of 3,4-Bis-methanesulfonyloxy-piperidine-1-carboxylic acid benzyl ester (1.62 g, 3.98 mmol) in DMF (100 mL) under argon and the reaction was heated at 120° C. for 24 h. The reaction was cooled to room temperature and poured into ice cold $H_2O$ and extracted with ethyl acetate (2×). The combined organic layers were washed with $H_2O$ and brine, dried over $Na_2SO_4$, filtered, and concentrated to provide 1.03 g of crude product which was carried to the next step without purification. ESI-MS m/z 324 (M+Na)$^+$.

Step 4. Synthesis of 3,4-Bis-tert-butoxycarbonylamino-piperidine-1-carboxylic acid benzyl ester A solution of 3,4-Diazido-piperidine-1-carboxylic acid benzyl ester (1.03 g, 3.42 mmol), triphenylphosphine (3.60 g, 13.7 mmol), $H_2O$ (0.6 mL, 33.3 mmol), and THF (35 mL) was heated at 70° C. for 20 h. The reaction was cooled to room temperature, diluted with ethyl acetate, and washed with 1N HCl (2×). The combined aqueous layers were basified to pH-13 with 1 0N NaOH and extracted with ethyl acetate (3×). The combined organic layers were dried over $Na_2SO_4$, filtered, and concentrated. The product was dissolved in DCM (15 mL) under argon. Triethylamine (1.1 mL, 7.89 mmol) and di-tert-butyldicarbonate (1.65 g, 7.54 mmol) in DCM (5 mL) were added and the reaction stirred at room temperature for 65 h. The reaction was quenched with saturated $NaHCO_3$ and extracted with DCM. The organic layer was dried over $Na_2SO_4$, filtered, and concentrated. Flash chromatography (0-50% EtOAc/hexane) provided 0.414 g (27%) of product as a white solid. ESI-MS m/z 450 (MH)$^+$.

Step 5. Synthesis of (4-tert-Butoxycarbonylamino-piperidin-3-yl)-carbamic acid tert-butyl ester A solution of 3,4-Bis-tert-butoxycarbonylamino-piperidine-1-carboxylic acid benzyl ester (0.414 g, 0.921 mmol) in methanol (9.0 mL) was purged with argon for 5 minutes. $Pd(OH)_2$ (0.043 g, 20% on carbon) was added, the flask evacuated, and the reaction placed under a hydrogen atmosphere for 43 h. The reaction was filtered through a Celite-plugged filter frit, washed with methanol and DCM, and concentrated in vacuo to afford 0.286 g of crude product as a white solid. ESI-MS m/z 316 (MH)$^+$.

Step 6. Synthesis of 3-[2-[2-(3,4-Bis-tert-butoxycarbonylamino-piperidin-1-yl)-acetylamino]-2-(2,9,9-trimethyl-3,5-dioxa-4-bora-tricyclo[6.1.1.02,6]dec-4-yl)-ethyl]-2-methoxy-benzoic acid tert-butyl ester Prepared from 2-Methoxy-3-(2,9,9-trimethyl-3,5-dioxa-4-bora-tricyclo[6.1.1.02,6]dec-4-ylmethyl)-benzoic acid tert-butyl ester and (4-tert-Butoxycarbonylamino-piperidin-3-yl)-carbamic acid tert-butyl ester following the procedure described in Step 2 of Example 24. The crude product was purified by a reverse phase preparative HPLC [Phenomenex Luna, 5 μm, 30×75 mm, 5-100% AcCN:$H_2O$ (with 0.1% TFA)] to give a 10% yield of product. ESI-MS m/z 785 (MH)$^+$.

Step 7. Synthesis of 3-[2-(3,4-Diamino-piperidin-1-yl)-acetylamino]-2-hydroxy-3,4-dihydro-2H-benzo[e][1,2]oxaborinine-8-carboxylic acid Prepared from 3-[2-[2-(3,4-Bis-tert-butoxycarbonylamino-piperidin-1-yl)-acetylamino]-2-(2,9,9-trimethyl-3,5-dioxa-4-bora-tricyclo[6.1.1.02,6]dec-4-yl)-ethyl]-2-methoxy-benzoic acid tert-butyl ester and $BCl_3$ following the procedure described in Step 5 of Example 1. The crude product was purified by reverse phase preparative HPLC [Waters Sunfire C18 OBD, 5 μm, 19×50 mm, 5-40% AcCN:

H₂O (with 0.1% TFA)] to give a 29% yield of product as a white solid. ESI-MS m/z 363 (MH)⁺.

Example 29: 3-[2-(4-Amino-3-aminomethyl-piperidin-1-yl)-acetylamino]-2-hydroxy-3,4-dihydro-2H-benzo[e][1,2]oxaborinine-8-carboxylic acid

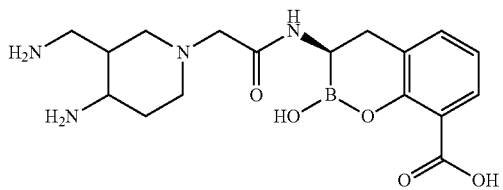 [SMILES: NCC1CN(CC(=O)N[C@H]2Cc3cccc(C(=O)O)c3OB2O)CCC1N]

Step 1. Synthesis of 4-tert-Butoxycarbonylamino-3-methanesulfonyloxy-piperidine-1-carboxylic acid benzyl ester To a solution of 4-tert-butoxycarbonylamino-3-hydroxy-piperidine-1-carboxylic acid benzyl ester (prepared in Example 20, step 4, 1.02 g, 2.91 mmol) in ethyl acetate (8.6 mL) and DCM (8.0 mL) was added triethylamine (0.51 mL, 3.66 mmol) under argon. The reaction was cooled to 0° C. and methanesulfonyl chloride (0.29 mL, 3.75 mmol) was added dropwise. The reaction was stirred at 0° C. for 50 minutes then warmed to room temperature for 3 h. The reaction was filtered, washed with ethyl acetate, and concentrated to provide crude product which was carried to the next step without purification. ESI-MS m/z 429 (MH)⁺.

Step 2. Synthesis of 4-tert-Butoxycarbonylamino-3-cyano-piperidine-1-carboxylic acid benzyl ester Tetrabutylammonium cyanide (1.57 g, 5.85 mmol) was added to a solution of 4-tert-butoxycarbonylamino-3-methanesulfonyloxy-piperidine-1-carboxylic acid benzyl ester (1.25 g, 2.91 mmol) in toluene (50 mL) under argon and the reaction was heated at 80° C. for 16.5 h. The reaction was diluted with ethyl acetate and washed with brine (2×). The organic layer was dried over Na₂SO₄, filtered, and concentrated to afford crude product which was carried to the next step without purification. ESI-MS m/z 360 (MH)⁺.

Step 3. 4-tert-Butoxycarbonylamino-3-(tert-butoxycarbonylamino-methyl)-piperidine-1-carboxylic acid benzyl ester A solution of 4-tert-Butoxycarbonylamino-3-cyano-piperidine-1-carboxylic acid benzyl ester (1.05 g, 2.91 mmol) in (50 mL) under argon was cooled to 0° C. Nickel (II) chloride hexahydrate (0.312 g, 1.31 mmol) and di-tert-butyldicarbonate (1.09 g, 4.99 mmol) were added followed by portionwise addition of sodium borohydride (0.739 g, 19.5 mmol) over 10 minutes. The reaction was stirred at 0° C. for 30 minutes then warmed to room temperature for 34 h. Diethylenetriamine (0.5 mL) was added and the reaction was concentrated to dryness. The residue was suspended in ethyl acetate and washed with 0.25N HCl, saturated NaHCO₃, and brine. The organic layer was dried over Na₂SO₄, filtered, and concentrated to give 1.12 g of crude product which was carried to the next step without purifi-cation. ESI-MS m/z 464 (MH)⁺. Step 4. Synthesis of [3-(tert-Butoxycarbonylamino-methyl)-piperidin-4-yl]-carbamic acid tert-butyl ester.

A solution of 4-tert-Butoxycarbonylamino-3-(tert-butoxycarbonylamino-methyl)-piperidine-1-carboxylic acid benzyl ester (1.12 g, 2.42 mmol) in methanol (24 mL) was purged with argon for 5 minutes. Pd(OH)₂ (0.113 g, 20% on carbon) was added, the flask evacuated, and the reaction placed under a hydrogen atmosphere for 18 h. The reaction was filtered through a Celite-plugged filter frit, washed with methanol and DCM, and concentrated in vacuo to afford 0.810 g of crude product. ESI-MS m/z 330 (MH)⁺.

Step 5. Synthesis of 3-[2-{2-[4-tert-Butoxycarbonylamino-3-(tert-butoxycarbonylamino-methyl)-piperidin-1-yl]-acetylamino}-2-(2,9,9-trimethyl-3,5-dioxa-4-bora-tricyclo[6.1.1.0²,⁶]dec-4-yl)-ethyl]-2-methoxy-benzoic acid tert-butyl ester Prepared from 2-Methoxy-3-(2,9,9-trimethyl-3,5-dioxa-4-bora-tricyclo[6.1.1.0²,⁶]dec-4-ylmethyl)-benzoic acid tert-butyl ester and [3-(tert-Butoxycarbonylamino-methyl)-piperidin-4-yl]-carbamic acid tert-butyl ester following the procedure described in Step 2 of Example 24. The crude product was purified by a reverse phase preparative HPLC [Phenomenex Luna, 5 μm, 30×75 mm, 5-100% AcCN:H₂O (with 0.1% TFA)] to give a 16% yield of product. ESI-MS m/z 799 (MH)⁺.

Step 6. Synthesis of 3-[2-(4-Amino-3-aminomethyl-piperidin-1-yl)-acetylamino]-2-hydroxy-3,4-dihydro-2H-benzo[e][1,2]oxaborinine-8-carboxylic acid Prepared from 3-[2-{2-[4-tert-Butoxycarbonylamino-3-(tert-butoxycarbonylamino-methyl)-piperidin-1-yl]-acetylamino}-2-(2,9,9-trimethyl-3,5-dioxa-4-bora-tricyclo[6.1.1.0²,⁶]dec-4-yl)-ethyl]-2-methoxy-benzoic acid tert-butyl ester and BCl₃ following the procedure described in Step 5 of Example 1. The crude product was purified by reverse phase preparative HPLC [Waters Sunfire C18 OBD, 5 μm, 19×50 mm, 5-30% AcCN:H₂O (with 0.1% TFA)] to give a 10% yield of product as a white solid. ESI-MS m/z 377 (MH)⁺.

Example 30: 3-{2-[4-(2-Amino-ethylamino)-piperidin-1-yl]-acetylamino}-2-hydroxy-3,4-dihydro-2H-benzo[e][1,2]oxaborinine-8-carboxylic acid

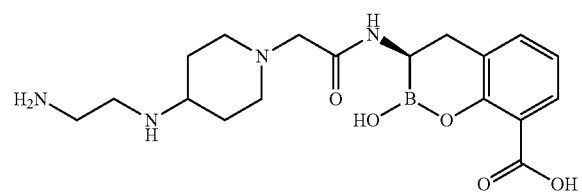 [SMILES: NCCNC1CCN(CC(=O)N[C@H]2Cc3cccc(C(=O)O)c3OB2O)CC1]

Step 1. Synthesis of 4-(2-tert-Butoxycarbonylamino-ethylamino)-piperidine-1-carboxylic acid benzyl ester A mixture of 4-amino-1-N-Cbz-piperidine (0.683 g, 2.91 mmol) and N-Boc-2-aminoacetaldehyde (0.463 g, 2.91 mmol) in methanol (12 mL) was stirred under argon at room temperature for 17 h. Sodium borohydride (0.220 g, 5.82 mmol) was added and the reaction stirred for additional 7 h. The reaction was quenched with water and extracted with DCM (2×). The combined organic layers were washed with brine, dried over Na₂SO₄, filtered, and concentrated. Flash chromatography (0-100% EtOAc/hexane then 5-10% CH₃OH:DCM) provided 0.250 g (23%) of product. ESI-MS m/z 378 (MH)⁺.

Step 2. Synthesis of 4-[tert-Butoxycarbonyl-(2-tert-butoxycarbonylamino-ethyl)-amino]-piperidine-1-carboxylic acid benzyl ester Triethylamine (0.16 mL, 1.15 mmol) and di-tert-butyldicarbonate (0.178 g, 0.816 mmol) were added to a solution of 4-(2-tert-Butoxycarbonylamino-ethylamino)-piperidine-1-carboxylic acid benzyl ester (0.250 g, 0.662 mmol) in DCM (7 mL) under argon. The reaction was stirred at room temperature for 21.5 h. The reaction was quenched with brine and extracted with DCM (2×). The combined organic layers were dried over Na₂SO₄, filtered, and concentrated to afford crude product which was carried to the next step without purification. ESI-MS m/z 478 (MH)⁺.

Step 3. Synthesis of (2-tert-Butoxycarbonylamino-ethyl)-piperidin-4-yl-carbamic acid tert-butyl ester A solution of 4-[tert-Butoxycarbonyl-(2-tert-butoxycarbonylamino-ethyl)-amino]-piperidine-1-carboxylic acid benzyl ester (0.377 g, 0.789 mmol) in methanol (8.0 mL) was purged with argon for 5 minutes. Pd(OH)₂ (0.062 g, 20% on carbon) was added, the flask evacuated, and the reaction placed under a hydrogen atmosphere for 18 h. The reaction was filtered through a Celite-plugged filter frit, washed with methanol and DCM, and concentrated in vacuo to afford 0.267 g of crude product. ESI-MS m/z 344 (MH)⁺.

Step 4. Synthesis of 3-[2-(2-{4-[tert-Butoxycarbonyl-(2-tert-butoxycarbonylamino-ethyl)-amino]-piperidin-1-yl}-acetylamino)-2-(2,9,9-trimethyl-3,5-dioxa-4-bora-tricyclo[6.1.1.02,6]dec-4-yl)-ethyl]-2-methoxy-benzoic acid tert-butyl ester Prepared from 2-Methoxy-3-(2,9,9-trimethyl-3,5-dioxa-4-bora-tricyclo[6.1.1.02,6]dec-4-ylmethyl)-benzoic acid tert-butyl ester and (2-tert-Butoxycarbonylamino-ethyl)-piperidin-4-yl-carbamic acid tert-butyl ester following the procedure described in Step 2 of Example 24. The crude product was purified by a reverse phase preparative HPLC [Phenomenex Luna, 5 μm, 30×75 mm, 5-100% AcCN:H₂O (with 0.1% TFA)] to give a 21% yield of product. ESI-MS m/z 813 (MH)⁺.

Step 5. Synthesis of 3-{2-[4-(2-Amino-ethylamino)-piperidin-1-yl]-acetylamino}-2-hydroxy-3,4-dihydro-2H-benzo[e][1,2]oxaborinine-8-carboxylic acid Prepared from 3-[2-(2-{4-[tert-Butoxycarbonyl-(2-tert-butoxycarbonylamino-ethyl)-amino]-piperidin-1-yl}-acetylamino)-2-(2,9,9-trimethyl-3,5-dioxa-4-bora-tricyclo[6.1.1.02,6]dec-4-yl)-ethyl]-2-methoxy-benzoic acid tert-butyl ester and BCl₃ following the procedure described in Step 5 of Example 1. The crude product was purified by reverse phase preparative HPLC [Waters Sunfire C18 OBD, 5 μm, 19×50 mm, 5-30% AcCN:H₂O (with 0.1% TFA)] to give a 16% yield of product as a white solid. ESI-MS m/z 391 (MH)⁺.

Example 31: 3-{3-[1-(2-Amino-ethyl)-piperidin-4-yl]-propionylamino}-2-hydroxy-3,4-dihydro-2H-benzo[e][1,2]oxaborinine-8-carboxylic acid

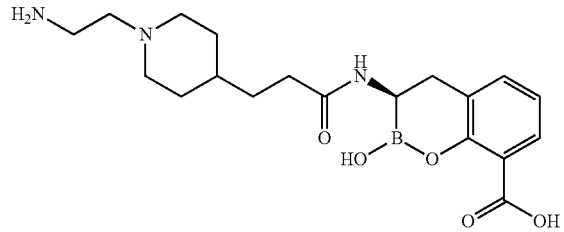 [SMILES: NCCN1CCC(CCC(=O)N[C@H]2Cc3cccc(C(=O)O)c3OB2O)CC1]

Step 1. Synthesis of 3-[1-(2-tert-Butoxycarbonylamino-ethyl)-piperidin-4-yl]-propionic acid Palladium (0.130 g, 10% on carbon) was added to a mixture of 3-piperidin-4-yl-propionic acid (0.403 g, 2.56 mmol) and (2-Oxo-ethyl)-carbamic acid tert-butyl ester (0.417 g, 2.62 mmol) in methanol (5.0 mL) under argon. The flask was evacuated and the reaction placed under a hydrogen atmosphere for 21 h. The reaction was filtered through a Celite-plugged filter frit, washed with methanol and DCM, and concentrated in vacuo to afford 0.775 g of crude product. ESI-MS m/z 323 (M+Na)⁺.

Step 2. Synthesis of 3-[2-{3-[1-(2-tert-Butoxycarbonylamino-ethyl)-piperidin-4-yl]-propionylamino}-2-(2,9,9-trimethyl-3,5-dioxa-4-bora-tricyclo[6.1.1.02,6]dec-4-yl)-ethyl]-2-methoxy-benzoic acid tert-butyl ester Prepared from 2-Methoxy-3-(2,9,9-trimethyl-3,5-dioxa-4-bora-tricyclo[6.1.1.02,6]dec-4-ylmethyl)-benzoic acid tert-butyl ester and 3-[1-(2-tert-Butoxycarbonylamino-ethyl)-piperidin-4-yl]-propionic acid following the procedure described in Step 1 of Example 8. The crude product was purified by a reverse phase column [Biotage Snap C18 30 g, 5-100% AcCN:H₂O (with 0.1% TFA)] to give a 31% yield of product. ESI-MS m/z 712 (MH)⁺.

Step 3. Synthesis of 3-{3-[1-(2-Amino-ethyl)-piperidin-4-yl]-propionylamino}-2-hydroxy-3,4-dihydro-2H-benzo[e][1,2]oxaborinine-8-carboxylic acid Prepared from 3-[2-{3-[1-(2-tert-Butoxycarbonylamino-ethyl)-piperidin-4-yl]-propionylamino}-2-(2,9,9-trimethyl-3,5-dioxa-4-bora-tricyclo[6.1.1.02,6]dec-4-yl)-ethyl]-2-methoxy-benzoic acid tert-butyl ester and BCl₃ following the procedure described in Step 5 of Example 1. The crude product was purified by reverse phase preparative HPLC [Waters Sunfire C18 OBD, 5 μm, 19×50 mm, 5-30% AcCN:H₂O (with 0.1% TFA)] to give a 5% yield of product as a white solid. ESI-MS m/z 390 (MH)⁺.

Example 32: 2-Hydroxy-3-(2-piperidin-4-yl-acetylamino)-3,4-dihydro-2H-benzo[e][1,2]oxaborinine-8-carboxylic acid

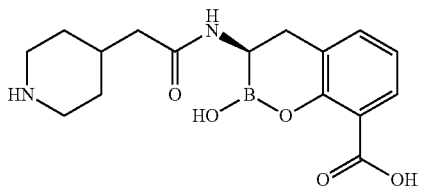

Step 1. Synthesis of tert-butyl 4-(2-((1R)-2-(3-(tert-butoxycarbonyl)-2-methoxyphenyl)-1-(2,9,9-trimethyl-3,5-dioxa-4-bora-tricyclo[6.1.1.0$^{2,6}$]dec-4-yl)ethylamino)-2-oxoethyl)piperidine-1-carboxylate Prepared from 2-Methoxy-3-(2,9,9-trimethyl-3,5-dioxa-4-bora-tricyclo[6.1.1.02,6]dec-4-ylmethyl)-benzoic acid tert-butyl ester and 2-(1-(tert-butoxycarbonyl)piperidin-4-yl)acetic acid following the procedure described in Step 1 of Example 8. The crude product was purified by flash chromatography on silica gel (Hexane/EtOAc, 2:1 to 1:2). ESI-MS m/z 655.1 (MH)⁺.

Step 2. Synthesis of 2-Hydroxy-3-(2-piperidin-4-yl-acetylamino)-3,4-dihydro-2H-benzo[e][1,2]oxaborinine-8-carboxylic acid Prepared from tert-butyl 4-(2-((1R)-2-(3-(tert-butoxycarbonyl)-2-methoxyphenyl)-1-(2,9,9-trimethyl-3,5-dioxa-4-bora-tricyclo[6.1.1.0$^{26}$]dec-4-yl)ethylamino)-2-oxoethyl)piperidine-1-carboxylate and BCl₃ following the procedure described in Step 5 of Example 1. The crude product was purified by reverse phase preparative HPLC [Waters Sunfire C18 OBD, 5 μm, 19×50 mm, 5-30% AcCN:H₂O (with 0.1% TFA)] to afford product as a white solid. ESI-MS m/z 333 (MH)⁺.

Example 33: 3-[2-(1-Carbamimidoyl-piperidin-4-yl)-acetylamino]-2-hydroxy-3,4-dihydro-2H-benzo[e][1,2]oxaborinine-8-carboxylic acid

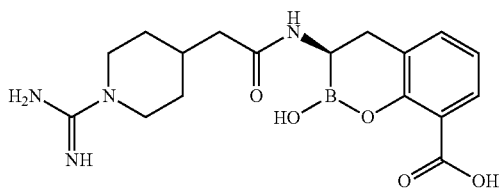 [SMILES: N=C(N)N1CCC(CC(=O)N[C@H]2Cc3cccc(C(=O)O)c3OB2O)CC1]

Step 1. Synthesis of 4-{[2-(3-tert-Butoxycarbonyl-2-methoxy-phenyl)-1-(2,9,9-trimethyl-3,5-dioxa-4-bora-tricyclo[6.1.1.02,6]dec-4-yl)-ethylcarbamoyl]-methyl}-piperidine-1-carboxylic acid benzyl ester Prepared from 2-Methoxy-3-(2,9,9-trimethyl-3,5-dioxa-4-bora-tricyclo[6.1.1.02,6]dec-4-ylmethyl)-benzoic acid tert-butyl ester and 2-(1-(benzyloxycarbonyl)piperidin-4-yl) acetic acid following the procedure described in Step 1 of Example 8. The crude product was purified by flash chromatography on silica gel (Hexane/EtOAc, 2:1 to 1:2). ESI-MS m/z 689 (MH)⁺.

Step 2. Synthesis of 2-Methoxy-3-[2-(2-piperidin-4-yl-acetylamino)-2-(2,9,9-trimethyl-3,5-dioxa-4-bora-tricyclo[6.1.1.02,6]dec-4-yl)-ethyl]-benzoic acid tert-butyl ester Palladium (0.039 g, 10% on carbon) was added to a solution of 4-{[2-(3-tert-Butoxycarbonyl-2-methoxy-phenyl)-1-(2,9,9-trimethyl-3,5-dioxa-4-bora-tricyclo[6.1.1.02,6]dec-4-yl)-ethylcarbamoyl]-methyl}-piperidine-1-carboxylic acid benzyl ester (0.437 g, 0.635 mmol) in methanol (6.7 mL) under argon. The flask was evacuated and the reaction placed under a hydrogen atmosphere for 16 h. The reaction was filtered through a Celite-plugged filter frit, washed with methanol and DCM, and concentrated in vacuo to afford 0.361 g of crude product. ESI-MS m/z 555 (MH)⁺.

Step 3. Synthesis of 3-[2-{2-[1-(tert-Butoxycarbonylamino-tert-butoxycarbonylimino-methyl)-piperidin-4-yl]-acetylamino}-2-(2,9,9-trimethyl-3,5-dioxa-4-bora-tricyclo[6.1.1.02,6]dec-4-yl)-ethyl]-2-methoxy-benzoic acid tert-butyl ester Triethylamine (0.03 mL, 0.215 mmol) and N,N'-di-Boc-1H-pyrazole-1-carboxamide (0.200 g, 0.644 mmol) were added to a solution of 2-Methoxy-3-[2-(2-piperidin-4-yl-acetylamino)-2-(2,9,9-trimethyl-3,5-dioxa-4-bora-tricyclo[6.1.1.02,6]dec-4-yl)-ethyl]-benzoic acid tert-butyl ester (0.120 g, 0.216 mmol) in methanol (4.2 mL) under argon and stirred at room temperature for 17 h. The reaction was concentrated to afford crude product which was carried to the next step without purification. ESI-MS m/z 797 (MH)⁺.

Step 4. Synthesis of 3-[2-(1-Carbamimidoyl-piperidin-4-yl)-acetylamino]-2-hydroxy-3,4-dihydro-2H-benzo[e][1,2]oxaborinine-8-carboxylic acid Prepared from 3-[2-{2-[1-(tert-Butoxycarbonylamino-tert-butoxycarbonylimino-methyl)-piperidin-4-yl]-acetylamino}-2-(2,9,9-trimethyl-3,5-dioxa-4-bora-tricyclo[6.1.1.02,6]dec-4-yl)-ethyl]-2-methoxy-benzoic acid tert-butyl ester and BCl₃ following the procedure described in Step 5 of Example 1. The crude product was purified by reverse phase preparative HPLC [Waters Sunfire C18 OBD, 5 μm, 19×50 mm, 5-50% AcCN:H₂O (with 0.1% TFA)] to afford a 10% yield of product as a white solid. ESI-MS m/z 375 (MH)⁺.

Example 34: 3-{3-[1-(2-Guanidino-ethyl)-piperidin-4-yl]-propionylamino}-2-hydroxy-3,4-dihydro-2H-benzo[e][1,2]oxaborinine-8-carboxylic acid

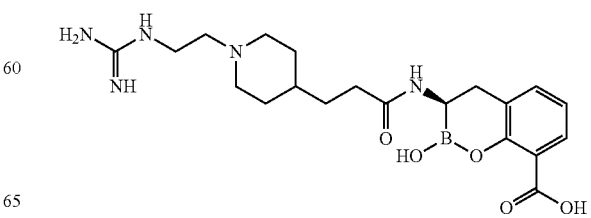

Step 1. Synthesis of 3-{3-[1-(2-Di-tert-butoxycarbo-nyl-guanidino-ethyl)-piperidin-4-yl]-propio-nylamino}-2-hydroxy-3,4-dihydro-2H-benzo[e][1,2]oxaborinine-8-carboxylic acid Prepared from 3-{3-[1-(2-Amino-ethyl)-piperidin-4-yl]-propionylamino}-2-hydroxy-3,4-dihydro-2H-benzo[e][1,2]oxaborinine-8-carboxylic acid following the procedure described in Step 3 of Example 33. The crude product was carried to the next step without purification. ESI-MS m/z 632 (MH)+.

Step 2. Synthesis of 3-{3-[1-(2-Guanidino-ethyl)-piperidin-4-yl]-propionylamino}-2-hydroxy-3,4-dihydro-2H-benzo[e][1,2]oxaborinine-8-carboxylic acid A solution of 3-{3-[1-(2-Di-tert-butoxycarbonyl-guanidino-ethyl)-piperidin-4-yl]-propionylamino}-2-hydroxy-3,4-dihydro-2H-benzo[e][1,2]oxaborinine-8-carboxylic acid (0.013 g, 0.020 mmol) in hydrochloric acid (4.0N in 1,4-dioxane, 1.9 mL, 7.60 mmol) was stirred at room temperature for 26 h. The reaction was concentrated and the crude product was purified by reverse phase preparative HPLC [Waters Sunfire C18 OBD, 5 µm, 19×50 mm, 5-50% AcCN:H2O (with 0.1% TFA)] to afford a 32% yield of product as a white solid. ESI-MS m/z 432 (MH)+.

Example 35: 3-[2-(1-Cyanomethyl-piperidin-4-yl)-acetylamino]-2-hydroxy-3,4-dihydro-2H-benzo[e][1,2]oxaborinine-8-carboxylic acid

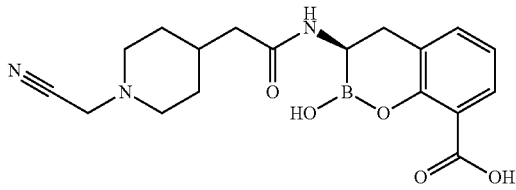 [SMILES: N#CCN1CCC(CC(=O)N[C@H]2Cc3cccc(C(=O)O)c3OB2O)CC1]

Step 1. Synthesis of 3-[2-[2-(1-Cyanomethyl-piperidin-4-yl)-acetylamino]-2-(2,9,9-trimethyl-3,5-dioxa-4-bora-tricyclo[6.1.1.02,6]dec-4-yl)-ethyl]-2-methoxy-benzoic acid tert butyl ester To a solution of 2-Methoxy-3-[2-(2-piperidin-4-yl-acetylamino)-2-(2,9,9-trimethyl-3,5-dioxa-4-bora-tricyclo[6.1.1.02,6]dec-4-yl)-ethyl]-benzoic acid tert-butyl ester (Step 2, Example 33, 0.250 g, 0.451 mmol) in acetonitrile (5.0 mL) was added potassium carbonate (0.132 g, 0.955 mmol) and bromoacetonitrile (0.08 mL, 1.15 mmol) under argon. The reaction was stirred at room temperature for 42 h. The reaction was quenched with water and extracted with diethyl ether (3×). The combined organic layers were dried over Na2SO4, filtered, and concentrated. The crude product was carried to the next step without purification. ESI-MS m/z 594 (MH)+.

Step 2. Synthesis of 3-[2-(1-Cyanomethyl-piperidin-4-yl)-acetylamino]-2-hydroxy-3,4-dihydro-2H-benzo[e][1,2]oxaborinine-8-carboxylic acid Prepared from 3-[2-[2-(1-Cyanomethyl-piperidin-4-yl)-acetylamino]-2-(2,9,9-trimethyl-3,5-dioxa-4-bora-tricyclo[6.1.1.02,6]dec-4-yl)-ethyl]-2-methoxy-benzoic acid tert-butyl ester and BCl3 following the procedure described in Step 5 of Example 1. The crude product was purified by reverse phase preparative HPLC [Waters Sunfire C18 OBD, 5 µm, 19×50 mm, 5-100% AcCN:H2O (with 0.1% TFA)] to provide a 44% yield of product as a white solid. ESI-MS m/z 372 (MH).

Example 36: 3-{2-[4-(2-Amino-ethyl)-2-oxo-piperazin-1-yl]-acetylamino}-2-hydroxy-3,4-dihydro-2H-benzo[e][1,2]oxaborinine-8-carboxylic acid

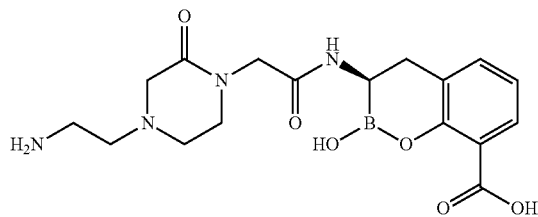 [SMILES: NCCN1CCN(CC(=O)N[C@H]2Cc3cccc(C(=O)O)c3OB2O)C(=O)C1]

Step 1. Synthesis of [4-(2-tert-Butoxycarbonylamino-ethyl)-2-oxo-piperazin-1-yl]-acetic acid Palladium (0.161 g, 10% on carbon) was added to a mixture of 2-Oxo-1-piperazineacetic acid (0.497 g, 3.14 mmol) and (2-Oxo-ethyl)-carbamic acid tert-butyl ester (0.503 g, 3.16 mmol) in methanol (6.2 mL) under argon. The flask was evacuated and the reaction placed under a hydrogen atmosphere for 22 h. The reaction was filtered through a Celite-plugged filter frit, washed with methanol and DCM, and concentrated in vacuo to afford crude product which was carried to the next step without purification. ESI-MS m/z 324 (M+Na)+.

Step 2. Synthesis of 3-[2-{2-[4-(2-tert-Butoxycarbonylamino-ethyl)-2-oxo-piperazin-1-yl]-acetylamino}-2-(2,9,9-trimethyl-3,5-dioxa-4-bora-tricyclo[6.1.1.02,6]dec-4-yl)-ethyl]-2-methoxy-benzoic acid tert-butyl ester Prepared from 2-Methoxy-3-(2,9,9-trimethyl-3,5-dioxa-4-bora-tricyclo[6.1.1.02,6]dec-4-ylmethyl)-benzoic acid tert-butyl ester and [4-(2-tert-Butoxycarbonylamino-ethyl)-2-oxo-piperazin-1-yl]-acetic acid following the procedure described in Step 1 of Example 8. The crude product was purified by reverse phase column [C18, 30 g, 5-100% AcCN:H2O (with 0.1% TFA)] to afford a 28% yield of product as a white solid. ESI-MS m/z 713 (MH)+.

Step 3. Synthesis of 3-{2-[4-(2-Amino-ethyl)-2-oxo-piperazin-1-yl]-acetylamino}-2-hydroxy-3,4-dihydro-2H-benzo[e][1,2]oxaborinine-8-carboxylic acid Prepared from 3-[2-{2-[4-(2-tert-Butoxycarbonylamino-ethyl)-2-oxo-piperazin-1-yl]-acetylamino}-2-(2,9,9-trimethyl-3,5-dioxa-4-bora-tricyclo[6.1.1.02,6]dec-4-yl)-ethyl]-2-methoxy-benzoic acid tert-butyl ester and BCl3 following the procedure described in Step 5 of Example 1. The crude product was purified by reverse phase preparative HPLC [Waters Sunfire C18 OBD, 5 µm, 19×50 mm, 5-100% AcCN:H2O (with 0.1% TFA)] to afford product as a white solid. ESI-MS m/z 391 (MH)+.

Example 37: 3-[2-(3-Guanidinomethyl-piperidin-1-yl)-acetylamino]-2-hydroxy-3,4-dihydro-2H-benzo[e][1,2]oxaborinine-8-carboxylic acid

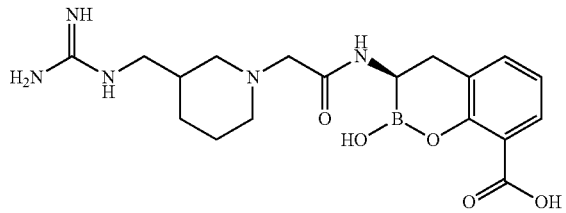 [SMILES: N=C(N)NCC1CCCN(CC(=O)N[C@H]2Cc3cccc(C(=O)O)c3OB2O)C1]

Step 1. Synthesis of 3-{3-[1-(2-Di-tert-butoxycarbonyl-guanidino-ethyl)-piperidin-4-yl]-propionylamino}-2-hydroxy-3,4-dihydro-2H-benzo[e][1,2]oxaborinine-8-carboxylic acid Prepared from 3-[2-(3-Aminomethyl-piperidin-1-yl)-acetylamino]-2-hydroxy-3,4-dihydro-2H-benzo[e][1,2]oxaborinine-8-carboxylic acid (Example 19) following the procedure described in Step 3 of Example 33. The crude product was carried to the next step without purification. ESI-MS m/z 604 (MH)+.

Step 2. Synthesis of 3-{3-[1-(2-Guanidino-ethyl)-piperidin-4-yl]-propionylamino}-2-hydroxy-3,4-dihydro-2H-benzo[e][1,2]oxaborinine-8-carboxylic acid Prepared from 3-{3-[1-(2-Di-tert-butoxycarbonyl-guanidino-ethyl)-piperidin-4-yl]-propionylamino}-2-hydroxy-3,4-dihydro-2H-benzo[e][1,2]oxaborinine-8-carboxylic acid and hydrochloric acid following the procedure described in Step 2 of Example 34. The reaction was concentrated and the crude product was purified by reverse phase preparative HPLC [Waters Sunfire C18 OBD, 5 μm, 19×50 mm, 5-50% AcCN:H2O (with 0.1% TFA)] to afford a 28% yield of product as a white solid. ESI-MS m/z 404 (MH)+.

Example 38: 3-{2-[4-(2-Guanidino-ethyl)-2-oxo-piperazin-1-yl]-acetylamino}-2-hydroxy-3,4-dihydro-2H-benzo[e][1,2]oxaborinine-8-carboxylic acid

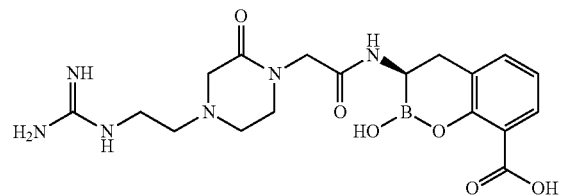 [SMILES: N=C(N)NCCN1CCN(CC(=O)N[C@H]2Cc3cccc(C(=O)O)c3OB2O)C(=O)C1]

Step 1. Synthesis of 3-{2-[4-(2-Di-tert-butoxycarbonyl-guanidino-ethyl)-2-oxo-piperazin-1-yl]-acetylamino}-2-hydroxy-3,4-dihydro-2H-benzo[e][1,2]oxaborinine-8-carboxylic acid Prepared from 3-{2-[4-(2-Amino-ethyl)-2-oxo-piperazin-1-yl]-acetylamino}-2-hydroxy-3,4-dihydro-2H-benzo[e][1,2]oxaborinine-8-carboxylic acid (Example 36) following the procedure described in Step 3 of Example 33. The crude product was carried to the next step without purification. ESI-MS m/z 633 (MH)+.

Step 2. 3-{2-[4-(2-Guanidino-ethyl)-2-oxo-piperazin-1-yl]-acetylamino}-2-hydroxy-3,4-dihydro-2H-benzo[e][1,2]oxaborinine-8-carboxylic acid Prepared from 3-{2-[4-(2-Di-tert-butoxycarbonyl-guanidino-ethyl)-2-oxo-piperazin-1-yl]-acetylamino}-2-hydroxy-3,4-dihydro-2H-benzo[e][1,2]oxaborinine-8-carboxylic acid and hydrochloric acid following the procedure described in Step 2 of Example 34. The reaction was concentrated and the crude product was purified by reverse phase preparative HPLC [Waters Sunfire C18 OBD, 5 μm, 19×50 mm, 5-50% AcCN:H2O (with 0.1% TFA)] to afford a 63% yield of product as a white solid. ESI-MS m/z 433 (MH)+.

Example 39: 2-Hydroxy-3-[2-(piperidin-4-yloxy)-acetylamino]-3,4-dihydro-2H-benzo[e][1,2]oxaborinine-8-carboxylic acid

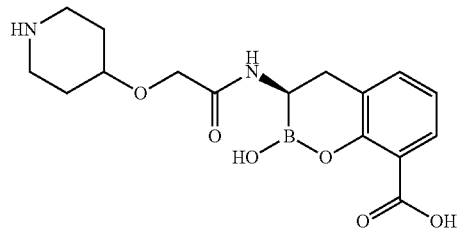 [SMILES: O=C(COC1CCNCC1)N[C@H]1Cc2cccc(C(=O)O)c2OB1O]

Step 1. Synthesis of 4-Ethoxycarbonylmethoxy-piperidine-1-carboxylic acid tert-butyl ester Sodium hydride (60%, 0.480 g, 12.0 mmol) was added to a solution of 1-Boc-4-hydroxypiperidine (1.61 g, 8.00 mmol) in THF (70 mL) under argon and the reaction mixture was stirred at room temperature for 25 minutes. Ethyl bromoacetate (2.0 mL, 18.0 mmol) was added and the reaction stirred for 17 h. The reaction was quenched with saturated NaHCO3 and extracted with ethyl acetate (2×). The combined organic layers were washed with H2O and brine, dried over Na2SO4, filtered, and concentrated to afford crude product which was carried to the next step without purification. ESI-MS m/z 310 (M+Na)+.

Step 2. Synthesis of 4-Carboxymethoxy-piperidine-1-carboxylic acid tert-butyl ester Sodium hydroxide (1M, 31 mL, 31.0 mmol) was added to a solution of 4-Ethoxycarbonylmethoxy-piperidine-1-carboxylic acid tert-butyl ester (2.30 g, 8.00 mmol) in methanol (65 mL) and THF (15 mL). The reaction was stirred at room temperature for 18 h. The reaction was concentrated to remove methanol and THF and the remaining aqueous layer was extracted with diethyl ether (2×). The aqueous layer was acidified to pH~1 with 3N HCl (~10.5 mL). Brine was added and extracted with ethyl acetate (3×). The combined organic layers were dried over Na$_2$SO$_4$, filtered, and concentrated to afford 0.610 g of product for a 29% yield over two steps. ESI-MS m/z 282 (M+Na)$^+$.

Step 3. Synthesis of 4-{[2-(3-tert-Butoxycarbonyl-2-methoxy-phenyl)-1-(2,9,9-trimethyl-3,5-dioxa-4-bora-tricyclo[6.1.1.02,6]dec-4-yl)-ethylcarbamoyl]-methoxy}-piperidine-1-carboxylic acid tert-butyl ester Prepared from 2-Methoxy-3-(2,9,9-trimethyl-3,5-dioxa-4-bora-tricyclo[6.1.1.02,6]dec-4-ylmethyl)-benzoic acid tert-butyl ester and 4-Carboxymethoxy-piperidine-1-carboxylic acid tert-butyl ester following the procedure described in Step 1 of Example 8. Flash chromatography (0-100% EtOAc/hexane) provided 0.378 g (31%) of product as an off white solid. ESI-MS m/z 671 (MH)$^+$.

Step 4. Synthesis of 2-Hydroxy-3-[2-(piperidin-4-yloxy)-acetylamino]-3,4-dihydro-2H-benzo[e][1,2] oxaborinine-8-carboxylic acid Prepared from 4-{[2-(3-tert-Butoxycarbonyl-2-methoxy-phenyl)-1-(2,9,9-trimethyl-3,5-dioxa-4-bora-tricyclo [6.1.1.02,6]dec-4-yl)-ethylcarbamoyl]-methoxy}-piperidine-1-carboxylic acid tert-butyl ester and BCl$_3$ following the procedure described in Step 5 of Example 1. The crude product was purified by reverse phase preparative HPLC [Waters Sunfire C18 OBD, 5 µm, 19×50 mm, 5-60% AcCN:H$_2$O (with 0.1% TFA)] to afford product as a white solid. ESI-MS m/z 349 (MH)$^+$.

Example 40: 2-Hydroxy-3-[2-(piperidin-4-ylamino)-acetylamino]-3,4-dihydro-2H-benzo[e][1,2]oxaborinine-8-carboxylic acid

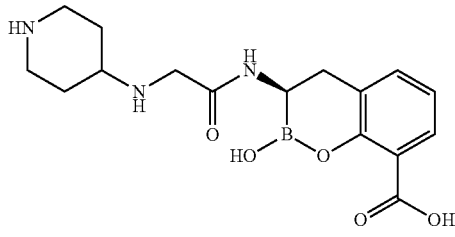 [SMILES: O=C(CNC1CCNCC1)N[C@H]1Cc2cccc(C(=O)O)c2OB1O]

Step 1. Synthesis of 4-(Ethoxycarbonylmethyl-amino)-piperidine-1-carboxylic acid tert-butyl ester To a solution of 4-amino-1-Boc-piperidine (0.817 g, 4.08 mmol) in acetonitrile (5.0 mL) were added diisopropylethylamine (1.4 mL, 8.04 mmol) and ethyl bromoacetate (0.45 mL, 4.06 mmol). The resulting suspension was stirred under argon at room temperature for 17 h. The reaction was concentrated in vacuo. The residue was diluted with H$_2$O and extracted with DCM (3×). The combined organic layers were dried over Na$_2$SO$_4$, filtered, and concentrated to provide crude product which was carried forward without purification. ESI-MS m/z 287 (MH).

Step 2. Synthesis of 4-(Benzyloxycarbonyl-ethoxycarbonylmethyl-amino)-piperidine-1-carboxylic acid tert-butyl ester A solution of 4-(Ethoxycarbonylmethyl-amino)-piperidine-1-carboxylic acid tert-butyl ester (1.09 g, 3.81 mmol) in DCM (15 mL) under argon was cooled to −10° C. Triethylamine (2.8 mL, 20.1 mmol) and benzyl chloroformate (1.4 mL, 9.67 mmol) were added slowly and the reaction was allowed to warm to room temperature and stir for 71 h. The reaction was diluted with DCM and washed successively with H$_2$O, saturated NaHCO$_3$, and brine. The organic layer was dried over Na$_2$SO$_4$, filtered, and concentrated to afford crude product which was carried forward without purification. ESI-MS m/z 421 (MH).

Step 3. Synthesis of 4-(Benzyloxycarbonyl-carboxymethyl-amino)-piperidine-1-carboxylic acid tert-butyl ester Prepared from 4-(Benzyloxycarbonyl-ethoxycarbonylmethyl-amino)-piperidine-1-carboxylic acid tert-butyl ester following the procedure described in Step 2 of Example 39. The crude product was carried forward without purification. ESI-MS m/z 415 (M+Na).

Step 4. Synthesis of 4-(Benzyloxycarbonyl-{[2-(3-tert-butoxycarbonyl-2-methoxy-phenyl)-1-(2,9,9-trimethyl-3,5-dioxa-4-bora-tricyclo[6.1.1.02,6]dec-4-yl)-ethylcarbamoyl]-methyl}-amino)-piperidine-1-carboxylic acid tert-butyl ester Prepared from 2-Methoxy-3-(2,9,9-trimethyl-3,5-dioxa-4-bora-tricyclo[6.1.1.02,6]dec-4-ylmethyl)-benzoic acid tert-butyl ester and 4-(Benzyloxycarbonyl-carboxymethyl-amino)-piperidine-1-carboxylic acid tert-butyl ester following the procedure described in Step 1 of Example 8. Flash chromatography (0-80% EtOAc/hexane) provided 0.202 g (14%) of product as a white solid. ESI-MS m/z 804 (MH)$^+$.

Step 5. Synthesis of 4-({[2-(3-tert-Butoxycarbonyl-2-methoxy-phenyl)-1-(2,9,9-trimethyl-3,5-dioxa-4-bora-tricyclo[6.1.1.02,6]dec-4-yl)-ethylcarbamoyl]-methyl}-amino)-piperidine-1-carboxylic acid tert-butyl ester A solution of 4-(Benzyloxycarbonyl-{[2-(3-tert-butoxycarbonyl-2-methoxy-phenyl)-1-(2,9,9-trimethyl-3,5-dioxa-4-bora-tricyclo[6.1.1.02,6]dec-4-yl)-ethylcarbamoyl]-methyl}-amino)-piperidine-1-carboxylic acid tert-butyl ester (0.202 g, 0.251 mmol) in methanol (4.0 mL) was purged with argon for ~5 minutes. Palladium on carbon (10%, 0.020 g) was added, flask evacuated, and the reaction stirred under H$_2$ atmosphere for 16 h. The reaction was filtered through a Celite-plugged filter frit, washed with methanol and DCM, and concentrated to give the crude product which was carried forward without purification. ESI-MS m/z 670 (MH)$^+$.

Step 6. Synthesis of 2-Hydroxy-3-[2-(piperidin-4-ylamino)-acetylamino]-3,4-dihydro-2H-benzo[e][1,2]oxaborinine-8-carboxylic acid Prepared from 4-({[2-(3-tert-Butoxycarbonyl-2-methoxy-phenyl)-1-(2,9,9-trimethyl-3,5-dioxa-4-bora-tricyclo[6.1.1.02,6]dec-4-yl)-ethylcarbamoyl]-methyl}-amino)-piperidine-1-carboxylic acid tert-butyl ester and BCl$_3$ following the procedure described in Step 5 of Example 1. The crude product was purified by reverse phase preparative HPLC [Waters Sunfire C18 OBD, 5 µm, 19×50 mm, 5-30% AcCN:H$_2$O (with 0.1% TFA)] to afford product as a white solid. ESI-MS m/z 348 (MH)$^+$.

Example 41: 3-{2-[1-(2-Amino-ethyl)-piperidin-4-yl]-acetylamino}-2-hydroxy-3,4-dihydro-2H-benzo[e][1,2]oxaborinine-8-carboxylic acid

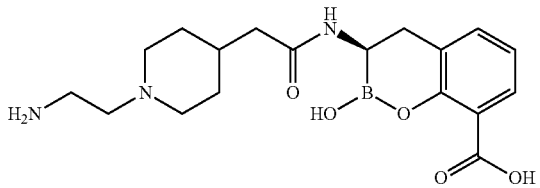

Step 1. Synthesis of 3-[2-{2-[1-(2-tert-Butoxycarbonylamino-ethyl)-piperidin-4-yl]-acetylamino}-2-(2,9,9-trimethyl-3,5-dioxa-4-bora-tricyclo[6.1.1.02,6]dec-4-yl)-ethyl]-2-methoxy-benzoic acid tert-butyl ester To a solution of 2-Methoxy-3-[2-(2-piperidin-4-yl-acetylamino)-2-(2,9,9-trimethyl-3,5-dioxa-4-bora-tricyclo[6.1.1.02,6]dec-4-yl)-ethyl]-benzoic acid tert-butyl ester (Step 2, Example 33, 0.102 g, 0.184 mmol) in methanol (2.5 mL) was added (2-Oxo-ethyl)-carbamic acid tert-butyl ester (0.060 g, 0.377 mmol) followed by palladium on carbon (10%, 0.017 g). The flask was evacuated and the reaction placed under $H_2$ for 18 h. The reaction was filtered through a Celite-plugged filter frit, washed with methanol and DCM, and concentrated. The crude product was carried forward without purification. ESI-MS m/z 698 (MH)$^+$.

Step 2. Synthesis of 3-{2-[1-(2-Amino-ethyl)-piperidin-4-yl]-acetylamino}-2-hydroxy-3,4-dihydro-2H-benzo[e][1,2]oxaborinine-8-carboxylic acid Prepared from 3-[2-{2-[1-(2-tert-Butoxycarbonylamino-ethyl)-piperidin-4-yl]-acetylamino}-2-(2,9,9-trimethyl-3,5-dioxa-4-bora-tricyclo[6.1.1.02,6]dec-4-yl)-ethyl]-2-methoxy-benzoic acid tert-butyl ester and $BCl_3$ following the procedure described in Step 5 of Example 1. The crude product was purified by reverse phase preparative HPLC [Waters Sunfire C18 OBD, 5 μm, 19×50 mm, 5-40% AcCN:$H_2O$ (with 0.1% TFA)] to afford a 38% yield of product as a white solid. ESI-MS m/z 376 (MH)$^+$.

Example 42: 3-{2-[1-(3-Amino-propyl)-piperidin-4-yl]-acetylamino}-2-hydroxy-3,4-dihydro-2H-benzo[e][1,2]oxaborinine-8-carboxylic acid

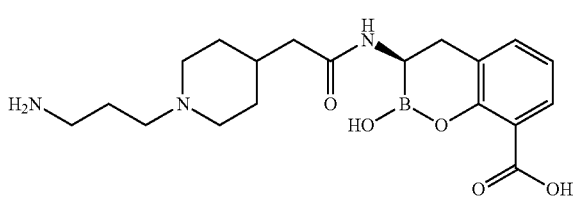 [SMILES: NCCCN1CCC(CC(=O)N[C@H]2Cc3cccc(C(=O)O)c3OB2O)CC1]

Step 1. Synthesis of 3-[2-{2-[1-(3-tert-Butoxycarbonylamino-propyl)-piperidin-4-yl]-acetylamino}-2-(2,9,9-trimethyl-3,5-dioxa-4-bora-tricyclo[6.1.1.02,6]dec-4-yl)-ethyl]-2-methoxy-benzoic acid tert-butyl ester Potassium carbonate (0.030 g, 0.217 mmol) was added to a solution of 2-Methoxy-3-[2-(2-piperidin-4-yl-acetylamino)-2-(2,9,9-trimethyl-3,5-dioxa-4-bora-tricyclo[6.1.1.02,6]dec-4-yl)-ethyl]-benzoic acid tert-butyl ester (Step 2, Example 33, 0.078 g, 0.141 mmol) and 3-(Boc-amino)propyl bromide (0.065 g, 0.273 mmol) in DMF (2.5 mL). The reaction was sealed and heated at 60° C. for 16 h. The reaction was cooled to room temperature, quenched with $H_2O$, and extracted with ethyl acetate (2×). The combined organic layers were washed with brine, dried over $Na_2SO_4$, filtered, and concentrated to provide crude product which was carried forward without purification. ESI-MS m/z 712 (MH)$^+$.

Step 2. Synthesis of 3-{2-[1-(3-Amino-propyl)-piperidin-4-yl]-acetylamino}-2-hydroxy-3,4-dihydro-2H-benzo[e][1,2]oxaborinine-8-carboxylic acid Prepared from 3-[2-{2-[1-(3-tert-Butoxycarbonylamino-propyl)-piperidin-4-yl]-acetylamino}-2-(2,9,9-trimethyl-3,5-dioxa-4-bora-tricyclo[6.1.1.02,6]dec-4-yl)-ethyl]-2-methoxy-benzoic acid tert-butyl ester and $BCl_3$ following the procedure described in Step 5 of Example 1. The crude product was purified by reverse phase preparative HPLC [Waters Sunfire C18 OBD, 5 μm, 19×50 mm, 5-50% AcCN:$H_2O$ (with 0.1% TFA)] to afford a 15% yield of product as a white solid. ESI-MS m/z 390 (MH)$^+$.

Example 43: 2-Hydroxy-3-[2-(methyl-piperidin-4-yl-amino)-acetylamino]-3,4-dihydro-2H-benzo[e][1,2]oxaborinine-8-carboxylic acid

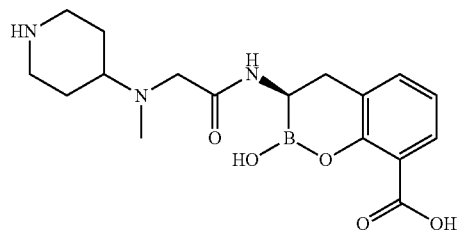 [SMILES: CN(CC(=O)N[C@H]1Cc2cccc(C(=O)O)c2OB1O)C1CCNCC1]

Step 1. Synthesis of 4-(Ethoxycarbonylmethyl-methyl-amino)-piperidine-1-carboxylic acid tert-butyl ester To a solution of 4-(Ethoxycarbonylmethyl-amino)-piperidine-1-carboxylic acid tert-butyl ester (Step 2, Example 40, 1.09 g, 3.81 mmol) in DCM (95 mL) under argon was added formaldehyde (37% in $H_2O$, 3.2 mL, 39.4 mmol), acetic acid (0.44 mL, 7.69 mmol), and sodium triacetoxyborohydride (1.61 g, 7.60 mmol). The reaction was stirred at room temperature for 20 h. The reaction was quenched with ice cold $H_2O$ and extracted with DCM (2×). The combined organic layers were washed with brine, dried over $Na_2SO_4$, filtered, and concentrated to provide crude product which was carried forward without purification. ESI-MS m/z 323 (M+Na)+.

Step 2. Synthesis of 4-(Carboxymethyl-methyl-amino)-piperidine-1-carboxylic acid tert-butyl ester Prepared from 4-(Ethoxycarbonylmethyl-methyl-amino)-piperidine-1-carboxylic acid tert-butyl ester following the procedure described in Step 2 of Example 39. The crude product was carried forward without purification. ESI-MS m/z 295 (M+Na)+.

Step 3. Synthesis of 4-({[2-(3-tert-Butoxycarbonyl-2-methoxy-phenyl)-1-(2,9,9-trimethyl-3,5-dioxa-4-bora-tricyclo[6.1.1.02,6]dec-4-yl)-ethylcarbamoyl]-methyl}-methyl-amino)-piperidine-1-carboxylic acid tert-butyl ester Prepared from 2-Methoxy-3-(2,9,9-trimethyl-3,5-dioxa-4-bora-tricyclo[6.1.1.02,6]dec-4-ylmethyl)-benzoic acid tert-butyl ester and 4-(Carboxymethyl-methyl-amino)-piperidine-1-carboxylic acid tert-butyl ester following the procedure described in Step 1 of Example 8. The crude product was purified by reverse phase preparative HPLC [Waters Sunfire C18 OBD, 5 μm, 19×50 mm, 5-100% AcCN:H2O (with 0.1% TFA)] to give an 8% yield of product as a white solid. ESI-MS m/z 684 (MH)+.

Step 4. Synthesis of 2-Hydroxy-3-[2-(methyl-piperidin-4-yl-amino)-acetylamino]-3,4-dihydro-2H-benzo[e][1,2]oxaborinine-8-carboxylic acid Prepared from 4-({[2-(3-tert-Butoxycarbonyl-2-methoxy-phenyl)-1-(2,9,9-trimethyl-3,5-dioxa-4-bora-tricyclo [6.1.1.02,6]dec-4-yl)-ethylcarbamoyl]-methyl}-methyl-amino)-piperidine-1-carboxylic acid tert-butyl ester and BCl3 following the procedure described in Step 5 of Example 1. The crude product was purified by reverse phase preparative HPLC [Waters Sunfire C18 OBD, 5 μm, 19×50 mm, 5-40% AcCN:H2O (with 0.1% TFA)] to afford a 27% yield of product as a white solid. ESI-MS m/z 362 (MH)+.

Example 44: 2-Hydroxy-3-[(piperidine-4-carbonyl)-amino]-3,4-dihydro-2H-benzo[e][1,2]oxaborinine-8-carboxylic acid

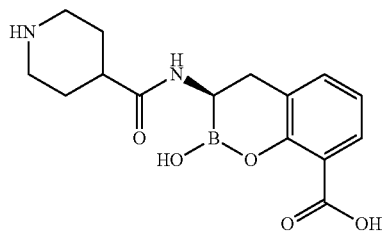

Step 1. Synthesis of 4-[2-(3-tert-Butoxycarbonyl-2-methoxy-phenyl)-1-(2,9,9-trimethyl-3,5-dioxa-4-bora-tricyclo[6.1.1.02,6]dec-4-yl)-ethylcarbamoyl]-piperidine-1-carboxylic acid tert-butyl ester Prepared from 2-Methoxy-3-(2,9,9-trimethyl-3,5-dioxa-4-bora-tricyclo[6.1.1.02,6]dec-4-ylmethyl)-benzoic acid tert-butyl ester and 1-(tert-butoxycarbonyl)piperidine-4-carboxylic acid following the procedure described in Step 1 of Example 8. The crude product was purified by flash chromatography on silica gel (Hexane/EtOAc, 2:1 to 1:2). ESI-MS m/z 641 (MH)+.

Step 2. Synthesis of 2-Hydroxy-3-[(piperidine-4-carbonyl)-amino]-3,4-dihydro-2H-benzo[e][1,2]oxaborinine-8-carboxylic acid Prepared 4-[2-(3-tert-Butoxycarbonyl-2-methoxy-phenyl)-1-(2,9,9-trimethyl-3,5-dioxa-4-bora-tricyclo[6.1.1.02, 6]dec-4-yl)-ethylcarbamoyl]-piperidine-1-carboxylic acid tert-butyl ester and BCl3 following the procedure described in Step 5 of Example 1. The crude product was purified by reverse phase preparative HPLC [Waters Sunfire C18 OBD, 5 μm, 19×50 mm, 5-50% AcCN:H2O (with 0.1% TFA)] to afford product as a white solid. ESI-MS m/z 319 (MH)+.

Example 45: 2-Hydroxy-3-[2-(1-methyl-piperidin-4-yl)-acetylamino]-3,4-dihydro-2H-benzo[e][1,2]oxaborinine-8-carboxylic acid

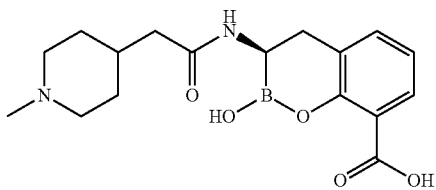 [SMILES: CN1CCC(CC(=O)N[C@H]2Cc3cccc(C(=O)O)c3OB2O)CC1]

Step 1. Synthesis of 2-Methoxy-3-[2-[2-(1-methyl-piperidin-4-yl)-acetylamino]-2-(2,9,9-trimethyl-3,5-dioxa-4-bora-tricyclo[6.1.1.02,6]dec-4-yl)-ethyl]-benzoic acid tert-butyl ester Prepared from 2-Methoxy-3-(2,9,9-trimethyl-3,5-dioxa-4-bora-tricyclo[6.1.1.02,6]dec-4-ylmethyl)-benzoic acid tert-butyl ester and (1-Methyl-piperidin-4-yl)-acetic acid following the procedure described in Step 1 of Example 8. The crude product was purified by flash chromatography on silica gel (Hexane/EtOAc, 2:1 to 1:2). ESI-MS m/z 569 (MH)+.

Step 2. Synthesis of 2-Hydroxy-3-[2-(1-methyl-piperidin-4-yl)-acetylamino]-3,4-dihydro-2H-benzo[e][1,2]oxaborinine-8-carboxylic acid Prepared 2-Methoxy-3-[2-[2-(1-methyl-piperidin-4-yl)-acetylamino]-2-(2,9,9-trimethyl-3,5-dioxa-4-bora-tricyclo [6.1.1.02,6]dec-4-yl)-ethyl]-benzoic acid tert-butyl ester and BCl3 following the procedure described in Step 5 of Example 1. The crude product was purified by reverse phase preparative HPLC [Waters Sunfire C18 OBD, 5 μm, 19×50 mm, 5-50% AcCN:H2O (with 0.1% TFA)] to afford product as a white solid. ESI-MS m/z 347 (MH)+.

Example 46: (R)-3-(azetidine-3-carboxamido)-2-hydroxy-3,4-dihydro-2H-benzo[e][1,2]oxaborinine-8-carboxylic acid

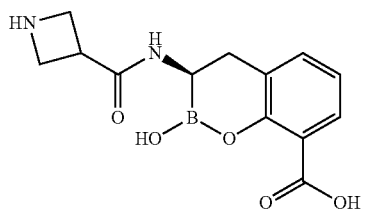 [SMILES: O=C(O)c1cccc2c1OB(O)[C@@H](NC(=O)C1CNC1)C2]

Step 1. Synthesis of 3-[2-(3-tert-Butoxycarbonyl-2-methoxy-phenyl)-1-(2,9,9-trimethyl-3,5-dioxa-4-bora-tricyclo[6.1.1.0²,⁶]dec-4-yl)-ethylcarbamoyl]-azetidine-1-carboxylic acid tert-butyl ester Prepared from 2-Methoxy-3-(2,9,9-trimethyl-3,5-dioxa-4-bora-tricyclo[6.1.1.02,6]dec-4-ylmethyl)-benzoic acid and 1-(tert-butoxycarbonyl)azetidine-3-carboxylic acid following the procedure described in Step 1 of Example 8. The crude product was purified by flash chromatography on silica gel (Hexane/EtOAc, 2:1 to 1:2). ESI-MS m/z 655 (MH)⁺.

Step 2. Synthesis of (R)-3-(azetidine-3-carboxamido)-2-hydroxy-3,4-dihydro-2H-benzo[e][1,2]oxaborinine-8-carboxylic acid Prepared from 3-[2-(3-tert-Butoxycarbonyl-2-methoxy-phenyl)-1-(2,9,9-trimethyl-3,5-dioxa-4-bora-tricyclo[6.1.1.0²'6]dec-4-yl)-ethylcarbamoyl]-azetidine-1-carboxylic acid tert-butyl ester and BCl₃ following the procedure described in Step 5 of Example 1. The crude product was purified by reverse phase preparative HPLC [Waters Sunfire C18 OBD, 5 m, 19×50 mm, 5-50% AcCN:H₂O (with 0.1% TFA)] to afford product as a white solid. ESI-MS m/z 333 (MH)⁺.

Example 47: (R)-3-(1-(4-(dimethylamino)phenylcarbamoyl)azetidine-3-carboxamido)-2-hydroxy-3,4-dihydro-2H-benzo[e][1,2]oxaborinine-8-carboxylic acid

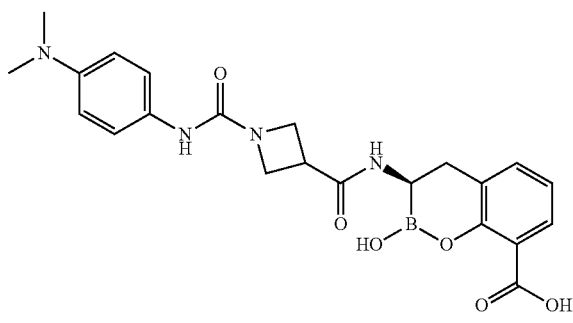 [SMILES: CN(C)c1ccc(NC(=O)N2CC(C(=O)N[C@H]3Cc4cccc(C(=O)O)c4OB3O)C2)cc1]

Step 1. Synthesis of (R)-3-(1-(4-(dimethylamino)phenylcarbamoyl)azetidine-3-carboxamido)-2-hydroxy-3,4-dihydro-2H-benzo[e][1,2]oxaborinine-8-carboxylic acid To 10 mg of (R)-3-(azetidine-3-carboxamido)-2-hydroxy-3,4-dihydro-2H-benzo[e][1,2]oxaborinine-8-carboxylic acid (Step 2, Example 46) in 1 mL of DMF was added 10 mg of 4-isocyanato-N,N-dimethylaniline. The resulting reaction mixture was stirred at room temperature overnight. The crude product was purified by reverse phase preparative HPLC [Waters Sunfire C18 OBD, 5 μm, 19×50 mm, 5-100% AcCN:H₂O (with 0.1% TFA)] to afford product as a white solid. ESI-MS m/z 453 (MH)⁺.

Example 48: (R)-2-hydroxy-3-(1-(pyrimidin-2-yl)azetidine-3-carboxamido)-3,4-dihydro-2H-benzo[e][1,2]oxaborinine-8-carboxylic acid

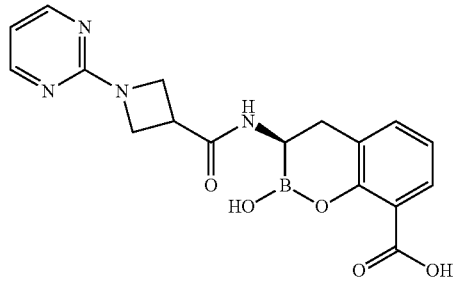 [SMILES: O=C(O)c1cccc2c1OB(O)[C@@H](NC(=O)C1CN(c3ncccn3)C1)C2]

Step 1. Synthesis of (R)-2-hydroxy-3-(1-(pyrimidin-2-yl)azetidine-3-carboxamido)-3,4-dihydro-2H-benzo[e][1,2]oxaborinine-8-carboxylic acid To 10 mg of (R)-3-(azetidine-3-carboxamido)-2-hydroxy-3,4-dihydro-2H-benzo[e][1,2]oxaborinine-8-carboxylic acid (Step 2, Example 46) in 1 mL of DMF was added 20 mg of 2-chloropyrimidine. The resulting reaction mixture was stirred at 100° C. for 5 h. The crude product was purified by reverse phase preparative HPLC [Waters Sunfire C18 OBD, 5 μm, 19×50 mm, 5-100% AcCN:H₂O (with 0.1% TFA)] to afford product as a white solid. ESI-MS m/z 369 (MH).

Example 49: 3-[(4-Amino-piperidine-4-carbonyl)-amino]-2-hydroxy-3,4-dihydro-2H-benzo[e][1,2]oxaborinine-8-carboxylic acid

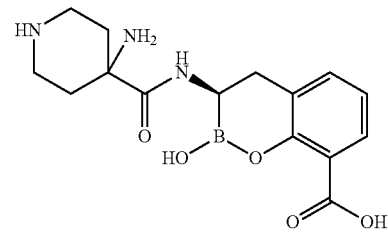 [SMILES: NC1(C(=O)N[C@H]2Cc3cccc(C(=O)O)c3OB2O)CCNCC1]

Step 1. Synthesis of tert-butyl 4-(benzyloxycarbonylamino)-4-((1R)-2-(3-(tert-butoxycarbonyl)-2-methoxyphenyl)-1-(2,9,9-trimethyl-3,5-dioxa-4-bora-tricyclo[6.1.1.0²,⁶]dec-4-yl)ethylcarbamoyl)piperidine-1-carboxylate Prepared from 4-(benzyloxycarbonylamino)-1-(tert-butoxycarbonyl) piperidine-4-carboxylic acid and 2-Methoxy-3-(2,9,9-trimethyl-3,5-dioxa-4-bora-tricyclo[6.1.1.02,6]dec-4-ylmethyl)-benzoic acid tert-butyl ester following the procedure described in Step 1 of Example 8. The crude product was purified by flash chromatography on silica gel (Hexane/EtOAc, 2:1 to 1:2). ESI-MS m/z 790 (MH).

Step 2. Synthesis of tert-butyl 4-amino-4-((1R)-2-(3-(tert-butoxycarbonyl)-2-methoxyphenyl)-1-(2,9,9-trimethyl-3,5-dioxa-4-bora-tricyclo[6.1.1.0²'6]dec-4-yl)ethylcarbamoyl)piperidine-1-carboxylate Prepared from tert-butyl 4-(benzyloxycarbonylamino)-4-((1R)-2-(3-(tert-butoxycarbonyl)-2-methoxyphenyl)-1-(2,9, 9-trimethyl-3,5-dioxa-4-bora-tricyclo[6.1.1.0²,⁶]dec-4-yl)ethylcarbamoyl)piperidine-1-carboxylate following procedure described in Step 2 of Example 33. ESI-MS m/z 656 (MH)⁺.

Step 3. Synthesis of 3-[(4-Amino-piperidine-4-carbonyl)-amino]-2-hydroxy-3,4-dihydro-2H-benzo[e][1,2]oxaborinine-8-carboxylic acid Prepared from tert-butyl 4-amino-4-((1R)-2-(3-(tert-butoxycarbonyl)-2-methoxyphenyl)-1-(2,9,9-trimethyl-3,5-dioxa-4-bora-tricyclo[6.1.1.0²,⁶]dec-4-yl)ethylcarbamoyl)piperidine-1-carboxylate and BCl₃ following the procedure described in Step 5 of Example 1. The crude product was purified by reverse phase preparative HPLC [Waters Sunfire C18 OBD, 5 μm, 19×50 mm, 5-50% AcCN:H₂O (with 0.1% TFA)] to afford product as a white solid. ESI-MS m/z 334 (MH)⁺.

Example 50: 2-Hydroxy-3-[(piperazine-2-carbonyl)-amino]-3,4-dihydro-2H-benzo[e][1,2]oxaborinine-8-carboxylic acid

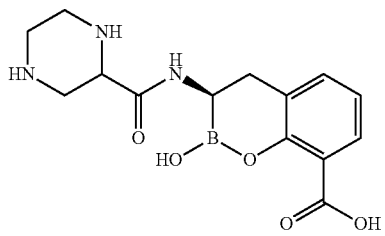

Step 1. Synthesis of 1-benzyl 4-tert-butyl 2-((1R)-2-(3-(tert-butoxycarbonyl)-2-methoxyphenyl)-1-(2,9,9-trimethyl-3,5-dioxa-4-bora-tricyclo[6.1.1.0²,⁶]dec-4-yl)ethylcarbamoyl)piperazine-1,4-dicarboxylate Prepared from 1-(benzyloxycarbonyl)-4-(tert-butoxycarbonyl)piperazine-2-carboxylic acid and 2-Methoxy-3-(2,9,9-trimethyl-3,5-dioxa-4-bora-tricyclo[6.1.1.02,6]dec-4-yl-methyl)-benzoic acid tert-butyl ester following the procedure described in Step 1 of Example 8. The crude product was purified by flash chromatography on silica gel (Hexane/EtOAc, 2:1 to 1:2). ESI-MS m/z 776 (MH)⁺.

Step 2. Synthesis of tert-butyl 3-((1R)-2-(3-(tert-butoxycarbonyl)-2-methoxyphenyl)-1-(2,9,9-trimethyl-3,5-dioxa-4-bora-tricyclo[6.1.1.0²,⁶]dec-4-yl)ethylcarbamoyl)piperazine-1-carboxylate Prepared from 1-benzyl 4-tert-butyl 2-((1R)-2-(3-(tert-butoxycarbonyl)-2-methoxyphenyl)-1-(2,9,9-trimethyl-3,5-dioxa-4-bora-tricyclo[6.1.1.0²,⁶]dec-4-yl)ethylcarbamoyl)piperazine-1,4-dicarboxylate following procedure described in Step 2 of Example 33. ESI-MS m/z 642 (MH)⁺.

Step 3. Synthesis of 2-Hydroxy-3-[(piperazine-2-carbonyl)-amino]-3,4-dihydro-2H-benzo[e][1,2]oxaborinine-8-carboxylic acid Prepared from tert-butyl 3-((1R)-2-(3-(tert-butoxycarbonyl)-2-methoxyphenyl)-1-(2,9,9-trimethyl-3,5-dioxa-4-bora-tricyclo[6.1.1.0²,⁶]dec-4-yl)ethylcarbamoyl)piperazine-1-carboxylate and BCl₃ following the procedure described in Step 5 of Example 1. The crude product was purified by reverse phase preparative HPLC [Waters Sunfire C18 OBD, 5 μm, 19×50 mm, 5-50% AcCN:H₂O (with 0.1% TFA)] to afford product as a white solid. ESI-MS m/z 320 (MH)⁺.

Example 51: 3-[(4-Dimethylamino-1-methyl-piperidine-4-carbonyl)-amino]-2-hydroxy-3,4-dihydro-2H-benzo[e][1,2]oxaborinine-8-carboxylic acid

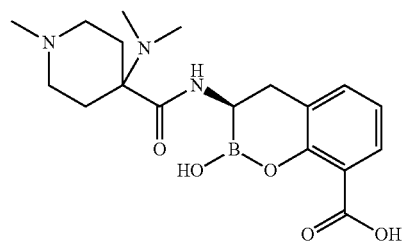 [SMILES: CN1CCC(C(=O)N[C@H]2Cc3cccc(C(=O)O)c3OB2O)(N(C)C)CC1]

Step 1. Synthesis of 3-[(4-Dimethylamino-1-methyl-piperidine-4-carbonyl)-amino]-2-hydroxy-3,4-dihydro-2H-benzo[e][1,2]oxaborinine-8-carboxylic acid To 3-[(4-Amino-piperidine-4-carbonyl)-amino]-2-hydroxy-3,4-dihydro-2H-benzo[e][1,2]oxaborinine-8-carboxylic acid (Step 3, Example 49, 10.0 mg) in methanol (5 mL) was added formaldehyde (1.0 mL, 37% solution), followed by 10% palladium on carbon (20 mg). The reaction mixture was hydrogenated under H₂ balloon for 3 h. The reaction mixture was filtrated and the solvent was removed under vacuum. The crude product was purified by reverse phase preparative HPLC [Waters Sunfire C18 OBD, 5 m, 19×50 mm, 5-100% AcCN:H₂O (with 0.1% TFA)] to afford product as a white solid. ESI-MS m/z 376 (MH)⁺.

Example 52: 3-{2-[1-(2-Amino-ethyl)-piperidin-4-ylamino]-acetylamino}-2-hydroxy-3,4-dihydro-2H-benzo[e][1,2]oxaborinine-8-carboxylic acid

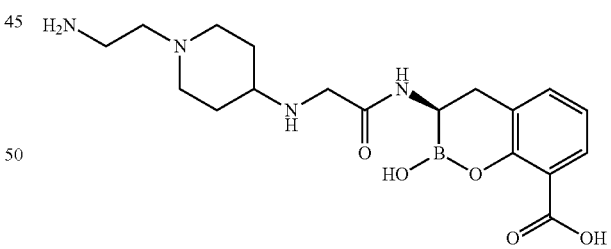

Step 1. Synthesis of 4-(Benzyloxycarbonylmethyl-amino)-piperidine-1-carboxylic acid tert-butyl ester Potassium carbonate (2.35 g, 17.0 mmol) and benzyl bromoacetate (0.74 mL, 4.67 mmol) were added to a solution of 4-amino-1-Boc-piperidine (0.850 g, 4.24 mmol) in acetonitrile (55 mL) under argon and stirred at room temperature for 20 h. The reaction was diluted with ethyl acetate and washed with sat. NaHCO₃ and brine. The organic layer was dried over Na₂SO₄, filtered, and concentrated. The crude product was carried forward without purification. ESI-MS m/z 349 (MH)⁺.

Step 2. Synthesis of 4-(Benzyloxycarbonyl-benzyloxycarbonylmethyl-amino)-piperidine-1-carboxylic acid tert-butyl ester Triethylamine (2.1 mL, 15.1 mmol) and 4-(dimethylamino)pyridine (0.262 g, 2.14 mmol) were added to a solution of 4-(Benzyloxycarbonylmethyl-amino)-piperidine-1-carboxylic acid tert-butyl ester (1.48 g, 4.25 mmol) in DCM (42 mL) under argon. The reaction mixture was cooled to 5° C. for 20 min. Benzyl chloroformate (1.3 mL, 8.90 mmol) was added slowly and the reaction allowed to warm to room temperature and stir for 18 h. The reaction was quenched with brine and extracted with DCM (3×). The combined organic layers were dried over $Na_2SO_4$, filtered, and concentrated. The crude product was purified by flash chromatography on silica gel (0-40% EtOAc:Hexane). ESI-MS m/z 483 $(MH)^+$.

Step 3. Synthesis of (Benzyloxycarbonyl-piperidin-4-yl-amino)-acetic acid benzyl ester To a solution of 4-(Benzyloxycarbonyl-benzyloxycarbonylmethyl-amino)-piperidine-1-carboxylic acid tert-butyl ester (0.860 g, 1.78 mmol) in DCM (15 mL) was added hydrochloric acid (4.0N in 1,4-dioxane, 2.2 mL, 8.80 mmol) and the reaction was stirred at room temperature for 17 h. The reaction was concentrated in vacuo and carried forward without purification. ESI-MS m/z 383 $(MH)^+$.

Step 4. Synthesis of {Benzyloxycarbonyl-[1-(2-tert-butoxycarbonylamino-ethyl)-piperidin-4-yl]-amino}-acetic acid benzyl ester A solution of (Benzyloxycarbonyl-piperidin-4-yl-amino)-acetic acid benzyl ester (0.681 g, 1.78 mmol) and (2-oxo-ethyl)-carbamic acid tert-butyl ester (0.325 g, 2.04 mmol) in methanol (12 mL) was stirred under argon for 7 h. Sodium triacetoxyborohydride (0.554 g, 2.61 mmol) was added and the reaction stirred overnight. The reaction was quenched with sat. $NaHCO_3$ and extracted with ethyl acetate (3×). The combined organic layers were washed with brine, dried over $Na_2SO_4$, filtered, and concentrated. The crude product was purified by flash chromatography on silica gel (0-100% EtOAc:Hexane). ESI-MS m/z 526 (MH).

Step 5. Synthesis of [1-(2-tert-Butoxycarbonylamino-ethyl)-piperidin-4-ylamino]-acetic acid A solution of {Benzyloxycarbonyl-[1-(2-tert-butoxycarbonylamino-ethyl)-piperidin-4-yl]-amino}-acetic acid benzyl ester (0.273 g, 0.519 mmol) in methanol (5.5 mL) was purged with argon for 5 min. Palladium on carbon (10%, 0.052 g) was added, flask evacuated, and the reaction stirred under a $H_2$ atmosphere at room temperature for 18 h. The reaction was filtered through a Celite-plugged filter frit, washed with methanol and DCM, and concentrated. The crude product was carried forward without purification. ESI-MS m/z 302 $(MH)^+$.

Step 6. Synthesis of {tert-Butoxycarbonyl-[1-(2-tert-butoxycarbonylamino-ethyl)-piperidin-4-yl]-amino}-acetic acid To a solution of [1-(2-tert-Butoxycarbonylamino-ethyl)-piperidin-4-ylamino]-acetic acid (0.156 g, 0.518 mmol) in THF (2.0 mL) and $H_2O$ (2.0 mL) was added di-tert-butyl dicarbonate (0.126 g, 0.577 mmol) and sodium bicarbonate (0.058 g, 0.690 mmol). The reaction was stirred at room temperature for 17 h. The reaction was quenched with 3N HCl, diluted with brine, and extracted with ethyl acetate (3×). The combined organic layers were dried over $Na_2SO_4$, filtered, and concentrated. The crude product was carried forward without purification. ESI-MS m/z 424 $(M+Na)^+$.

Step 7. Synthesis of 3-[2-(2-{tert-Butoxycarbonyl-[1-(2-tert-butoxycarbonylamino-ethyl)-piperidin-4-yl]-amino}-acetylamino)-2-(2,9,9-trimethyl-3,5-dioxa-4-bora-tricyclo[6.1.1.02,6]dec-4-yl)-ethyl]-2-methoxy-benzoic acid tert-butyl ester Prepared from 2-Methoxy-3-(2,9,9-trimethyl-3,5-dioxa-4-bora-tricyclo[6.1.1.02,6]dec-4-ylmethyl)-benzoic acid tert-butyl ester and {tert-Butoxycarbonyl-[1-(2-tert-butoxycarbonylamino-ethyl)-piperidin-4-yl]-amino}-acetic acid following the procedure described in Step 1 of Example 8. The crude product was purified by reverse phase column [C18, 30 g, 5-100% $AcCN:H_2O$ (with 0.1% TFA)] to afford product as a white solid. ESI-MS m/z 813 $(MH)^+$.

Step 8. Synthesis of 3-{2-[1-(2-Amino-ethyl)-piperidin-4-ylamino]-acetylamino}-2-hydroxy-3,4-dihydro-2H-benzo[e][1,2]oxaborinine-8-carboxylic acid Prepared from 3-[2-(2-{tert-Butoxycarbonyl-[1-(2-tert-butoxycarbonylamino-ethyl)-piperidin-4-yl]-amino}-acetylamino)-2-(2,9,9-trimethyl-3,5-dioxa-4-bora-tricyclo[6.1.1.02,6]dec-4-yl)-ethyl]-2-methoxy-benzoic acid tert-butyl ester and $BCl_3$ following the procedure described in Step 5 of Example 1. The crude product was purified by reverse phase preparative HPLC [Phenomenex Luna C18, 5 µm, 19×50 mm, 5-40% $AcCN:H_2O$ (with 0.1% TFA)] to afford product as a white solid. ESI-MS m/z 391 $(MH)^+$.

TABLE 1

Examples of Compounds

| Example | Structure | MW | ESI-MS (m/z) for [MH]+ |
|---|---|---|---|
| 1 | 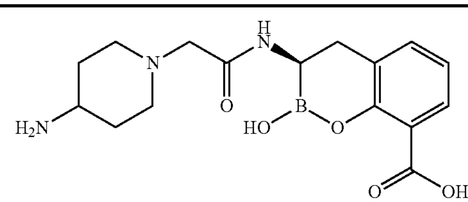 | 347 | 348 |

TABLE 1-continued

Examples of Compounds

| Example | Structure | MW | ESI-MS (m/z) for [MH]+ |
|---|---|---|---|
| 2 | 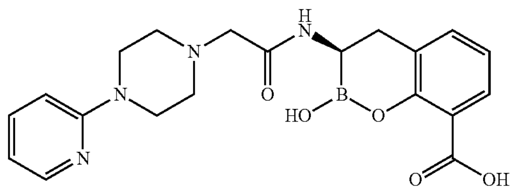 [SMILES: O=C(CN1CCN(c2ccccn2)CC1)N[C@H]1Cc2cccc(C(=O)O)c2OB1O] | 410 | 411 |
| 3 | 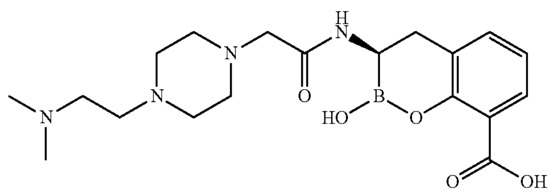 [SMILES: CN(C)CCN1CCN(CC(=O)N[C@H]2Cc3cccc(C(=O)O)c3OB2O)CC1] | 404 | 405 |
| 4 | 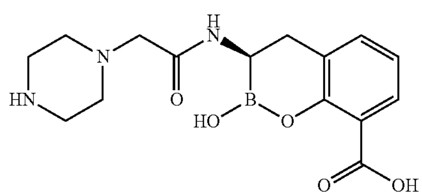 [SMILES: O=C(CN1CCNCC1)N[C@H]1Cc2cccc(C(=O)O)c2OB1O] | 333 | 334 |
| 5 | 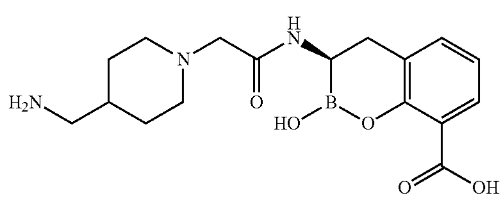 [SMILES: NCC1CCN(CC(=O)N[C@H]2Cc3cccc(C(=O)O)c3OB2O)CC1] | 361 | 362 |
| 6 | 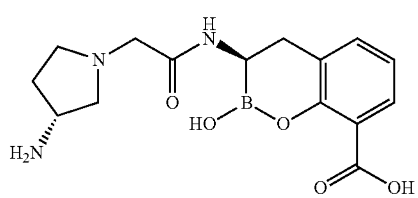 [SMILES: N[C@@H]1CCN(CC(=O)N[C@H]2Cc3cccc(C(=O)O)c3OB2O)C1] | 333 | 334 |
| 7 | 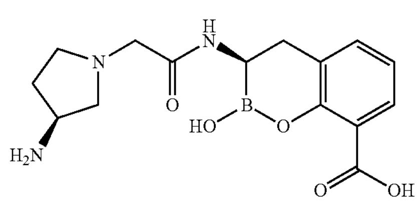 [SMILES: N[C@H]1CCN(CC(=O)N[C@H]2Cc3cccc(C(=O)O)c3OB2O)C1] | 333 | 334 |
| 8 | 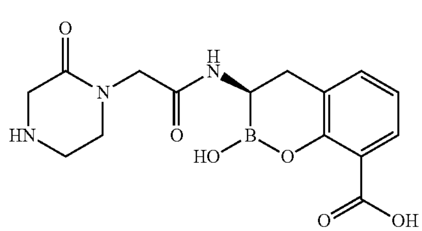 [SMILES: O=C(CN1CCNCC1=O)N[C@H]1Cc2cccc(C(=O)O)c2OB1O] | 347 | 348 |

TABLE 1-continued

Examples of Compounds

| Example | Structure | MW | ESI-MS (m/z) for [MH]+ |
|---|---|---|---|
| 9 | 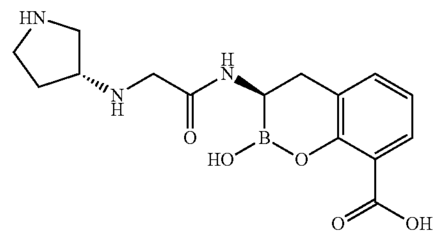 [SMILES: O=C(CN[C@@H]1CCNC1)N[C@H]1Cc2cccc(C(=O)O)c2OB1O] | 333 | 334 |
| 10 | 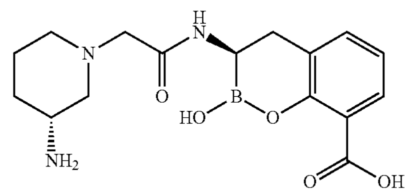 [SMILES: N[C@@H]1CCCN(CC(=O)N[C@H]2Cc3cccc(C(=O)O)c3OB2O)C1] | 347 | 348 |
| 11 | 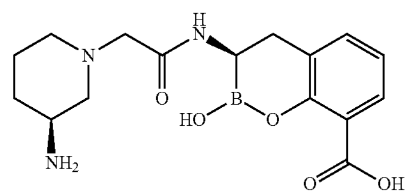 [SMILES: N[C@H]1CCCN(CC(=O)N[C@H]2Cc3cccc(C(=O)O)c3OB2O)C1] | 347 | 348 |
| 12 | 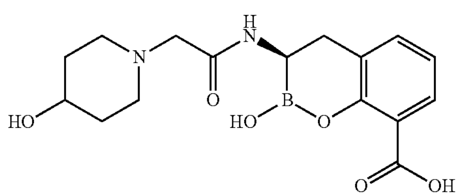 [SMILES: O=C(CN1CCC(O)CC1)N[C@H]1Cc2cccc(C(=O)O)c2OB1O] | 348 | 349 |
| 13 | 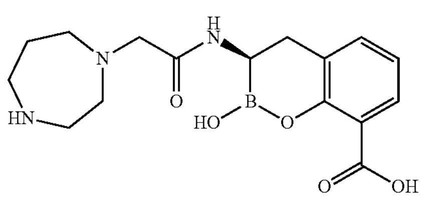 [SMILES: O=C(CN1CCCNCC1)N[C@H]1Cc2cccc(C(=O)O)c2OB1O] | 347 | 348 |
| 14 | 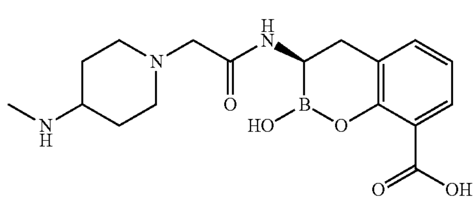 [SMILES: CNC1CCN(CC(=O)N[C@H]2Cc3cccc(C(=O)O)c3OB2O)CC1] | 361 | 362 |
| 15 | 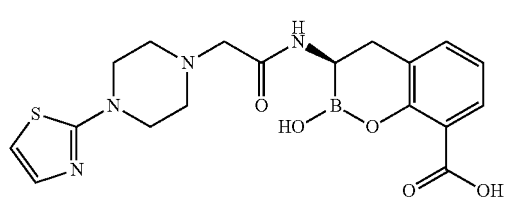 [SMILES: O=C(CN1CCN(c2nccs2)CC1)N[C@H]1Cc2cccc(C(=O)O)c2OB1O] | 416 | 417 |

TABLE 1-continued

Examples of Compounds

| Example | Structure | MW | ESI-MS (m/z) for [MH]+ |
|---|---|---|---|
| 16 | 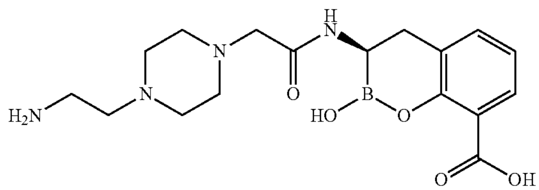 [SMILES: NCCN1CCN(CC(=O)N[C@H]2Cc3cccc(C(=O)O)c3OB2O)CC1] | 376 | 377 |
| 17 | 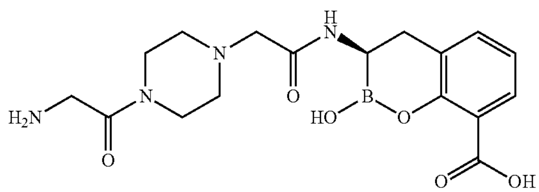 [SMILES: NCC(=O)N1CCN(CC(=O)N[C@H]2Cc3cccc(C(=O)O)c3OB2O)CC1] | 390 | 391 |
| 18 | 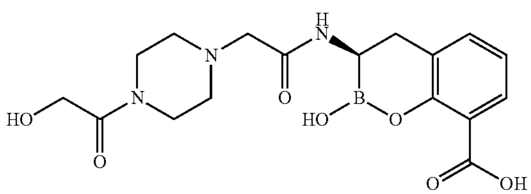 [SMILES: O=C(CN1CCN(C(=O)CO)CC1)N[C@H]1Cc2cccc(C(=O)O)c2OB1O] | 377 | 378 |
| 19 | 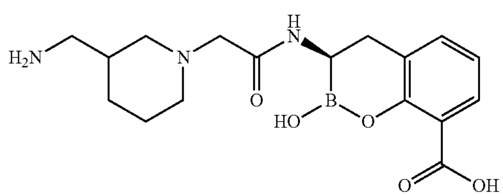 [SMILES: NCC1CCCN(CC(=O)N[C@H]2Cc3cccc(C(=O)O)c3OB2O)C1] | 361 | 362 |
| 20 | 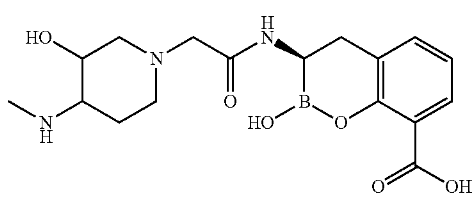 [SMILES: CNC1CCN(CC(=O)N[C@H]2Cc3cccc(C(=O)O)c3OB2O)CC1O] | 377 | 378 |
| 21 | 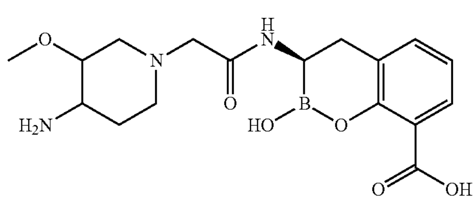 [SMILES: COC1CN(CC(=O)N[C@H]2Cc3cccc(C(=O)O)c3OB2O)CCC1N] | 377 | 378 |
| 22 | 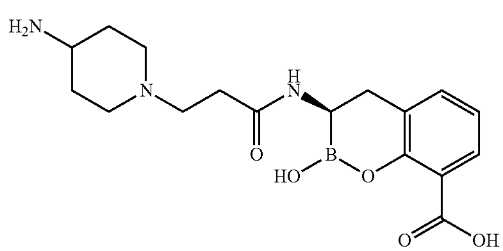 [SMILES: NC1CCN(CCC(=O)N[C@H]2Cc3cccc(C(=O)O)c3OB2O)CC1] | 361 | 362 |

TABLE 1-continued

Examples of Compounds

| Example | Structure | MW | ESI-MS (m/z) for [MH]+ |
|---|---|---|---|
| 23 | 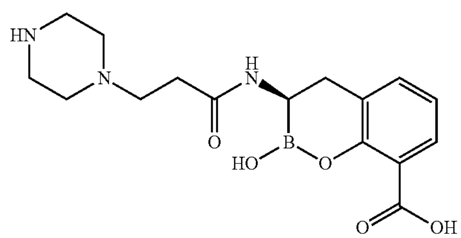 | 347 | 348 |
| 24 | 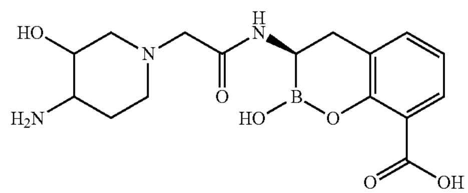 [SMILES: NC1CCN(CC(=O)N[C@H]2Cc3cccc(C(=O)O)c3OB2O)CC1O] | 363 | 364 |
| 25 | 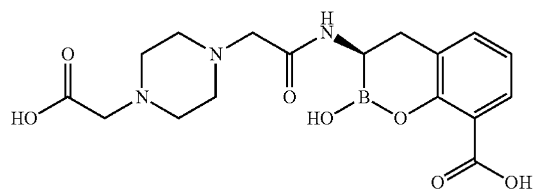 [SMILES: O=C(O)CN1CCN(CC(=O)N[C@H]2Cc3cccc(C(=O)O)c3OB2O)CC1] | 391 | 392 |
| 26 | 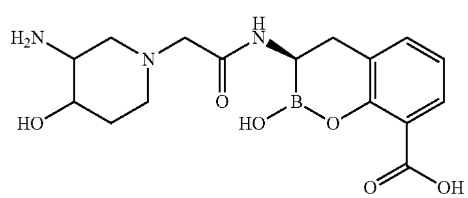 [SMILES: NC1CN(CC(=O)N[C@H]2Cc3cccc(C(=O)O)c3OB2O)CCC1O] | 363 | 364 |
| 27 | 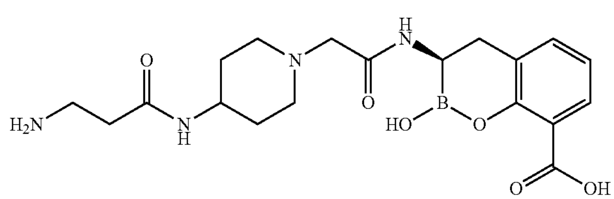 [SMILES: NCCC(=O)NC1CCN(CC(=O)N[C@H]2Cc3cccc(C(=O)O)c3OB2O)CC1] | 418 | 419 |
| 28 | 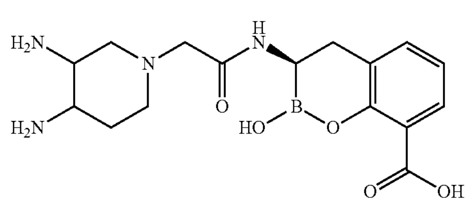 [SMILES: NC1CCN(CC(=O)N[C@H]2Cc3cccc(C(=O)O)c3OB2O)CC1N] | 362 | 363 |
| 29 | 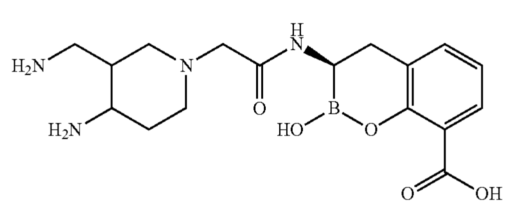 [SMILES: NCC1CN(CC(=O)N[C@H]2Cc3cccc(C(=O)O)c3OB2O)CCC1N] | 376 | 377 |

TABLE 1-continued

Examples of Compounds

| Example | Structure | MW | ESI-MS (m/z) for [MH]+ |
|---|---|---|---|
| 30 | 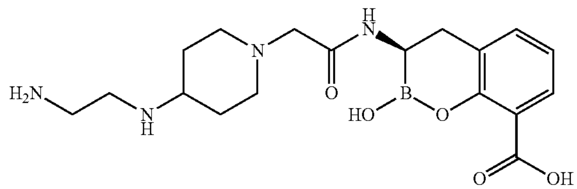 [SMILES: NCCNC1CCN(CC(=O)N[C@H]2Cc3cccc(C(=O)O)c3OB2O)CC1] | 390 | 391 |
| 31 | 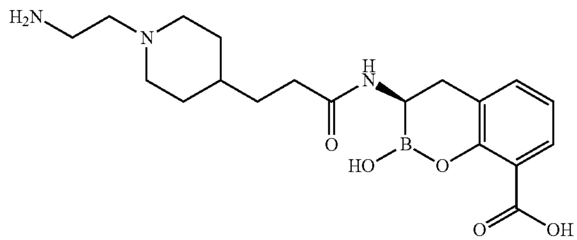 [SMILES: NCCN1CCC(CCC(=O)N[C@H]2Cc3cccc(C(=O)O)c3OB2O)CC1] | 389 | 390 |
| 32 | 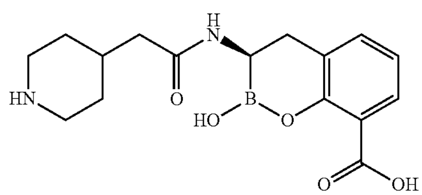 [SMILES: O=C(CC1CCNCC1)N[C@H]1Cc2cccc(C(=O)O)c2OB1O] | 332 | 333 |
| 33 | 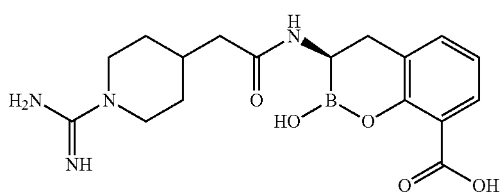 [SMILES: N=C(N)N1CCC(CC(=O)N[C@H]2Cc3cccc(C(=O)O)c3OB2O)CC1] | 374 | 375 |
| 34 | 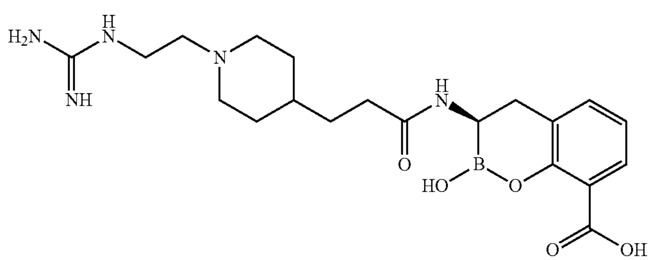 [SMILES: N=C(N)NCCN1CCC(CCC(=O)N[C@H]2Cc3cccc(C(=O)O)c3OB2O)CC1] | 431 | 432 |
| 35 | 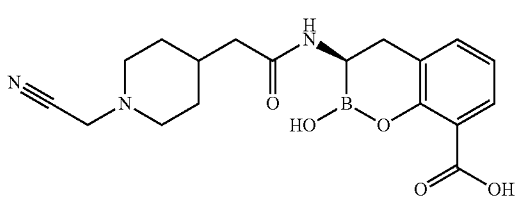 [SMILES: N#CCN1CCC(CC(=O)N[C@H]2Cc3cccc(C(=O)O)c3OB2O)CC1] | 371 | 372 |
| 36 | 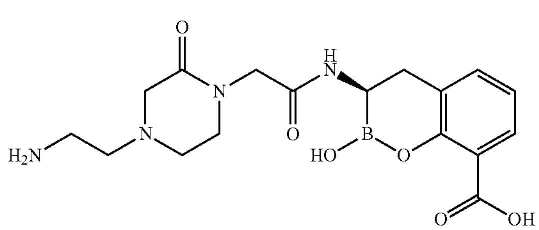 [SMILES: NCCN1CCN(CC(=O)N[C@H]2Cc3cccc(C(=O)O)c3OB2O)C(=O)C1] | 390 | 391 |

TABLE 1-continued

Examples of Compounds

| Example | Structure | MW | ESI-MS (m/z) for [MH]+ |
|---|---|---|---|
| 37 | 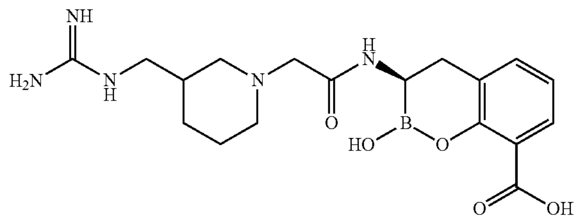 [SMILES: N=C(N)NCC1CCCN(CC(=O)N[C@H]2Cc3cccc(C(=O)O)c3OB2O)C1] | 403 | 404 |
| 38 | 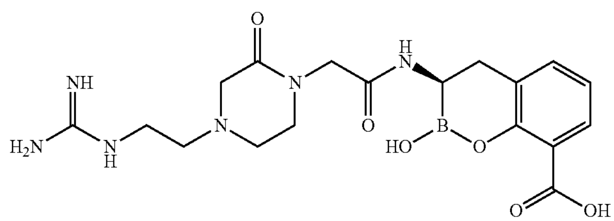 [SMILES: N=C(N)NCCN1CCN(CC(=O)N[C@H]2Cc3cccc(C(=O)O)c3OB2O)C(=O)C1] | 432 | 433 |
| 39 | 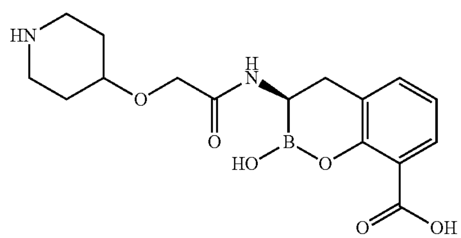 | 348 | 349 |
| 40 | 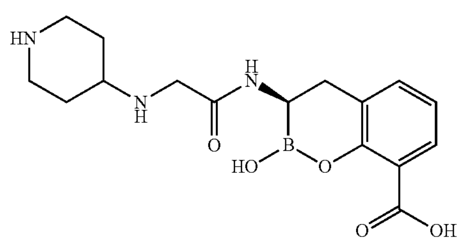 | 347 | 348 |
| 41 | 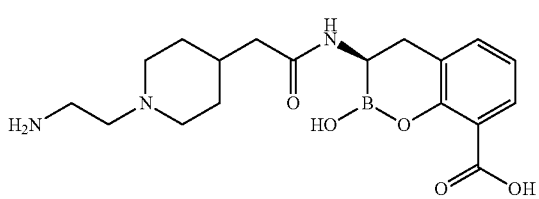 [SMILES: NCCN1CCC(CC(=O)N[C@H]2Cc3cccc(C(=O)O)c3OB2O)CC1] | 375 | 376 |
| 42 | 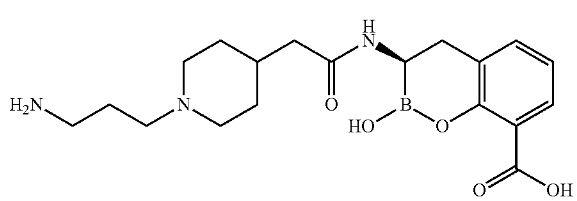 [SMILES: NCCCN1CCC(CC(=O)N[C@H]2Cc3cccc(C(=O)O)c3OB2O)CC1] | 389 | 390 |

TABLE 1-continued

Examples of Compounds

| Example | Structure | MW | ESI-MS (m/z) for [MH]+ |
|---|---|---|---|
| 43 | 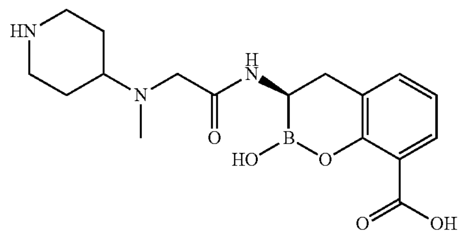 | 361 | 362 |
| 44 | 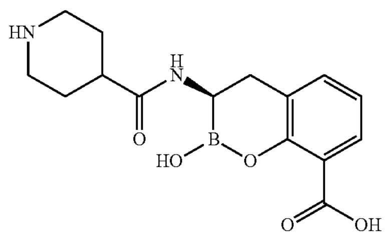 [SMILES: O=C(O)c1cccc2c1OB(O)[C@@H](NC(=O)C1CCNCC1)C2] | 318 | 319 |
| 45 | 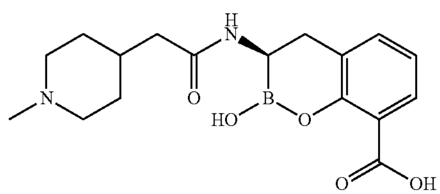 [SMILES: CN1CCC(CC(=O)N[C@H]2Cc3cccc(C(=O)O)c3OB2O)CC1] | 346 | 347 |
| 46 | 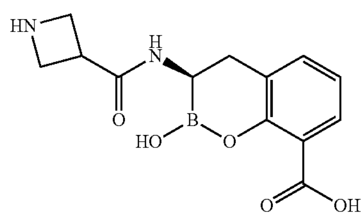 [SMILES: O=C(O)c1cccc2c1OB(O)[C@@H](NC(=O)C1CNC1)C2] | 332 | 333 |
| 47 | 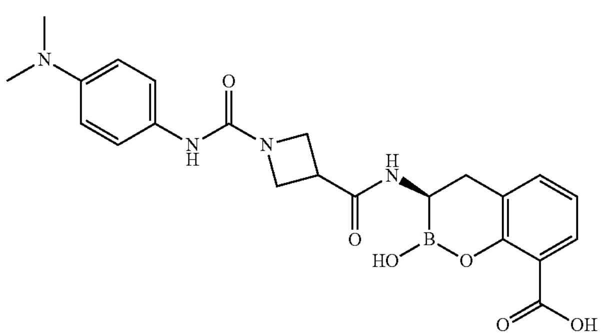 [SMILES: CN(C)c1ccc(NC(=O)N2CC(C(=O)N[C@H]3Cc4cccc(C(=O)O)c4OB3O)C2)cc1] | 452 | 453 |
| 48 | 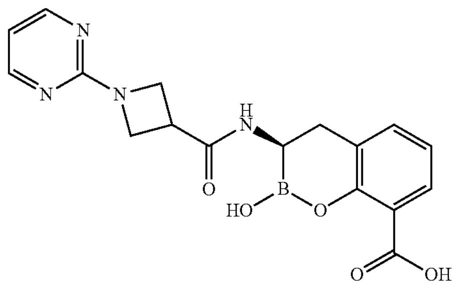 [SMILES: O=C(O)c1cccc2c1OB(O)[C@@H](NC(=O)C1CN(c3ncccn3)C1)C2] | 368 | 369 |

TABLE 1-continued

Examples of Compounds

| Example | Structure | MW | ESI-MS (m/z) for [MH]+ |
|---|---|---|---|
| 49 | 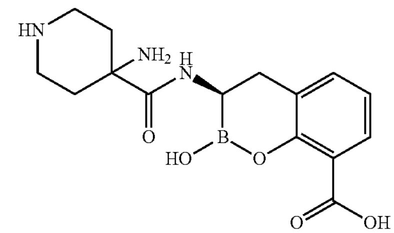 [SMILES: NC1(C(=O)N[C@H]2Cc3cccc(C(=O)O)c3OB2O)CCNCC1] | 333 | 334 |
| 50 | 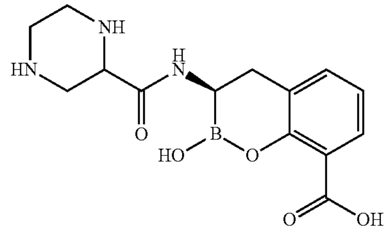 [SMILES: O=C(O)c1cccc2c1OB(O)[C@@H](NC(=O)C1CNCCN1)C2] | 319 | 320 |
| 51 | 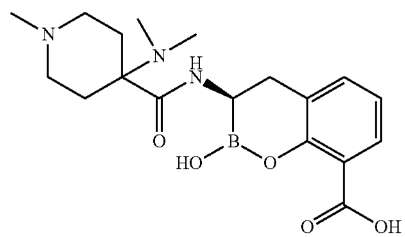 [SMILES: CN1CCC(C(=O)N[C@H]2Cc3cccc(C(=O)O)c3OB2O)(N(C)C)CC1] | 375 | 376 |
| 52 | 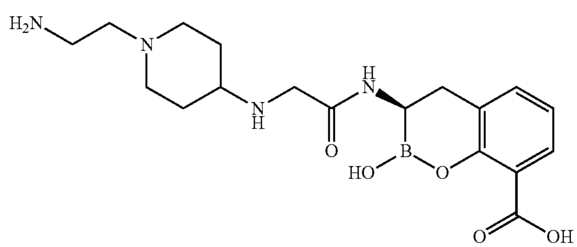 [SMILES: NCCN1CCC(NCC(=O)N[C@H]2Cc3cccc(C(=O)O)c3OB2O)CC1] | 390 | 391 |
| 53 | 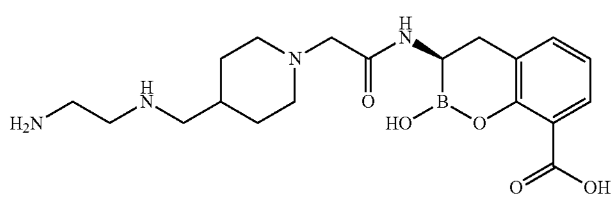 [SMILES: NCCNCC1CCN(CC(=O)N[C@H]2Cc3cccc(C(=O)O)c3OB2O)CC1] | | |
| 54 | 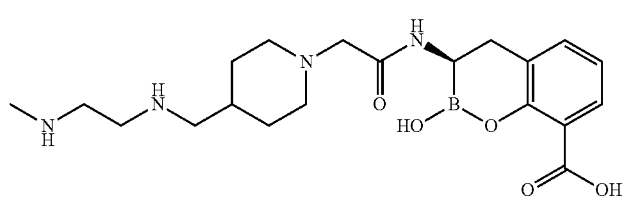 [SMILES: CNCCNCC1CCN(CC(=O)N[C@H]2Cc3cccc(C(=O)O)c3OB2O)CC1] | | |

TABLE 1-continued

Examples of Compounds

| Example | Structure | MW | ESI-MS (m/z) for [MH]+ |
|---------|-----------|----|-----|
| 55 | 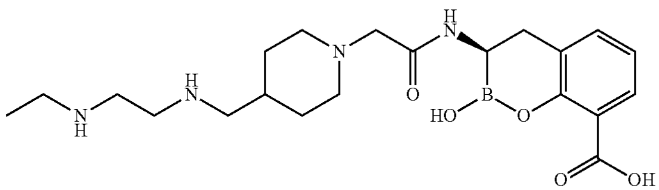 [SMILES: CCNCCNCC1CCN(CC(=O)N[C@H]2Cc3cccc(C(=O)O)c3OB2O)CC1] | | |
| 56 | 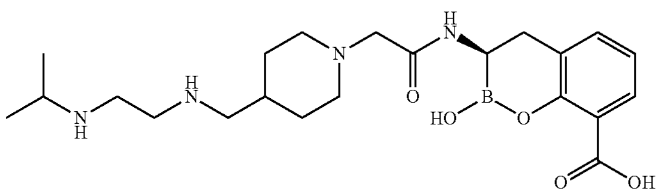 [SMILES: CC(C)NCCNCC1CCN(CC(=O)N[C@H]2Cc3cccc(C(=O)O)c3OB2O)CC1] | | |
| 57 | 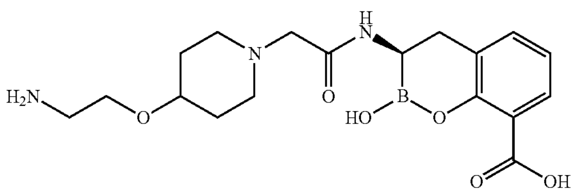 [SMILES: NCCOC1CCN(CC(=O)N[C@H]2Cc3cccc(C(=O)O)c3OB2O)CC1] | | |
| 58 | 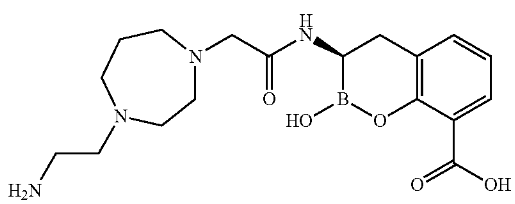 [SMILES: NCCN1CCCN(CC(=O)N[C@H]2Cc3cccc(C(=O)O)c3OB2O)CC1] | | |
| 59 | 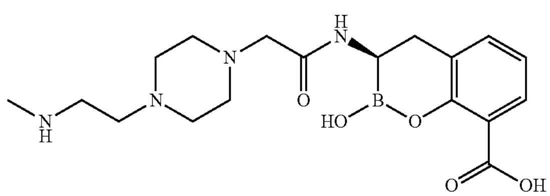 [SMILES: CNCCN1CCN(CC(=O)N[C@H]2Cc3cccc(C(=O)O)c3OB2O)CC1] | | |
| 60 | 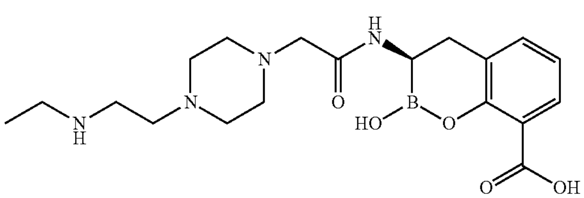 [SMILES: CCNCCN1CCN(CC(=O)N[C@H]2Cc3cccc(C(=O)O)c3OB2O)CC1] | | |
| 61 | 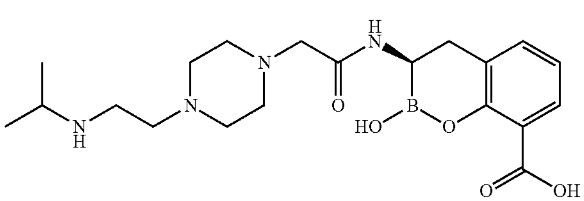 [SMILES: CC(C)NCCN1CCN(CC(=O)N[C@H]2Cc3cccc(C(=O)O)c3OB2O)CC1] | | |

TABLE 1-continued

Examples of Compounds

| Example | Structure | MW | ESI-MS (m/z) for [MH]+ |
|---|---|---|---|
| 62 | 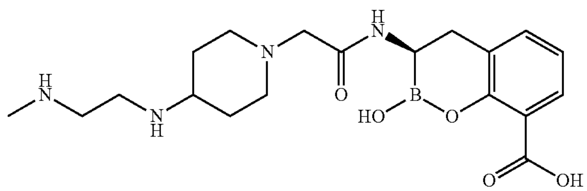 [SMILES: CNCCNC1CCN(CC(=O)N[C@H]2Cc3cccc(C(=O)O)c3OB2O)CC1] | | |
| 63 | 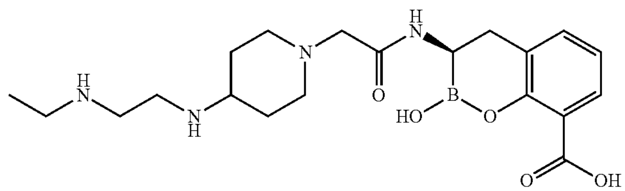 [SMILES: CCNCCNC1CCN(CC(=O)N[C@H]2Cc3cccc(C(=O)O)c3OB2O)CC1] | | |
| 64 | 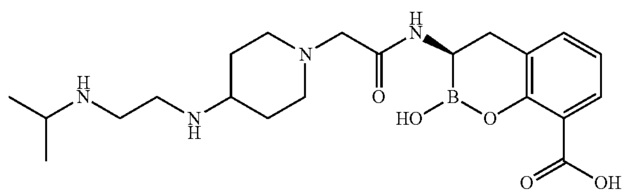 [SMILES: CC(C)NCCNC1CCN(CC(=O)N[C@H]2Cc3cccc(C(=O)O)c3OB2O)CC1] | | |
| 65 | 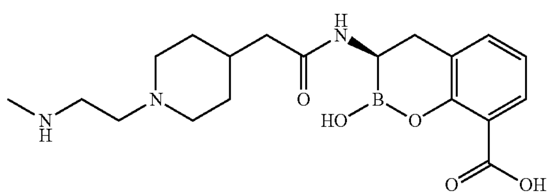 [SMILES: CNCCN1CCC(CC(=O)N[C@H]2Cc3cccc(C(=O)O)c3OB2O)CC1] | | |
| 66 | 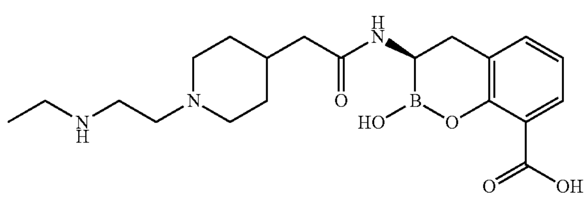 [SMILES: CCNCCN1CCC(CC(=O)N[C@H]2Cc3cccc(C(=O)O)c3OB2O)CC1] | | |
| 67 | 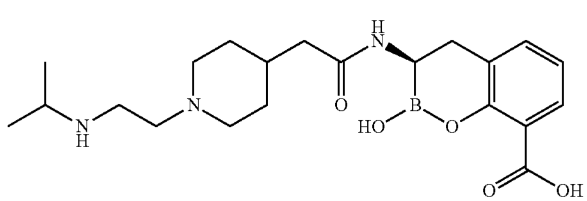 [SMILES: CC(C)NCCN1CCC(CC(=O)N[C@H]2Cc3cccc(C(=O)O)c3OB2O)CC1] | | |
| 68 | 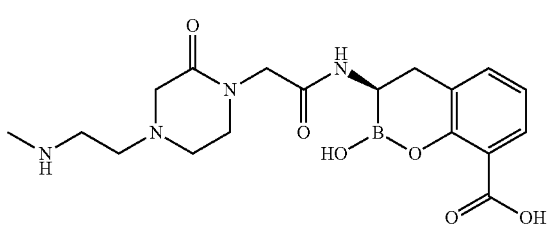 [SMILES: CNCCN1CCN(CC(=O)N[C@H]2Cc3cccc(C(=O)O)c3OB2O)C(=O)C1] | | |

TABLE 1-continued

Examples of Compounds

| Example | Structure | MW | ESI-MS (m/z) for [MH]+ |
|---|---|---|---|
| 69 | 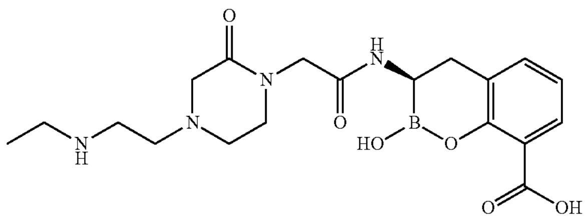 [SMILES: CCNCCN1CCN(CC(=O)N[C@H]2Cc3cccc(C(=O)O)c3OB2O)C(=O)C1] | | |
| 70 | 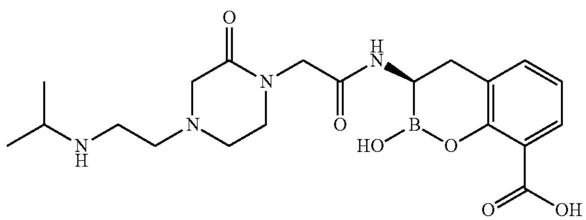 [SMILES: CC(C)NCCN1CCN(CC(=O)N[C@H]2Cc3cccc(C(=O)O)c3OB2O)C(=O)C1] | | |
| 71 | 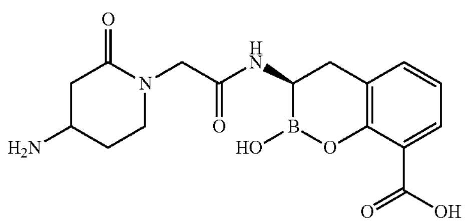 [SMILES: NC1CCN(CC(=O)N[C@H]2Cc3cccc(C(=O)O)c3OB2O)C(=O)C1] | | |
| 72 | 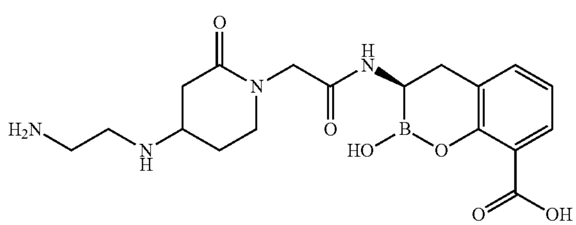 [SMILES: NCCNC1CCN(CC(=O)N[C@H]2Cc3cccc(C(=O)O)c3OB2O)C(=O)C1] | | |
| 73 | 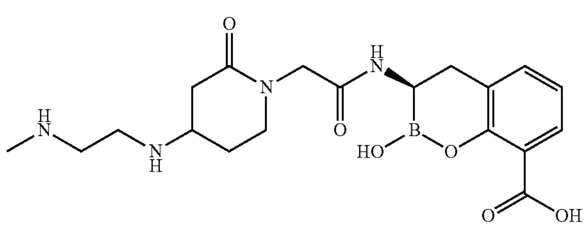 [SMILES: CNCCNC1CCN(CC(=O)N[C@H]2Cc3cccc(C(=O)O)c3OB2O)C(=O)C1] | | |
| 74 | 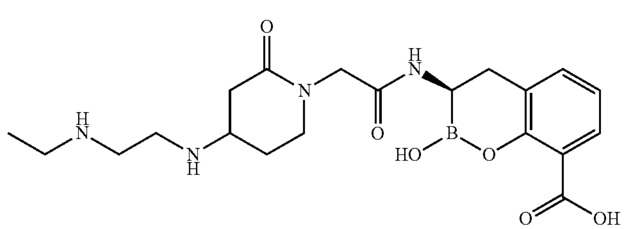 [SMILES: CCNCCNC1CCN(CC(=O)N[C@H]2Cc3cccc(C(=O)O)c3OB2O)C(=O)C1] | | |

TABLE 1-continued

Examples of Compounds

| Example | Structure | MW | ESI-MS (m/z) for [MH]+ |
|---|---|---|---|
| 75 | 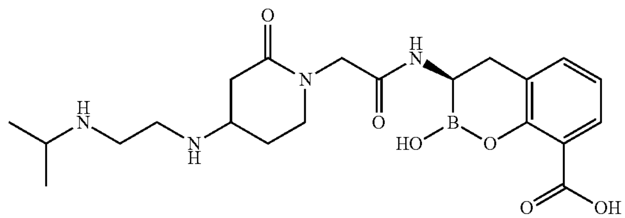 [SMILES: CC(C)NCCNC1CCN(CC(=O)N[C@H]2Cc3cccc(C(=O)O)c3OB2O)C(=O)C1] | | |
| 76 | 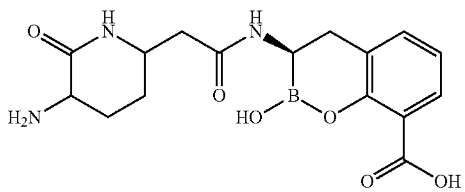 [SMILES: NC1CCC(CC(=O)N[C@H]2Cc3cccc(C(=O)O)c3OB2O)NC1=O] | | |
| 77 | 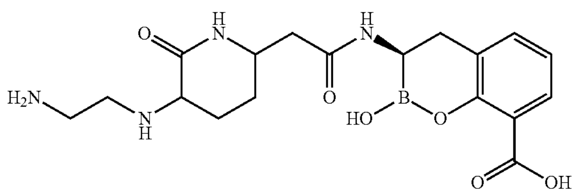 [SMILES: NCCNC1CCC(CC(=O)N[C@H]2Cc3cccc(C(=O)O)c3OB2O)NC1=O] | | |
| 78 | 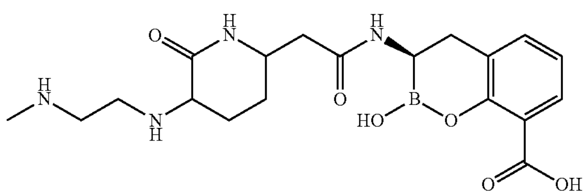 [SMILES: CNCCNC1CCC(CC(=O)N[C@H]2Cc3cccc(C(=O)O)c3OB2O)NC1=O] | | |
| 79 | 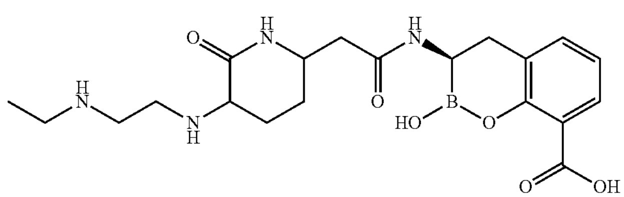 [SMILES: CCNCCNC1CCC(CC(=O)N[C@H]2Cc3cccc(C(=O)O)c3OB2O)NC1=O] | | |
| 80 | 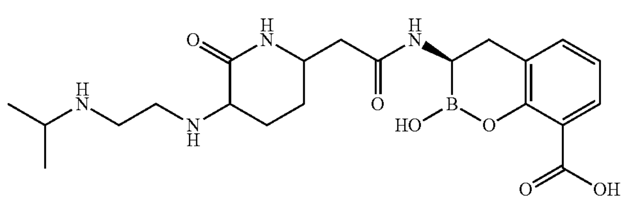 [SMILES: CC(C)NCCNC1CCC(CC(=O)N[C@H]2Cc3cccc(C(=O)O)c3OB2O)NC1=O] | | |
| 81 | 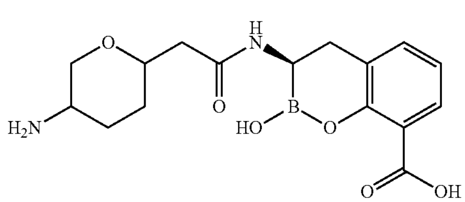 | | |

TABLE 1-continued

Examples of Compounds

| Example | Structure | MW | ESI-MS (m/z) for [MH]+ |
|---|---|---|---|
| 82 | 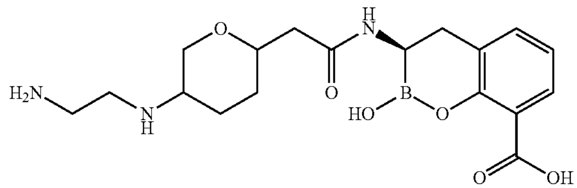 [SMILES: NCCNC1CCC(CC(=O)N[C@H]2Cc3cccc(C(=O)O)c3OB2O)OC1] | | |
| 83 | 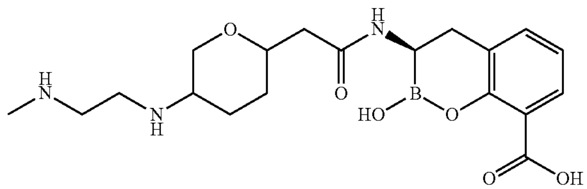 [SMILES: CNCCNC1CCC(CC(=O)N[C@H]2Cc3cccc(C(=O)O)c3OB2O)OC1] | | |
| 84 | 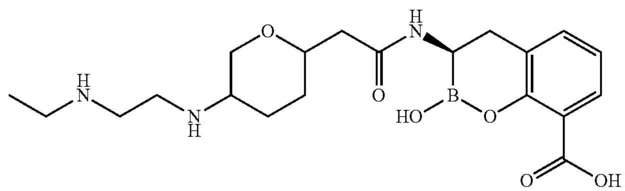 [SMILES: CCNCCNC1CCC(CC(=O)N[C@H]2Cc3cccc(C(=O)O)c3OB2O)OC1] | | |
| 85 | 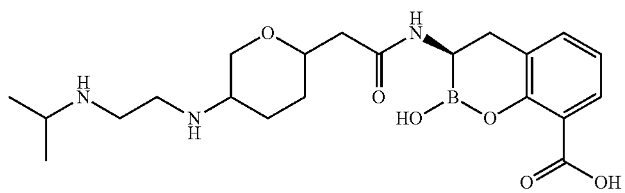 [SMILES: CC(C)NCCNC1CCC(CC(=O)N[C@H]2Cc3cccc(C(=O)O)c3OB2O)OC1] | | |

Example 53: Parenteral Composition of a Compound of Formula I or Formula Ia

To prepare a parenteral pharmaceutical composition suitable for administration by injection, 100 mg of a compound of Formula I or Formula Ia, or a water soluble pharmaceutically acceptable salt thereof, is dissolved in DMSO and then mixed with 10 ml of 0.9% sterile saline solution. The mixture is incorporated into a dosage unit suitable for administration by injection.

Example 54: Oral Composition of a Compound of Formula I or Formula Ia

To prepare a pharmaceutical composition for oral delivery, 400 mg of a compound of Formula I or Formula Ia and the following ingredients are mixed intimately and pressed into single scored tablets.

| Tablet Formulation | |
|---|---|
| Ingredient | Quantity per tablet mg |
| compound | 400 |
| cornstarch | 50 |
| croscarmellose sodium | 25 |
| lactose | 120 |
| magnesium stearate | 5 |

The following ingredients are mixed intimately and loaded into a hard-shell gelatin capsule.

| Capsule Formulation | |
|---|---|
| Ingredient | Quantity per capsule mg |
| compound | 200 |
| lactose spray dried | 148 |
| magnesium stearate | 2 |

Biological Examples

Example I: Experimental Method for β-Lactamase Enzyme Assays

Isolation of β-Lactamases

For SHV-5, Kpc-2, p99AmpC and OXA-1 β-lactamases, E. coli BL21(DE3) bacterial cells carrying expression plasmids (expressed as native untagged proteins) for the individual β-lactamases were grown in 1 L of Superbroth (Teknova Inc. Hollister, Calif.) supplemented with 100 µg/ml kanamycin selection and 1×5052 (0.5% glycerol, 0.05% glucose and 0.2% α-lactose) at 35° C. for 18-20 hours. Cells were harvested by centrifugation (4,000×g, 4° C., 20 min), resuspended in 50 ml of 10 mM HEPES pH 7.5 (1/20 of the initial volume). The cells were lysed by sonication (5 pulses of 45 seconds) at 45 W on ice. The lysates were clarified by centrifugation at 10,000×g for 40 minutes at 4° C. Samples were diluted 5-fold in 50 mM sodium acetate pH 5.0, stored overnight at 4° C., after which they were centrifuged at 10,000×g for 30 minutes to clarify, and filtered through 0.45 µm filters. The samples were loaded onto a 5 ml Capto S sepharose cation exchange column (GE Healthcare) pre-equilibrated with 50 mM sodium acetate pH 5.0. The column was washed with 5 column volumes of 50 mM sodium acetate pH 5.0 to wash out unbound protein and a linear gradient of NaCl (0 to 500 mM) was used to elute the protein (over 16 CV) from the column. Fractions were assayed for β-lactamase activity using Centa (Calbiochem, Gibbstown, N.J.) or Nitrocefin (EMD Millipore chemicals, Darmstadt, Germany) as a reporter β-lactamase substrate for activity in the isolated fractions. Active fractions were pooled, concentrated and further purified by gel filtration chromatography on a Superdex 75 prep grade gel filtration column (GE Healthcare, Piscataway, N.J.) pre-equilibrated in 50 mM Hepes pH 7.5, 150 mM NaCl. Active fractions were pooled concentrated, quantitated by BCA protein determination (Thermo Scientific, Rockford, Ill.), dialyzed into PBS and frozen at −80° C. in 20% glycerol until use.

For Vim-2 metallo β-lactamase, the procedure was identical with the following exceptions, first the protein was not pH adjusted to pH 5 with 50 mM sodium acetate, second, the chromatography step was changed to a 5 ml Q sepharose anion exchange column pre-equilibrated with 50 mM Hepes pH 7.5, and elution of the protein was achieved by a linear gradient of NaCl (0-600 mM). Finally, the VIM-2 purification required a second run (3$^{rd}$ step) on the Q sepharose anion exchange column to achieve acceptable purity (>90%).

β-Lactamase Inhibition.

To determine the level of inhibition of β-lactamase enzymes, compounds were diluted in PBS at pH 7.4 to yield concentrations ranging from 100 to 0.00005 µM in 96-well microtiter plates. An equal volume of diluted enzyme stock was added, and the plates were incubated at 37° C. for 15 min. Nitrocefin was used as substrate for p99 AmpC, VIM-2 and OXA-1 and dispensed into each well at a final concentration of 100 µM. Absorbance at 486 nm was immediately monitored for 10 min using a Biotek Powerwave XS2 microplate spectrophotometer using the GEN5 softweare package (Biotek Instruments, Winooski Vt.). In an analogous fashion, imipenem was used as substrate for Kpc-2 and Cefotaxime was used for SHV-5, while changes in absorbance upon hydrolysis of the β-lactam ring were monitored at 300 nm and 260 nm respectively in UV-transparent 96-well microtiter assay plates. Maximum rates of hydrolysis were compared to those in control wells (without inhibitors), and percentages of enzyme inhibition were calculated for each concentration of inhibitor. The concentration of inhibitor needed to reduce the initial rate of hydrolysis of substrate by 50% ($IC_{50}$) was calculated as the residual activity of β-lactamase at 486 nm using GraFit version 7 kinetics software package (Erithacus Software, Surrey, UK).

Example II: Inhibition of Diverse β-Lactamases by Exemplary Compounds

Using the methodology described above, examples of the current invention were evaluated for their ability to inhibit β-lactamase enzymes from all four Ambler classifications (A through D). The results of these assays are summarized in Table 2 for representative enzymes across different subtypes (note SHV-5 represents an Ambler Class A Extended Spectrum β-Lactamases, KPC-2 exemplifies a Class A carbapenemase, P99 represents chromosomal Class C AmpC, OXA-1 represents a Class D oxacillinase and VIM-2 represents a class B zinc-dependent metallo-β-lactamase also possessing carbapenemase activity), where A represents an $IC_{50}$ of 10-100 µM, B represents an $IC_{50}$ of 1 to 10 µM, C represents an $IC_{50}$ of 0.1 to 1 µM, and D represents an $IC_{50}$ of <0.1 µM. NT=Not tested.

TABLE 2

Inhibition of Diverse β-Lactamases by Exemplary Compounds

| | Class A | | Class B | Class C | Class D |
|---|---|---|---|---|---|
| EXAMPLE | SHV-5 | KPC-2 | VIM-2 | AmpC | OXA-1 |
| 1 | D | D | A | D | C |
| 2 | D | C | B | D | C |
| 3 | D | D | B | D | C |
| 4 | D | D | B | D | C |
| 5 | B | D | C | D | D |
| 6 | D | C | B | D | C |
| 7 | D | C | B | D | C |
| 8 | A | C | B | D | D |
| 9 | D | D | A | D | D |
| 10 | D | C | B | D | C |
| 11 | D | C | B | D | C |
| 12 | D | D | C | D | D |
| 13 | C | B | A | D | C |
| 14 | C | C | B | D | C |
| 15 | C | B | B | D | C |
| 16 | D | C | B | D | D |
| 17 | D | C | B | D | D |
| 18 | C | C | C | D | D |
| 19 | D | C | A | D | D |
| 20 | C | C | B | D | D |
| 21 | D | C | B | D | D |
| 22 | C | C | B | D | C |
| 23 | D | D | B | D | D |
| 24 | C | C | A | D | C |
| 25 | D | C | A | D | D |
| 26 | C | C | A | D | C |
| 27 | C | C | A | D | C |
| 28 | A | D | A | D | D |
| 29 | B | C | A | C | C |
| 30 | D | D | B | D | D |
| 31 | C | D | B | D | D |
| 32 | A | C | A | D | C |
| 33 | D | C | B | D | NT |
| 34 | D | C | A | C | C |
| 35 | C | C | A | C | C |
| 36 | D | C | B | D | D |
| 37 | C | C | C | D | C |
| 38 | C | B | B | D | NT |
| 39 | C | D | C | D | D |
| 40 | D | C | C | D | D |
| 41 | D | C | C | D | D |

TABLE 2-continued

Inhibition of Diverse β-Lactamases by Exemplary Compounds

| | Class A | | Class B | Class C | Class D |
|---|---|---|---|---|---|
| EXAMPLE | SHV-5 | KPC-2 | VIM-2 | AmpC | OXA-1 |
| 42 | D | D | B | D | NT |
| 43 | D | D | C | D | D |
| 44 | D | D | A | D | D |
| 45 | D | D | C | D | C |
| 46 | D | C | B | D | C |
| 47 | D | D | C | D | C |
| 48 | D | D | B | D | D |
| 49 | D | D | B | D | D |
| 50 | D | D | B | D | D |
| 51 | B | D | B | D | C |
| 52 | D | D | B | D | D |

Example III: In Vitro Antibacterial Assays of β-Lactamase Inhibition

To determine the ability of test compounds to potentiate the inhibition of the growth of bacterial strains that produce beta-lactamase enzymes, classic cell based broth microdilution MIC assays were employed. Six bacteria strains producing beta-lactamase enzymes were used: E. coli expressing the Class A Extended Spectrum Beta-Lactamase (ESBL) CTX-M-15, E. cloacae expressing the Class C P99, K. pneumoniae expressing the Class A carbapenemase KPC-3, P. aeruginosa expressing the Class B carbapenemase VIM-2, K. pneumoniae expressing the class A carbapenemase KPC-2 and the class B carbapenemase VIM-4, and S. aureus producing the Class A penicillinase PC-1. The assay was conducted in Cation Adjusted Mueller Hinton Broth (CAMHB, BD #212322, BD Diagnostic Systems, Sparks, Md.). Bacteria strains were grown for 3-5 hours in CAMBH broth. Test compounds (Examples 1-30) were added to a microtiter plate in 2-fold serial dilutions in CAMHB in a final concentration range of 32 µg/mL to 0.25 µg/ml. An overlay of CAMHB containing a Beta-lactam was added to the compounds at a final static concentration of 4 µg/ml. Ceftazidime (CAZ, Sigma#C3809-1 G, Sigma-Aldrich, St. Louis, Mo.) was used as the partner antibiotic for E. coli expressing Ambler Class A ESBL CTX-M-15 (MIC alone>128 µg/ml), and E. cloacae expressing Class C P99 (MIC alone=128 µg/mL). Meropenem (Mero, USP #1392454, U.S. Pharmacopeia, Rockville, Md.) was used as the partner antibiotic for K. pneumoniae expressing Ambler Class A carbapenemase KPC-3 (MIC alone>128 µg/mL), P. aeruginosa expressing Class A carbapenemase VIM-2 (MIC alone=16 g/mL), and K. pneumoniae expressing the Ambler Class A carbapenemase KPC-2 and Ambler Class B carbapenemase VIM-4 (MIC alone=64 µg/mL). Piperacillin (Pip, Fisher #ICN15626801, MP Biomidicals, Solon, Ohio) was used as the partner antibiotic for S. aureus producing the Class A penicillinase PC-1 (MIC alone=64 µg/ml). Titration of test compounds with MIC readout indicates the concentration of test article needed to sufficiently inhibit beta-lactamase enzyme activity and protect the intrinsic antibacterial activity of the beta-lactam. In addition to the titration of test compounds the MICs of a panel of control beta-lactams is also tested to ensure the strains are behaving consistently from test to test. Once the test compound and antibiotics are added the plates can be inoculated according to CLSI broth microdilution method. After inoculation the plates are incubated for 16-20 hours at 37° C. then the Minimal Inhibitory Concentration (MIC) of the test compound is determined visually.

Using the methodology described above, examples of the current invention were evaluated for their ability to inhibit the growth of β-lactamase-producing bacteria in the presence of a β-lactam antibiotic.

Representative results are shown in Table 3 where A represents an MIC>16 g/mL, B represents an MIC between 1 and 16 µg/mL inclusive, and C represents an MIC of <1 µg/mL. NT=Not Tested.

Example IV: In Vitro Antibacterial Activity of Exemplary Compounds

Using the methodology described above in EXAMPLE III, exemplary compounds for Formula I or Formula Ia were evaluated for their ability to inhibit the growth of β-lactamase producing bacteria in the presence of a β-lactam antibiotic.

Representative results are shown in Table 3 where A represents an MIC of the fixed β-lactam antibiotic in the presence of >32 g/mL of a β-lactamase inhibitor of exemplary Compounds, B represents the MIC in the presence of between 8 and 32 g/mL of a β-lactamase inhibitor of exemplary Compounds, and C represents the MIC in the presence of <4 µg/mL of a β-lactamase inhibitor of exemplary Compounds. NT=Not Tested.

TABLE 3

Broad spectrum inhibition of bacterial growth. MIC of example compounds of the invention in the presence of a fixed amount (4 (µg/mL) of designated β-lactam antibiotics ceftazidime (CAZ), meropenem (Mero), Piperacillin (Pip).

MIC (µg/mL) of Examples 1-52 in presence of fixed β-lactams

| | Fixed CAZ ESBLs | | Fixed Mero Carbapenemases (Classes A and B) | | | Fixed Pip |
|---|---|---|---|---|---|---|
| | (Class A and C) | | | | K. P. | Penicillinase |
| EXAMPLE | E. coli ESBL4 CTX-M-15 | E. cl. 144200 p99 AmpC | K. P. 156319 KPC-3 | P. aerug. Ps296 VIM-2 | A-1797 KPC-2 VIM-4 | S. aureus MSSA-7 PC-1 |
| 1 | C | B | N/T | A | A | C |
| 2 | C | C | B | A | A | C |
| 3 | C | C | C | C | B | C |
| 4 | C | C | C | B | B | C |
| 5 | C | C | C | B | C | B |

TABLE 3-continued

Broad spectrum inhibition of bacterial growth. MIC of example compounds of the invention in the presence of a fixed amount (4 (µg/mL) of designated β-lactam antibiotics ceftazidime (CAZ), meropenem (Mero), Piperacillin (Pip).

MIC (µg/mL) of Examples 1-52 in presence of fixed β-lactams

| EXAMPLE | Fixed CAZ ESBLs (Class A and C) | | Fixed Mero Carbapenemases (Classes A and B) | | | Fixed Pip Penicillinase |
|---|---|---|---|---|---|---|
| | *E. coli* ESBL4 CTX-M-15 | *E. cl.* 144200 p99 AmpC | *K. P.* 156319 KPC-3 | *P. aerug.* Ps296 VIM-2 | *K. P.* A-1797 KPC-2 VIM-4 | *S. aureus* MSSA-7 PC-1 |
| 6 | C | C | C | B | B | A |
| 7 | C | C | C | A | A | C |
| 8 | C | C | C | A | A | C |
| 9 | C | C | C | A | A | C |
| 10 | C | C | C | A | C | B |
| 11 | C | C | C | A | A | A |
| 12 | C | C | C | B | B | C |
| 13 | C | C | C | B | B | C |
| 14 | C | C | C | B | B | C |
| 15 | C | C | C | C | B | C |
| 16 | C | C | C | C | B | C |
| 17 | B | C | B | A | A | C |
| 18 | B | C | C | B | B | A |
| 19 | C | C | B | A | A | B |
| 20 | C | C | C | B | A | C |
| 21 | C | C | C | B | A | C |
| 22 | C | C | B | A | A | C |
| 23 | C | C | C | B | B | C |
| 24 | C | C | B | B | B | C |
| 25 | C | C | B | B | B | C |
| 26 | C | C | C | C | C | A |
| 27 | C | B | B | B | B | A |
| 28 | C | C | C | C | B | C |
| 29 | C | C | C | C | B | C |
| 30 | C | C | C | B | A | A |
| 31 | C | C | C | C | B | C |
| 32 | C | C | A | A | A | C |
| 33 | C | C | B | A | B | C |
| 34 | C | C | A | A | A | C |
| 35 | C | C | B | A | B | C |
| 36 | C | C | B | B | B | C |
| 37 | C | C | C | A | B | C |
| 38 | C | C | C | B | A | N/T |
| 39 | C | C | C | C | B | C |
| 40 | C | C | B | C | B | C |
| 41 | C | C | C | C | C | C |
| 42 | C | C | C | B | A | C |
| 43 | C | C | C | C | C | C |
| 44 | C | C | C | A | A | C |
| 45 | C | C | C | C | C | B |
| 46 | C | C | B | A | A | C |
| 47 | C | C | C | C | B | B |
| 48 | C | C | C | C | B | C |
| 49 | C | C | C | B | A | C |
| 50 | C | C | C | C | A | C |
| 51 | C | C | C | C | A | C |
| 52 | C | C | C | B | B | C |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound of Formula (I) or Formula (Ia), a pharmaceutically acceptable salt, polymorph, solvate, prodrug, N-oxide, or stereoisomer thereof:

Formula (I)

$(Y)_p$–(HetA)–$(CR^1R^2)_m$–M–$(CR^1R^2)_n$–Z–N(...)

Formula (Ia)

$(Y)_p$–(HetA)–$(CR^1R^2)_m$–M–$(CR^1R^2)_n$–Z–N(...)

wherein:
M is a bond;
m is 0, 1, or 2;
  provided that when HetA is attached to $(CR^1R^2)_m$ through a ring nitrogen atom, m=0 or 2;
n is 0, 1, 2, or 3;
provided that m or n is 1;
p is 0,1,2,3 or 4;
$X^1$ and $X^2$ are independently selected from —OH, —OR$^8$, or F;
Z is >C=O, >C=S, or >SO$_2$;
HetA is an optionally substituted non-aromatic heterocyclic ring system;
Y is selected from the group consisting fluoro, chloro, —CN, optionally substituted $C_1$-$C_6$ alkyl, —OH, —OR$^{10}$, —NR$^4$R$^5$, —(CR$^6$R$^7$)$_v$NR$^4$R$^5$, —NR$^4$(CR$^6$R$^7$)$_v$NR$^4$R$^5$, —O(CR$^6$R$^7$)$_v$NR$^4$R$^5$, —N(R$^4$)C(O)(CR$^6$R$^7$)$_v$NR$^4$R$^5$, —(CR$^6$R$^7$)$_v$N(R$^4$)C(O)(CR$^6$R$^7$)$_v$NR$^4$R$^5$, —C(O)NR$^4$(CR$^6$R$^7$)$_v$NR$^4$R$^5$, —S(O)$_{0,1,2}$NR$^4$(CR$^6$R$^7$)$_v$NR$^4$R$^5$, —NR$^5$C(O)NR$^4$(CR$^6$R$^7$)$_v$NR$^4$R$^5$, —OC(O)NR$^4$(CR$^6$R$^7$)$_v$NR$^4$R$^5$, —NR$^5$C(=NR$^7$)NR$^4$(CR$^6$R$^7$)$_v$NR$^4$R$^5$, —N(R$^4$)C(=NR$^5$)R$^6$, —(CR$^6$R$^7$)$_v$N(R$^4$)C(=NR$^5$)R$^6$, —NR$^4$(CR$^6$R$^7$)$_v$N(R$^4$)C(=NR$^5$)R$^6$, —O(CR$^6$R$^7$)$_v$N(R$^4$)C(=NR$^5$)R$^6$, —(CR$^6$R$^7$)$_v$C(=NR$^5$)NR$^4$R$^5$, —NR$^4$(CR$^6$R$^7$)$_v$C(=NR$^5$)NR$^4$R$^5$, —O(CR$^6$R$^7$)$_v$C(=NR$^5$)NR$^4$R$^5$, —(CR$^6$R$^7$)$_v$N(R$^4$)C(=NR$^5$)NR$^4$R$^5$, —NR$^4$(CR$^6$R$^7$)$_v$N(R$^4$)C(=NR$^5$)NR$^4$R$^5$, —O(CR$^6$R$^7$)$_v$N(R$^4$)C(=NR$^5$)NR$^4$R$^5$, —NR$^4$C(=NR$^5$)NR$^4$C(=NR$^5$)NR$^4$R$^5$, —(CR$^6$R$^7$)$_v$C(=NR$^4$)NR$^5$C(=NR$^4$)NR$^4$R$^5$, —NR$^4$(CR$^6$R$^7$)$_v$C(=NR$^4$)NR$^5$C(=NR$^4$)NR$^4$R$^5$, —O(CR$^6$R$^7$)$_v$C(=NR$^4$)NR$^5$C(=NR$^4$)NR$^4$R$^5$, —NR$^4$C(=NR$^4$)NR$^4$C(=NR$^4$)NR$^4$R$^5$, —NR$^4$C(=NR$^5$)NR$^4$R$^5$, —C(=NR$^4$)NR$^4$R$^5$, —C(=NR$^4$)NR$^4$C(O)R$^6$, —NR$^4$SO$_2$R$^6$, —NR$^4$C(O)R$^6$, —NR$^4$C(=O)OR$^6$, —C(O)NR$^4$R$^5$, —(CR$^6$R$^7$)$_v$C(O)NR$^4$R$^5$, -Heteroaryl-NR$^4$R$^5$, -Heterocyclyl-NR$^4$R$^5$, -Heteroaryl-N(R$^4$)C(=NR$^5$)NR$^4$R$^5$, -Heterocyclyl-N(R$^4$)C(=NR$^5$)NR$^4$R$^5$, —N(R$^4$)—Heteroaryl-NR$^4$R$^5$, —N(R$^4$)—Heterocyclyl-NR$^4$R$^5$, —(CR$^6$R$^7$)$_v$Heteroaryl-NR$^4$R$^5$, —(CR$^6$R$^7$)$_v$Heterocyclyl-NR$^4$R$^5$, —(CR$^6$R$^7$)$_v$Heteroaryl-N(R$^4$)C(=NR)NR$^4$R$^5$, —(CR$^6$R$^7$)$_v$Heterocyclyl-N(R$^4$)C(=NR$^5$)NR$^4$R$^5$, —(CR$^6$R$^7$)$_v$Heteroaryl, —(CR$^6$R$^7$)$_v$Heterocyclyl, —O-Heteroaryl, —O-Heterocyclyl, —NR$^4$(CR$^6$R$^7$)$_v$Heteroaryl, —NR$^4$(CR$^6$R$^7$)$_v$Heterocyclyl, —O(CR$^6$R$^7$)$_v$Heteroaryl, —O(CR$^6$R$^7$)$_v$Heterocyclyl, and —O(CR$^6$R$^7$)$_v$O-Heterocyclyl;
v is 1-4; w is 2-4;
R$^a$, R$^b$, and R$^c$ are independently selected from the group consisting of hydrogen, fluoro, chloro, bromo, optionally substituted $C_1$-$C_6$ alkyl, optionally substituted $C_3$-$C_6$ cycloalkyl, optionally substituted heterocyclyl, optionally substituted aryl, optionally substituted heteroaryl, —OH, —OR$^{10}$, —NR$^4$R$^5$, and —SR$^{10}$;
R$^1$ and R$^2$ are independently selected from the group consisting of hydrogen, fluoro, chloro, bromo, optionally substituted $C_1$-$C_6$ alkyl, optionally substituted $C_3$-$C_6$ cycloalkyl, —OH, —OR$^{10}$, —SR$^{10}$, and —NR$^4$R$^5$,
  or R$^1$ and R$^2$ taken together form an oxo, oxime, or an optionally substituted carbocycle or optionally substituted heterocycle with the carbon to which they are attached;
R$^3$ is hydrogen, optionally substituted $C_1$-$C_6$ alkyl, or a pharmaceutically acceptable prodrug;
R$^d$, R$^4$ and R$^5$ are independently selected from the group consisting of hydrogen, —OH, —CN, optionally substituted $C_1$-$C_6$ alkyl, optionally substituted alkoxyalkyl, optionally substituted hydroxyalkyl, optionally substituted aminoalkyl, optionally substituted cycloalkyl, optionally substituted heterocyclyl, optionally substituted aryl, optionally substituted heteroaryl, optionally substituted cycloalkylalkyl, optionally substituted heterocyclylalkyl, optionally substituted aralkyl, optionally substituted heteroaralkyl, (poly-ethylene-glycol)-ethyl, and an optionally substituted saccharide;
  or R$^4$ and R$^5$ taken together form an optionally substituted heterocycle with the nitrogen to which they are attached;
R$^6$ and R$^7$ are independently selected from the group consisting of hydrogen, fluoro, chloro, bromo, optionally substituted $C_1$-$C_6$ alkyl, optionally substituted alkoxyalkyl, optionally substituted hydroxyalkyl, optionally substituted $C_3$-$C_6$ cycloalkyl, —OH, —OR$^{10}$, —SR$^{10}$, —NR$^4$R$^5$, —NR$^4$C(O)R$^5$, —C(O)NR$^4$R$^5$, —NR$^4$SO$_2$R$^5$, optionally substituted heterocyclyl, optionally substituted aryl, and optionally substituted heteroaryl;
  or R$^6$ and R$^7$ taken together form an oxo, oxime, or an optionally substituted carbocycle or an optionally substituted heterocycle with the carbon to which they are attached;
R$^8$ is optionally substituted $C_1$-$C_6$ alkyl, optionally substituted $C_3$-$C_6$ cycloalkyl, or a pharmaceutically acceptable boronate ester group;
R$^9$ is optionally substituted $C_1$-$C_6$ alkyl; and
R$^{10}$ is optionally substituted $C_1$-$C_6$ alkyl or optionally substituted $C_3$-$C_6$ cycloalkyl.

2. The compound of claim 1, wherein $R^a$, $R^b$, and $R^c$ are independently hydrogen, fluoro, or chloro.

3. The compound of claim 1, wherein $R^a$, $R^b$, and $R^c$ are hydrogen.

4. The compound of claim 1, wherein $R^3$ is hydrogen.

5. The compound of claim 1, wherein $X^1$ and $X^2$ are —OH.

6. The compound of claim 1, wherein $R^d$ is hydrogen or $C_1$-$C_4$-alkyl.

7. The compound of claim 1, wherein Z is >C=O.

8. The compound of claim 1, wherein HetA is selected from the group consisting of azetidine, oxetane thietane, pyrrolidine oxazolidine, isoxazolidine, thiazolidine, isothiazolidine, imidazolidine, pyrazolidine, 2,5-dihydro-1H-pyrrole, 3,4-dihydro-2H-pyrrole, 4,5-dihydrooxazole, 4,5-dihydroisoxazole, 4,5-dihydrothiazole, 4,5-dihydroisothiazole, 4,5-dihydro-1H-pyrazole, 4,5-dihydro-1H-imidazole, 2,5-dihydro-1H-pyrrole, piperidine, morpholine, thiomorpholine, tetrahydrothiopyran, tetrahydropyran, tetrahydrofuran, 1,4-oxathiane, piperazine, hexahydropyrimidine, hexahydropyridazine, 1,4,5,6-tetrahydropyrimidine, 1,3-oxazinane, 5,6-dihydro-4H-1,3-oxazine, 1,3-thiazinane, 5,6-dihydro-4H-1,3-thiazine, 1,4,5,6-tetrahydropyridazine, 1,2,3,6-tetrahydropyrazine, 1,2,3,6-tetrahydropyridine, 1,2,3,6-tetrahydropyridazine, azepane, 1,3-oxazepane, 1,4-oxazepane, 1,3-diazepane, 1,4-diazepane, 1,3-thiazepane, 1,4-thiazepane, diazepane, oxazepane, thiazepane, 3,4,5,6-tetrahydro-2H-azepine, 4,5,6,7-tetrahydro-1H-1,3-diazepine, 4,5,6,7-tetrahydro-1,3-oxazepine, 4,5,6,7-tetrahydro-1,3-thiazepine, 2,3,4,7-tetrahydro-1H-1,3-diazepine, and 2,3,4,7-tetrahydro-1,3-oxazepine.

9. The compound of claim 8, wherein HetA is selected from the group consisting of piperidine, piperazine, pyrrolidine, tetrahydropyran, and tetrahydrofuran.

10. The compound of claim 1, wherein Y is selected from the group consisting fluoro, chloro, —CN, optionally substituted $C_1$-$C_6$ alkyl, —OH, —$NR^4R^5$, —$(CR^6R^7)_vNR^4R^5$, —$NR^4(CR^6R^7)_vNR^4R^5$, —$O(CR^6R^7)_vNR^4R^5$, —$C(O)NR^4(CR^6R^7)_vNR^4R^5$, —$NR^5C(O)NR^4(CR^6R^7)_vNR^4R^5$, —$NR^5C(=NR^7)NR^4(CR^6R^7)_vNR^4R^5$, —$N(R^4)C(=NR^5)R^6$, —$(CR^6R^7)_vN(R^4)C(=NR^5)R^6$, —$NR^4(CR^6R^7)_vN(R^4)C(=NR^5)R^6$, —$(CR^6R^7)_vC(=NR^5)NR^4R^5$, —$NR^4(CR^6R^7)_vC(=NR^5)NR^4R^5$, —$(CR^6R^7)_vN(R^4)C(=NR^5)NR^4R^5$, —$NR^4(CR^6R^7)_vN(R^4)C(=NR^5)NR^4R^5$, —$NR^4C(=NR^5)NR^4C(=NR^5)NR^4R^5$, —$(CR^6R^7)_vC(=NR^4)NR^5C(=NR^4)NR^4R^5$, —$C(=NR^4)NR^4C(O)R^6$, —$NR^4C(O)R^6$, —$(CR^6R^7)_vC(O)NR^4R^5$, -Heteroaryl-$NR^4R^5$, -Heteroaryl-$N(R^4)C(=NR^5)NR^4R^5$, —$N(R^4)$-Heterocyclyl-$NR^4R^5$, —$(CR^6R^7)_v$Heteroaryl-$NR^4R^5$, —$(CR^6R^7)_v$Heterocyclyl-$N(R^4)C(=NR^5)NR^4R^5$, —$(CR^6R^7)_v$Heteroaryl, and —$NR^4(CR^6R^7)_v$-Heterocyclyl.

11. The compound of claim 1, wherein Y is selected from the group consisting of —$NR^4R^5$, —$NR^4C(=NR^5)NR^4R^5$, —$C(=NR^4)NR^4R^5$, —$N(R^4)C(=NR^5)R^6$, —$(CR^6R^7)_vNR^4R^5$, —$(CR^6R^7)_vN(R^4)C(=NR^5)NR^4R^5$, —$NR^4(CR^6R^7)_vNR^4R^5$, —$NR^4(CR^6R^7)_vOR^{10}$, —$(CR^6R^7)_vNR^4(CR^6R^7)_vNR^4R^5$, $NR^5C(=NR^5)NR^4(CR^6R^7)_vNR^4R^5$, —$NR^4(CR^6R^7)_vN(R^4)C(=NR^5)NR^4R^5$, —$NR^5C(O)CR^6(NR^4R^5)(CR^6R^7)_vNR^4R^5$, —$(CR^6R^7)_vC(=NR^5)NR^4R^5$, —$(CR^6R^7)_vN(R^4)C(O)(CR^6R^7)_vNR^4R^5$, —$C(=NR^4)NR^4C(O)R^6$, —$NR^4(CR^6R^7)_v$Heteroaryl, and —$O(CR^6R^7)_vNR^4R^5$.

12. The compound of claim 1, wherein p is 1 or 2.

13. The compound of claim 1, wherein $R^4$ and $R^5$ are independently hydrogen or optionally substituted $C_1$-$C_6$ alkyl.

14. The compound of claim 1, wherein $R^6$ and $R^7$ are independently hydrogen, fluoro, or optionally substituted $C_1$-$C_6$ alkyl.

15. The compound of claim 1, wherein the compound is selected from the group represented by the following structures:

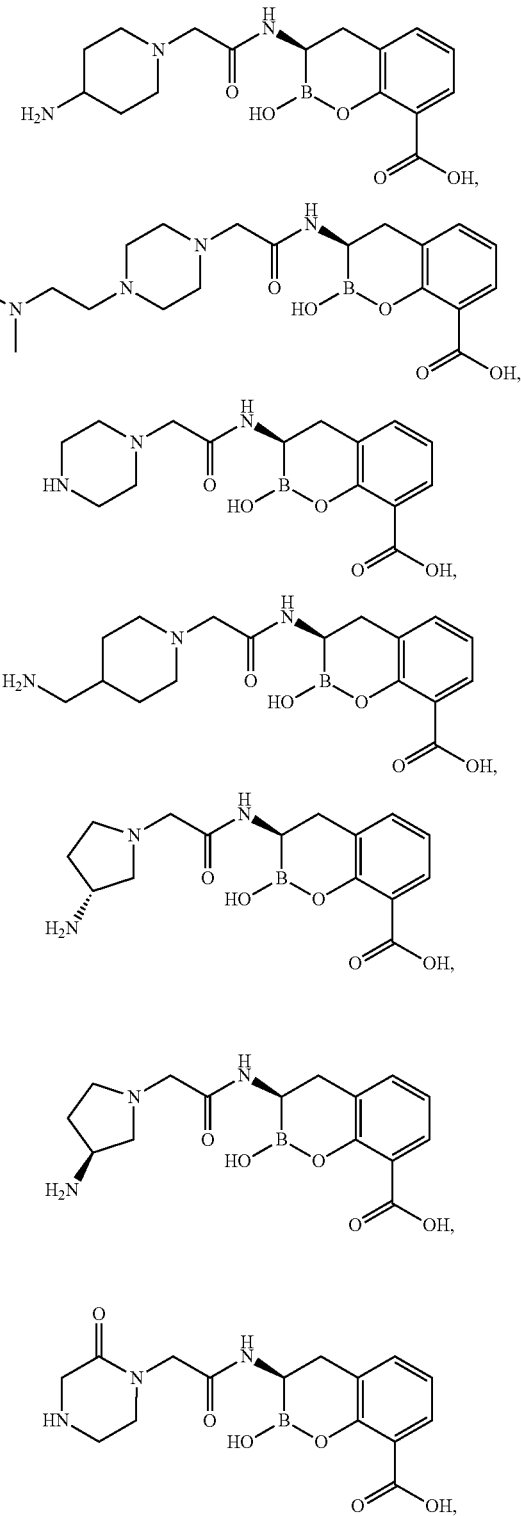

173
-continued
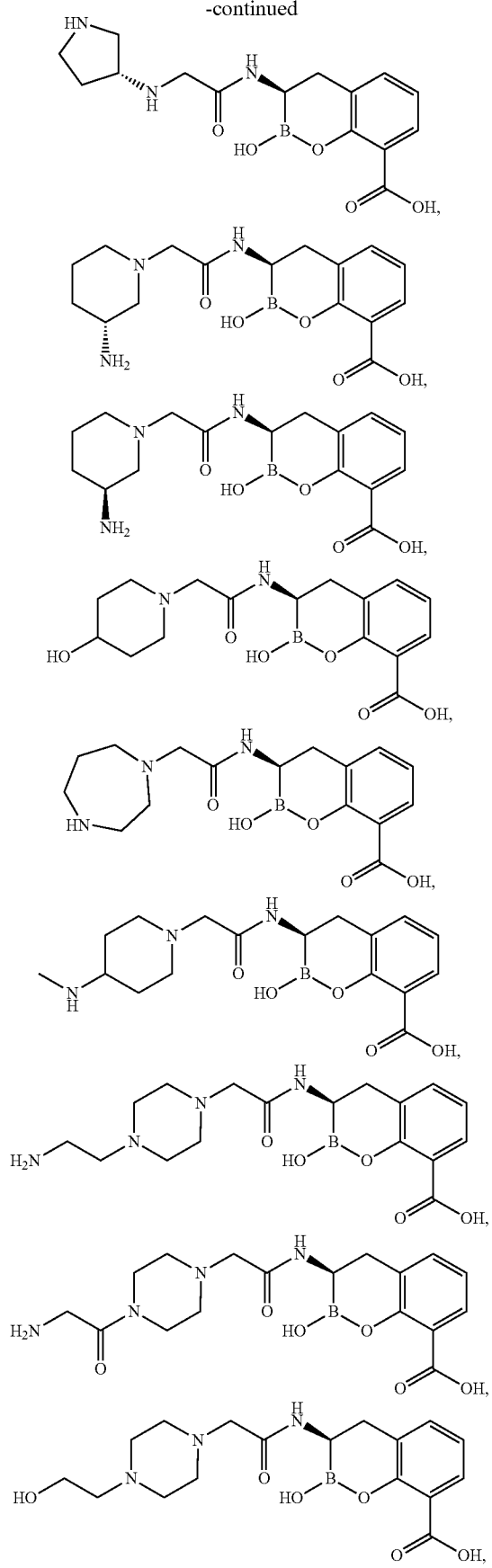
174
-continued
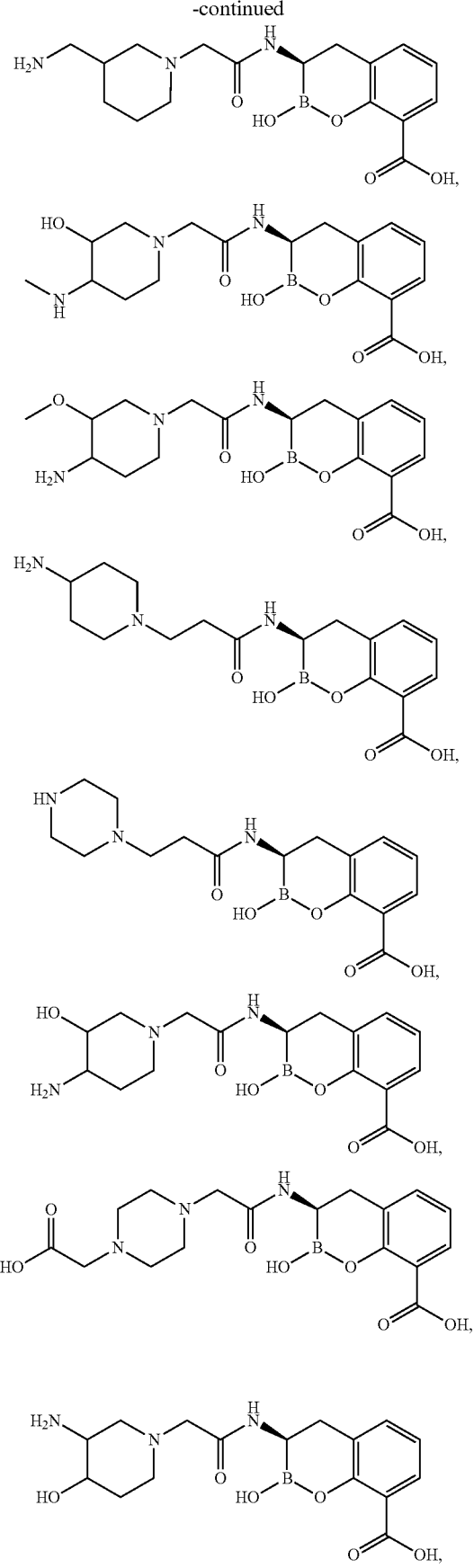

175
-continued
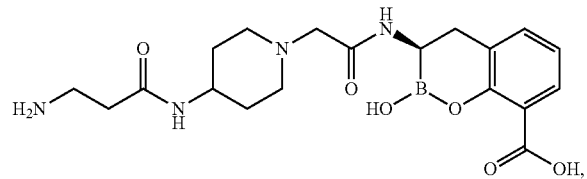
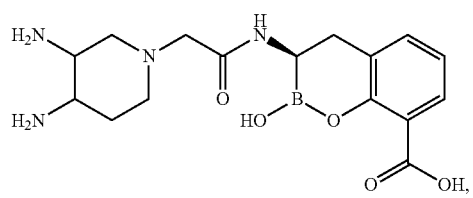
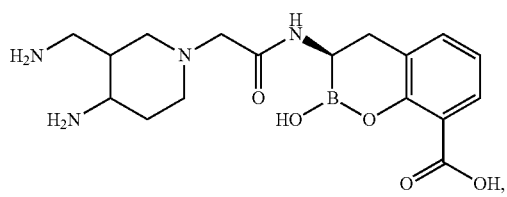
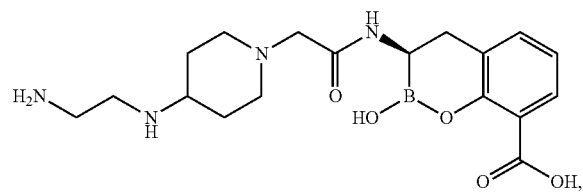
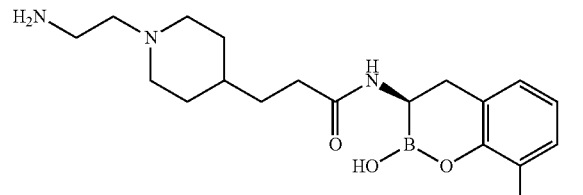
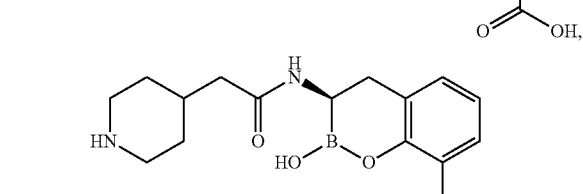
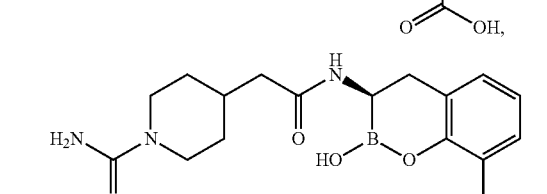
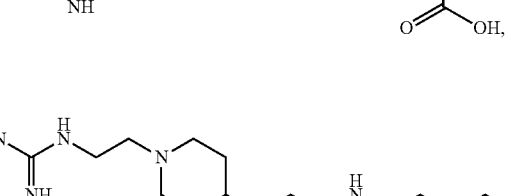
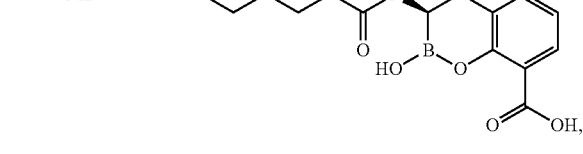
176
-continued
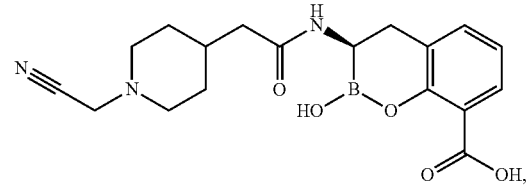
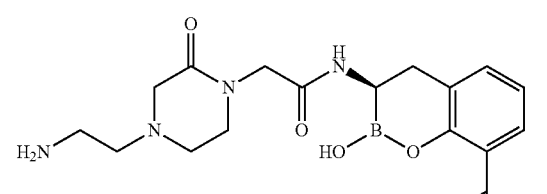
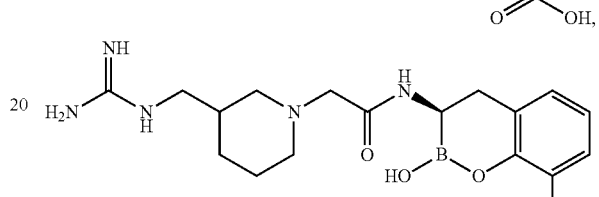
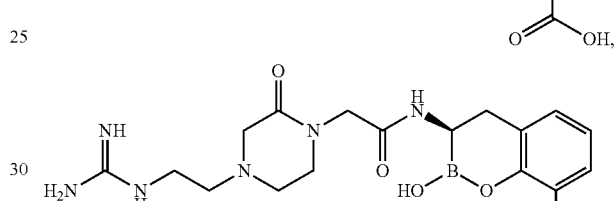
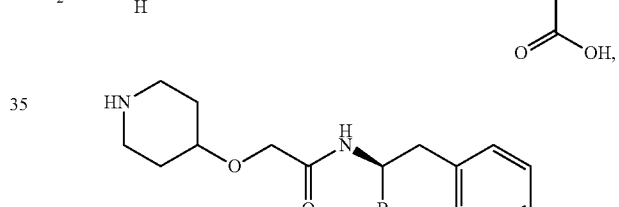
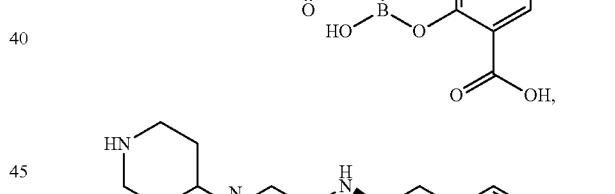
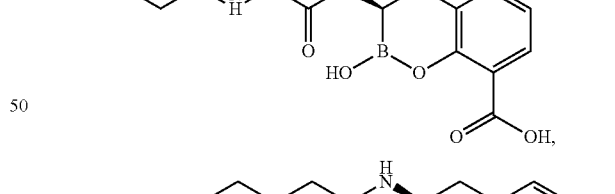
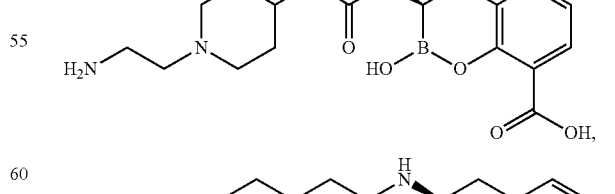
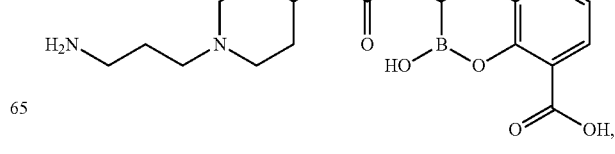

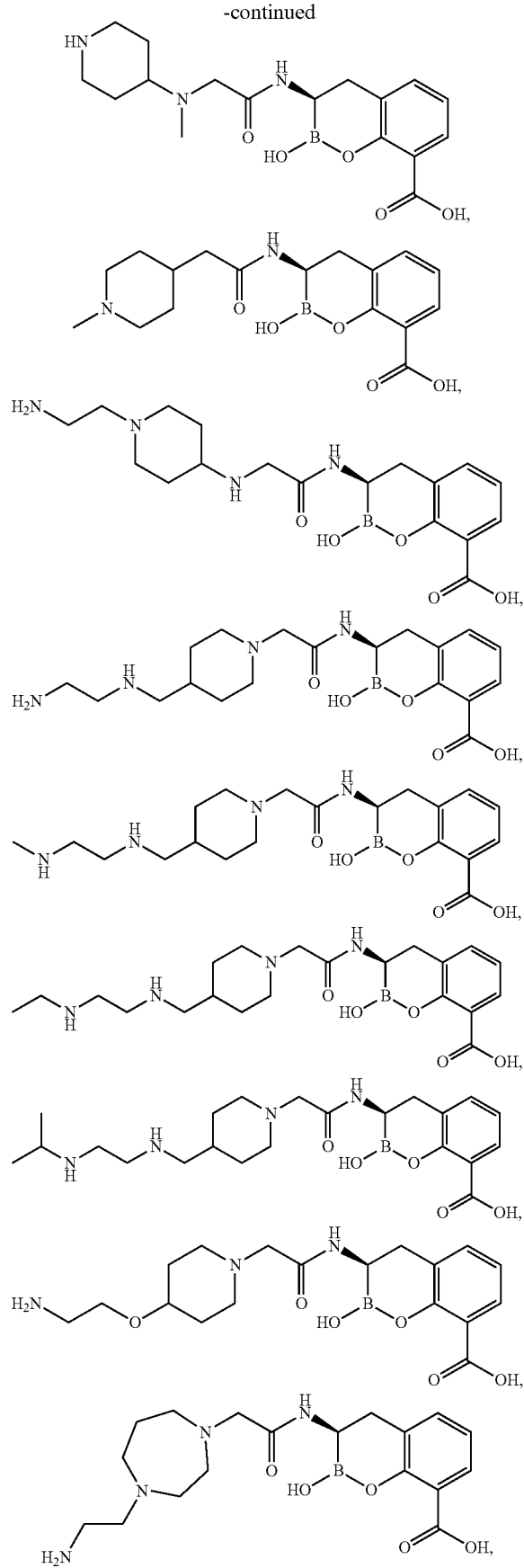
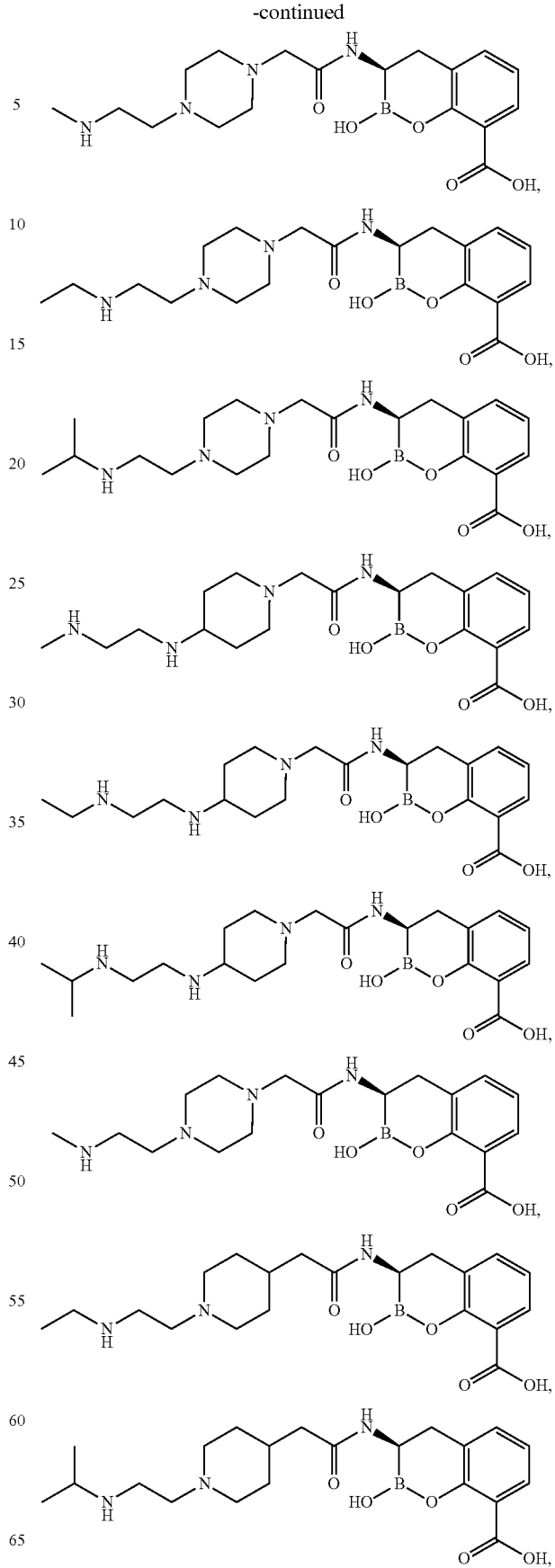

179
-continued

180
-continued

-continued
and

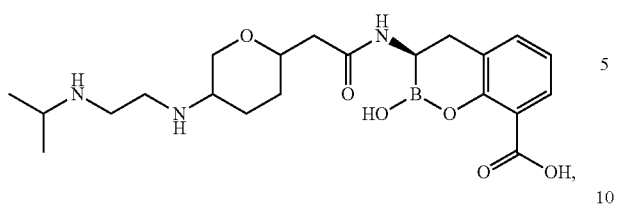

or a pharmaceutically acceptable salt, polymorph, solvate, prodrug, N-oxide, or stereoisomer thereof, wherein the compound is present in a closed, cyclic form according to Formula (I) and as shown in the structures above, in an open, acyclic form according to Formula (Ia), or mixtures thereof.

16. A pharmaceutical composition comprising a compound of claim 1 or a pharmaceutically acceptable salt, polymorph, solvate, prodrug, N-oxide, or stereoisomer thereof, and a pharmaceutically acceptable excipient.

17. The pharmaceutical composition of claim 16, further comprising a beta-lactam antibiotic.

18. The pharmaceutical composition of claim 17, wherein the beta-lactam antibiotic is a penicillin, cephalosporin, carbapenem, monobactam, bridged monobactam, or a combination thereof.

19. A method of treating a bacterial infection in a subject, comprising administering to the subject a pharmaceutical composition of claim 16, optionally in combination with a beta-lactam antibiotic.

* * * * *

UNITED STATES PATENT AND TRADEMARK OFFICE
CERTIFICATE OF CORRECTION

PATENT NO. : 9,944,658 B2
APPLICATION NO. : 14/773717
DATED : April 17, 2018
INVENTOR(S) : Burns et al.

It is certified that error appears in the above-identified patent and that said Letters Patent is hereby corrected as shown below:

In the Claims

In Claim 15, Column 173, Lines 1-10, delete the following structure:

"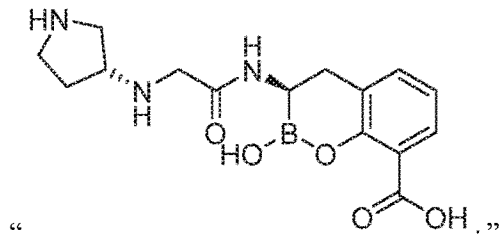,"

In Claim 15, Column 176, Lines 35-50, delete the following structures:

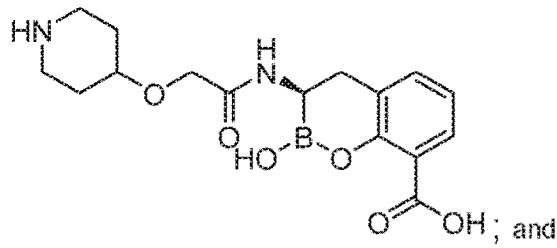; and

"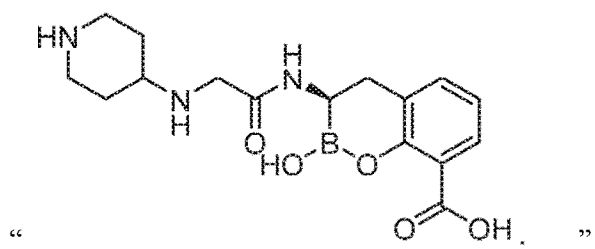."

Signed and Sealed this
Fourth Day of December, 2018

Andrei Iancu
*Director of the United States Patent and Trademark Office*

CERTIFICATE OF CORRECTION (continued)
U.S. Pat. No. 9,944,658 B2

In Claim 15, Column 177, Lines 1-10, delete the following structure:

"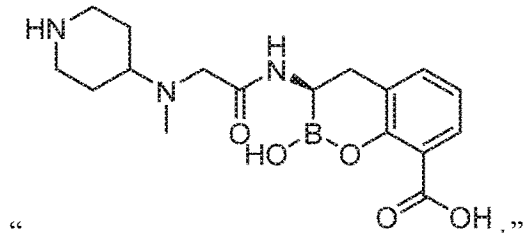"

In Claim 15, Column 177, Lines 17-25, delete the following structure:

"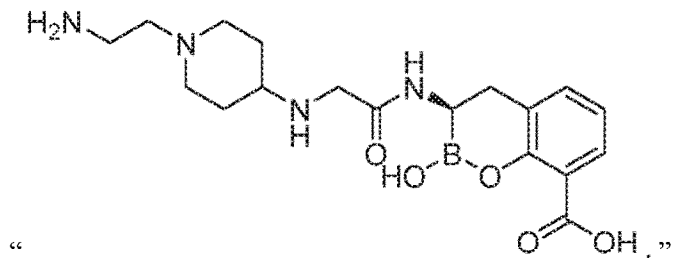"